(12) United States Patent
Hakonarson et al.

(10) Patent No.: US 12,365,946 B2
(45) Date of Patent: Jul. 22, 2025

(54) COMPOSITIONS AND METHODS FOR THE DIAGNOSIS AND TREATMENT OF LYMPHATIC SYSTEM DISORDERS

(71) Applicant: THE CHILDREN'S HOSPITAL OF PHILADELPHIA, Philadelphia, PA (US)

(72) Inventors: Hakon Hakonarson, Malvern, PA (US); Yoav Dori, Wynnewood, PA (US); Dong Li, Drexel Hill, PA (US); Michael March, Lansdowne, PA (US); Charlly Kao, Philadelphia, PA (US); Christoph Seiler, Philadelphia, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 969 days.

(21) Appl. No.: 17/274,263

(22) PCT Filed: Sep. 9, 2019

(86) PCT No.: PCT/US2019/050196
§ 371 (c)(1),
(2) Date: Mar. 8, 2021

(87) PCT Pub. No.: WO2020/051580
PCT Pub. Date: Mar. 12, 2020

(65) Prior Publication Data
US 2022/0112558 A1    Apr. 14, 2022

Related U.S. Application Data

(60) Provisional application No. 62/728,444, filed on Sep. 7, 2018.

(51) Int. Cl.
C12Q 1/68       (2018.01)
A61K 31/4184    (2006.01)
(Continued)

(52) U.S. Cl.
CPC ........ *C12Q 1/6883* (2013.01); *A61K 31/4184* (2013.01); *A61K 45/06* (2013.01);
(Continued)

(58) Field of Classification Search
None
See application file for complete search history.

(56) References Cited

U.S. PATENT DOCUMENTS

2005/0272083 A1 *  12/2005  Seshagiri ............... A61K 31/19
                                                      514/249

FOREIGN PATENT DOCUMENTS

WO   WO-2008022335 A2 *  2/2008  .......... C12Q 1/6883
WO      2014/186750 A2   11/2014
(Continued)

OTHER PUBLICATIONS

International Search Report and Written Opinion, dated Dec. 31, 2019, issued in corresponding International Application No. PCT/US2019/050196, filed Sep. 9, 2019.
(Continued)

*Primary Examiner* — Aaron A Priest
(74) *Attorney, Agent, or Firm* — Howson & Howson LLP; Kathleen D. Rigaut; Richard F. Kane

(57) ABSTRACT

Compositions and methods for the diagnosis and treatment of lymphatic anomaly are disclosed.

15 Claims, 31 Drawing Sheets

Specification includes a Sequence Listing.

| | | Baseline | | | | Post therapy | | | | |
|---|---|---|---|---|---|---|---|---|---|---|
| | | March 17, 2017 | | April 4, 2017 | | May 4, 2017 | | October 23, 2017 | | March 8, 2018 |
| Parameter | Unit | Per | % ref | Per | % ref | Per | % ref | Per | % ref | Per | % ref |
| Weight | kg | 38 | | 40 | | 42 | | 40 | | 39 | |
| Height | cm | 142 | | 142 | | 143 | | 145 | | 148 | |
| FVC | L | 0.58 | 23 | 0.88 | 35 | 0.88 | 31 | 0.95 | 35 | 1.18 | 40 |
| FEV$_1$ | L | 0.52 | 23 | 0.77 | 34 | 0.72 | 31 | 0.85 | 35 | 1.09 | 42 |
| FEV$_1$/FVC | % | 89.8 | 105 | 87 | 102 | 89.3 | 105 | 89.0 | 105 | 92.0 | 108 |
| FEF$_{25-75}$ | L/s | 0.8 | 29 | 1.12 | 41 | 1.10 | 39 | 1.46 | 50 | 1.79 | 58 |
| TLC | L | 0.93 | 29 | 1.23 | 38 | 1.28 | 39 | 1.51 | 45 | 1.98 | 58 |
| RV | L | 0.27 | 31 | 0.35 | 40 | 0.48 | 55 | 0.56 | 62 | 0.80 | 86 |
| RV/TLC | % | 28.94 | 107 | 28 | 104 | 37.67 | 140 | 37 | 137 | 40 | 154 |
| DLCO [Hb] | ml min$^{-1}$ mmHg$^{-1}$ | – | – | – | – | – | – | 9.99 | 54 | 9.9 | 52 |
| DLCO/VA | ml min$^{-1}$ mmHg$^{-1}$ | – | – | – | – | – | – | 9.08 | 135 | 7.67 | 116 |
| MIP | cmH$_2$O | 51.6 | 71 | – | – | 62.2 | 82 | 70.0 | 95 | 85.0 | 115 |
| MEP | cmH$_2$O | 69.4 | 66 | – | – | 77.6 | 74 | 89.0 | 85 | 83.0 | 75 |
| O$_2$ Sat | % | 92 | | – | | 97 | | 100 | | 97 | |

(51) Int. Cl.
  *A61K 45/06* (2006.01)
  *C12Q 1/6827* (2018.01)
  *C12Q 1/6869* (2018.01)
  *C12Q 1/6883* (2018.01)

(52) U.S. Cl.
  CPC ......... *C12Q 1/6827* (2013.01); *C12Q 1/6869* (2013.01); *C12Q 2600/106* (2013.01)

(56) References Cited

FOREIGN PATENT DOCUMENTS

| WO | 2018/045078 A2 | 3/2018 |
|---|---|---|
| WO | 2018/126192 A1 | 7/2018 |

OTHER PUBLICATIONS

Trenor, Cameron C. et al., "Complex lymphatic anomalies," Seminars in Pediatric Surgery, vol. 23, No. 4, Aug. 2014, pp. 186-190.
Collins, Francis S. et al., "A New Initiative on Precision Medicine," The New England Journal of Medicine, vol. 372, No. 9, Feb. 2015, pp. 793-795.
Adams, Denise M. et al., "Efficacy and Safety of Sirolimus in the Treatment of Complicated Vascular Anomalies," Pediatrics, vol. 137, No. 2, Feb. 2016, e20153257, pp. 1-10.
Hammill, Adrienne M. et al., "Sirolimus for the treatment of complicated vascular anomalies in children," Pediatric Blood and Cancer, vol. 57, No. 6, Dec. 2011, pp. 1018-1024.
McCormick, Andrew et al. "A Case of a Central Conducting Lymphatic Anomaly Responsive to Sirolimus," Pediatrics, vol. 137, No. 1, Jan. 2016, e20152694.
Hilliard, R. I. et al., "Congenital abnormalities of the lymphatic system: a new clinical classification," Pediatrics, vol. 86, No. 6, Dec. 1990, pp. 988-994.
Evine, C., "Primary disorders of the lymphatic vessels—a unified concept," Journal of Pediatric Surgery, vol. 24, No. 3, Mar. 1989, pp. 233-240.
Smeltzer, D. M. et al., "Primary lymphatic dysplasia in children: chylothorax, chylous ascites, and generalized lymphatic dysplasia," European Journal of Pediatrics, vol. 145, No. 4, Sep. 1986, pp. 286-292.
Wassef, Michel et al., "Vascular Anomalies Classification: Recommendations From the International Society for the Study of Vascular Anomalies," Pediatrics, vol. 136, No. 1, Jul. 2015, pp. e203-e214.
Chen, Wendy et al., "Generalized lymphatic malformation with chylothorax: long-term management of a highly morbid condition in a pediatric patient," Journal of Pediatric Surgery, vol. 48, No. 3, Mar. 2013, pp. e9-e12.
Lala, Shailee et al., "Gorham-Stout disease and generalized lymphatic anomaly-clinical, radiologic, and histologic differentiation," Skeletal Radiology, vol. 42, No. 7, Jul. 2013, pp. 917-924.
Clemens, Robert K. et al., "Combined and complex vascular malformations," VASA, vol. 44, No. 2, Mar. 2015, pp. 92-105.
Li, Dong et al., "Pathogenic variant in EPHB4 results in central conducting lymphatic anomaly," Human Molecular Genetics, vol. 27, No. 18, Sep. 2018, pp. 3233-3245.
Wellbrock, Claudia et al., "The RAF proteins take centre stage," Nature Reviews: Molecular Cell Biology, vol. 5, No. 11, Nov. 2004, pp. 875-885.
Lavoie, Hugo et al., "Regulation of RAF protein kinases in ERK signaling," Nature Reviews: Molecular Cell Biology, vol. 16, No. 5, May 2015, pp. 281-298.
Molzan, Manuela et al., "Impaired Binding of 14-3-3 to C-RAF in Noonan Syndrome Suggests New Approaches in Diseases with Increased Ras Signaling," Molecular and Cellular Biology, vol. 30, No. 19, Oct. 2010, pp. 4698-4711.
Jung, Hyun Min et al., "Development of the larval lymphatic system in zebrafish," Development, vol. 144, No. 11, Jun. 2017, pp. 2070-2081.
Karkkainen, Marika J. et al., "Vascular endothelial growth factor C is required for sprouting of the first lymphatic vessels from embryonic veins," Nature Immunology, vol. 5, No. 1, Jan. 2004, pp. 74-80.
Carmeliet, Peter et al., "Molecular mechanisms and clinical applications of angiogenesis," Nature, vol. 473, No. 7347, May 2011, pp. 298-307.
Karaman, Sinem et al., "Vascular endothelial growth factor signaling in development and disease," Development, vol. 145, No. 14, Jul. 2018, dev151019.
Potente, Michael et al., "Vascular heterogeneity and specialization in development and disease," Nature Reviews: Molecular Cell Biology, vol. 18, No. 8, Aug. 2017, pp. 477-494.
Coso, Sanja et al., "Pressing the right buttons: signaling in lymphangiogenesis," Blood, vol. 123, No. 17, Apr. 2014, op. 2614-2624.
Brouillard, Pascal et al., "Genetics of lymphatic anomalies," The Journal of Clinical Investigation, vol. 124, No. 3, Mar. 2014, pp. 898-904.
Bulow, Luzie et al., "Hydrops, fetal pleural effusions and chylothorax in three patients with CBL mutations," American Journal of Medical Genetics, vol. 167A, No. 2, Feb. 2015, pp. 394-399.
Gargano, Giancarlo et al., "Hydrops fetalis in a preterm newborn heterozygous for the c.4A>G SHOC2 mutation," American Journal of Medical Genetics, vol. 164A, No. 4, Apr. 2014, pp. 1015-1020.
Gos, Monika et al., "Contribution of RIT1 mutations to the pathogenesis of Noonan syndrome: Four new cases and further evidence of heterogeneity," American Journal of Genetics, vol. 164A, No. 9, Sep. 2014, pp. 2310-2316.
Hanson, Helen L. et al., "Germline CBL mutation associated with a noonan-like syndrome with primary lymphedema and teratoma associated with acquired uniparental isodisomy of chromosome 11q23," American Journal of Medical Genetics, vol. 164A, No. 4, Apr. 2014, pp. 1003-1009.
Milosavljevic, Doris et al., "Two cases of RIT1 associated Noonan syndrome: Further delineation of the clinical phenotype and review of the literature," American Journal of Medical Genetics, vol. 170, No. 7, Jul. 2016, pp. 1874-1880.
Koenighofer, Martin et al., "Mutations in RIT1 cause Noonan syndrome—additional functional evidence and expanding the clinical phenotype," Clinical Genetics, vol. 89, No. 3, Mar. 2016, pp. 359-366.
Leee, K. A. et al., "PTPN11 analysis for the prenatal diagnosis of Noonan syndrome in fetuses with abnormal ultrasound findings," Clinical Genetics, vol. 75, No. 2, Feb. 2009, pp. 190-194.
Croonen, Ellen A. et al., "Prenatal diagnostic testing of the Noonan syndrome genes in fetuses with abnormal ultrasound findings," European Journal of Human Genetics, vol. 21, No. 9, Sep. 2013, pp. 936-942.
Joyce, Sarah et al., "The lymphatic phenotype in Noonan and Cardiofaciocutaneous syndrome," European Journal of Human Genetics, vol. 24, No. 5, May 2016, pp. 690-696.
Yaoita, Masako et al., "Spectrum of mutations and genotype-phenotype analysis in Noonan syndrome patients with RIT1 mutations," Human Genetics, vol. 135, No. 2, Feb. 2016, pp. 209-222.
Lo, I. F. M. et al., "Severe neonatal manifestations of Costello syndrome," Journal of Medical Genetics, vol. 45, No. 3, Mar. 2008, pp. 167-171.
Ebrahimi-Fakari, Darius et al., "Congenital Chylothorax as the Initial Presentation of PTPN11Associated Noonan Syndrome," The Journal of Pediatrics, vol. 185, Jun. 2017, pp. 248-248.e1.
Morcaldi, G. et al., "Lymphodysplasia and Kras mutation: a case report and literature review," Lymphology, vol. 48, No. 3, Sep. 2015, pp. 121-127.
Manevitz-Mendelson, Eugenia et al., "Somatic NRAS mutation in patient with generalized lymphatic anomaly," Angiogenesis, vol. 21, No. 2, May 2018, pp. 287-298.
Barclay, Sarah F. et al., "A Somatic Activating NRAS Variant Associated with Kaposiform Lymphangiomatosis," Genetics in Medicine, vol. 21, No. 7, Jul. 2019, pp. 1517-1524.
Gao, Jianjiong et al., "Integrative analysis of complex cancer genomics and clinical profiles using the cBioPortal," Science Signaling, vol. 6, No. 269, Apr. 2013, pl1, pp. 1-34.

(56) References Cited

OTHER PUBLICATIONS

Mielinski, Marcin et al., "Oncogenic and sorafenib-sensitive ARAF mutations in lung adenocarcinoma," The Journal of Clinical Investigation, vol. 124, No. 4, Apr. 2014, pp. 1582-1586.

* cited by examiner

Figure 4A
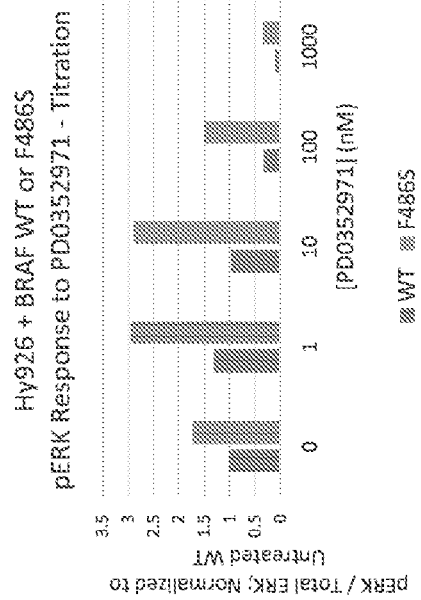
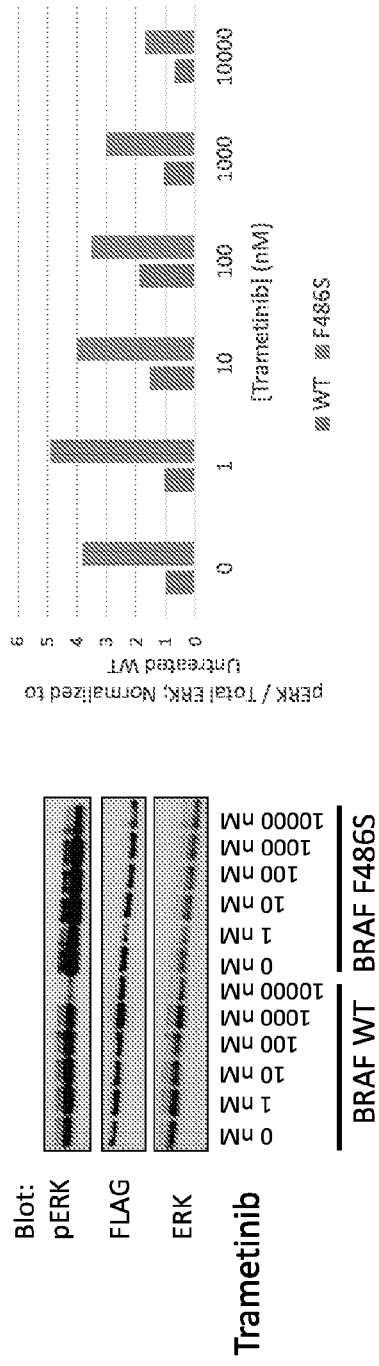

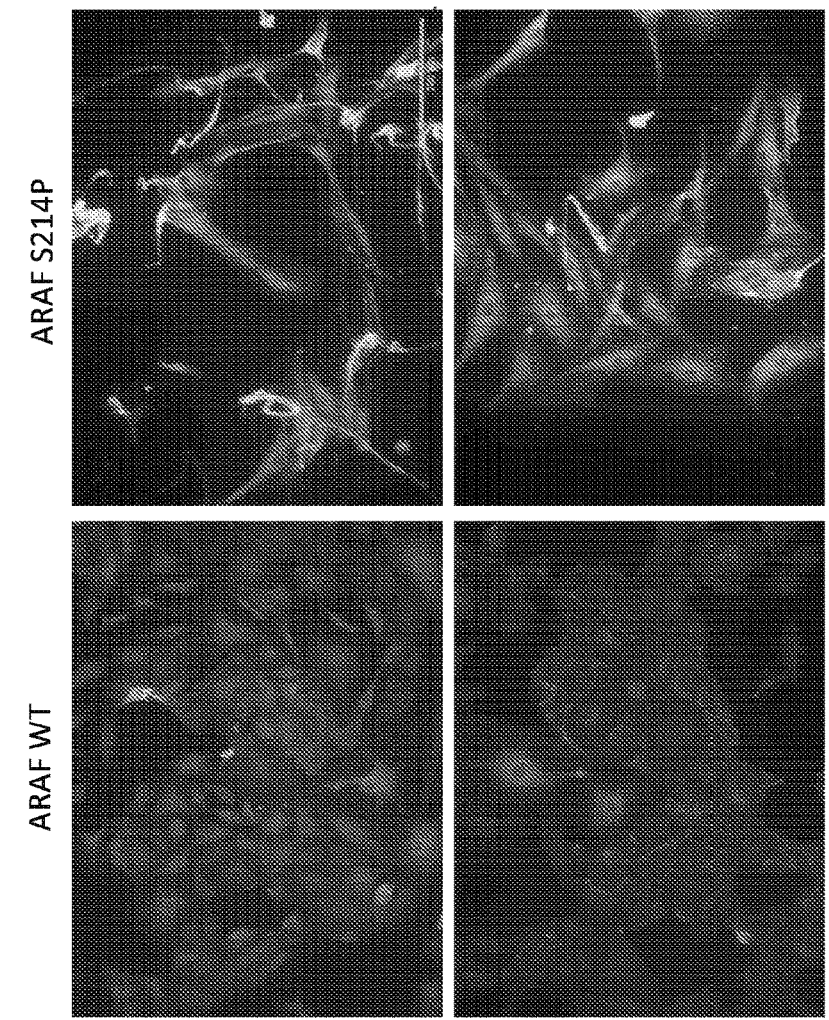
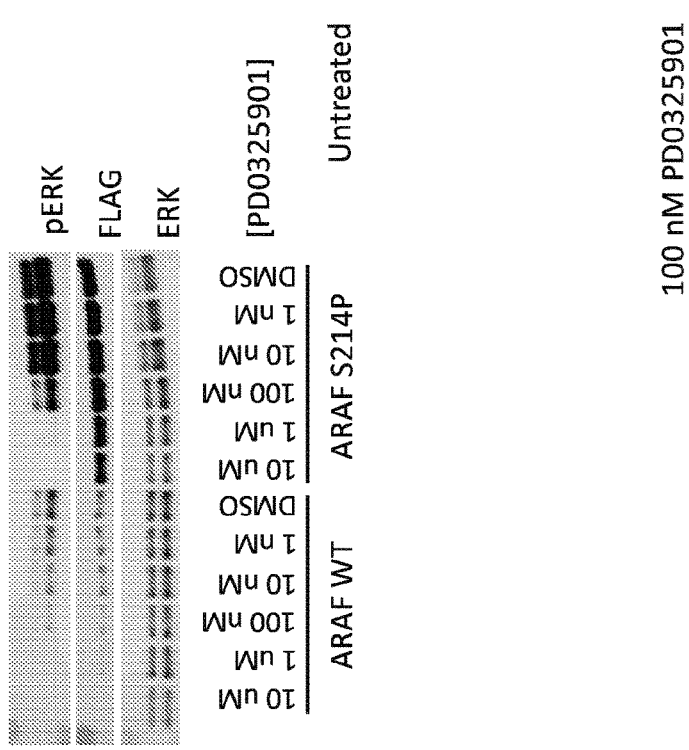
Figure 6

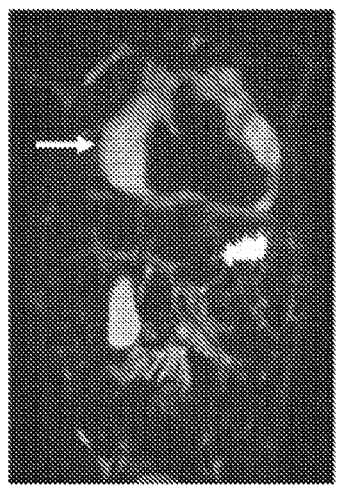 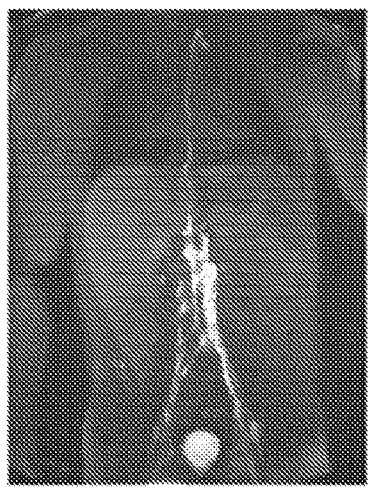 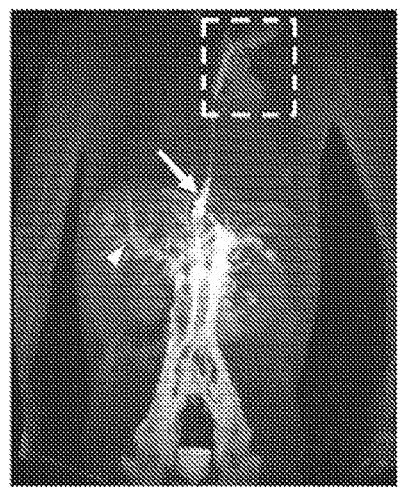
Fig. 22A  Fig. 22B  Fig. 22C
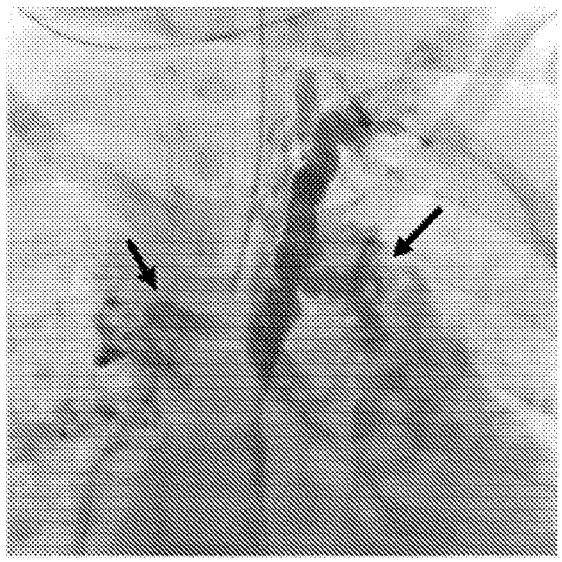 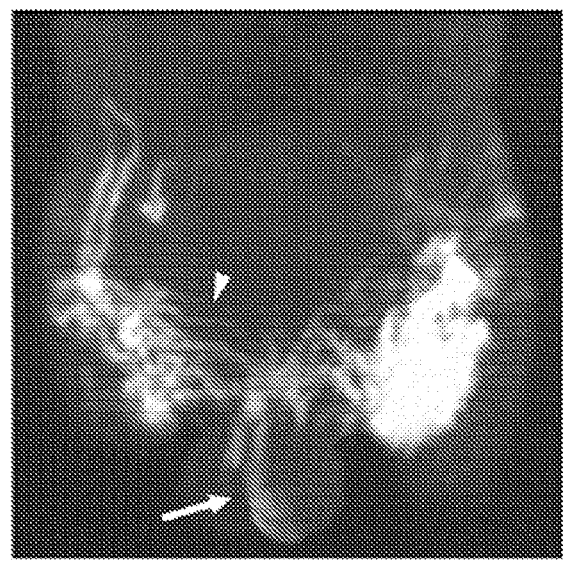
Fig. 22D  Fig. 22E Fig. 23C
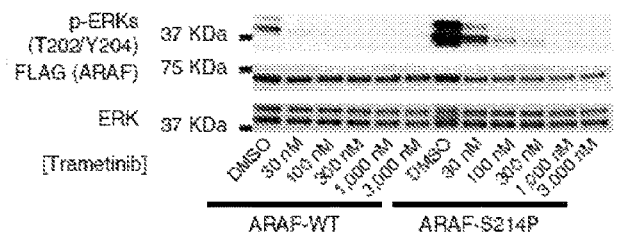
Fig. 23D
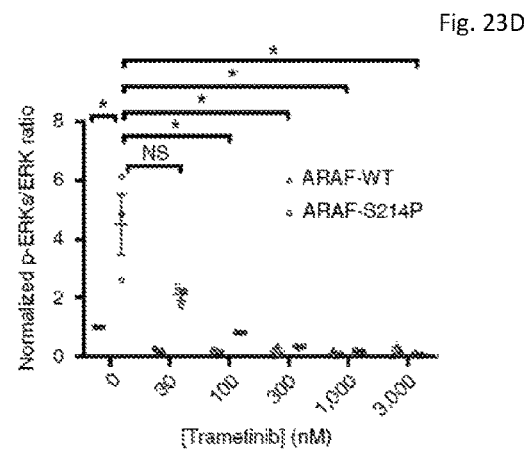
Fig. 24E
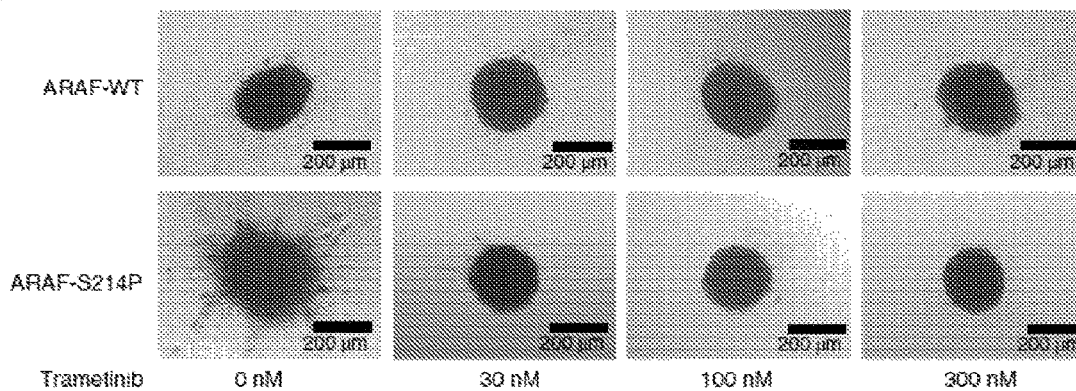
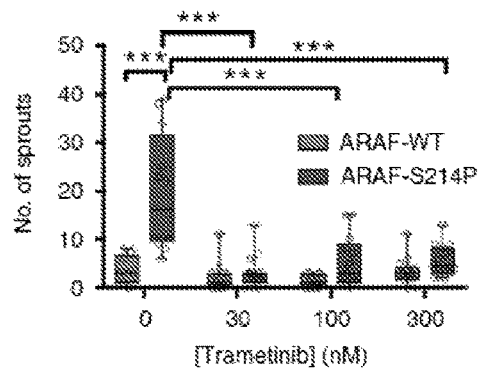
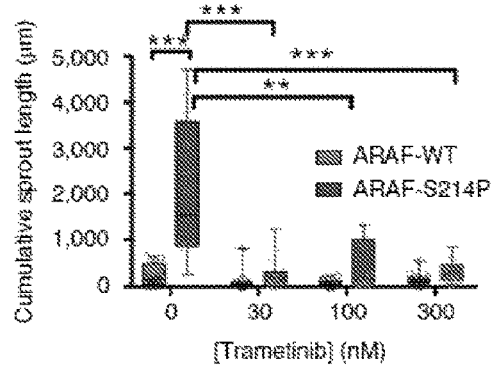
Fig. 23F

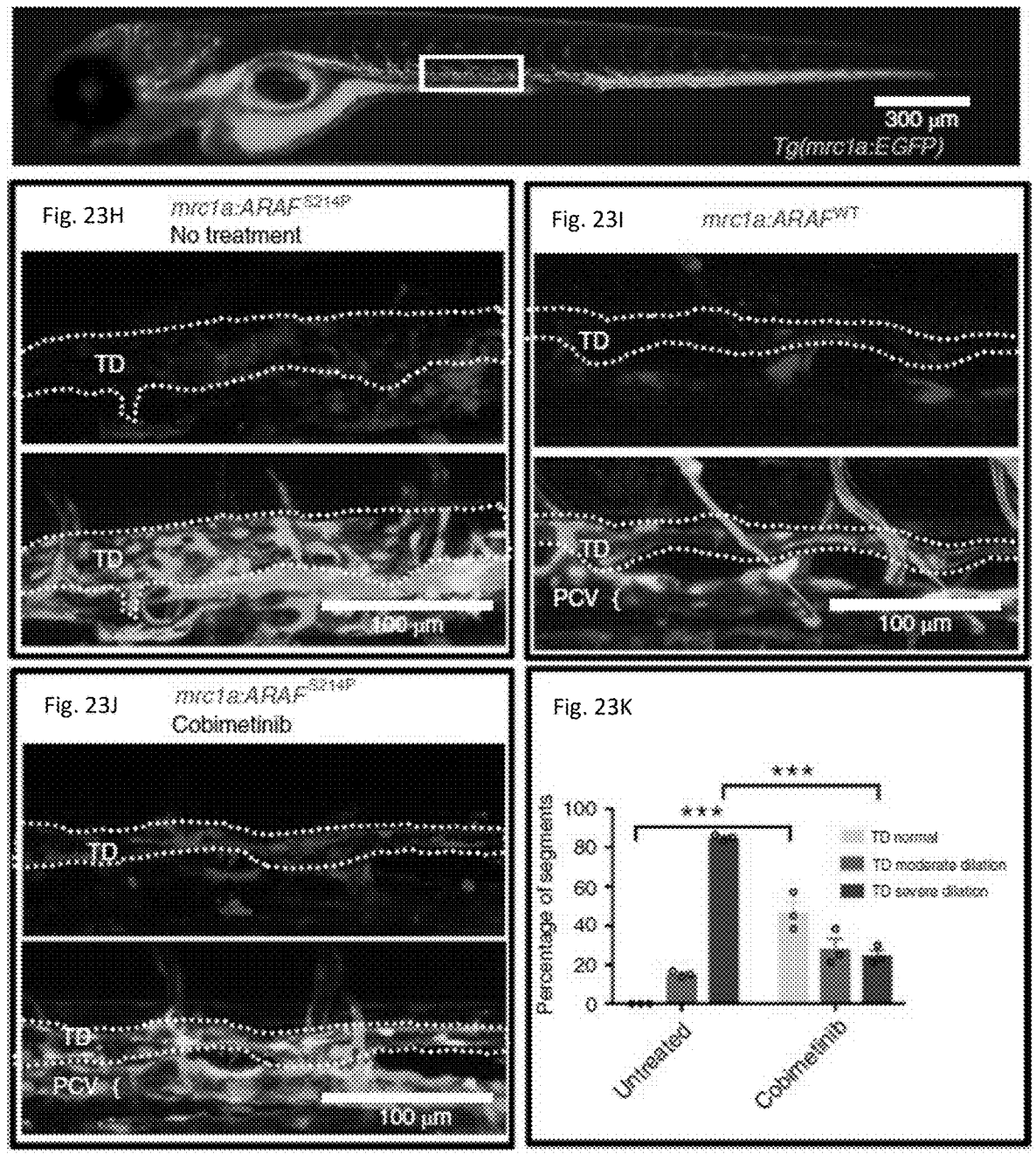

| Parameter | Unit | Baseline | | | | Post therapy | | | | | |
|---|---|---|---|---|---|---|---|---|---|---|---|
| | | March 17, 2017 | | April 4, 2017 | | May 4, 2017 | | October 23, 2017 | | March 8, 2018 | |
| | | Per | % ref | Per | % ref | Per | % ref | Per | % ref | Per | % ref |
| Weight | kg | 38 | | 40 | | 42 | | 40 | | 39 | |
| Height | cm | 142 | | 142 | | 143 | | 145 | | 148 | |
| FVC | L | 0.58 | 23 | 0.88 | 35 | 0.88 | 31 | 0.95 | 35 | 1.18 | 40 |
| $FEV_1$ | L | 0.52 | 23 | 0.77 | 34 | 0.72 | 31 | 0.85 | 35 | 1.09 | 42 |
| $FEV_1/FVC$ | % | 89.8 | 105 | 87 | 102 | 89.3 | 105 | 89.0 | 105 | 92.0 | 108 |
| $FEF_{25-75}$ | L/s | 0.8 | 29 | 1.12 | 41 | 1.10 | 39 | 1.46 | 50 | 1.79 | 58 |
| TLC | L | 0.93 | 29 | 1.23 | 38 | 1.28 | 39 | 1.51 | 45 | 1.98 | 56 |
| RV | L | 0.27 | 31 | 0.35 | 40 | 0.48 | 55 | 0.56 | 62 | 0.80 | 86 |
| RV/TLC | % | 28.94 | 107 | 28 | 104 | 37.67 | 140 | 37 | 137 | 40 | 154 |
| DLCO [Hb] | ml min$^{-1}$ mmHg$^{-1}$ | – | – | – | – | – | – | 9.99 | 54 | 9.9 | 52 |
| DLCO/VA | ml min$^{-1}$ mmHg$^{-1}$ | – | – | – | – | – | – | 9.08 | 135 | 7.67 | 116 |
| MIP | $cmH_2O$ | 51.6 | 71 | – | – | 62.2 | 82 | 70.0 | 95 | 85.0 | 115 |
| MEP | $cmH_2O$ | 69.4 | 66 | – | – | 77.6 | 74 | 89.0 | 85 | 83.0 | 75 |
| $O_2$ Sat | % | 92 | | – | | 97 | | 100 | | 97 | |

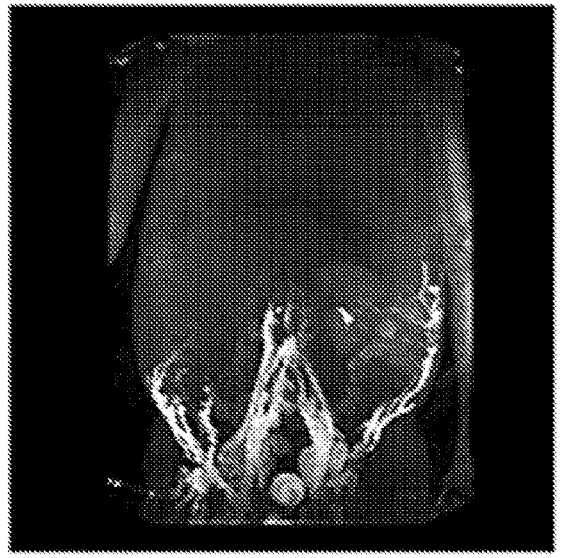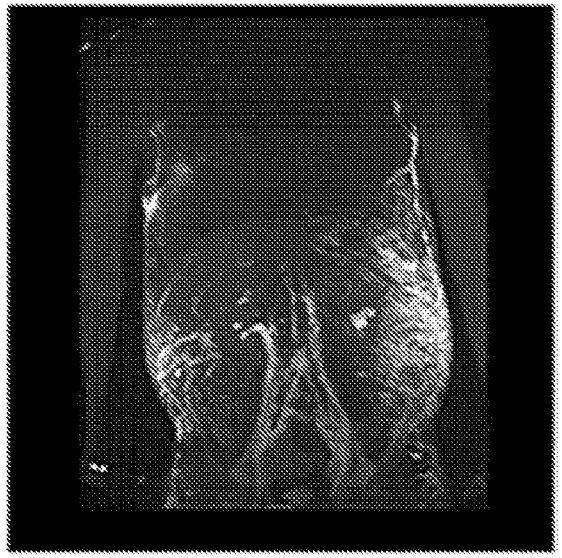
Fig. 24C
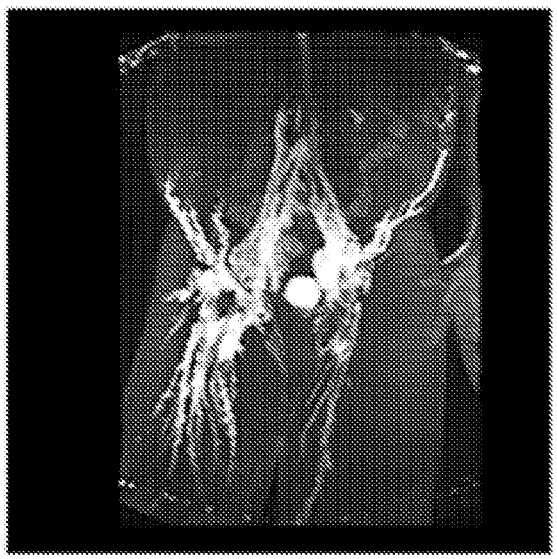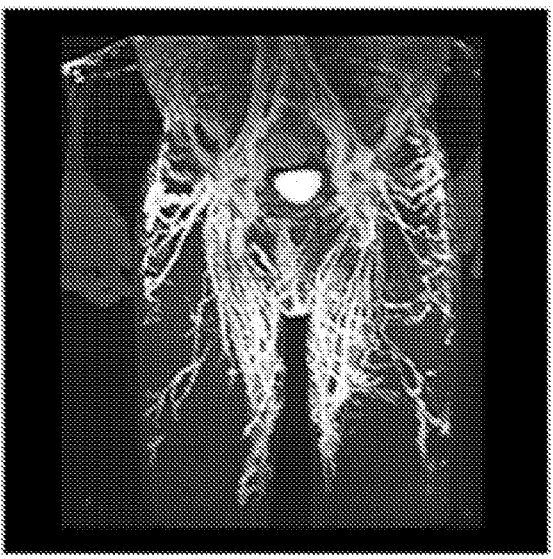
Fig. 24D

COMPOSITIONS AND METHODS FOR THE DIAGNOSIS AND TREATMENT OF LYMPHATIC SYSTEM DISORDERS This application is a § 371 of International Application No, PCT/US2019/050196, filed Sep. 9, 2019, which claims priority to U.S. Provisional Application No. 62/728,444 filed Sep. 7, 2018, the entire contents of each being incorporated herein by reference as though set forth in full.

INCORPORATION-BY-REFERENCE OF MATERIAL SUBMITTED IN ELECTRONIC FORM

Incorporated herein by reference in its entirety is the Sequence Listing submitted via EFS-Web as a text file named 6613WO00_SeqListing_ST25.txt, created Mar. 8, 2021 and having a size of 74,836 bytes.

FIELD OF THE INVENTION

This invention relates to the fields of genetics, personalized medicine and malformations of the lymphatic system. More specifically the invention provides new genetic targets and therapeutic treatment regimens for amelioration of symptoms associated with Lymphangiomatosis and other generalized lymphatic anomalies (GLAs).

BACKGROUND OF THE INVENTION

Several publications and patent documents are cited throughout the specification in order to describe the state of the art to which this invention pertains. Each of these citations is incorporated by reference herein as though set forth in full.

The lymphatic system plays a pivotal role in maintaining the body fluid circulation, defending the body against disease and in absorbing dietary fats in the small intestine (1). Complex lymphatic anomalies are characterized by abnormal formation of lymphatic vessels and tissue overgrowth. Patients often present with overlapping symptoms which may lead to serious pulmonary disease (2, 3). Examples of lymphatic anomalies include generalized lymphatic anomaly (GLA), lymphangiectasia, and chylous effusions (pericardial, pleural or peritoneal). Research on complex lymphatic anomalies has been hampered by the inconsistence in classification and nomenclature because of significant challenge in diagnosis (3-6). Although the molecular genetic etiology of complex lymphatic anomalies is poorly understood, congenital malformations of lymphatic system appear to have related underlying genetic etiology (7-9). Indeed, both germline and somatic mutations have been identified in genes which converge on the PI3K/mTOR and Ras/MAPK pathways (1, 8).

Disruption or aberrations of the PI3K/mTOR and Ras/MAPK signaling pathways have been shown to impair normal expansion and remodeling during construction of a mature lymphatic network, wherein such disruptions are associated with lymphatic disease. Gain of function mutations in AKT1 and PIK3CA, resulting in elevated mammalian target of rapamycin complex 1 (mTORC1) activity, were identified in patients with lymphatic malformations that comprise part of a syndrome, such as Proteus syndrome (OMIM 176920), CLOVES syndrome (OMIM 612918) and Klippel-Trenaunay-Weber syndrome (OMIM 149000) (9-11). Mutations in KRAS, HRAS, RAF1, PTPN11, SOS1 and RASA1, resulting in dysregulated RAS pathway activity, cause lymphedema or lymphangiectasia in Noonan syndrome (OMIM 163950), Costello syndrome (OMIM 218040), cardiofaciocutaneous syndrome (OMIM 115150) and capillary malformation-arteriovenous malformation (CM-AVM) syndrome (OMIM 608354) (12-17).

Despite these understandings, genetic biomarkers for use in identifying patients with lymphatic disorders and lymphatic anomalies, such as lymphangiomatosis/lymphangiectasia (LAM), generalized lymphatic anomaly (GLA), and chylous effusions are lacking, as are therapeutics that target the genetic markers associated with these disorders.

SUMMARY OF THE INVENTION

Accordingly, in one embodiment of the invention, a method for diagnosing a lymphatic anomaly in a human patient is provided. An exemplary method comprises obtaining a biological sample comprising nucleic acid from the patient. assaying the nucleic acid to determine whether i) a single nucleotide variant (SNV) in one or more of PTPN11, KRAS, BRAF, SOS1, ITGA9, RASA1, RAF1, RIT1, PEIZO1, EPHB4, NF1, CBL and ARAF is present or ii) an SNV in linkage disequilibrium with an SNV in one or more of PTPN11, KRAS, BRAF, SOS1, ITGA9, RASA1, RAF1, RIT1, PEIZO1, EPHB4, NF1, CBL and ARAF is present; and diagnosing the patient with a lymphatic anomaly if an SNV of i) or ii) is present. In another aspect, a method for diagnosing a lymphatic anomaly in a human patient entails obtaining genotype sequence information from a human patient, determining from the sequence information whether i) a single nucleotide variant (SNV) in one or more of PTPN11, KRAS, BRAF, SOS1, ITGA9, RASA1, RAF1, RIT1, PEIZO1, EPHB4, NF1, CBL and ARAF is present or ii) an SNV in linkage disequilibrium with an SNV in one or more of PTPN11, KRAS, BRAF, SOS1, ITGA9, RASA1, RAF1, RIT1, PEIZO1, EPHB4, NF1, CBL, and ARAF is present; and diagnosing the patient with a lymphatic anomaly if an SNV of i) or ii) is present.

The invention also provides a method for treating a lymphatic anomaly in a human patient. An exemplary method comprises obtaining a biological sample comprising nucleic acid from the patient; assaying the nucleic acid to determine whether i) a single nucleotide variant (SANV) in one or more of PTPN11, KRAS, BRAF, SOS1, ITGA9, RASA1, RAF1, RIT1, PEIZO1, EPHB4, NF1, and CBL is present or ii) an SNV in linkage disequilibrium with an SNV in one or more of PTPN11, KRAS, BRAF, SOS1, ITGA9, RASA1, RAF1, RIT1, PEIZO1, EPHB4, NF1, and CBL is present; and administering one or more agents suitable for treatment of said lymphatic anomaly to the patient identified as having one or more SNVs of i) or ii), thereby treating the lymphatic anomaly. In alternative embodiment of this method, genotype information is obtained from a patient and assayed to determine whether i) a single nucleotide variant (SNV) in one or more of PTPN11, KRAS, BRAF, SOS1, ITGA9, RASA1, RAF1, RIT1, PEIZO1, EPHB4, NF1, and CBL is present or ii) an SNV in linkage disequilibrium with an SNV in one or more of PTPN11, KRAS, BRAF, SOS1, ITGA9, RASA1, RAF1, RIT1, PEIZO1, EPHB4, NF1, and CBL is present; and administering one or more agents suitable for treatment of said lymphatic anomaly to the patient identified as having one or more SNVs of i) or ii), thereby treating the lymphatic anomaly. In alternative embodiment of this method, genotype information is obtained from a patient.

In certain embodiments, the lymphatic anomaly is characterized by abnormal formation of lymphatic vessels and/or tissue overgrowth. In other embodiments, the lymphatic anomaly is lymphangiomatosis (LAM). In another embodiment, the lymphatic anomaly is generalized lymphatic anomaly (GLA). The lymphatic anomaly can be characterized by chylous effusions, including pericardial, pleural, or peritoneal effusions.

The diagnostic methods can further comprise generating a report identifying the SNV after detection in the biological sample. The methods of treatment described above can further comprise generating a report identifying suggested treatment(s) for the lymphatic anomaly based upon the SNV identified in the method.

In some embodiments, the agent administered to a SNV positive subject is 1) a MEK/ERK inhibitor; 2) an agent/inhibitor listed in Tables 1 and 2; 3) a combination of a MEK/ERK inhibitor and one or more agent/inhibitor listed in Tables 1 and 2; and/or 4) a combination of 1) an mTOR inhibitor and/or a PIK3K inhibitor; and 2) one or more MEK/ERK inhibitors. In yet another embodiment, the diagnostic methods described herein can further comprise administering an effective amount of one or more agents suitable for treating said lymphatic anomaly to the diagnosed patient.

In certain embodiments of the methods for treatment, the agent to be administered, such as to patients harboring one or more lymphatic anomaly associated SNVs, is selected from one or more MEK/ERK inhibitors, and a combination of one or more of any of said inhibitors. In some embodiments, the agent to be administered is a MEK/ERK inhibitor. In some embodiments, the agent to be administered is one or more agent listed in Tables 1 and 2. In some embodiments, the agent to be administered is a MEK/ERK inhibitor and one or more agent listed in Tables 1 and 2. In some embodiments, the agent to be administered is a combination of 1) an mTOR inhibitor and/or a PIK3K inhibitor; and 2) one or more MEK/ERK inhibitors. In some embodiments, when the agent is an mTor inhibitor, rapamycin and or BEZ-235 (dactolisib) is administered. In certain embodiments, the one or more mTOR inhibitors, one or more PIK3K inhibitors, and/or one or more MEK/ERK inhibitors has an IC50 of less than 100 µM, less than 10 µM, less than 1 µM, less than 100 nM, less than 10 nM, or less than 1 nM.

In some embodiments, the patient does not have an SNV in PTPN11. In some embodiments, the patient does not have an SNV in BRAF. In some embodiments, the patient does not have an SNV in KRAS. In some embodiments, the patient does not have an SNV in SOS1. In some embodiments, the patient does not have an SNV in ITGA9.

In some embodiments, the agents listed in Tables 1 and 2 are used in combination. These combinations include, without limitation, a) Ridaforolimus and Trametinib; b) Ridaforolimus and Selumetinib or Cobimetinib; c) BEZ235 and Selumetinib; d) Omipalisib and Selumetinib or Trametinib; e) Everolimus and Trametinib or Selumetinib; f) Sirolimus, Ridaforolimus and Selumetinib; g) Sirolimus, Ridaforolimus and Trametinib; h) Torkinib and Trametinib; i) BEZ235, Torkinib and Trametinib; and j) Sirolimus and Gedatolisib and Trametinib. In other embodiments, the treatment further comprises administering systemic chemotherapy, interferon alfa, radiotherapy, and/or surgery.

In some embodiments, the SNV is selected from an SNV selected from c.1504T>G:pS502A, c.1510A>G:pM504V, and/or c.1507G>C:pG503R in the PTPN11 gene, a c.35G>A:pG12D in KRAS, a c.1403T>C:pF468S in the BRAF gene, a c.2536G>A:pE846K in the SOS1 gene, and a compound mutation comprising c.1236+4A>G and c.289T>G:p.C97G in the ITGA9 gene, where "c." designates a coding DNA sequence, and "p." designates a protein sequence.

In some embodiments, the diagnostic method comprises detection of one or more of the SNVs described above. In some embodiments, the diagnostic method further comprises administering one or more agents known to treat lymphatic anomaly to the subject. In some embodiments, the agent is a MEK/ERK inhibitors. In some embodiments, the agent to be administered is one or more agent listed in Tables 1 and 2. In some embodiments, the agent to be administered is a MEK/ERK inhibitor and one or more agent listed in Tables 1 and 2. In some embodiments, the agent to be administered is a combination of 1) an mTOR inhibitor and/or a PIK3K inhibitor; and 2) one or more MEK/ERK inhibitors. The administration of the agent(s) improves one or more of lymph structure, decreases chylous pleural effusions, improves respiratory function, allows tapering of concomitant medication usage, and/or increasing survival.

In some embodiments, the diagnostic method comprises detecting one or more of c.1504T>G:pS502A, c.1510A>G:pM504V, and/or c.1507G>C:pG503R in the PTPN11 gene and administering at least one or more MEK/ERK inhibitors alone or in combination. In other embodiments, the agent is selected from Tables 1-2, thereby improving one or more of lymphatic structure, decreasing chylous pleural effusions, improving respiratory function, allowing tapering of concomitant medication usage, or increasing survival.

In some embodiments, the diagnostic method comprises detection of a c.1403T>C:pF468S in the BRAF gene. In some embodiments, the diagnostic method further comprises treating said patient with one or more MEK/ERK inhibitors alone or in combination.

In other embodiments, agents are selected from Tables 1-2, thereby improving one or more of lymph structure, decreasing chylous pleural effusions, improving respiratory function, allowing tapering of concomitant medication usage, or increasing survival.

In some embodiments, the diagnostic method comprises detecting a c.35G>A:pG12D in KRAS and administering one or more mTor inhibitors, and one or more MEK/ERK inhibitors alone or in combination. In other embodiments, at least one agent is selected from Tables 1-2 for administration, thereby improving one or more of lymphatic structure, decreasing chylous pleural effusions, improving respiratory function, allowing tapering of concomitant medication usage, or increasing survival.

In some embodiments, the diagnostic method comprises detection of a c.2536G>A:pE846K in the SOS1 gene. In some embodiments, the diagnostic method further comprises treating said patient with one or more MEK/ERK inhibitors alone or in combination. In other embodiments, agents from Tables 1-2 are selected, thereby improving one or more of lymph structure, decreasing chylous pleural effusions, improving respiratory function, allowing tapering of concomitant medication usage, or increasing survival.

In some embodiments, the diagnostic method comprises detecting a c.1236+4A>G and/or c.289T>G:p.C97G in the ITGA9 gene and administering one or more MEK/ERK inhibitors alone or in combination. In some embodiments, at least one agent from Tables 1-2 is administered, thereby improving one or more of lymphatic structure, decreasing chylous pleural effusions, improving respiratory function, allowing tapering of concomitant medication usage, or increasing survival.

ERK/MEK inhibitors suitable for treatment include, without limitation, Selumetinib (AZD6244), PD0325901, Trametinib (GSK1120212), PD184352 (CI-1040), Pimasertib (AS-703026), TAK-733, AZD8330, Binimetinib (MEK162, ARRY-162, ARRY-438162), SL-327, Refametinib (RDEA119, Bay 86-9766), and Cobimetinib (GDC-0973, RG7420).

In some embodiments, the step of assaying the nucleic acid to determine whether a single nucleotide variant (SNV) in one or more of c.1504T>G:pS502A, c.1510A>G: pM504V, and/or c.1507G>C:pG503R in the PTPN11 gene, a c.35G>A:pG12D in KRAS, a c.1403T>C:pF468S in the BRAF gene, a c.2536G>A:pE846K in the SOS1 gene, and a compound mutation comprising c.1236+4A>G and c.289T>G:p.C97G in the ITGA9 gene is present further comprises the step of analyzing a polynucleotide sample to determine the presence of said SNV by performing a process selected from the group consisting of detection of specific hybridization, measurement of allele size, restriction fragment length polymorphism analysis, allele-specific hybridization analysis, single base primer extension reaction, and sequencing of an amplified polynucleotide.

In some embodiments, the biological sample comprises DNA.

In some embodiments, the biological sample comprises RNA.

In some embodiments, nucleic acids comprising said SNV(s) are obtained from an isolated cell of the human patient.

In some embodiments, an isolated vector encodes a nucleic acid with a SNV, wherein the SNV is selected from c.1504T>G:pS502A, c.1510A>G:pM504V, and/or c.1507G>C:pG503R in the PTPN11 gene, a c.35G>A: pG12D in KRAS, a c.1403T>C:pF468S in the BRAF gene, a c.2536G>A:pE846K in the SOS1 gene, and a compound mutation comprising c.1236+4A>G and c.289T>G:p.C97G in the ITGA9 gene.

In some embodiments, a host cell comprises an isolated vector encoding a nucleic acid with a SNV. In some embodiments, a transgenic animal comprises a host cell. In some embodiments, the transgenic animal is a mouse or zebrafish.

In some embodiments, a method of screening for effects of an agent comprises contacting a host cell or a transgenic animal with one or more the inhibitors described herein alone or in combination, or an agent from Tables 1-2 is encompassed. In some embodiments, the effect of an agent that is screened is caudal rescue or branching rescue in zebrafish.

In some embodiments, a method for identifying an agent that alters cellular signaling, comprises providing cells expressing at least one nucleic acid comprising at least one SNV as described above, providing cells which express the cognate wild type sequences lacking the SNV; contacting both cell populations with a test agent; and analyzing whether said agent alters cellular signaling of cells harboring the SNV containing nucleic acid relative to cells lacking said SNV.

BRIEF DESCRIPTION OF THE DRAWINGS

FIGS. 4A-4B. MEK inhibitors reduce ERK activation/ phosphorylation in cells overexpression BRAF WT and F486S mutant. FIG. 4b—MEK inhibitors reduce ERK activation/phosphorylation in cells overexpression BRAF WT and F486S mutant.

FIG. 6. Effects of PD0325901 on HDLECs expressing ARAF mutation S214P. The cell morphological differences induced by ARAF-S214P was rescued by PD0325901, as illustrated by reduced levels of pERK and increased VE-cadherin accumulation at the cell membrane. Green is for HA staining, which marks ARAF expressing cells; red is for VE-Cadherin staining.

FIGS. 22A-22G. Clinical images in the lead proband with lymphatic anomaly and molecular analysis. FIG. 22A) The coronal slice of a T2-weighted non-contrast lymphangiogram, demonstrating a large pericardial effusion (arrow). FIG. 22B) The maximal intensity projection of a dynamic contrast-enhanced magnetic resonance lymphangiogram in a healthy control person, showing a normal TD coursing towards the left innominate vein. FIG. 22C) The maximal intensity projection of a dynamic contrast-enhanced magnetic resonance lymphangiogram in P1, showing dilated lumber lymphatic networks with retrograde liver hilar flow (arrowhead) and a dilated and tortuous TD (arrow) coursing towards the innominate vein on the left and also supplying retrograde perfusion to the mediastinum and pericardium (box). FIG. 22D) The contrast lymphangiogram of the boxed region in c, demonstrating dilated and tortuous distal TD with retrograde flow towards the mediastinum, pericardium and lungs through dilated lymphatic networks originating at the distal TD (arrows). FIG. 22E) The coronal maximal intensity projection of the pelvis and genitalia, demonstrating multiple dilated ducts (arrowhead) originating in bilateral groin lymph nodes and supplying retrograde flow into the penis and scrotum (arrow). FIG. 22F) The pedigrees and genotypes of a recurrent mutation, c.640T>C (p.S214P), in ARAF identified in unrelated kindreds. FIG. 22G), The schematic topology of the ARAF protein, where the asterisk indicates the position of the p.S214P mutation in CR2. The Ser 214 residue is highly conserved across vertebrate species and all RAF isoforms.

FIG. 23A-23K. The ARAF-S214P mutation increases ERK1/2 activity, enhances lymphangiogenic capacity and alters actin skeleton and VE-cadherin junctions in HDLECs, and results in dilation of the thoracic duct (TD) in zebrafish that is reversed by cobimetinib. FIG. 23A), ARAF mutant transfection in HEK293T cells impairs association with 14-3-3 proteins and increases p-ERKs. The normalized 14-3-3/FLAG ratio is illustrated by the panel on the right, showing reduced co-immunoprecipitation of 14-3-3 proteins in the mutant. The data are shown as the mean±s.e.m. of three independent experiments. Two-tailed unpaired t-test (with 4 degrees of freedom (df)), **$P=8.6\times10^{-6}$. The images were cropped for better presentation. FIG. 23B), ARAF mutant transfection in HEK293T cells induces increased expression of p-ERK1/2 compared with cells expressing the WT ($P=0.0026$; two-tailed unpaired t-test; df=8). Phosphorylation of AKT, p70S6K, mTOR and p38 was not altered by ARAF-S214P. Normalized ratios are illustrated by the box and whisker plot on the right (minimum to maximum, showing all the points), where the center line represents the median, the box limits represent the interquartile range and the whiskers represent the minimum to maximum data range. Six independent experiments were performed. The images were cropped for better presentation. FIG. 23C) Primary HDLECs transduced with ARAF-WT or ARAF-S214P were cultured in increasing concentrations of trametinib. The results with cells from three independent transductions were quantified and graphed on a scatter dot plot with each individual value as a dot superimposed. The data are shown as the mean±s.e.m. (error bars) of the three independent experiments. Transduction of ARAF-S214P significantly increased the level of p-ERKs (*$P=0.03$; two-tailed unpaired t-test with 4 df). Trametinib treatment led to a significant reduction of p-ERKs (*$P=0.02$ for 100 nM trametinib treatment and 300 nM trametinib treatment; *$P=0.01$ for 1,000 nM trametinib treatment and 3,000 nM trametinib treatment; two-tailed unpaired t-test with 4 df); NS, not significant. The images were cropped for better presentation. FIG. 23D) Three-dimensional lymphatic spheroid sprouting assay shows the elevated sprouting activity in HDLECs expressing ARAF-S214P compared with ARAF-WT as measured by both number of sprouts (*$P=0.0002$) and sprout length on the bottom (*$P=0.0005$). Two-tailed unpaired t-test with 22 df. Spheroids were also cultured in increasing concentrations of trametinib, which significantly reduces both the number of sprouts at concentrations of 30 nM (**$P=4.68\times10^{-5}$; df=25), 100 nM (*$P=9.5\times10^{-4}$; df=23) and 300 nM (*$P=4.4\times10^{-4}$; df=24) and sprout length at concentrations of 30 nM (*$P=1.8\times10^{-4}$; df=25), 100 nM ($P=0.001$; df=23) and 300 nM (*$P=3.2\times10^{-4}$; df=24). Two-tailed unpaired t-test. Three experiments performed with independent transductions of HDLECs were quantified, and points from all three experiments are plotted (15 points per condition) on the interleaved box and whisker plot (three to six spheroids per experiment), where the center line represents the median, the box limits represent the interquartile range and the whiskers represent the minimum to maximum data range. FIG. 23E) The ARAF mutant affects VE-cadherin localization (**$P=1.88\times10^{-26}$), and treatment with trametinib results in increased cell surface localization of VE-cadherin ($P=1.63\times10^{-19}$). The red arrowheads point to staining referred to as plasma membrane staining, and the yellow arrowheads indicate intracellular staining. Three experiments performed with independent transductions of HDLECs were quantified for intracellular and plasma membrane staining, and points from all three experiments are plotted (75 points per condition) on the left box and whisker plot (minimum to maximum), where the center line represents the median, the box limits represent the interquartile range and the whiskers represent the minimum to maximum data range. Two-tailed unpaired t-test with 148 df; NS, not significant. The maximum length and width of cells from the experiment in FIG. 23E were measured, and the length-to-width ratios were calculated and plotted on the right box and whisker plot (minimum to maximum; bottom right), where the center line represents the median, the box limits represent the interquartile range and the whiskers represent the minimum to maximum data range. ARAF-S214P expression causes a significantly increased length/width ratio (P=9.57×10-15) and treatment with trametinib normalizes the ratio (P=7.51×10$^{-17}$; two-tailed unpaired t-test with 148 df; NS, not significant). FIG. 23F) MTT (3-(4,5-dimethylthiazol-2-yl)-2,5-diphenyltetrazolium bromide) assay shows that ARAF-S214P leads to no increase in proliferation in transduced HDLECs. The metabolic activity is measured at two wavelengths (550 and 700 nm). The contents of triplicate wells (n=3 independent wells) were collected at the indicated times, as described in the Methods. The trend lines connect the means for each transductant at each time point, and the points show the measured values for all data points. This experiment is representative of results from two independent retroviral transductions. FIG. 23G): an overview of the fish lymphatic system; the white frame indicates the area investigated in FIG. 23H-2JK which shows an overlay (maximum intensity projection) of confocal scans. The TD and posterior cardinal vein (PCV) are labeled green (tg(mrc1a:EGFP)), and the TD is outlined by a dotted line in FIG. 23H-23J. ARAF transgenic (mrc1a: araf) cells are marked red (green+red→yellow). FIG. 23H) ARAF-S214P expression leads to severe dilation of the TD. FIG. 23I) ARAF-WT (red) expression has no effect on the morphology of the TD and PCV (both green). FIG. 23J) Cobimetinib (1 uM) partially reverses dilation induced by the mutation. Three independent experiments were repeated with similar findings in FIGS. 23H-23J. FIG. 23K), Phenotype scoring categories of body segments for dilation with and without cobimetinib treatment: normal, moderate dilation (TD expanded but can be separated from the PCV) and severe dilation (TD and PCV overlapping). Cobimetinib treatment led to a significant reduction of severe dilation (P=1.33×10$^{-5}$; one-tailed unpaired t-test; blue histograms) and rescue to normal morphology (*P=0.00051; one-tailed unpaired t-test; green histogram). In three independent experiments, a total of 40 larvae and 120 body segments were analyzed. The data are shown as the mean±s.e.m. of three independent experiments. Unprocessed blot images are available as source data.

FIGS. 24A-24F. Pulmonary function tests and clinical images in the lead proband before and after MEK inhibitor therapy. FIG. 24A) Results from pulmonary function tests before MEK inhibitor therapy, and after therapy. Note the significant improvements in all spirometry measures, with FEV1 improving from 23% to 42% predicated value, TLC improving from 29% to 56% predicted value and maximal inspiratory pressure (MIP) improving from 71% to 115% predicted value (marked in red). FVC, forced vital capacity; FEF25-75, mid forced expiratory flow rates; RV, residual volume; RV/TLC, ratio of RV to TLC; DLCO [Hb], diffusing capacity of the lung for carbon monoxide corrected for hemoglobin; DLCO/VA, DLCO divided by the alveolar volume (VA); MEP, maximal expiratory pressure; 02 Sat, oxygen saturation. FIG. 24B) Coronal maximal intensity projections of a T2-weighted non-contrast lymphangiogram just before initiation of medical therapy (left) and 12 months after MEK inhibitor therapy began (right) demonstrate near-complete resorption of massively dilated and beading subcutaneous lymphatic ducts. FIG. 24C) Coronal maximal intensity projections of contrast lymphangiograms of the pelvis and chest before treatment (left) demonstrate paucity of central lymphatic ducts, lack of central lymphatic flow above the diaphragm, and massively dilated and beading bilateral subcutaneous ducts coursing along the abdominal wall. Twelve months after the start of treatment (right) there is resorption of the dilated subcutaneous ducts, with formation of new, more normal-appearing lymphatic networks now extending along the abdominal wall and into the chest. FIG. 24D) Coronal maximal intensity projections of contrast lymphangiograms of the pelvis and thighs before treatment (left) also demonstrate paucity of ducts in the thighs and massive dilation and beading of the lymphatic ducts. After treatment (right), again there is resorption of the abnormal dilated ducts and formation of new and more normal appearing lymphatic networks. FIG. 24E) Chest X-rays before (left) and 12 months after treatment (right) showing reduced effusions and notably improved lung volumes. FIG. 24F) The patient's growth chart (left). Treatment with trametinib was initiated just before age 13 (*) and improvement in lymphedema and clinical status was observed starting approximately 3-6 months after initiation of treatment. A picture of the patient's lower extremities immediately after removal of compression stockings at his peak weight is shown at the top right. The bottom right image shows the corresponding picture of the lower extremities.

DETAILED DESCRIPTION OF THE INVENTION

Figure 1:
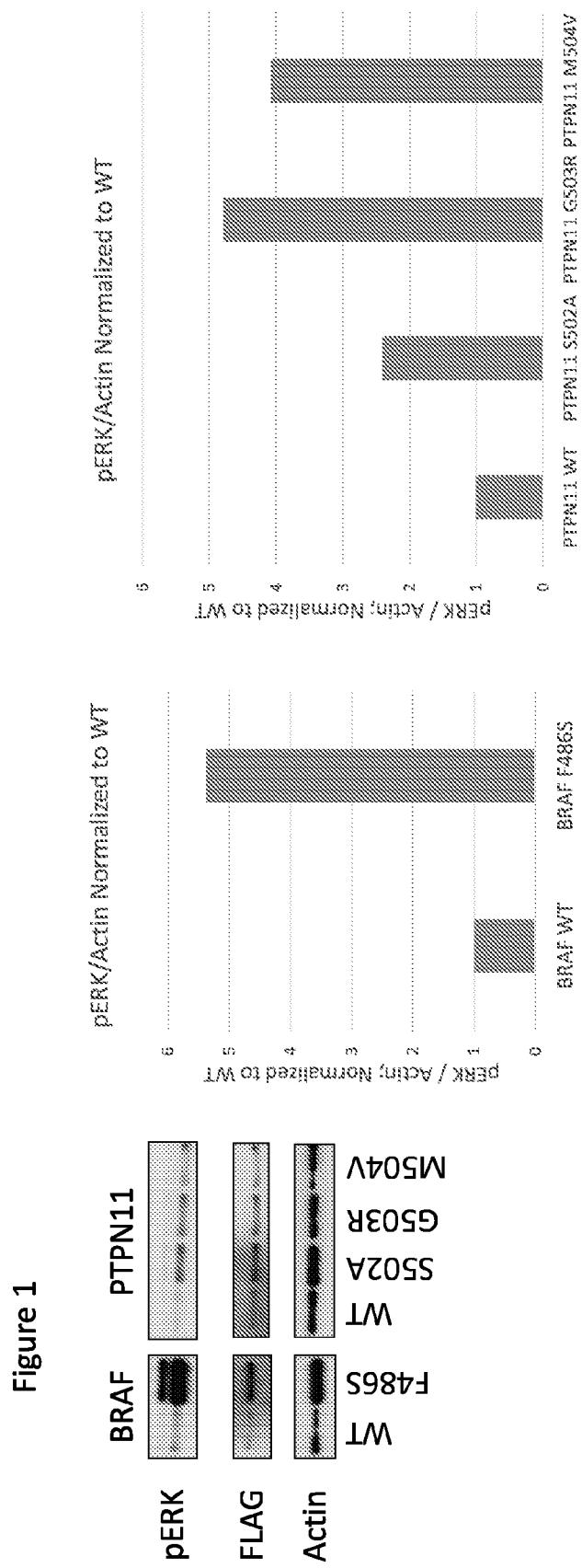
FIG. 1. Overexpression of BRAF and PTPN11 mutants in the Ea.hy926 cell line activates ERK signaling.

The Ras/mitogen-activated protein kinase (MAPK) pathway plays a vital role in cellular proliferation, migration, differentiation, and apoptosis, all of which are essential to normal development. Central conducting lymphatic anomalies (CCLA) are complex lymphatic anomalies characterized by dilated lymphatic channels, lymphatic channel dysmotility, and distal obstruction affecting lymphatic drainage. First described by Trenor III and Chaudry, and Clemens et al, CCLA was classified as channel-type lymphatic malformation by the International Society for the Study of Vascular Anomalies (ISSVA) in 2015, presenting significant overlapping patterns of clinical symptoms with its closely related diagnosis—generalized lymphatic anomaly (GLA), including but not limited to chylothorax, chylous ascites, leakage or reflux of lymph fluid, and extremity swelling. We recently identified a gain of function mutation in ARAF as causative for lymphatic anomalies, including LAM, GLA, and CCLA. Here we describe gain of function mutations in KRAS, BIRAF and PNPN11 as causative variants in lymphatic anomalies, including LAM, GLA, and CCLA. Other mutations in SOS1, ITAG9, RASA1, RAF1, RIT1, PIEZO1, EPHB4, NF1, CBL and ARAF which contribute to the pathogenesis of this disorder, are also described.

The treatment of lymphatic anomaly, a rare devastating disease spectrum of mostly unknown etiologies, depends on the patient manifestations. Identifying the causal genes will allow for developing affordable therapies in keeping with precision medicine implementation.

In Example II, we characterized a recurrent gain-of-function ARAF mutation (c.640T>C:p.S214P) in a 12-year-old boy with advanced anomalous lymphatic disease unresponsive to conventional sirolimus therapy and in another, unrelated, adult patient. The mutation led to loss of a conserved phosphorylation site. Cells transduced with ARAF-S214P showed elevated ERK1/2 activity, enhanced lymphangiogenic capacity, and disassembly of actin skeleton and VE-cadherin junctions, which were rescued using the MEK inhibitor trametinib. The functional relevance of the mutation was also validated by recreating a lymphatic phenotype in a zebrafish model, with rescue of the anomalous phenotype using a MEK inhibitor. Subsequent therapy of the lead proband with a MEK inhibitor led to dramatic clinical improvement, with remodeling of the patient's lymphatic system with resolution of the lymphatic edema, marked improvement in his pulmonary function tests, cessation of supplemental oxygen requirements and near normalization of daily activities. Our results provide a representative demonstration of how knowledge of genetic classification and mechanistic understanding guides biologically based medical treatments, which in our instance was life-saving.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Before describing the present teachings in detail, it is to be understood that the disclosure is not limited to specific compositions or process steps, as such may vary. It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

It will be appreciated that there is an implied "about" prior to the temperatures, concentrations, times, etc. discussed in the present disclosure, such that slight and insubstantial deviations are within the scope of the present teachings herein. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims).

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, a compound "selected from the group consisting of" refers to one or more of the compounds in the list that follows, including mixtures (i.e., combinations) of two or more of the compounds. According to the present invention, an isolated, or biologically pure molecule is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route.

"Lymphatic anomaly" refers to a disease or disorder characterized by abnormal formation of lymphatic vessels and tissue overgrowth. Non-limiting examples of lymphatic anomalies include "Lymphangiomatosis" or "lymphangiectasia" (referred to collectively herein as LAM), lymphangiomas, generalized lymphatic anomaly (GLA), and chylous effusions, generalized lymphangioma, systemic cystic angiomatosis, multiple lymphangiectasias, generalized lymphatic malformation, CCLA, diffuse lymphatic malformation, Kaposiform LAM and Gorham-Stout disease (GSD), a rare vascular disorder of lymphatic origin characterized by progressive bone osteolysis.

Clinically, lymphangiomas are classified into several types. These include (1) Simplex, which is made up of capillary sized, thin-walled lymphatic channels. This type usually affects the skin (lymphangioma circumscriptum); (2) Cystic lymphangioma (or cystic hygroma): this may range in size from a few millimeters to several centimeters, seen in a young age, commonly in the neck or the axilla; (3) Cavernosum: this type is made up of dilated lymphatic channels, often with fibrous adventitial coats. This is the type which usually affects organs in the thorax, abdomen, and bones. Each of these lymphangiomas are encompassed in the invention.

A "single nucleotide variation (SNV)" refers to a position in genomic DNA where there is a single base that differs from the usual base at that position. An SNV is similar to an SNP except that an SNP generally refers to an SNV that occurs with some frequency (e.g., occurring in greater than a certain percentage of the population), whereas SNV provides no frequency information. Millions of SNV's have been cataloged in the human genome. Some SNVs are responsible for disease, while other SNVs are normal variations in the genome.

A "lymphatic anomaly-associated-SNV or -specific marker" is an SNV that is associated with an increased risk of developing a lymphatic anomaly, and is not found in patients who do not have this disease. Such markers may include, but are not limited to, nucleic acids, proteins encoded thereby, or other small molecules.

The term "genetic alteration," as used herein, refers to a change from the wild-type or reference sequence of one or more nucleic acid molecules. Genetic alterations include without limitation, SNVs and SNPs, copy number variations (CNVs), base pair substitutions, additions, and deletions of at least one nucleotide from a nucleic acid molecule of a known sequence.

"Linkage" describes the tendency of genes, alleles, loci or genetic markers to be inherited together as a result of their location on the same chromosome, and is measured by percent recombination (also called recombination fraction, or θ) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causative mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

The term "solid matrix," as used herein, refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose. A solid matrix can comprise nucleic acids immobilized thereon such that they are not removable from the matrix in solution.

"Target nucleic acid," as used herein, refers to a previously defined region of a nucleic acid present in a complex nucleic acid mixture wherein the defined wild-type region contains at least one known nucleotide variation, which may or may not be associated with a lymphatic anomaly. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-to 5-fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus, if a nucleic acid sequence contains the following sequence of bases: thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any lymphatic anomaly-specific marker nucleic acid, but does not hybridize to other nucleotides. Such markers include, for example the lymphatic anomaly-specific markers shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$T_m = 81.5"C + 16.6 \text{ Log } [Na+] + 0.41(\% \text{ G+C}) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C.

below the $T_m$ of the hybrid. In certain aspects, the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein, is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe," as used herein, refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe (in certain cases nucleic acids associated with a specified rs number associated with a single nucleotide polymorphism available in the dbSNP database) typically contains 15-25, 15-35, 20-50, or 100 or more nucleotides, although it may contain fewer nucleotides, provided the site of the SNV is included in the probe. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer," as used herein, refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25, 15-40, 20-50, etc. or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNAs of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, CA, USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting Lymphangiomatosis mRNA, for example, may be between 15-35 nucleotides in length, and more typically about 21 nucleotides in length.

The term "vector" relates to a single- or double-stranded circular nucleic acid molecule that can be infected, transfected or transformed into cells and replicate independently or within the host cell genome. A circular double-stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together. When cloning a genetic region containing a duplication or a deletion, the skilled artisan is well aware that flanking sequences upstream and downstream of the affected region of a suitable length (e.g., between 50-100 or more nucleotides) would be employed in the cloning process. Such vectors would have utility, for example in cell lines for studying the effects such alterations have on the encoded proteins.

Many techniques are available to those skilled in the art to facilitate transformation, transfection, or transduction of the expression construct into a prokaryotic or eukaryotic organism. The terms "transformation," "transfection," and "transduction" refer to methods of inserting a nucleic acid and/or an expression construct into a cell or host organism. These methods involve a variety of techniques, such as treating the cells with high concentrations of salt, an electric field, or detergent, to render the host cell outer membrane or wall permeable to nucleic acid molecules of interest, micro-injection, PEG-fusion, and the like.

The term "'promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the lymphatic anomaly-specific marker nucleic acid molecule such that the latter is transcribed into mRNA. Host cell machinery then translates mRNA into a polypeptide. Promoter elements may drive constitutive or inducible expression of a coding region of interest.

Those skilled in the art will recognize that a nucleic acid vector can contain nucleic acid elements other than the promoter element and the lymphatic anomaly-specific marker encoding nucleic acid. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single- or double-stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system," "reporter gene," or "reporter gene product" shall mean an operative genetic system in which a nucleic acid comprises a gene that encodes a product that when expressed produces a reporter signal that is readily measurable, e.g., by biological assay, immunoassay, radio immunoassay, or by colorimetric, fluorogenic, chemiluminescent or other methods. The nucleic acid may be either RNA or DNA, linear or circular, single- or double-stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g., enhancers) in an expression vector.

The terms "recombinant organism" or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism. Example transgenic organisms include zebrafish or mice.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably a lymphatic anomaly-specific marker molecule, such as a marker shown in the tables provided below. Samples may include but are not limited to cells, body fluids, including blood, serum, plasma, urine, lymph, saliva, tears, pleural fluid and the like.

"Genotype sequence information" generally refers to any information related to the sequence of a subject's DNA or RNA. Genotype sequence information comprises whole genome, whole exome sequencing, exome sequencing, or targeted sequencing of areas of interest within the genome of a subject. Genotype sequence information may also include generation of data on the presence or absence of specific SNVs, such as those found herein to be associated with lymphatic anomalies. In addition, genotype sequence information would include use of probes to detect the presence of and/or expression of one or more lymphatic anomaly-associated SNVs. Examples of how probes may be used to obtain genotype sequence information include, but are not limited to: (1) in situ hybridization; (2) southern hybridization (3) northern hybridization; and (4) assorted amplification reactions such as polymerase chain reactions (PCR).

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the SNV containing nucleic acids described herein or their encoded proteins. Exemplary agents include, without limitation, at least one MEK inhibitor. Additional agents also include those listed in Tables 1-2. Agents are evaluated for potential biological activity by inclusion in screening assays described herein below.

"Treatment," as used herein, covers any administration or application of a therapeutic for disease in a mammal, including a human, and includes inhibiting the disease or progression of the disease, inhibiting or slowing the disease or its progression, arresting its development, partially or fully relieving the disease, preventing the onset of the disease, or preventing a recurrence of symptoms of the disease. Exemplary treatments include administration of at least one MEK inhibitor and or at least one of the agents listed in Tables 1-2, at efficacious doses.

The terms "inhibition" or "inhibit" refer to a decrease or cessation of any event (such as protein ligand binding) or to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. It is not necessary that the inhibition or reduction be complete. For example, in certain embodiments, "reduce" or "inhibit" refers to the ability to cause an overall decrease of 20% or greater. In another embodiment, "reduce" or "inhibit" refers to the ability to cause an overall decrease of 50% or greater. In yet another embodiment, "reduce" or "inhibit" refers to the ability to cause an overall decrease of 75%, 85%, 90%, 95%, or greater.

The term "inhibitor" refers to an agent that slows down or prevents a particular chemical reaction, signaling pathway or other process, or that reduces the activity of a particular reactant, catalyst, or enzyme.

The terms "patient" and "subject" are used interchangeably to mean a mammal, including human.

The term "MEK" refers to the MAPK/ERK pathway (also known as the Ras-Raf-MEK-ERK pathway) which comprise a chain of proteins in the cell that communicate a signal from a receptor on the surface of the cell to the DNA in the nucleus of the cell. The signal starts when a signaling molecule binds to the receptor on the cell surface and ends when the DNA in the nucleus expresses a protein and produces some change in the cell, such as cell division. The pathway includes many proteins, including MAPK (mitogen-activated protein kinases, originally called ERK, extracellular signal-regulated kinases), which communicate by adding phosphate groups to a neighboring protein, which acts as an "on" or "off" switch.

The term "MEK inhibitor" or "MEK/ERK inhibitor" refers to an agent that inhibits the mitogen-activated protein kinase enzymes MEK1, MEK2, and/or ERK. They can be used to affect the MAPK/ERK pathway which is often overactive in some cancers. The term "cellular signaling" would comprise mTOR signaling as well as any other signal transduction pathway process that governs cells homeostasis or activity.

Diagnosing Patients with Lymphatic Anomalies

In some embodiments, patients with lymphatic anomalies are diagnosed based on the presence of an SNV after obtaining genotype sequence information from a biological sample obtained from a patient. In some embodiments, patients with lymphatic anomalies are diagnosed based on detecting the presence of one or more SNV in a gene selected from PTPN11, KRAS, BRAF, SOS1, ITGA9, RASA1, RAF1, RIT1, PEIZO1, EPHB4, NF1, ARAF and CBL, or an SNV in linkage disequilibrium with an SNV in a gene selected from PTPN11, KRAS, BRAF, SOS1, ITGA9, RASA1, RAF1, RIT1, PEIZO1, EPHB4, NF1, ARAF and CBL associated with lymphatic anomaly. In some embodiments, this one or more SNV is a c.1504T>G: pS502A, c.1510A>G:pM504V, and/or c.1507G>C:pG503R in the PTPN11 gene, a c.35G>A:pG12D in KRAS, a c.1403T>C:pF468S in the BRAF gene, ac.2536G>A: pE846K in the SOS1 gene, and a compound mutation comprising c.1236+4A>G and c.289T>G:p.C97G in the ITGA9 gene or any of the mutations listed in Table 3.

In some embodiments, a report identifying the SNV(s) present in a particular subject may be generated from experimental data. In some embodiments, a report identifying suggested treatment(s) for the lymphatic anomaly may be generated based upon the data on SNV(s) identified using genotype sequence information.

In some embodiments, diagnosis based on detecting the presence of one or more SNV in a gene selected from PTPN11, KRAS, BRAF, SOS1, ITGA9, RASA1, RAF1, RIT1, PEIZO1, EPHB4, NF1, ARAF, and CBL, or an SNV in linkage disequilibrium with an SNV in a gene selected from PTPN11, KRAS, BRAF, SOS1, ITGA9, RASA1, RAF1, RIT1, PEIZO1, EPHB4, NF1, ARAF and CBL, after obtaining genotype sequence information from a biological sample obtained from a patient guides the choice of treatment for the patient. In some embodiments, diagnosis based on detecting the presence of one or more SNV in a gene selected from PTPN11, KRAS, BRAF, SOS1, ITGA9, RASA1, RAF1, RIT1, PEIZO1, EPHB4, NF1, ARAF and CBL, or an SNV in linkage disequilibrium with an SNV in a gene selected from PTPN11, KRAS, BRAF, SOS1, ITGA9, RASA1, RAF1, RIT1, PEIZO1, EPHB4, NF1, ARAF and CBL, after obtaining genotype sequence information from a biological sample obtained from a patient does not guide or impact the choice of treatment for the patient.

In some embodiments, diagnosis of a lymphatic anomaly is made solely based on clinical presentation, scanning results, and/or family history. In some embodiments, diagnosis of a lymphatic anomaly is made without testing for genetic sequence information. In some embodiments, diagnosis of a lymphatic anomaly is made based on clinical presentation together with genetic sequence information.

The lymphatic anomaly-related SNVs disclosed in this invention can be used in a number of ways to diagnose lymphatic anomalies.

For example, nucleic acids comprising lymphatic anomaly-associated SNVs may be used as probes to detect the presence of and/or expression of lymphatic anomaly-specific markers. Methods in which lymphatic anomaly-associated marker nucleic acids may be utilized as probes for such assays include, but are not limited to: (1) in situ hybridization; (2) Southern hybridization (3) northern hybridization; and (4) assorted amplification reactions such as polymerase chain reactions (PCR).

Further, assays for detecting lymphatic anomaly-associated SNVs, or the proteins encoded thereby, may be conducted on any type of biological sample, including but not limited to body fluids (including blood, urine, serum, gastric lavage), any type of cell (such as brain cells, white blood cells, mononuclear cells) or body tissue.

Lymphatic anomaly-associated SNV-containing nucleic acids, vectors expressing the same, lymphatic anomaly-associated SNV-containing marker proteins and anti-lymphatic anomaly-specific marker antibodies can be used to detect lymphatic anomaly-associated SNVs in body tissue, cells, or fluid, and alter lymphatic anomaly-associated SNV-containing marker protein expression for purposes of detecting and diagnosing lymphatic anomalies.

Methods for detecting and/or diagnosing lymphatic anomalies based on lymphatic anomaly-associated SNVs are encompassed. The method may comprise detecting lymphatic anomaly-associated SNVs, the lymphatic anomaly-associated SNV containing nucleic acid in the sample will initially be amplified, e.g. using PCR, to increase the amount of the templates as compared to other sequences present in the sample. This allows the target sequences to be detected with a high degree of sensitivity if they are present in the sample. This initial step may be avoided by using highly sensitive array techniques that are becoming increasingly important in the art.

Alternatively, new detection technologies can overcome this limitation and enable analysis of small samples containing as little as 1 μg of total RNA. Using Resonance Light Scattering (RLS) technology, as opposed to traditional fluorescence techniques, multiple reads can detect low quantities of mRNAs using biotin-labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus, any of the aforementioned techniques may be used to detect or quantify lymphatic anomaly-associated SNV marker expression and accordingly and to diagnose lymphatic anomalies or a risk of development thereof.

Treating Patients with Lymphatic Anomalies

The elucidation of the role played by lymphatic anomaly-associated SNVs described herein in modulating the lymphatic anomaly phenotype facilitates the repurposing of existing therapies, and the development of new therapies, useful for treatment of lymphatic anomalies. In some embodiments, the invention comprises administering one or more mTOR inhibitors, one or more PIK3K inhibitors, and/or one or more MEK inhibitors (e.g., one or more of the agents of Tables 1-2) to a patient having a lymphatic anomaly.

In some embodiments, the patient with a lymphatic anomaly to be treated has been diagnosed based on symptoms and a positive family history of lymphatic anomalies. In some embodiments, a variety of scanning technologies, such as plain film radiography, bone scanning, computed tomography, magnetic resonance imaging, and lymphoscintigraphy are used together with clinical presentation to diagnose a lymphatic anomaly. In some embodiments, a biopsy is performed to diagnose a lymphatic anomaly. In some embodiments, a lymphatic anomaly is diagnosed based on lymph vessel overgrowth. In some embodiments, a lymphatic anomaly is diagnosed based on abnormal formation of lymphatic vessels. In some embodiments, a lymphatic anomaly is diagnosed based on chylous effusions, including pericardial, pleural, or peritoneal effusions.

In some embodiments, the patient with a lymphatic anomaly to be treated has been diagnosed according to the diagnostic methods described herein.

In some embodiments, one or more MEK inhibitors (e.g., one or more of the agents of Tables 1-2; Example II) are useful in the preparation of a medicament to treat lymphatic anomalies. The one or more agent(s) may be formulated with a pharmaceutically acceptable excipient, carrier, buffer, stabilizer or other material well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, nasal, aerosolized, intramuscular, and intraperitoneal routes. In vitro systems or transgenic organisms comprising lymphatic anomaly-associated mutations may be used to select a particular agent for treatment of humans.

Agents useful for treatment include, but are not limited to, the agents of Tables 1 and 2. Some agents are listed on both Table 1 and 2, and the fact that they are not listed on both tables should be given no meaning.

TABLE 1

| | | |
|---|---|---|
| Rapamycin (Sirolimus) | Rapamycin (Sirolimus) is a specific mTOR inhibitor with IC50 of ~0.1 nM HEK293 cells. | Nat Genet, 2014, 46(4): 364-70 Cancer Cell, 2011, 19(6): 792-804 Cell Res, 2012, 22(6): 1003-21 |
| Everolimus (RAD001) | Everolimus (RAD001) is an mTOR inhibitor of FKBP12 with IC50 of 1.6-2.4 nM in a cell-free assay. | Cell, 2012, 149(3): 656-70 Nat Med, 2015, 10.1038/nm.3855 Cancer Cell, 2015, 27(4): 533-46 |
| AZD8055 | AZD8055 is a novel ATP-competitive mTOR inhibitor with IC50 of 0.8 nM in MDA-MB-468 cells with excellent selectivity (~1,000-fold) against PI3K isoforms and ATM/DNA-PK. Phase 1. | Nat Med, 2015, 10.1038/nm.3855 Cancer Cell, 2015, 27(1): 97-108 Cancer Cell, 2015, 27(4): 533-46 |

TABLE 1-continued

| | | |
|---|---|---|
| Temsirolimus (CCI-779, NSC 683864) | Temsirolimus (CCI-779, NSC 683864) is a specific mTOR inhibitor with IC50 of 1.76 μM in a cell-free assay. | Autophagy, 2011, 7(2): 176-87<br>Cancer Res, 2014, 74(14): 3947-58<br>Mol Oncol, 2014, 10.1016/j.molonc.2014.05.005 |
| KU-0063794 | KU-0063794 is a potent and highly specific dual-mTOR inhibitor of mTORC1 and mTORC2 with IC50 of ~10 nM in cell-free assays; no effect on PI3Ks. | Cell Stem Cell, 2012, 10(2): 210-7<br>Circ Res, 2010, 107(10): 1265-74<br>Oncogene, 2013, 10.1038/onc.2013.509 |
| MHY1485 | MHY1485 is a potent, and cell-permeable mTOR activator, and also potently inhibits autophagy. | |
| BEZ235 (NVP-BEZ235, Dactolisib) | BEZ235 (NVP-BEZ235, Dactolisib) is a dual ATP-competitive PI3K and mTOR inhibitor for p110α/γ/δ/β and mTOR(p70S6K) with IC50 of 4 nM/5 nM/7 nM/75 nM/6 nM in cell-free assays, respectively. Inhibits ATR with IC50 of 21 nM in $3T3^{TopBP1-ER}$ cell. | Nature, 2012, 487(7408): 505-9<br>Nat Med, 2015, 10.1038/nm.3855<br>Cancer Cell, 2012, 21(2): 155-67 |
| PI-103 | PI-103 is a multi-targeted PI3K inhibitor for p110α/β/δ/γ with IC50 of 2 nM/3 nM/3 nM/15 nM in cell-free assays, less potent to mTOR/DNA-PK with IC50 of 30 nM/23 nM. | Cell, 2013, 153(4): 840-54<br>Leukemia, 2013, 27(3): 650-60<br>Leukemia, 2012, 26(5): 927-33 |
| Torkinib (PP242) | Torkinib (PP242) is a selective mTOR inhibitor with IC50 of 8 nM in cell-free assays; targets both mTOR complexes with > 10- and 100-fold selectivity for mTOR than PI3Kδ or PI3Kα/β/γ, respectively. | J Clin Invest, 2015, 10.1172/JCI78018<br>Nat Chem Biol, 2013, 9(11): 708-14<br>Autophagy, 2012, 8(6): 903-14 |
| Tacrolimus (FK506) | Tacrolimus (FK506) is a 23-membered macrolide lactone, it reduces peptidyl-prolyl isomerase activity in T cells by binding to the immunophilin FKBP12 (FK506 binding protein) creating a new complex. | Biomed Pharmacother, 2013, 67(6): 469-73<br>Universidad de Cantabria, 2012, Garcia Diaz<br>Biochim Biophys Acta, 2012, 1833(3): 652-62 |
| Selumetinib (AZD6244) | Selumetinib (AZD6244) is a potent, highly selective MEK1 inhibitor with IC50 of 14 nM in cell-free assays, also inhibits ERK1/2 phosphorylation with IC50 of 10 nM, no inhibition to p38α, MKK6, EGFR, ErbB2, ERK2, B-Raf, etc. | Nature, 2012, 487(7408): 505-9<br>Nature, 2010, 468(7326): 968-72<br>Nature, 2016, 10.1038/nature19347 |
| PD0325901 | PD0325901 is a selective and non ATP-competitive MEK inhibitor with IC50 of 0.33 nM in cell-free assays, roughly 500-fold more potent than CI-1040 on phosphorylation of ERK1 and ERK2. Phase 2. | Nature, 2015, 10.1038/nature14413<br>Nature, 2015, 517(7534): 391-5<br>Cell, 2015, 160(1-2): 161-76 |
| Trametinib (GSK1120212) | Trametinib (GSK1120212) is a highly specific and potent MEK1/2 inhibitor with IC50 of 0.92 nM/1.8 nM in cell-free assays, no inhibition of the kinase activities of c-Raf, B-Raf, ERK1/2. | Nature, 2015, 517(7534): 391-5<br>Nature, 2014, 510(7504): 283-7<br>Nature, 2014, 508(7494): 118-22 |
| PD184352 (CI-1040) | PD184352 (CI-1040) is an ATP non-competitive MEK1/2 inhibitor with IC50 of 17 nM in cell-based assays, 100-fold more selective for MEK1/2 than MEK5. Phase 2. | Science, 2011, 331(6019): 912-6<br>Nat Genet, 2011, 44(2): 133-9<br>Cancer Cell, 2016, 10.1016/j.ccell.2016.01.006 |
| Pimasertib (AS-703026) | Pimasertib (AS-703026) is a highly selective, potent, ATP non-competitive allosteric inhibitor of MEK1/2 with IC50 of 5 nM-2 μM in MM cell lines. Phase 2. | Nat Commun, 2015, 6: 6683 FASEB J, 2014, 10.1096/fj.13-247924 Oncotarget, 2016, 7(4): 4265-78 |
| TAK-733 | TAK-733 is a potent and selective MEK allosteric site inhibitor for MEK1 with IC50 of 3.2 nM, inactive to Abl1, AKT3, c-RAF, CamK1, CDK2, c-Met, etc. | Nat Commun, 2016, 7: 13701<br>Oncotarget, 2014, 5(20): 9609-18<br>Mol Cancer Ther, 2014, 13(2): 353-63 |
| AZD8330 | AZD8330 is a novel, selective, non-ATP competitive MEK1/2 inhibitor with IC50 of 7 nM. | Cell, 2012, 32(34): 4034-42<br>Oncotarget, 2016, 7(13): 16273-81 |

TABLE 1-continued

| | | |
|---|---|---|
| Binimetinib (MEK162, ARRY-162, ARRY-438162) SL-327 | Binimetinib (MEK162, ARRY-162, ARRY-438162) is a potent inhibitor of MEK1/2 with IC50 of 12 nM in a cell-free assay. SL327 is a selective inhibitor for MEK1/2 with IC50 of 0.18 μM/ 0.22 μM, no activity towards Erk1, MKK3, MKK4, c-JUN, PKC, PKA, or CamKII; capable of transport through the blood-brain barrier. | Stem Cells, 2015, 10.1002/stem.1990 Mol Oncol, 2014, 8(3): 544-54 Tumour Biol, 2015, 10.1007/s13277-015-3244-2 Psychopharmacology (Berl). 2011 Jul;216(1): 63-73. |
| Refametinib (RDEA119, Bay 86-9766) | Refametinib (RDEA119, Bay 86-9766) is a potent, ATP non-competitive and highly selective inhibitor of MEK1 and MEK2 with IC50 of 19 nM and 47 nM, respectively. | J Neurosci, 2012, 32(14): 4887-900 EBioMedicine, 2017, 15: 90-99 Am J Cancer Res, 2016, 6(10): 2235-2251 |
| Cobimetinib (GDC-0973, RG7420) | Cobimetinib (GDC-0973, RG7420) is a potent and highly selective MEK1 inhibitor with IC50 of 4.2 nM, showing more than 100-fold selectively for MEK1 over MEK2 and showed no significant inhibition when tested against a panel of more than 100 of serine-threonine and tyrosine kinases. | Cancer Discov, 2015, 10.1158/2159-8290.CD-15-0913 Mol Cell Proteomics, 2017, 16(2): 265-277 Cancer Discov, 2016, 6(2): 154-65 |
| Ulixertinib | Ulixertinib (BVD-523; VRT752271) is a potent, orally active, highly selective, ATP-competitive and reversible covalent inhibitor of ERK1/2 kinases, with an $IC_{50}$ of < 0.3 nM against ERK2. Ulixertinib (BVD-523; VRT752271) inhibits the phosphorylated ERK2 (pERK) and downstream kinase RSK (pRSK) in an A375 melanoma cell line. | J Pharm Biomed Anal. 2016 Jun 5;125: 140-4. J Med Chem. 2015 Jun 11;58(11): 4790-801. |

Table 2 provides agents that can be used alone, or in combination with any of the agents in Table 1 or in Table 2 to treat lymphatic anomalies.

TABLE 2

| Inhibitor Name | mTOR | mTORC1 | mTORC2 | Other Targets |
|---|---|---|---|---|
| BEZ235 (NVP-BEZ235, Dactolisib) | +++ | | | p110α, p110γ, p110δ |
| Rapamycin (Sirolimus) | ++++ | | | |
| Everolimus (RAD001) | +++ | | | |
| AZD8055 | ++++ | | | DNA-PK, PI3Kδ, PI3Kα |
| Temsirolimus (CCI-779, NSC 683864) | + | | | |
| PI-103 | + | | | p110α, p110δ, p110β |
| KU-0063794 | | ++ | ++ | |
| Torkinib (PP242) | ++ | | | p110δ, PDGFR, DNA-PK |
| Ridaforolimus (Deforolimus, MK-8669) | ++++ | | | |
| INK 128 (MLN0128) | ++++ | | | PI3Kα, PI3Kγ, PI3Kδ |
| Voxtalisib (SAR245409, XL765) | + | | | PI3Kγ, PI3Kα, PI3Kδ |
| Torin 1 | +++ | +++ | ++ | DNA-PK, p110γ, C2α |
| Omipalisib (GSK2126458, GSK458) | | ++++ | ++++ | p110α, p110δ, p110γ |
| OSI-027 | +++ | + | + | PI3Kγ, DNA-PK, PI3Kα |
| PF-04691502 | + | | | PI3Kδ, PI3Kα, PI3Kγ |
| Apitolisib (GDC-0980, RG7422) | + | | | p110α, p110δ, p110γ |
| GSK1059615 | ++ | | | PI3Kα, PI3Kβ, PI3Kδ |
| Gedatolisib (PF-05212384, PKI-587) | +++ | | | PI3Kα, PI3Kγ |
| WYE-354 | +++ | | | PI3Kα, PI3Kγ |
| AZD2014 | +++ | | | P-Akt (S473), pS6 (S235/236) |
| Torin 2 | ++++ | | | ATM, ATR, DNA-PK |
| WYE-125132 (WYE-132) | ++++ | | | |
| PP121 | ++ | | | PDGFR, Hck, VEGFR |
| WYE-687 | ++ | | | PI3Kα, PI3Kγ, p38α |
| CH5132799 | + | | | PI3Kα, PI3Kγ, PI3Kβ |
| WAY-600 | ++ | | | PI3Kα, PI3Kγ |
| ETP-46464 | ++++ | | | ATR, DNA-PK, PI3Kα |

TABLE 2-continued

| Inhibitor Name | mTOR | mTORC1 | mTORC2 | Other Targets |
|---|---|---|---|---|
| GDC-0349 | +++ | | | PI3Kα |
| XL388 | ++ | ++ | + | CYP2C9, CYP3A4 |
| Zotarolimus (ABT-578) | +++ | | | |
| Tacrolimus (FK506) | √ | | | |
| BGT226 (NVP-BGT226) | √ | | | PI3Kα, PI3Kγ, PI3Kβ |
| Palomid 529 (P529) | | √ | | |
| Chrysophanic Acid | √ | | | EGFR |
| TAK-733 | | | | MEK |
| PD-325901 | | | | MEK |
| Selumetinib | | | | MEK |
| Binimetinib (MEK162) | | | | MEK |
| Cobimetinib (XL518) | | | | MEK |
| Trametinib (GSK1120212 | | | | MEK |
| Pimasertib (AS-70326) | | | | MEK |
| Trametinib | | | | MEK |
| PD184352 | | | | MEK |
| SL-327 | | | | MEK |
| AZD8330 | | | | MEK |
| ISO-027* | √ | √ | | |

*structure of ISO-27 (Mateo et al. (2016) Br. J. Cancer 114(8): 889-96

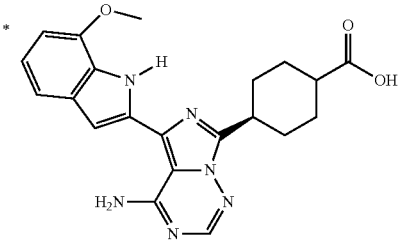

In order to treat an individual having a lymphatic anomaly, or to alleviate a sign or symptom of the disease, suitable agents targeting the genes disclosed herein can be administered in combination in order to provide therapeutic benefit to the patient. Such agents should be administered in an effective dose.

Once the genetic alteration(s) is/are identified, therapy is then devised to modulate biological and signaling pathways affected by the altered gene. For example, in cases where it is desirable to inhibit the MAPK (MEK1/MEK2) and ERK pathways, MEK inhibitors can used alone or in combination with other MEK/ERK inhibitors. In certain embodiments, treatment entails administration of an agent listed in Table 1 or 2 such as an mTOR inhibitor together with PIK3K inhibitor. In other embodiments, mTOR and MEK/ERK inhibitors are combined to provide therapeutic benefit to the patient. In another approach, PIK3K and MEK/ERK inhibitor are combined to ameliorate symptoms of disease. For the specific ARAF gain of function mutation described herein, an effective therapy comprises administration of a MEK/ERK inhibitor. The combinatorial therapies described above can act in an additive fashion. In other embodiments, the combined agents act synergistically to alleviate symptoms.

First, a biological sample, and/or genotyping information may be obtained from a patient. Genetic information gleaned from nucleic acids present in the sample would then be assessed for the presence or absence of the lymphatic anomaly-associated SNV for example. The presence of these mutations indicating the presence of a lymphatic anomaly risk or disease, along with the simultaneous identification of the genes affected, provides the clinician with guidance as to which therapeutic agents are appropriate. The total treatment dose or doses (when two or more targets are to be modulated) can be administered to a subject as a single dose or can be administered using a fractionated treatment protocol, in which multiple/separate doses are administered over a more prolonged period of time, for example, over the period of a day to allow administration of a daily dosage or over a longer period of time to administer a dose over a desired period of time. One skilled in the art would know that the amount of lymphatic anomaly agent required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having a lymphatic anomaly.

The effective dose of lymphatic anomaly therapeutic agent(s) will depend on the mode of administration, and the weight of the individual being treated. The dosages described herein are generally those for an average adult but can be adjusted for the treatment of children. The dose will generally range from about 0.001 mg to about 1000 mg.

In an individual suffering from a lymphatic anomaly in particular, a more severe form of the disease, administration of lymphatic anomaly therapeutic agents can be particularly useful when administered in combination, for example, with a conventional agent for treating such a disease. The skilled artisan would administer lymphatic anomaly therapeutic agent(s), alone or in combination and would monitor the effectiveness of such treatment using routine methods such as pulmonary, bowel, thyroid, or inflammatory function determination, radiologic or immunologic assays, or, where indicated, histopathologic methods. Other agents for the treatment of lymphatic anomaly include systemic chemotherapy, interferon alfa therapy, radiotherapy, or surgery, to alleviate the symptoms underlying the disease.

Administration of the pharmaceutical preparation is preferably in an "effective amount" this being sufficient to show benefit to the individual. This amount prevents, alleviates, abates, or otherwise reduces the severity of lymphatic anomaly symptoms in a patient. Treatment of patients having lymphatic anomaly with an efficacious amount of a MEK inhibitor and or an agent from Tables 1-2) may produce improvements in lymph structure, decreased chylous pleural effusions, improved respiratory function, tapering of concomitant medication usage, or increased survival.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

Pharmaceutical compositions that are useful in the methods of the invention may be administered systemically in parenteral, oral solid and liquid formulations, subcutaneously, intradermally, intramuscularly, sublingually, topically, auricularly (OTIC), buccally, conjunctivally, cutaneously, dentally, via electro-osmosis, endo-cervically, via the sinus or trachea, enteral, epidurally, via infiltration, interstitially, intra-abdominally, intra-arterially, intra-articular, intra-biliary, intra-bronchially, intra-bursal, intra-cardiac, intra-cartilaginous, intra-caudal, intracavernous, intracavitary, intracerebral, intradermal, intra-lymphatic, intrapericardially, intraperitoneal, nasally, percutaneous, respiratory, ophthalmic, suppository, aerosol, topical or other known routes of administration. In addition to the agent(s) useful for treating a lymphatic anomaly, the pharmaceutical compositions may contain pharmaceutically-acceptable carriers and other ingredients known to enhance and facilitate drug administration. Thus, such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to deliver/administer the appropriate agent to a patient according to the methods of the invention. The use of nanoparticles to deliver such agents, as well as cell membrane permeable peptide carriers that can be used are described in Crombez et al., Biochemical Society Transactions v35:p44 (2007).

Administration of agent(s) useful for treating a lymphatic anomaly may be done following successfully detecting or quantifying lymphatic anomaly-associated SNV marker expression and accordingly, diagnosing a lymphatic anomaly or a risk of development thereof. Detecting or quantifying lymphatic anomaly-associated SNV marker expression may guide the selection of the specific agent used for treatment. Detecting or quantifying lymphatic anomaly-associated SNV marker expression may indicate that a particular treatment is not appropriate for a given subject.

In other embodiments, treatment for a lymphatic anomaly may be done based on clinical diagnosis of disease and treatment may be initiated in the absence of detecting or quantifying genetic sequence information. In other embodiments, treatment for a lymphatic anomaly may be done based on clinical diagnosis of disease and treatment may be initiated in the absence of detecting or quantifying lymphatic anomaly-associated SNV marker expression.

In other embodiments, treatment for a lymphatic anomaly may be done based on clinical diagnosis of disease and treatment may be initiated when lymphatic anomaly-associated SNV marker expression is not different from controls.

In some embodiments, treatment is administered in patients who do not have an SNV in PTPN11, KRAS, BRAF, SOS1, ITGA9, RASA1, RAF1, RIT1, PEIZO1, EPHB4, NF1, ARAF and CBL.

In some embodiments, the inhibitor is an MEK1/2 inhibitor which inhibits the mitogen-activated protein kinase enzymes MEK1 and/or MEK2. They can be used to affect the MAPK/ERK pathway which is often overactive in some cancers and other disorders.

In some embodiments, the agent(s) to co-administered is rapamycin or BEZ-235 (dactolisib). Rapamycin, an mTOR inhibitor, is also known as sirolimus. BEZ-235, also known as dactolisib or NVP-BEZ235, is a compound with known activity against p110, PI3K, and mTOR.

In some embodiments, the agent to be administered in the treatment methods is selected from Rapamycin (Sirolimus), Everolimus (RAD001), AZD8055, Temsirolimus (CCI-779, NSC 683864), KU-0063794, MHY1485, BEZ235 (NVP-BEZ235, Dactolisib), PI-103, Torkinib (PP242), Tacrolimus (FK506), Ridaforolimus (Deforolimus, MK-8669), INK 128 (MLN0128), Voxtalisib (SAR245409, XL765), Torin 1, Omipalisib (GSK2126458, GSK458), OSI-027, PF-04691502, Apitolisib (GDC-0980, RG7422), GSK1059615, Gedatolisib (PF-05212384, PKI-587), WYE-354, AZD2014, Torin 2, WYE-125132 (WYE-132), PP121, WYE-687, CH5132799, WAY-600, ETP-46464, GDC-0349, XL388, Zotarolimus (ABT-578), Tacrolimus (FK506), BGT226 (NVP-BGT226), Palomid 529 (P529), and Chrysophanic Acid.

In some embodiments, the agent to be administered is an MEK inhibitor selected from Selumetinib (AZD6244). PD0325901, Trametinib (GSK1120212), PD184352 (CI-1040), Pimasertib (AS-703026), TAK-733, AZD8330, Binimetinib (MEK162, ARRY-162, ARRY-438162), SL-327, Refametinib (RDEA119, Bay 86-9766), and Cobimetinib (GDC-0973, RG7420).

Combinations of the agents described above may also be used in the methods of treatment described herein to treat lymphatic anomalies. In some embodiments, the combinations below can act additively or synergistically to treat lymphatic anomalies, including GLA and LAM. In certain embodiments, the combinations for administration are selected from 1) Ridaforolimus and Trametinib; 2) Ridaforolimus and Selumetinib or Cobimetinib; 3) BEZ235 and Selumetinib; 4) Omipalisib and Selumetinib or Trametinib; 5) Everolimus and Trametinib or Selumetinib; 6) Sirolimus, Ridaforolimus and Selumetinib; 7) Sirolimus, Ridaforolimus and Trametinib; 8) Torkinib and Trametinib; 9) BEZ235, Torkinib and Trametinib; and 10) Sirolimus and Gedatolisib and Trametinib.

In some embodiments, treatment with an agent(s) listed herein is used in combination with one or more of systemic chemotherapy, interferon alfa, radiotherapy, and/or surgery.

Methods of Identifying Additional Useful Therapeutic Reagents

Since the SNVs identified herein have been associated with the etiology of lymphatic anomaly, methods for identifying agents that modulate the activity of the genes and their encoded products containing such SNVs should result in the generation of efficacious therapeutic agents for the treatment of this condition.

The chromosomal regions described herein contain protein coding regions which provide suitable targets for the rational design of therapeutic agents which modulate their activity. Small peptide molecules corresponding to these regions may be used to advantage in the design of therapeutic agents which effectively modulate the activity of the encoded proteins.

Molecular modeling should facilitate the identification of specific organic molecules with capacity to bind to the active site of the proteins encoded by the SNV-containing nucleic acids based on conformation or key amino acid residues required for function. A combinatorial chemistry approach will be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, NJ), Microsource (New Milford, CT), Aldrich (Milwaukee, WI), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, CA), ChemDiv, (San Diego, CA), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, NJ), Interbioscreen (Moscow, Russia), Interchim (Montlucon, France), Life Chemicals, Inc. (Orange, CT), Microchemistry Ltd. (Moscow, Russia), Otava, (Toronto, ON), PharmEx Ltd.(Moscow, Russia), Princeton Biomolecular (Monmouth Junction, NJ), Scientific Exchange (Center Ossipee, NH), Specs (Delft, Netherlands), TimTec (Newark, DE), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

A further technique for drug screening involves the use of host eukaryotic cell lines, cells (such as endothelial cells) or whole animal models (e.g., transgenic mice or zebrafish) which have a nonfunctional or altered lymphatic anomaly-associated gene. In some cases, the transgenic organism comprises cells that have mutation of c.1504T>G:pS502A, c.1510A>G:pM504V, and/or c.1507G>C:pG503R in the PTPN11 gene, a c.35G>A:pG12D in KRAS, a c.1403T>C:pF468S in the BRAF gene, ac.2536G>A:pE846Kin the SOS1 gene, and a compound mutation comprising c.1236+4A>G and c.289T>G:p.C97G in the ITGA9 gene or one or more of the mutations shown in Table 3. These host cell lines, cells or transgenic animals are defective at the polypeptide level. The host cell lines or cells are grown in the presence of drug compound. For example, in a zebra fish model, the rescue of caudal and or D/V vessel structure can be assessed. Additionally, induction of phosphorylation by mTOR in a host cell line may be assessed.

An example method of drug screening would be a method for identifying an agent that alters cellular signaling, such as an agent listed in Tables 1-2. This method would comprise providing cells expressing at least one nucleic acid comprising at least one lymphatic anomaly-associated SNV; providing cells which express the cognate wild type sequences corresponding to the lymphatic anomaly-associated SNV; contacting the cells expressing at least one lymphatic anomaly-associated SNV and cells expressing the cognate wild type sequence with a test agent; and analyzing whether said agent alters cellular signaling.

Host cells expressing the lymphatic anomaly-associated SNVs of the present invention or functional fragments thereof provide a system in which to screen potential compounds or agents for the ability to modulate the development of lymphatic anomalies. Thus, in one embodiment, the nucleic acid molecules of the invention may be used to create recombinant cell lines for use in assays to identify agents which modulate aspects of aberrant MAPK signaling associated with lymphatic anomalies and aberrant vessel formation. Also provided herein are methods to screen for compounds capable of modulating the function of proteins encoded by SNV-containing nucleic acids.

Another approach entails the use of phage display libraries engineered to express fragment of the polypeptides encoded by the SNV containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

In another embodiment, the availability of lymphatic anomaly-associated altered nucleic acids enables the production of strains of laboratory mice carrying the altered nucleic acids of the invention. These lymphatic anomaly-associated altered nucleic acids may be c.1504T>G: pS502A, c.1510A>G:pM504V, and/or c.1507G>C:pG503R in the PTPN11 gene, a c.35G>A:pG12D in KRAS, a c.1403T>C:pF468S in the BRAF gene, ac.2536G>A: pE846K in the SOS1 gene, and a compound mutation comprising c.1236+4A>G and c.289T>G:p.C97G in the ITGA9 gene or any of the other mutations shown in Table 3. Transgenic mice expressing the lymphatic anomaly-associated mutations of the invention provide a model system in which to examine the role of the protein encoded by the mutated nucleic acid in the development and progression towards lymphatic anomalies. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various processes associated with the lymphatic anomaly phenotypes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of altered lymphatic anomaly-associated nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

One type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated, mutation-containing lymphatic anomaly-associated genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Non-homologous plasmid-chromosome interactions are more frequent occurring at levels $10^5$-fold to $10^2$-fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists.

The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing mutated lymphatic anomaly-associated nucleic acid as a targeted insertional cassette provides means to detect a successful insertion as visualized, for example, by acquisition of immunoreactivity to an antibody immunologically specific for the polypeptide encoded by EPHB4 nucleic acid and, therefore, facilitates screening/selection of ES cells with the desired genotype.

As used herein, a knock-in animal is one in which the endogenous murine gene, for example, has been replaced with human lymphatic anomaly-associated gene of the invention. Such knock-in animals provide an ideal model system for studying the development of lymphatic anomalies.

As used herein, the expression of a mutated lymphatic anomaly-associated nucleic acid, fragment thereof, or a lymphatic anomaly-associated fusion protein can be targeted in a "tissue specific manner" or "cell type specific manner" using a vector in which nucleic acid sequences encoding all or a portion of lymphatic anomaly-associated nucleic acid are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein. Alternatively, the transgene may be under the control of an inducible promoter which may function in a tissue specific or "whole body" manner.

The nucleic acid sequence encoding the lymphatic anomaly-associated mutant of the invention may be operably linked to a variety of different promoter sequences for expression in transgenic animals. Such promoters include, but are not limited to a prion gene promoter such as a hamster or mouse Thy-1 promoter; a PGK promoter; or a CMV promoter for the expression of transgenes in desired cell types.

Methods of use for the transgenic mice of the invention are also provided herein. Transgenic mice into which a nucleic acid containing the mutated lymphatic anomaly-associated nucleic acid or its encoded protein have been introduced are useful, for example, to develop screening methods to screen therapeutic agents to identify those capable of modulating the development of lymphatic anomalies.

Detection Products and Kits

Compositions or products that are useful in detecting lymphatic anomaly SNVs are encompassed. For example, lymphatic anomaly-associated SNV-containing nucleic acids, vectors expressing the same, lymphatic anomaly-associated SNV-containing marker proteins and anti-lymphatic anomaly-specific marker antibodies are products capable of detecting SNVs c.1504T>G:pS502A, c.1510A>G:pM504V, and/or c.1507G>C:pG503R in the PTPN11 gene, a c.35G>A:pG12D in KRAS, a c.1403T>C: pF468S in the BRAF gene, ac.2536G>A:pE846K in the SOS1 gene, and a compound mutation comprising c.1236+ 4A>G and c.289T>G:p.C97G in the ITGA9 gene. Nucleic acid probes having sufficient length and characteristics to detect SNVs c.1504T>G:pS502A, c.1510A>G:pM504V, and/or c.1507G>C:pG503R in the PTPN11 gene, a c.35G>A:pG12D in KRAS, a c.1403T>C:pF468S in the BRAF gene, ac.2536G>A:pE846K in the SOS1 gene, and a compound mutation comprising c.1236+4A>G and c.289T>G:p.C97G in the ITGA9 gene are also encompassed. Detection products may be labeled such that they can be detected.

Any products useful in detecting the lymphatic-anomaly-associated SNVs can be incorporated into a kit. Any products useful in treating lymphatic anomalies can be incorporated into a kit. Kits containing such detection and therapeutic products are encompassed. The kit may contain one or more of a lymphatic anomaly-associated SNV specific marker polynucleotide or one or a collection of such markers immobilized on a solid support, gene chip, an oligonucleotide, a polypeptide, a peptide, an antibody, a label, a marker, a reporter, a pharmaceutically acceptable carrier, a physiologically acceptable carrier, instructions for use, a container, a vessel for administration, an assay substrate, or any combination thereof.

The following examples are provided to illustrate certain embodiments of the invention. They are not intended to limit the invention in any way.

Example I

As described for other lymphatic malformations, CCLA is the result of congenital errors of lymphatic development. To identify the genetic basis of CCLA, we performed whole exome sequencing on DNA samples from seven patients, all of which have dysmorphic lymphatics imaged by dynamic contrast magnetic resonance lymphangiogram (DCMRL), a new advanced imaging technique, allowing better diagnosis of this group of patients. We examined five patients for missense, nonsense, splice-altering, and coding indel mutations that could possibly explain the phenotypes. Results were filtered to exclude synonymous variants, variants with minor allele frequency (MAF) greater than 0.5%, and variants previously identified in controls by our in-house exome variant database. Relevant candidates were taken forward for manual curation. As a result, we identified one somatic and five de novo missense mutations in four different genes (PTPN11, KRAS, BRAF, and SOS1) which are all involved in the Ras/MAPK signaling pathway (Table 3). In additional, two heterozygous variants, c.1236+4A>G and c.289T>G:p.C97G, in ITGA9 were discovered in one patient with primary lymphedema and retrograde lymph flow. ITGA9 encodes intergrin alpha-9, which is a cell surface glycoprotein that mediate cell-cell adhesion and cell-matrix interactions. Integrin alpha-9 binds VEGF-C and inactivation of Itga9 causes chylothorax and disrupts lymphatic valve formation in mice.

The sequences for each of these proteins can be found in the NCBI database and are set forth below.

a) c.1504T>G:pS502A in PTPN11;
S502 present in NCBI Reference Sequence: NP_002825.3
b) c.1510A>G:pM504V in PTPN11;
M504 present NCBI Reference Sequence: NP_002825.3
c) c.1507G>C:pG503R in PTPN1;
G503 present NCBI Reference Sequence: NP_002825.3
d) c.35G>A:pG12D in KRAS;
G12 present in NCBI Reference Sequence: NP_203524.1.
e) c.1403T>C:pF468S in BRAF;
F 468 present in NCBI Reference Sequence: NP_004324.2
f) c.2536G>A:pE846K in the SOS1;
E 846 present in NCBI Reference Sequence: NP_005624.2
g) c.1236+4A*>G and c.289T>G:p.C97G in ITGA9:
pC97 present in NCBI Reference Sequence: NP_002198.2.

*variant is 4-bp away from the exon-intron junction and is present in an intron

TABLE 3

Mutations in genes causative of lymphatic disorders

| Gene | Mutation | Phenotype | Inheritance | Mechanism |
| --- | --- | --- | --- | --- |
| PTPN11 | NM_002834.3 c.1504T > G:pS502A | Noonan syndrome, central conducting lymphatic anomaly | Germline and de novo | Interfering with ability to transition from active to inactive conformation |
| PTPN11 | NM_002834.3 C1510A > G:pM504V | Noonan syndrome, lymphatic anomaly | Germline and de novo | Interfering with ability to transition from active to inactive conformation |
| PTPN11 | NM_002834.3 c.1507G > C:pG503R | Noonan syndrome, lymphatic anomaly | Germline and de novo | Interfering with ability to transition from active to inactive conformation |
| KRAS | NM_004985.4 c.35G > A:pG12D | lymphatic anomaly | Somatic mosaic | Reduced intrinsic GTPase activity of Ras |
| BRAF | NM_004333.4 c.1403T > C:pF468S | Cardiofaciocutaneous syndrome with chylothorax | Germline and de novo | Increased kinase activity |
| BRAF | NM_004333.4 c.2128-1G > T | Congenital chylothorax | Somatic mosaic | |
| SOS1 | NM_005633.3 c.2536G > A:pE846K | Noonan syndrome with lymphatic anomaly and protein losing enteropathy | Germline and de novo | Disrupt the autoinhibition of SOS1 Ras GEF activity |

TABLE 3-continued

Mutations in genes causative of lymphatic disorders

| Gene | Mutation | Phenotype | Inheritance | Mechanism |
|---|---|---|---|---|
| ITGA9 | NM_002207.2 c.1236 + 4A > G and NM_002207.2 c.289T > G:p.C97G | Primary lymphedema and retrograde lymph flow | Autosomal recessive | Loss of function increased permeability of cell-cell junction |
| RASA1 | NM_002890.2 c.475_476del:p.(L159Gfs * 20) | Lymphatic disorder with chylous pericardial effusion and non-immune hydrops | Germline and de novo | Gain of function and upregulation of MEK/ERK |
| RASA1 | NM_002890.2 c.2246G > C p.R749P | congenital lymphatic disorder | Germline inherited | Gain of function and upreg MEK/ERK |
| RAF1 | NM_002880.3 c.433A > C:p.T145P | Noonan; Chylothorax, Lymphatic disorder, Valvular pulmonary stenosis | Presumably germline de novo | Gain of function and upreg MEK/ERK |
| RIT1 | NM_194456.1 c.270G > T:p.M90I | Noonan syndrome, pulmonary lymphangiectasis and plastic bronchitis | Presumably germline de novo | Gain of function and upreg MEK/ERK |
| PIEZ01 | NM_001142864.2 c.7289C > T:p.P2430L | Lymphedema and lymphatic conduction disorder | Recessive | Loss of function |
| EPHB4 | NM_004444.4 c.2288G > A:p.R763Q | Central Conducting Lymphatic Anomaly | Germline inherited | Loss of function |
| EPHB4 | NM_004444.4 c.2654A > G:p.K885R | prenatal onset nonimmune hydrops, ascites, and subcutaneous edema | Germline inherited | Loss of function |
| NF1 | NM_000267.3 c.1034_1043del:p.(L345Pfs * 28 | Pleural effusion, retrograde flow | Germline de novo | Gain of function and upreg MEK/ERK |
| CBL | NM_005188.3 c.1096-1G > T | Central Conducting Lymphatic Anomaly | Germline de novo | Gain of function and upreg ME |
| CBL | NM_005188.3 c.2322T > G:p.Y774* | Kaposiform lymphangiomatosis | Somatic mosaic | Gain of function and upreg MEK/ERK K/ERK |

NM_002834.3:381-2162 Homo sapiens protein tyrosine phosphatase, non-receptor
type 11 (PTPN11), transcript variant 1, mRNA
(SEQ ID NO: 1)

ATGACATCGCGGAGATGGTTTCACCCAAATATCACTGGTGTGGAGGCAGAAAACCTACTGTTGACAAGAG

GAGTTGATGGCAGTTTTTTGGCAAGGCCTAGTAAAAGTAACCCTGGAGACTTCACACTTTCCGTTAGAAG

AAATGGAGCTGTCACCCACATCAAGATTCAGAACACTGGTGATTACTATGACCTGTATGGAGGGGAGAAA

TTTGCCACTTTGGCTGAGTTGGTCCAGTATTACATGGAACATCACGGGCAATTAAAAGAGAAGAATGGAG

ATGTCATTGAGCTTAAATATCCTCTGAACTGTGCAGATCCTACCTCTGAAAGGTGGTTTCATGGACATCT

CTCTGGGAAAGAAGCAGAGAAATTATTAACTGAAAAAGGAAAACATGGTAGTTTTCTTGTACGAGAGAGC

CAGAGCCACCCTGGAGATTTTGTTCTTTCTGTGCGCACTGGTGATGACAAAGGGGAGAGCAATGACGGCA

AGTCTAAAGTGACCCATGTTATGATTCGCTGTCAGGAACTGAAATACGACGTTGGTGGAGGAGAACGGTT

TGATTCTTTGACAGATCTTGTGGAACATTATAAGAAGAATCCTATGGTGGAAACATTGGGTACAGTACTA

CAACTCAAGCAGCCCCTTAACACGACTCGTATAAATGCTGCTGAAATAGAAAGCAGAGTTCGAGAACTAA

GCAAATTAGCTGAGACCACAGATAAAGTCAAACAAGGCTTTTGGGAAGAATTTGAGACACTACAACAACA

GGAGTGCAAACTTCTCTACAGCCGAAAAGAGGGTCAAAGGCAAGAAAACAAAACAAAAATAGATATAAA

AACATCCTGCCCTTTGATCATACCAGGGTTGTCCTACACGATGGTGATCCCAATGAGCCTGTTTCAGATT

ACATCAATGCAAATATCATCATGCCTGAATTTGAAACCAAGTGCAACAATTCAAAGCCCAAAAAGAGTTA

CATTGCCACACAAGGCTGCCTGCAAAACACGGTGAATGACTTTTGGCGGATGGTGTTCCAAGAAAACTCC

```
CGAGTGATTGTCATGACAACGAAAGAAGTGGAGAGAGGAAAGAGTAAATGTGTCAAATACTGGCCTGATG

AGTATGCTCTAAAAGAATATGGCGTCATGCGTGTTAGGAACGTCAAAGAAAGCGCCGCTCATGACTATAC

GCTAAGAGAACTTAAACTTTCAAAGGTTGGACAAGGGAATACGGAGAGAACGGTCTGGCAATACCACTTT

CGGACCTGGCCGGACCACGGCGTGCCCAGCGACCCTGGGGGCGTGCTGGACTTCCTGGAGGAGGTGCACC

ATAAGCAGGAGAGCATCATGGATGCAGGGCCGGTCGTGGTGCACTGCAGTGCTGGAATTGGCCGGACAGG

GACGTTCATTGTGATTGATATTCTTATTGACATCATCAGAGAGAAAGGTGTTGACTGCGATATTGACGTT

CCCAAAACCATCCAGATGGTGCGGTCTCAGAGGTCAGGGATGGTCCAGACAGAAGCACAGTACCGATTTA

TCTATATGGCGGTCCAGCATTATATTGAAACACTACAGCGCAGGATTGAAGAAGAGCAGAAAAGCAAGAG

GAAAGGGCACGAATATACAAATATTAAGTATTCTCTAGCGGACCAGACGAGTGGAGATCAGAGCCCTCTC

CCGCCTTGTACTCCAACGCCACCCTGTGCAGAAATGAGAGAAGACAGTGCTAGAGTCTATGAAAACGTGG

GCCTGATGCAACAGCAGAAAAGTTTCAGATGA

>NM_004985.4:193-759 Homo sapiens KRAS proto-oncogene, GTPase (KRAS),
transcript variant b, mRNA
                                                              (SEQ ID NO: 2)
ATGACTGAATATAAACTTGTGGTAGTTGGAGCTGGTGGCGTAGGCAAGAGTGCCTTGACGATACAGCTAA

TTCAGAATCATTTTGTGGACGAATATGATCCAACAATAGAGGATTCCTACAGGAAGCAAGTAGTAATTGA

TGGAGAAACCTGTCTCTTGGATATTCTCGACACAGCAGGTCAAGAGGAGTACAGTGCAATGAGGGACCAG

TACATGAGGACTGGGGAGGGCTTTCTTTGTGTATTTGCCATAAATAATACTAAATCATTTGAAGATATTC

ACCATTATAGAGAACAAATTAAAAGAGTTAAGGACTCTGAAGATGTACCTATGGTCCTAGTAGGAAATAA

ATGTGATTTGCCTTCTAGAACAGTAGACACAAAACAGGCTCAGGACTTAGCAAGAAGTTATGGAATTCCT

TTTATTGAAACATCAGCAAAGACAAGACAGGGTGTTGATGATGCCTTCTATACATTAGTTCGAGAAATTC

GAAAACATAAAGAAAAGATGAGCAAAGATGGTAAAAAGAAGAAAAAGAAGTCAAAGACAAAGTGTGTAAT

TATGTAA

>NM_004333.4:62-2362 Homo sapiens B-Raf proto-oncogene, serine/threonine
kinase (BRAF), mRNA
                                                              (SEQ ID NO: 3)
ATGGCGGCGCTGAGCGGTGGCGGTGGTGGCGGCGCGGAGCCGGGCCAGGCTCTGTTCAACGGGGACATGG

AGCCCGAGGCCGGCGCCGGCGCCGGCGCCGCGGCCTCTTCGGCTGCGGACCCTGCCATTCCGGAGGAGGT

GTGGAATATCAAACAAATGATTAAGTTGACACAGGAACATATAGAGGCCCTATTGGACAAATTTGGTGGG

GAGCATAATCCACCATCAATATATCTGGAGGCCTATGAAGAATACACCAGCAAGCTAGATGCACTCCAAC

AAAGAGAACAACAGTTATTGGAATCTCTGGGGAACGGAACTGATTTTTCTGTTTCTAGCTCTGCATCAAT

GGATACCGTTACATCTTCTTCCTCTTCTAGCCTTTCAGTGCTACCTTCATCTCTTTCAGTTTTTCAAAAT

CCCACAGATGTGGCACGGAGCAACCCCAAGTCACCACAAAAACCTATCGTTAGAGTCTTCCTGCCCAACA

AACAGAGGACAGTGGTACCTGCAAGGTGTGGAGTTACAGTCCGAGACAGTCTAAAGAAAGCACTGATGAT

GAGAGGTCTAATCCCAGAGTGCTGTGCTGTTTACAGAATTCAGGATGGAGAGAAGAAACCAATTGGTTGG

GACACTGATATTTCCTGGCTTACTGGAGAAGAATTGCATGTGGAAGTGTTGGAGAATGTTCCACTTACAA

CACACAACTTTGTACGAAAACGTTTTTCACCTTAGCATTTTGTGACTTTTGTCGAAAGCTGCTTTTCCA

GGGTTTCCGCTGTCAAACATGTGGTTATAAATTTCACCAGCGTTGTAGTACAGAAGTTCCACTGATGTGT

GTTAATTATGACCAACTTGATTTGCTGTTTGTCTCCAAGTTCTTTGAACACCACCCAATACCACAGGAAG

AGGCGTCCTTAGCAGAGACTGCCCTAACATCTGGATCATCCCCTTCCGCACCCGCCTCGGACTCTATTGG

GCCCCAAATTCTCACCAGTCCGTCTCCTTCAAAATCCATTCCAATTCCACAGCCCTTCCGACCAGCAGAT

GAAGATCATCGAAATCAATTTGGGCAACGAGACCGATCCTCATCAGCTCCCAATGTGCATATAAACACAA

TAGAACCTGTCAATATTGATGACTTGATTAGAGACCAAGGATTTCGTGGTGATGGAGGATCAACCACAGG

TTTGTCTGCTACCCCCCCTGCCTCATTACCTGGCTCACTAACTAACGTGAAAGCCTTACAGAAATCTCCA
```

-continued

```
GGACCTCAGCGAGAAAGGAAGTCATCTTCATCCTCAGAAGACAGGAATCGAATGAAAACACTTGGTAGAC

GGGACTCGAGTGATGATTGGGAGATTCCTGATGGGCAGATTACAGTGGGACAAAGAATTGGATCTGGATC

ATTTGGAACAGTCTACAAGGGAAAGTGGCATGGTGATGTGGCAGTGAAAATGTTGAATGTGACAGCACCT

ACACCTCAGCAGTTACAAGCCTTCAAAAATGAAGTAGGAGTACTCAGGAAAACACGACATGTGAATATCC

TACTCTTCATGGGCTATTCCACAAAGCCACAACTGGCTATTGTTACCCAGTGGTGTGAGGGCTCCAGCTT

GTATCACCATCTCCATATCATTGAGACCAAATTTGAGATGATCAAACTTATAGATATTGCACGACAGACT

GCACAGGGCATGGATTACTTACACGCCAAGTCAATCATCCACAGAGACCTCAAGAGTAATAATATATTTC

TTCATGAAGACCTCACAGTAAAAATAGGTGATTTTGGTCTAGCTACAGTGAAATCTCGATGGAGTGGGTC

CCATCAGTTTGAACAGTTGTCTGGATCCATTTTGTGGATGGCACCAGAAGTCATCAGAATGCAAGATAAA

AATCCATACAGCTTTCAGTCAGATGTATATGCATTTGGAATTGTTCTGTATGAATTGATGACTGGACAGT

TACCTTATTCAAACATCAACAACAGGGACCAGATAATTTTTATGGTGGGACGAGGATACCTGTCTCCAGA

TCTCAGTAAGGTACGGAGTAACTGTCCAAAAGCCATGAAGAGATTAATGGCAGAGTGCCTCAAAAAGAAA

AGAGATGAGAGACCACTCTTTCCCCAAATTCTCGCCTCTATTGAGCTGCTGGCCCGCTCATTGCCAAAAA

TTCACCGCAGTGCATCAGAACCCTCCTTGAATCGGGCTGGTTTCCAAACAGAGGATTTTAGTCTATATGC

TTGTGCTTCTCCAAAAACACCCATCCAGGCAGGGGGATATGGTGCGTTTCCTGTCCACTGA
```

>NM_005633.3:42-4043 *Homo sapiens* SOS Ras/Rac guanine nucleotide exchange factor 1 (SOS1), mRNA (SEQ ID NO: 4)

```
ATGCAGGCGCAGCAGCTGCCCTACGAGTTTTTCAGCGAAGAGAACGCGCCCAAGTGGCGGGGACTACTGG

TGCCTGCGCTGAAAAAGGTCCAGGGGCAAGTTCATCCTACTCTCGAGTCTAATGATGATGCTCTTCAGTA

TGTTGAAGAATTAATTTTGCAATTATTAAATATGCTATGCCAAGCTCAGCCCCGAAGTGCTTCAGATGTA

GAGGAACGTGTTCAAAAAGTTTCCCTCATCCAATTGATAAATGGGCAATAGCTGATGCCCAATCAGCTA

TTGAAAAGAGGAAGCGAAGAAACCCTTTATCTCTCCCAGTAGAAAAAATTCATCCTTTATTAAAGGAGGT

CCTAGGTTATAAAATTGACCACCAGGTTTCTGTTTACATAGTAGCAGTCTTAGAATACATTTCTGCAGAC

ATTTTAAAGCTGGTTGGGAATTATGTAAGAAATATACGGCATTATGAAATTACAAAACAAGATATTAAG

TGGCAATGTGTGCTGACAAGGTATTGATGGATATGTTTCATCAAGATGTAGAAGATATTAATATATTATC

TTTAACTGACGAAGAGCCTTCCACCTCAGGAGAACAAACTTACTATGATTTGGTAAAAGCATTTATGGCA

GAAATTCGACAATATATAAGGGAACTAAATCTAATTATAAAAGTTTTTAGAGAGCCCTTTGTCTCCAATT

CAAAATTGTTTTCAGCTAATGATGTAGAAAATATATTTAGTCGCATAGTAGATATACATGAACTTAGTGT

AAAGTTACTGGGCCATATAGAAGATACAGTAGAAATGACAGATGAAGGCAGTCCCCATCCACTAGTAGGA

AGCTGCTTTGAAGACTTAGCAGAGGAACTGGCATTTGATCCATATGAATCGTATGCTCGAGATATTTTGC

GACCTGGTTTTCATGATCGTTTCCTTAGTCAGTTATCAAAGCCTGGGGCAGCACTTTATTTGCAGTCAAT

AGGCGAAGGTTTCAAAGAAGCTGTTCAATATGTTTTACCCAGGCTGCTTCTGGCCCCTGTTTACCACTGT

CTCCATTACTTTGAACTTTTGAAGCAGTTAGAAGAAAAAGTGAAGATCAAGAAGACAAGGAATGTTTAA

AACAAGCAATAACAGCTTTGCTTAATGTTCAGAGTGGTATGGAAAAAATATGTTCTAAAAGTCTTGCAAA

ACGAAGACTGAGTGAATCTGCATGTCGGTTTTATAGTCAGCAAATGAAGGGGAAACAACTAGCAATCAAG

AAGATGAACGAGATTCAGAAGAATATTGATGGTTGGGAGGGAAAAGACATTGGACAGTGTTGTAATGAAT

TTATAATGGAAGGAACTCTTACACGTGTAGGAGCCAAACATGAGAGACACATATTTCTCTTTGATGGCTT

AATGATTTGCTGTAAATCAAATCATGGGCAGCCAAGACTTCCTGGTGCTAGCAATGCAGAATATCGTCTT

AAAGAAAAGTTTTTTATGCGAAAGGTACAAATTAATGATAAAGATGACACCAATGAATACAAGCATGCTT

TTGAAATAATTTTAAAAGATGAAAATAGTGTTATATTTTCTGCCAAGTCAGCTGAAGAGAAAAACAATTG

GATGGCAGCATTGATATCTTTACAGTACCGGAGTACACTGGAAAGGATGCTTGATGTAACAATGCTACAG
```

-continued

```
GAAGAGAAAGAGGAGCAGATGAGGCTGCCTAGTGCTGATGTTTATAGATTTGCAGAGCCTGACTCTGAAG

AGAATATTATATTTGAAGAGAACATGCAGCCCAAGGCTGGAATTCCAATTATCAAAGCAGGAACTGTTAT

TAAACTTATAGAGAGGCTTACGTACCATATGTACGCAGATCCCAATTTTGTTCGGACATTTCTTACAACA

TACAGATCCTTTTGCAAACCTCAAGAACTACTGAGTCTTATAATAGAAAGGTTTGAAATTCCAGAGCCTG

AGCCAACAGAAGCTGATCGCATAGCTATAGAGAATGGAGATCAACCCTTGAGTGCAGAACTGAAAAGATT

TAGAAAAGAATATATACAGCCTGTGCAACTGCGAGTATTAAATGTATGTCGGCACTGGGTAGAGCACCAC

TTCTATGATTTTGAAAGAGATGCATATCTTTTGCAACGAATGGAAGAATTTATTGGAACAGTAAGAGGTA

AAGCAATGAAAAAATGGGTTGAATCCATCACTAAAATAATCCAAAGGAAAAAAATTGCAAGAGACAATGG

ACCAGGTCATAATATTACATTTCAGAGTTCACCTCCCACAGTTGAGTGGCATATAAGCAGACCTGGGCAC

ATAGAGACTTTTGACCTGCTCACCTTACACCCAATAGAAATTGCTCGACAACTCACTTTACTTGAATCAG

ATCTATACCGAGCTGTACAGCCATCAGAATTAGTTGGAAGTGTGTGGACAAAAGAAGACAAAGAAATTAA

CTCTCCTAATCTTCTGAAAATGATTCGACATACCACCAACCTCACTCTGTGGTTTGAGAAATGTATTGTA

GAAACTGAAAATTTAGAAGAAAGAGTAGCTGTGGTGAGTCGAATTATTGAGATTCTACAAGTCTTTCAAG

AGTTGAACAACTTTAATGGTGTCCTTGAGGTTGTCAGTGCTATGAATTCATCACCTGTTTACAGACTAGA

CCACACATTTGAGCAAATACCAAGTCGCCAGAAGAAAATTTTAGAAGAAGCTCATGAATTGAGTGAAGAT

CACTATAAGAAATATTTGGCAAAACTCAGGTCTATTAATCCACCATGTGTGCCTTTCTTTGGAATTTATC

TCACTAATATCTTGAAAACAGAAGAAGGCAACCCTGAGGTCCTAAAAAGACATGGAAAAGAGCTTATAAA

CTTTAGCAAAAGGAGGAAAGTAGCAGAAATAACAGGAGAGATCCAGCAGTACCAAAATCAGCCTTACTGT

TTACGAGTAGAATCAGATATCAAAAGGTTCTTTGAAAACTTGAATCCGATGGGAAATAGCATGGAGAAGG

AATTTACAGATTATCTTTTCAACAAATCCCTAGAAATAGAACCACGAAACCCTAAGCCTCTCCCAAGATT

TCCAAAAAAATATAGCTATCCCCTAAAATCTCCTGGTGTTCGTCCATCAAACCCAAGACCAGGTACCATG

AGGCATCCCACACCTCTGCAGCAGGAGCCAAGGAAAATTAGTTATAGTAGGATCCCTGAAAGTGAAACAG

AAAGTACAGCATCTGCACCAAATTCTCCAAGAACACCGTTAACACCTCCGCCTGCTTCTGGTGCTTCCAG

TACCACAGATGTTTGCAGTGTATTTGATTCCGATCATTCGAGCCCTTTTCACTCAAGCAATGATACCGTC

TTTATCCAAGTTACTCTGCCCCATGGCCCAAGATCTGCTTCTGTATCATCTATAAGTTTAACCAAAGGCA

CTGATGAAGTGCCTGTCCCTCCTCCTGTTCCTCCACGAAGACGACCAGAATCTGCCCCAGCAGAATCTTC

ACCATCTAAGATTATGTCTAAGCATTTGGACAGTCCCCCAGCCATTCCTCCTAGGCAACCCACATCAAAA

GCCTATTCACCACGATATTCAATATCAGACCGGACCTCTATCTCAGACCCTCCTGAAAGCCCTCCCTTAT

TACCACCACGAGAACCTGTGAGGACACCTGATGTTTTCTCAAGCTCACCACTACATCTCCAACCTCCCCC

TTTGGGCAAAAAAGTGACCATGGCAATGCCTTCTTCCCAAACAGCCCTTCCCCCTTTACACCACCTCCT

CCTCAAACACCTTCTCCTCACGGCACAAGAAGGCATCTGCCATCACCACCATTGACACAAGAAGTGGACC

TTCATTCCATTGCTGGGCCGCCTGTTCCTCCACGACAAAGCACTTCTCAACATATCCCTAAACTCCCTCC

AAAAACTTACAAAAGGGAGCACACACACCCATCCATGCACAGAGATGGACCACCACTGTTGGAGAATGCC

CATTCTTCCTGA

>NM_002207.2:54-3161 Homo sapiens integrin subunit alpha 9 (ITGA9), mRNA
                                                               (SEQ ID NO: 5)
ATGGGCGGCCCGGCTGCGCCGAGGGGCGCCGGGAGGCTCCGCGCGCTGCTGCTGGCGCTGGTGGTCGCGG

GGATCCCCGCGGGCGCCTACAACCTCGACCCGCAGCGCCCCGTGCACTTCCAGGGCCCCGCTGACTCGTT

CTTCGGCTACGCAGTTCTGGAGCATTTCCACGACAACACGCGCTGGGTCCTTGTGGGCGCACCAAAGGCA

GATTCCAAATACAGCCCTTCAGTGAAGTCTCCTGGGGCTGTGTTTAAGTGCCGTGTTCACACCAACCCTG

ACCGGAGATGCACCGAACTGGACATGGCTCGAGGGAAGAATCGGGGCACGTCCTGCGGAAAGACCTGCCG
```

-continued

```
GGAAGACCGCGATGATGAGTGGATGGGGGTGAGCCTGGCCCGACAGCCCAAGGCTGATGGCCGTGTGTTG

GCCTGTGCTCATCGCTGGAAGAACATCTACTATGAAGCCGACCACATCCTACCCCATGGCTTCTGCTACA

TCATCCCCTCCAACCTCCAGGCCAAAGGCAGGACGCTGATCCCTTGCTATGAAGAGTATAAGAAGAAGTA

CGGAGAGGAACACGGCTCCTGCCAGGCTGGGATAGCGGGCTTCTTCACCGAGGAGCTGGTGGTGATGGGT

GCTCCAGGGTCATTTTATTGGGCTGGAACCATCAAAGTGCTGAACCTTACGGACAACACCTATTTAAAAC

TGAACGACGAAGTGATCATGAACAGGCGGTACACCTACCTGGGCTACGCAGTGACCGCTGGCCACTTCTC

TCACCCGTCCACCATTGATGTGGTAGGAGGTGCCCCACAGGACAAAGGCATCGGCAAGGTTTATATTTTC

AGAGCTGACCGAAGATCAGGCACCTTAATTAAGATCTTTCAAGCATCAGGTAAAAAGATGGGCTCTTACT

TCGGCTCCTCCTTGTGCGCAGTTGACCTGAATGGGGACGGCCTCTCTGACCTGCTGGTGGGGCCCCCAT

GTTTTCTGAGATCAGGGATGAGGGACAGGTCACTGTCTACATCAACAGAGGAAATGGAGCCCTCGAGGAG

CAGCTGGCTCTGACTGGGGATGGTGCCTACAATGCGCACTTTGGAGAGAGCATTGCCAGCCTGGACGATC

TGGACAATGATGGGTTCCCAGATGTGGCCATTGGTGCACCCAAGGAGGATGACTTCGCAGGGGCGGTCTA

TATCTATCATGGTGATGCCGGTGGGATAGTCCCTCAGTACTCAATGAAACTGTCTGGGCAGAAGATAAAT

CCAGTGCTCCGGATGTTTGGTCAGTCCATATCGGGAGGCATTGATATGGATGGAAATGGCTATCCTGATG

TCACTGTTGGAGCCTTCATGTCCGACAGCGTGGTTCTTCTCAGAGCAAGGCCTGTCATTACGGTGGATGT

CTCCATCTTCCTCCCGGGCTCCATCAACATCACAGCGCCTCAGTGTCACGACGGACAGCAGCCTGTGAAC

TGCCTGAACGTCACCACCTGCTTCAGCTTCCATGGCAAACACGTTCCAGGAGAGATTGGCCTGAATTATG

TTCTGATGGCTGACGTGGCCAAAAAGGAGAAGGGCCAGATGCCCAGGGTCTACTTTGTGCTGCTGGGAGA

GACCATGGGTCAGGTCACAGAGAAGCTGCAGCTGACTTACATGGAGGAGACGTGTCGTCACTATGTGGCC

CATGTGAAGCGGAGGGTGCAGGACGTCATCAGCCCGATCGTGTTTGAAGCAGCCTACAGCCTCAGTGAGC

ATGTGACTGGAGAGGAGGAGAGGGAACTGCCGCCTCTGACACCAGTTCTCCGCTGGAAAAAGGGACAAAA

GATTGCCCAAAAGAATCAGACTGTTTTTGAAAGGAATTGCCGTTCAGAGGACTGTGCCGCAGACCTGCAG

CTTCAGGGTAAACTGCTGCTCTCCAGTATGGATGAGAAAACCCTGTATCTAGCTTTGGGGGCTGTGAAGA

ACATCTCCCTAAACATCTCTATCTCCAACCTCGGAGATGATGCCTATGATGCCAACGTGTCCTTCAATGT

TTCCCGGGAGCTCTTCTTCATCAACATGTGGCAGAAGGAGGAGATGGGCATCTCCTGTGAGCTGCTGGAA

TCGGACTTCCTCAAATGCAGCGTGGGATTTCCTTTCATGAGGTCAAAGTCAAAGTATGAATTCAGCGTGA

TCTTTGATACAAGCCACCTGTCTGGGGAAGAGGAAGTTCTCAGCTTCATTGTTACTGCTCAGAGTGGCAA

CACGGAGCGCTCTGAATCCCTGCATGACAACACCCTCGTGCTGATGGTGCCACTGATGCACGAGGTGGAC

ACGTCCATCACCGGAATCATGTCTCCAACCTCCTTTGTATATGGCGAGTCCGTGGACGCAGCCAACTTCA

TTCAGCTGGATGACCTGGAGTGTCACTTTCAGCCCATCAATATCACCCTTCAGGTCTACAACACTGGCCC

AAGCACCCTTCCAGGGTCATCTGTCAGCATCTCTTTCCCTAATCGACTCTCATCTGGTGGTGCAGAGATG

TTTCATGTCCAGGAAATGGTGGTGGGCCAAGAGAAGGGAAACTGCTCTTTCCAGAAAAACCCAACTCCCT

GCATCATCCCTCAAGAACAAGAAAATATCTTCCACACAATATTTGCTTTTTTCACAAAGTCTGGAAGAAA

AGTCTTGGACTGTGAAAAACCAGGAATTTCTTGCCTAACAGCACACTGTAACTTTAGTGCTCTTGCTAAA

GAAGAAAGTCGTACTATAGACATTTACATGCTGCTGAACACAGAAATACTGAAAAAGGACAGTTCGTCTG

TCATCCAGTTCATGTCCCGCGCCAAGGTGAAGGTGGATCCTGCCCTAAGGGTGGTGGAAATAGCTCATGG

GAACCCAGAAGAGGTGACGGTGGTCTTCGAGGCCCTGCACAATCTGGAGCCCCGTGGCTACGTCGTGGGG

TGGATCATCGCCATCAGTTTGTTGGTGGGAATCCTCATCTTCCTGCTGCTGGCCGTGCTGCTCTGGAAGA

TGGGCTTCTTTCGCCGAAGGTACAAAGAAATTATCGAAGCTGAGAAGAACCGGAAAGAGAATGAAGACAG

TTGGGACTGGGTCCAGAAAAACCAGTGA
```

NM_002890.2 4402 bp mRNA *Homo sapiens* RAS p21 protein activator 1 (RASA1), transcript (SEQ ID NO: 6)

```
   1 cgtaacccag gcagctgggg agcctgggct gtggccctag gaggggggcgc ggcggcgggc
  61 tctctccttt tgttgttgtt tcctcagcct ggggagctga aggggagacg cgtctgggtg
 121 gggctgctcg gagcccgggc ctggtggccc ctggggctcc cggcgggca gggtagggca
 181 gagtagagcg ggcttcaaca tgatggcggc cgaggccggc agtgaggagg gcggcccggt
 241 aacagccgga gctggaggag gcggcgcggc agcgggctcc agtgcctatc ccgcagtgtg
 301 tcgggtgaag atacccgcgg ccctgcctgt ggcagccgcc ccctatcctg ggctggtgga
 361 gaccggagtg gctggaactc tgggtggcgg agccgctttg gggtcagagt tcctaggagc
 421 cgggtctgtg gcaggggcac tgggggagc tggactgaca gggggaggta ctgctgctgg
 481 cgtagctggt gctgctgctg gcgtggccgg tgctgctgtt gctggaccta gtggagacat
 541 ggctctcacc aaactgccca cttcgttgct tgctgagact ctcgggccag gcggcggttt
 601 tcccctctg cccctcccc cttacctgcc cctttgggg gcgggcctcg ggacagtgga
 661 cgaaggtgac tctctggatg accagaata cgaggaggaa gaggtggcca taccgttgac
 721 cgctcctcca actaaccagt ggtatcacgg aaaacttgac agaacgatag cagaagaacg
 781 cctcaggcag gcagggaagt ctggcagtta tcttataaga gagagtgatc ggaggccagg
 841 gtcctttgta ctttcatttc ttagccagat gaatgttgtc aaccatttta ggattattgc
 901 tatgtgtgga gattactaca ttggtggaag acgtttttct tcactgtcag acctaatagg
 961 ttattacagt catgtttctt gtttgcttaa aggagaaaaa ttactttacc cagttgcacc
1021 accagagcca gtagaagata gaaggcgtgt acgagctatt ctaccttaca caaaagtacc
1081 agacactgat gaaataagtt tcttaaaagg agatatgttc attgttcata tgaattaga
1141 agatggatgg atgtgggtta caaatttaag aacagatgaa caaggcctta ttgttgaaga
1201 cctagtagaa gaggtgggcc gggaagaaga tccacatgaa ggaaaaatat ggttccatgg
1261 gaagatttcc aaacaggaag cttataattt actaatgaca gttggtcaag tctgcagttt
1321 tcttgtgagg ccctcagata atactcctgg cgattattca ctttatttcc ggaccaatga
1381 aaatattcag cgatttaaaa tatgtccaac gccaaacaat cagtttatga tgggaggccg
1441 gtattataac agcattgggg acatcataga tcactatcga aaagaacaga ttgttgaagg
1501 atattatctt aaggaacctg taccaatgca ggatcaagaa caagtactca atgacacagt
1561 ggatggcaag gaaatctata ataccatccg tcgtaaaaca aaggatgcct tttataaaaa
1621 cattgttaag aaaggttatc ttctgaaaaa gggcaaagga aaacgttgga aaaatttata
1681 ttttatctta gagggtagtg atgcccaact tatttatttt gaaagcgaaa acgagctac
1741 caaaccaaaa ggattaatag atctcagtgt atgttctgtc tatgtcgttc atgatagtct
1801 ctttggcagg ccaaactgtt tcagatagt agttcagcac tttagtgaag aacattacat
1861 cttttacttt gcaggagaaa ctccagaaca agcagaggat tggatgaaag tctgcaggc
1921 attttgcaat ttacggaaaa gtagtccagg acatccaat aaacgccttc gtcaggtcag
1981 cagccttgtt ttacatattg aagaagccca taaactccca gtaaacatt ttactaatcc
2041 atattgtaac atctacctga atagtgtcca gtagcaaaa actcatgcaa gggaagggca
2101 aaacccagta tggtcagaag agtttgtctt tgatgatctt cctcctgaca tcaatagatt
2161 tgaaataact cttagtaata aaacaaagaa aagcaaagat cctgatatct tatttatgcg
2221 ctgccagttg agccgattac agaaagggca tgccacagat gaatggtttc tgctcagctc
2281 ccatatacca ttaaaaggta ttgaaccagg gtccctgcgt gttcgagcac gatactctat
```

-continued

```
2341 ggaaaaaatc atgccagaag aagagtacag tgaatttaaa gagcttatac tgcaaaagga
2401 acttcatgta gtctatgctt tatcacatgt atgtggacaa gaccgaacac tactggccag
2461 catcctactg aggattttc ttcacgaaaa gcttgaatcg ttgttgttat gcacactaaa
2521 tgacagagaa ataagcatgg aagatgaagc cactacccta tttcgagcca caacacttgc
2581 aagcaccttg atggagcagt atatgaaagc cactgctaca cagtttgttc atcatgcttt
2641 gaaagactct attttaaaga taatggaaag caagcagtct tgtgagttaa gtccatcaaa
2701 gttagaaaaa aatgaagatg tgaacactaa tttaacacac ctattgaaca tactttcaga
2761 gcttgtggag aaaatattca tggcttcaga aatacttcca ccgacattga gatatattta
2821 tgggtgttta cagaaatctg ttcagcataa gtggcctaca ataccacca tgagaacaag
2881 agttgttagt ggttttgttt ttcttcgact catctgtcct gccatcctga atccacggat
2941 gttcaatatc atctcagatt ctccatctcc tattgctgca agaacactga tattagtggc
3001 taaatctgtg cagaacttag caaatcttgt ggaatttgga gctaaggagc cctacatgga
3061 aggtgtcaat ccattcatca aaagcaacaa acatcgtatg atcatgtttt tagatgaact
3121 tgggaatgta cctgaacttc cggacactac agagcattct agaacggacc tgtcccgtga
3181 tttagcagca ttgcatgaga tttgcgtggc tcattcagat gaacttcgaa cgctcagtaa
3241 tgagcgtggt gcacagcagc acgtattgaa aaagcttctg gctataacag aactgcttca
3301 acaaaaacaa aaccagtata caaaaaccaa tgatgtcagg tagcagcctt cgccccagtg
3361 ttctgcatgg attcagcatg tccaacatgg taattcactt cagtttaatg tctccttttgc
3421 tcttgccaaa aaatagcaca cttttccaca ttccagtgat gtgtgagcta tgcaaacaaa
3481 atccaagatt ctgctggtga ataactatgc cagcaacctt gtaagctatc tgtgcaggat
3541 atttgcacta tttccacatg gaatcaatct ttaacaacct ctgagccttg gtgtacagac
3601 caccttcac aaaacgaaat gctatgactg tatcttgata tctcgaactt tcaaaatata
3661 ttttcagtac acccagttgc caaagttttg ctgtctctta gagaaagaac tatgaaatca
3721 actgacaaga aacacattct tattgacaat tgtgtataac tggattgcag actgttctta
3781 ctgtaactac ttcctgatta ggaatatgac catttgactg ttcaatgatt atttgtattt
3841 acagtttcca gagtttgtca ttataatagg aacaatcttt gctgtatact tttaaaaaat
3901 actctgctat ttctcttgct ggaactgttg aaagaaaata tatagaatga tctattgctc
3961 atcagcttta ttttttaaac atacgactta ttttgttgaa attgtcaaag actgtattta
4021 gatctcataa tgctttgtta aatgtttaca agtaaatagt ttgaattcag taaatattat
4081 tggttgttgt attgatcaat gcatgttacc cattcaacca ttttatagac taccaatttc
4141 ttttatgtta actagaatgc ttttgttaaa agttatttgt tcattatttg tgctacccct
4201 ttgattatgc agacaacctc atcagctgcc taacttatcc atctttgaac ttctgactac
4261 ttgttgtatc tgctggatat ttagttcaac tgtatagttt tatttacttc tgtatgtgta
4321 tttttgtgaa gtattcacaa aggttaagtt aaaataaaac caagggatat cttgcataat
4381 tgattaaaaa aaaaaaaaaa aa
```

NM_002880.2 3291 bp mRNA Homo sapiens Raf-1 proto-oncogene, serine/threonine kinase (RAF1), transcript variant 2, mRNA.

SEQ ID NO: 7)

```
  1 agaatcggag agccggtggc gtcgcaggtc gggaggacga gcaccgagtc gagggctcgc
 61 tcgtctgggc cgcccgagag tcttaatcgc gggcgcttgg gccgccatct tagatggcgg
121 gagtaagagg aaaacgattg tgaggcggga acggctttct gctgcctttt ttgggccccg
181 aaaagggtca gctggccggg ctttggggcg cgtgccctga ggcgcggagc gcgtttgcta
```

-continued

```
 241 cgatgcgggg gctgctcggg gctccgtccc ctgggctggg gacgcgccga atgtgaccgc 301 ctcccgctcc ctcacccgcc gcggggagga ggagcgggcg agaagctgcc gccgaacgac 361 aggacgttgg ggcggcctgg ctccctcagg tttaagaatt gtttaagctg catcaatgga 421 gcacatacag ggagcttgga agacgatcag caatggtttt ggattcaaag atgccgtgtt 481 tgatggctcc agctgcatct ctcctacaat agttcagcag tttggctatc agcgccgggc 541 atcagatgat ggcaaactca cagatccttc taagacaagc aacactatcc gtgttttctt 601 gccgaacaag caaagaacag tggtcaatgt gcgaaatgga atgagcttgc atgactgcct 661 tatgaaagca ctcaaggtga ggggcctgca accagagtgc tgtgcagtgt tcagacttct 721 ccacgaacac aaaggtaaaa agcacgctt agattggaat actgatgctg cgtctttgat 781 tggagaagaa cttcaagtag atttcctgga tcatgttccc ctcacaacac acaactttgc 841 tcggaagacg ttcctgaagc ttgccttctg tgacatctgt cagaaattcc tgctcaatgg 901 atttcgatgt cagacttgtg ctacaaatt tcatgagcac tgtagcacca agtacctac 961 tatgtgtgtg gactggagta acatcagaca actcttattg tttccaaatt ccactattgg 1021 tgatagtgga gtcccagcac taccttcttt gactatgcgt cgtatgcgag agtctgtttc 1081 caggatgcct gttagttctc agcacagata ttctacacct cacgccttca cctttaacac 1141 ctccagtccc tcatctgaag gttccctctc cagaggcag aggtcgacat ccacacctaa 1201 tgtccacatg gtcagcacca ccctgcctgt ggacagcagg atgattgagg atgcaattcg 1261 aagtcacagc gaatcagcct caccttcagc cctgtccagt agcccaaca atctgagccc 1321 aacaggctgg tcacagccga aaccccgt gccagcacaa agagagcggg caccagtatc 1381 tgggacccag gagaaaaaca aaattaggcc tcgtggacag agagattcaa gctattattg 1441 ggaaatagaa gccagtgaag tgatgctgtc cactcggatt gggtcaggct cttttggaac 1501 tgtttataag ggtaaatggc acggagatgt tgcagtaaag atcctaaagg ttgtcgaccc 1561 aaccccagag caattccagg ccttcaggaa tgaggtggct gttctgcgca aaacacggca 1621 tgtgaacatt ctgctttca tggggtacat gacaaaggac aacctggcaa ttgtgaccca 1681 gtggtgcgag ggcagcagcc tctacaaaca cctgcatgtc caggagacca agtttcagat 1741 gttccagcta attgacattg cccggcagac ggctcaggga atggactatt tgcatgcaaa 1801 gaacatcatc catagagaca tgaaatccaa caatatattt ctccatgaag gcttaacagt 1861 gaaaattgga gattttggtt tggcaacagt aaagtcacgc tggagtggtt ctcagcaggt 1921 tgaacaacct actggctctg tcctctggat ggccccagag gtgatccgaa tgcaggataa 1981 caacccattc agtttccagt cggatgtcta ctcctatggc atcgtattgt atgaactgat 2041 gacgggggag cttccttatt ctcacatcaa caaccgagat cagatcatct tcatggtggg 2101 ccgaggatat gcctccccag atcttagtaa gctatataag aactgcccca agcaatgaa 2161 gaggctggta gctgactgtg tgaagaaagt aaaggaagag aggcctcttt ttccccagat 2221 cctgtcttcc attgagctgc tccaacactc tctaccgaag atcaaccgga gcgcttccga 2281 gccatccttg catcgggcag cccacactga ggatatcaat gcttgcacgc tgaccacgtc 2341 cccgaggctg cctgtcttct agttgacttt gcacctgtct tcaggctgcc aggggaggag 2401 gagaagccag caggcaccac ttttctgctc cctttctcca gaggcagaac acatgttttc 2461 agagaagctg ctgctaagga ccttctagac tgctcacagg gccttaactt catgttgcct 2521 tcttttctat ccctttgggc cctgggagaa ggaagccatt tgcagtgctg gtgtgtcctg 2581 ctccctcccc acattcccca tgctcaaggc ccagccttct gtagatgcgc aagtggatgt
```

-continued

```
2641 tgatggtagt acaaaaagca gggcccagc cccagctgtt ggctacatga gtatttagag 2701 gaagtaaggt agcaggcagt ccagccctga tgtggagaca catgggattt tggaaatcag 2761 cttctggagg aatgcatgtc acaggcggga cttctcag agagtggtgc agcgccagac 2821 attttgcaca taaggcacca aacagcccag gactgccgag actctggccg cccgaaggag 2881 cctgctttgg tactatggaa cttttcttag gggacacgtc ctcctttcac agcttctaag 2941 gtgtccagtg cattgggatg gttttccagg caaggcactc ggccaatccg catctcagcc 3001 ctctcaggga gcagtcttcc atcatgctga attttgtctt ccaggagctg cccctatggg 3061 gcggggccgc agggccagcc ttgtttctct aacaaacaaa caaacaaaca gccttgtttc 3121 tctagtcaca tcatgtgtat acaaggaagc caggaataca ggttttcttg atgatttggg 3181 ttttaatttt gtttttattg cacctgacaa aatacagtta tctgatggtc cctcaattat 3241 gttattttaa taaataaat taaatttagg tgtaaaaaaa aaaaaaaaaa a
```

NM_001142864 7833 bp mRNA *Homo sapiens* piezo-type mechanosensitive ion channel component 1 (PIEZO1), mRNA.

(SEQ ID NO: 8)

```
   1 atggagccgc acgtgctcgg cgcggtcctg tactggctgc tgctgcccctg cgcgctgctg 61 gctgcctgcc tgctccgctt cagcggactc tcgctggtct acctgctctt cctgctgctg 121 ctgccctggt tccccggccc caccgatgc ggcctccaag gtcacacagg ccgcctcctg 181 cgggcattgc tgggcctcag cctgctcttc ctggtggccc atctcgccct ccagatctgc 241 ctgcatattg tgccccgcct ggaccagctc ctgggaccca gctgcagccg ctgggagacc 301 ctctcgcgac acatagggt cacaaggctg acctgaagg acatcccaa cgccatccgg 361 ctggtggccc ctgacctggg catcttggtg gtctcctctg tctgcctcgg catctgcggg 421 cgccttgcaa ggaacacccg gcagagccca catccacggg agctggatga tgatgagagg 481 gatgtggatg ccagcccgac ggcagggctg caggaagcag caacgctggc ccctacacgg 541 aggtcacggc tggccgctcg tttccgagtc acggcccact ggctgctggt ggcggctggg 601 cgggtcctgg ccgtaacact gcttgcactg gcaggcatcg cccacccctc ggccctctcc 661 agtgtctacc tgctgctctt cctggccctc tgcacctggt gggcctgcca ctttcccatc 721 agcactcggg gcttcagcag actctgcgtc gcggtggggt gcttcggcgc cggccatctc 781 atctgcctct actgctacca gatgcccttg gcacaggctc tgctcccgcc tgccggcatc 841 tgggctaggg tgctgggtct caaggacttc gtgggtccca ccaactgctc cagcccccac 901 gcgctggtcc tcaacaccgg cctggactgg cctgtgtatg ccagccccgg cgtcctcctg 961 ctgctgtgct acgccacggc ctctctgcgc aagctccgcg cgtaccgccc ctccggccag 1021 aggaaggagg cggcaaaggg gtatgaggct cgggagctgg agctagcaga gctggaccag 1081 tggccccagg aacgggagtc tgaccagcac gtggtgccca gcacccgga caccgaggct 1141 gataactgca tcgtgcacga gctgaccggc cagagctccg tcctgcggcg gcctgtgcgg 1201 cccaagcggc tgagcccag ggaggcgtct ccgctccaca gctgggcca cctcatcatg 1261 gaccagagct atgtgtgcgc gctcattgcc atgatggtat ggagcatcac ctaccacagc 1321 tggctgacct tcgtactgct gctctgggcc tgcctcatct ggacggtgcg cagccgccac 1381 caactggcca tgctgtgctc gccctgcatc ctgctgtatg gatgacgct gtgctgccta 1441 cgctacgtgt gggccatgga cctgcgcccc gagctgccca ccaccctggg ccccgtcagc 1501 ctgcgccagc tggggctgga gcacacccgc taccccctgtc tggaccttgg tgccatgttg 1561 ctctacaccc tgacccttctg gctcctgctg cgccagtttg tgaaagagaa gctgctgaag 1621 tgggcagagt ctccagctgc gctgacggag gtcaccgtgg cagacacaga gcccacgcgg
```

-continued

```
1681 acgcagacgc tgttgcagag cctgggggag ctggtgaagg gcgtgtacgc caagtactgg 1741 atctatgtgt gtgctggcat gttcatcgtg gtcagcttcg ccggccgcct cgtggtctac 1801 aagattgtct acatgttcct cttcctgctc tgcctcaccc tcttccaggt ctactacagc 1861 ctgtggcgga agctgctcaa ggccttctgg tggctcgtgg tggcctacac catgctggtc 1921 ctcatcgccg tctacacctt ccagttccag gacttccctg cctactggcg caacctcact 1981 ggcttcaccg acgagcagct gggggacctg ggcctggagc agttcagcgt gtccgagctc 2041 ttctccagca tcctggtgcc cggcttcttc ctcctggcct gcatcctgca gctgcactac 2101 ttccacaggc ccttcatgca gctcaccgac atggagcacg tgtccctgcc tggcacgcgc 2161 ctcccgcgct gggctcacag gcaggatgca gtgagtggga ccccactgct gcgggaggag 2221 cagcaggagc atcagcagca gcagcaggag gaggaggagg aggaggagga ctccagggac 2281 gaggggctgg gcgtggccac tccccaccag gccacgcagg tgcctgaagg ggcagccaag 2341 tggggcctgg tggctgagcg gctgctggag ctggcagccg gcttctcgga cgtcctctca 2401 cgcgtgcagg tgttcctgcg gcggctgctg gagcttcacg ttttcaagct ggtggccctg 2461 tacaccgtct gggtggccct gaaggaggtg tcggtgatga acctgctgct ggtggtgctg 2521 tgggccttcg ccctgcccta cccacgcttc cggcccatgg cctcctgcct gtccaccgtg 2581 tggacctgcg tcatcatcgt gtgtaagatg ctgtaccagc tcaaggttgt caacccccag 2641 gagtattcca gcaactgcac cgagcccttc cccaacagca ccaacttgct gcccacggag 2701 atcagccagt ccctgctgta ccggggggcc gtggaccctg ccaactggtt tggggtgcgg 2761 aaagggttcc ccaacctggg ctacatccag aaccacctgc aagtgctgct gctgctggta 2821 ttcgaggcca tcgtgtaccg gcgccaggag cactaccgcc ggcagcacca gctggccccg 2881 ctgcctgccc aggccgtgtt tgccagcggc acccgccagc agctggacca ggatctgctc 2941 ggctgcctca agtacttcat caacttcttc ttctacaaat tcgggctgga gatctgcttc 3001 ctgatgccgc tgaacgtgat cgggcagcgc atgaactttc tggtgaccct gcacggttgc 3061 tggctggtgg ccatcctcac ccgcaggcac cgccaggcca ttgcccgcct ctggcccaac 3121 tactgcctct tcctggcgct gttcctgctg taccagtacc tgctgtgcct ggggatgccc 3181 ccggccctgt gcattgatta tccctggcgc tggagccggg ccgtccccat gaactccgca 3241 ctcatcaagt ggctgtacct gcctgatttc ttccgggccc ccaactccac caacctcatc 3301 agcgactttc tcctgctgct gtgcgcctcc cagcagtggc aggtgttctc agctgagcgc 3361 acagaggagt ggcagcgcat ggctggcgtc aacaccgacc gcctggagcc gctgcgggg 3421 gagcccaacc ccgtgcccaa ctttatccac tgcaggtcct accttgacat gctgaaggtg 3481 gccgtcttcc gatacctgtt ctggctggtg ctggtggtgg tgtttgtcac ggggggccacc 3541 cgcatcagca tcttcgggct gggctacctg ctggcctgct ctacctgct gctcttcggc 3601 acggccctgc tgcagaggga cacacggggc cgcctcgtgc tgtgggactg cctcattctg 3661 tacaacgtca ccgtcatcat ctccaagaac atgctgtcgc cctggcctg cgtcttcgtg 3721 gagcagatgc agaccggctt ctgctgggtc atccagctct tcagccttgt atgcaccgtc 3781 aagggctact atgaccccaa ggagatgatg gacagagacc aggactgcct gctgcctgtg 3841 gaggaggctg gcatcatctg ggacagcgtc tgcttcttct tcctgctgct gcagcgccgc 3901 gtcttcctta gccattacta cctgcacgtc agggccgacc tccaggccac cgccctgcta 3961 gcctccaggg gcttcgccct ctacaacgct gccaacctca agagcattga ctttcaccgc 4021 aggatagagg agaagtccct ggcccagctg aaaagacaga tggagcgtat ccgtgccaag 4081 caggagaagc acaggcaggg ccgggtggac cgcagtcgcc cccaggacac cctgggcccc
```

-continued

```
4141 aaggacaccg gcctggagcc agggcccgac agtccagggg gctcctcccc gccacggagg
4201 cagtggtggc ggccctggct ggaccacgcc acagtcatcc actccgggga ctacttcctg
4261 tttgagtccg acagtgagga agaggaggag gctgttcctg aagacccgag gccgtcggca
4321 cagagtgcct tccagctggc gtaccaggca tgggtgacca acgcccaggc ggtgctgagg
4381 cggcggcagc aggagcagga gcaggcaagg caggaacagg caggacagct acccacagga
4441 ggtggtccca gccaggaggt ggagccagca gagggccccg aggaggcagc ggcaggccgg
4501 agccatgtgg tgcagagggt gctgagcacg gcgcagttcc tgtggatgct ggggcaggcg
4561 ctagtggatg agctgacacg ctggctgcag gagttcaccc ggcaccacgg caccatgagc
4621 gacgtgctgc gggcagagcg ctacctcctc acacaggagc tcctgcaggg cggcgaagtg
4681 cacaggggcg tgctggatca gctgtacaca agccaggccg aggccacgct gccaggcccc
4741 accgaggccc ccaatgcccc aagcaccgtg tccagtgggc tgggcgcgga ggagccactc
4801 agcagcatga cagacgacat gggcagcccc ctgagcaccg ctaccacac gcgcagtggc
4861 agtgaggagg cagtcaccga ccccggggag cgtgaggctg gtgcctctct gtaccaggga
4921 ctgatgcgga cggccagcga gctgctcctg gacaggcgcc tgcgcatccc agagctggag
4981 gaggcagagc tgtttgcgga ggggcagggc cgggcgctgc ggctgctgcg ggccgtgtac
5041 cagtgtgtgg ccgcccactc ggagctgctc tgctacttca tcatcatcct caaccacatg
5101 gtcacggcct ccgccggctc gctggtgctg cccgtgctcg tcttcctgtg gccatgctg
5161 tcgatcccga ggcccagcaa gcgcttctgg atgacggcca tcgtcttcac cgagatcgcg
5221 gtggtcgtca agtacctgtt ccagtttggg ttcttcccct ggaacagcca cgtggtgctg
5281 cggcgctacg agaacaagcc ctacttcccg ccccgcatcc tgggcctgga aagactgac
5341 ggctacatca agtacgacct ggtgcagctc atggcccttt tcttccaccg ctcccagctg
5401 ctgtgctatg gcctctggga ccatgaggag gactcaccat ccaaggagca tgacaagagc
5461 ggcgaggagg agcagggagc cgaggagggg ccaggggtgc ctgcggccac caccgaagac
5521 cacattcagg tggaagccag ggtcggaccc acggacggga ccccagaacc ccaagtggag
5581 ctcaggcccc gtgatacgag gcgcatcagt ctacgtttta aagaaggaa gaaggagggc
5641 ccagcacgga aaggagcggc agccatcgaa gctgaggaca gggaggaaga agaggggag
5701 gaagagaaag aggcccccac ggggagagag aagaggccaa gccgctctgg aggaagagta
5761 agggcggccg ggcggcggct gcagggcttc tgcctgtccc tggcccaggg cacatatcgg
5821 ccgctacggc gcttcttcca cgacatcctg cacaccaagt accgcgcagc caccgacgtc
5881 tatgccctca tgttcctggc tgatgttgtc gacttcatca tcatcatttt tggcttctgg
5941 gcctttggga agcactcggc ggccacagac atcacgtcct ccctatcaga cgaccaggta
6001 cccgaggctt tcctggtcat gctgctgatc cagttcagta ccatggtggt tgaccgcgcc
6061 ctctacctgc gcaagaccgt gctgggcaag ctggccttcc aggtggcgct ggtgctggcc
6121 atccacctat ggatgttctt catcctgccc gccgtcactg agaggatgtt caaccagaat
6181 gtggtggccc agctctggta cttcgtgaag tgcatctact cgccctgtc cgcctaccag
6241 atccgctgcg gctaccccac ccgcatcctc ggcaacttcc tcaccaagaa gtacaatcat
6301 ctcaacctct tcctcttcca ggggttccgg ctggtgccgt tcctggtgga gctgcgggca
6361 gtgatggact gggtgtggac ggacaccacg ctgtccctgt ccagctggat gtgtgtggag
6421 gacatctatg ccaacatctt catcatcaaa tgcagccgag agacagagaa gaaatacccg
6481 cagcccaaag ggcagaagaa gaagaagatc gtcaagtacg gcatgggtgg cctcatcatc
```

-continued

```
6541 ctcttcctca tcgccatcat ctggttccca ctgctcttca tgtcgctggt gcgctccgtg 6601 gttggggttg tcaaccagcc catcgatgtc accgtcaccc tgaagctggg cggctatgag 6661 ccgctgttca ccatgagcgc ccagcagccg tccatcatcc ccttcacggc ccaggcctat 6721 gaggagctgt cccggcagtt tgaccccag ccgctggcca tgcagttcat cagccagtac 6781 agccctgagg acatcgtcac ggcgcagatt gagggcagct ccggggcgct gtggcgcatc 6841 agtccccca gccgtgccca gatgaagcgg gagctctaca acggcacggc cgacatcacc 6901 ctgcgcttca cctggaactt ccagagggac ctggcgaagg gaggcactgt ggagtatgcc 6961 aacgagaagc acatgctggc cctgccccc aacagcactg cacggcggca gctggccagc 7021 ctgctcgagg gcacctcgga ccagtctgtg gtcatcccta tctcttccc caagtacatc 7081 cgtgccccca acgggcccga agccaaccct gtgaagcagc tgcagcccaa tgaggaggcc 7141 gactacctcg gcgtgcgtat ccagctgcgg agggagcagg tgcgggggc caccggcttc 7201 ctcgaatggt gggtcatcga gctgcaggag tgccggaccg actgcaacct gctgcccatg 7261 gtcattttca gtgacaaggt cagcccaccg agcctcggct tcctggctgg ctacggcatc 7321 atggggctgt acgtgtccat cgtgctggtc atcggcaagt tcgtgcgcgg attcttcagc 7381 gagatctcgc actccattat gttcgaggag ctgccgtgcg tggaccgcat cctcaagctc 7441 tgccaggaca tcttcctggt gcgggagact cgggagctgg agctggagga ggagttgtac 7501 gccaagctca tcttcctcta ccgctcaccg gagaccatga tcaagtggac tcgtgagaag 7561 gagtaggagc tgctgctggc ccccgagagg gaaggagccg gcctgctggg cagcgtggcc 7621 acaaggggcg gcactcctca ggccggggga gccactgccc cgtccaaggc cgccagctgt 7681 gatgcatcct cccggcctgc ctgagccctg atgctgctgt cagagaagga cactgcgtcc 7741 ccacggcctg cgtggcgctg ccgtccccca cgtgtactgt agagttttt ttttaattaa 7801 aaaatgtttt atttatacaa atggacaatc aga
```

NM_004444 4369 bp mRNA *homo sapiens* EPH receptor B4 (EPHB4), mRNA.
(SEQ ID NO: 9)

```
   1 ttccagcgca gctcagcccc tgcccggccc ggcccgcccg gctccgcgcc gcagtctccc 61 tccctcccgc tccgtccccg ctcgggctcc caccatcccc gcccgcgagg agagcactcg 121 gcccggcggc gcgagcagag ccactccagg gaggggggga daccgcgagc ggccggctca 181 gcccccgcca cccggggcgg daccccgagg ccccggaggg accccaactc cagccacgtc 241 ttgctgcgcg cccgcccggc gcggccactg ccagcacgct ccgggcccgc cgcccgcgcg 301 cgcggcacag acgcggggcc acacttggcg ccgccgcccg gtgccccgca cgctcgcatg 361 ggcccgcgct gagggccccg acgaggagtc ccgcgcggag tatcggcgtc cacccgccca 421 gggagagtca gacctggggg ggcgagggcc ccccaaactc agttcggatc ctacccgagt 481 gaggcggcgc catggagctc cgggtgctgc tctgctgggc ttcgttggcc gcagctttgg 541 aagagaccct gctgaacaca aaattggaaa ctgctgatct gaagtgggtg acattccctc 601 aggtggacgg gcagtgggag gaactgagcg gcctggatga ggaacagcac agcgtgcgca 661 cctacgaagt gtgtgacgtg cagcgtgccc cgggccaggc ccactggctt cgcacaggtt 721 gggtcccacg gcggggcgcc gtccacgtgt acgccacgct gcgcttcacc atgctcgagt 781 gcctgtccct gcctcgggct gggcgctcct gcaaggagac cttcaccgtc ttctactatg 841 agagcgatgc ggacacggcc acggcccctca cgccagcctg gatggagaac ccctacatca 901 aggtggacac ggtggccgcg agcatctca cccggaagcg ccctgggcc gaggccaccg 961 ggaaggtgaa tgtcaagacg ctgcgtctgg gaccgctcag caaggctggc ttctacctgg 1021 ccttccagga ccagggtgcc tgcatggccc tgctatccct gcacctcttc tacaaaaagt
```

```
1081  gcgcccagct gactgtgaac ctgactcgat tcccggagac tgtgcctcgg gagctggttg
1141  tgcccgtggc cggtagctgc gtggtggatg ccgtccccgc ccctggcccc agccccagcc
1201  tctactgccg tgaggatggc cagtgggccg aacagccggt cacgggctgc agctgtgctc
1261  cggggttcga ggcagctgag gggaacacca agtgccgagc ctgtgcccag ggcaccttca
1321  agccctgtc aggagaaggg tcctgccagc catgcccagc caatagccac tctaacacca
1381  ttggatcagc cgtctgccag tgccgcgtcg ggtacttccg ggcacgcaca gaccccgggg
1441  gtgcaccctg caccacccct ccttcggctc cgcggagcgt ggtttcccgc ctgaacggct
1501  cctccctgca cctggaatgg agtgccccc tggagtctgg tggccgagag gacctcacct
1561  acgccctccg ctgccgggag tgccgacccg gaggctcctg tgcgccctgc gggggagacc
1621  tgacttttga ccccggcccc cgggacctgg tggagccctg ggtggtggtt cgagggctac
1681  gtcctgactt cacctatacc tttgaggtca ctgcattgaa cggggtatcc tccttagcca
1741  cggggcccgt cccatttgag cctgtcaatg tcaccactga ccgagaggta cctcctgcag
1801  tgtctgacat ccgggtgacg cggtcctcac ccagcagctt gagcctggcc tgggctgttc
1861  cccgggcacc cagtggggct gtgctggact acgaggtcaa ataccatgag aagggcgccg
1921  aggtcccag cagcgtgcgg ttcctgaaga cgtcagaaaa ccgggcagag ctgcggggc
1981  tgaagcgggg agccagctac ctggtgcagg tacgggcgcg ctctgaggcc ggctacgggc
2041  ccttcggcca ggaacatcac agccagaccc aactggatga gagcgagggc tggcgggagc
2101  agctggccct gattgcgggc acggcagtcg tgggtgtggt cctggtcctg gtggtcattg
2161  tggtcgcagt tctctgcctc aggaagcaga gcaatgggag agaagcagaa tattcggaca
2221  aacacggaca gtatctcatc ggacatggta ctaaggtcta catcgacccc ttcacttatg
2281  aagaccctaa tgaggctgtg agggaatttg caaaagagat cgatgtctcc tacgtcaaga
2341  ttgaagaggt gattggtgca ggtgagtttg gcgaggtgtg ccgggggcgg ctcaaggccc
2401  cagggaagaa ggagagctgt gtggcaatca agacactgaa gggtggctac acggagcggc
2461  agcggcgtga gtttctgagc gaggcctcca tcatgggcca gttcgagcac cccaatatca
2521  tccgcctgga gggcgtggtc accaacagca tgcccgtcat gattctcaca gagttcatgg
2581  agaacggcgc cctggactcc ttcctgcggc taaacgacgg acagttcaca gtcatccagc
2641  tcgtgggcat gctgcgggc atcgcctcgg gcatgcggta ccttgccgag atgagctacg
2701  tccaccgaga cctggctgct cgcaacatcc tagtcaacag caacctcgtc tgcaaagtgt
2761  ctgactttgg cctttcccga ttcctggagg agaactcttc cgatcccacc tacacgagct
2821  ccctgggagg aaagattccc atccgatgga ctgccccgga ggccattgcc ttccggaagt
2881  tcacttccgc cagtgatgcc tggagttacg ggattgtgat gtgggaggtg atgtcatttg
2941  gggagaggcc gtactgggac atgagcaatc aggacgtgat caatgccatt gaacaggact
3001  accggctgcc cccgcccca gactgtccca cctccctcca ccagctcatg ctggactgtt
3061  ggcagaaaga ccggaatgcc cggccccgct tcccccaggt ggtcagcgcc ctggacaaga
3121  tgatccggaa ccccgccagc ctcaaaatcg tggcccggga aatggcggg cctcacacc
3181  ctctcctgga ccagcggcag cctcactact cagcttttgg ctctgtgggc gagtggcttc
3241  gggccatcaa aatgggaaga tacgaagaaa gtttcgcagc cgctggcttt ggctccttcg
3301  agctggtcag ccagatctct gctgaggacc tgctccgaat cggagtcact ctggcgggac
3361  accagaagaa aatcttggcc agtgtccagc acatgaagtc ccaggccaag ccgggaaccc
3421  cgggtgggac aggaggaccg gccccgcagt actgacctgc aggaactccc caccccaggg
```

-continued

```
3481 acaccgcctc cccatttttcc ggggcagagt ggggactcac agaggccccc agccctgtgc 3541 cccgctggat tgcactttga gcccgtgggg tgaggagttg gcaatttgga gagacaggat 3601 ttgggggttc tgccataata ggaggggaaa atcacccccc agccacctcg gggaactcca 3661 gaccaagggt gagggcgcct ttccctcagg actgggtgtg accagaggaa aaggaagtgc 3721 ccaacatctc ccagcctccc caggtgcccc cctcaccttg atgggtgcgt tcccgcagac 3781 caaagagagt gtgactccct tgccagctcc agagtggggg ggctgtccca ggggcaaga 3841 aggggtgtca gggcccagtg acaaaatcat tggggtttgt agtcccaact tgctgctgtc 3901 accaccaaac tcaatcattt ttttcccttg taaatgcccc tcccccagct gctgccttca 3961 tattgaaggt ttttgagttt tgtttttggt cttaattttt ctccccgttc ccttttttgtt 4021 tcttcgtttt gttttttctac cgtccttgtc ataactttgt gttggaggga acctgtttca 4081 ctatggcctc ctttgcccaa gttgaaacag gggcccatca tcatgtctgt ttccagaaca 4141 gtgccttggt catcccacat ccccggaccc cgcctgggac ccccaagctg tgtcctatga 4201 aggggtgtgg ggtgaggtag tgaaaagggc ggtagttggt ggtggaaccc agaaacggac 4261 gccggtgctt ggaggggttc ttaaattata tttaaaaaag taacttttg tataaataaa 4321 agaaaatggg acgtgtccca gctccagggg taaaaaaaaa aaaaaaaa
```

NM_000267 12381 bp mRNA *Homo sapiens* neurofibromin 1 (NF1), transcript variant 2, mRNA.
(SEQ ID NO: 10)

```
   1 aatctctagc tcgctcgcgc tccctctccc cgggccgtgg aaaggatccc acttccggtg 61 gggtgtcatg gcggcgtctc ggactgtgat ggctgtgggg agacggcgct agtggggaga 121 gcgaccaaga ggccccctcc cctccccggg tccccttccc ctatccccct cccccagcc 181 tccttgccaa cgccccttt ccctctcccc ctcccgctcg gcgctgaccc cccatcccca 241 cccccgtggg aacactggga gcctgcactc cacagaccct ctccttgcct cttccctcac 301 ctcagcctcc gctccccgcc ctcttcccgg cccagggcgc cggcccaccc ttccctccgc 361 cgccccccgg ccgcggggag gacatggccg cgcacaggcc ggtggaatgg gtccaggccg 421 tggtcagccg cttcgacgag cagcttccaa taaaaacagg acagcagaac acacatacca 481 aagtcagtac tgagcacaac aaggaatgtc taatcaatat ttccaaatac aagttttctt 541 tggttataag cggcctcact actatttaa agaatgttaa caatatgaga atatttggag 601 aagctgctga aaaaaattta tatctctctc agttgattat attggataca ctggaaaaat 661 gtcttgctgg gcaaccaaag gacacaatga gattagatga aacgatgctg gtcaaacagt 721 tgctgccaga aatctgccat tttcttcaca cctgtcgtga aggaaaccag catgcagctg 781 aacttcggaa ttctgcctct ggggttttat tttctctcag ctgcaacaac ttcaatgcag 841 tctttagtcg catttctacc aggttacagg aattaactgt tgttcagaa acaatgttg 901 atgttcatga tatagaattg ttacagtata tcaatgtgga ttgtgcaaaa ttaaaacgac 961 tcctgaagga aacagcattt aaatttaaag ccctaagaa ggttgcgcag ttagcagtta 1021 taaatagcct ggaaaaggca ttttggaact gggtagaaaa ttatccagat gaatttacaa 1081 aactgtacca gatcccacag actgatatgg ctgaatgtgc agaaaagcta tttgacttgg 1141 tggatggttt tgctgaaagc accaaacgta agcagcagt ttggccacta caaatcattc 1201 tccttatctt gtgtccagaa ataatccagg atatatccaa agacgtggtt gatgaaaaca 1261 acatgaataa gaagttattt ctggacagtc tacgaaaagc tcttgctggc catggaggaa 1321 gtaggcagct gacagaaagt gctgcaattg cctgtgtcaa actgtgtaaa gcaagtactt 1381 acatcaattg ggaagataac tctgtcattt tcctacttgt tcagtccatg gtggttgatc
```

-continued

```
1441 ttaagaacct gcttttaat ccaagtaagc cattctcaag aggcagtcag cctgcagatg 1501 tggatctaat gattgactgc cttgtttctt gctttcgtat aagccctcac aacaaccaac 1561 actttaagat ctgcctggct cagaattcac cttctacatt tcactatgtg ctggtaaatt 1621 cactccatcg aatcatcacc aattccgcat tggattggtg gcctaagatt gatgctgtgt 1681 attgtcactc ggttgaactt cgaaatatgt ttggtgaaac acttcataaa gcagtgcaag 1741 gttgtggagc acacccagca atacgaatgg caccgagtct tacatttaaa gaaaaagtaa 1801 caagccttaa atttaaagaa aaacctacag acctggagac aagaagctat aagtatcttc 1861 tcttgtccat ggtgaaacta attcatgcag atccaaagct cttgctttgt aatccaagaa 1921 aacaggggcc cgaaacccaa ggcagtacag cagaattaat tacagggctc gtccaactgg 1981 tccctcagtc acacatgcca gagattgctc aggaagcaat ggaggctctg ctggttcttc 2041 atcagttaga tagcattgat ttgtggaatc ctgatgctcc tgtagaaaca ttttgggaga 2101 ttagctcaca aatgcttttt tacatctgca agaaattaac tagtcatcaa atgcttagta 2161 gcacagaaat tctcaagtgg ttgcgggaaa tattgatctg caggaataaa tttcttctta 2221 aaaataagca ggcagataga agttcctgtc actttctcct tttttacggg gtaggatgtg 2281 atattccttc tagtggaaat accagtcaaa tgtccatgga tcatgaagaa ttactacgta 2341 ctcctggagc ctctctccgg aagggaaaag ggaactcctc tatggatagt gcagcaggat 2401 gcagcggaac ccccccgatt tgccgacaag cccagaccaa actagaagtg gccctgtaca 2461 tgtttctgtg gaaccctgac actgaagctg ttctggttgc catgtcctgt ttccgccacc 2521 tctgtgagga agcagatatc cggtgtgggg tggatgaagt gtcagtgcat aacctcttgc 2581 ccaactataa cacattcatg gagtttgcct ctgtcagcaa tatgatgtca acaggaagag 2641 cagcacttca gaaagagtg atggcactgc tgaggcgcat tgagcatccc actgcaggaa 2701 acactgaggc ttgggaagat acacatgcaa aatgggaaca agcaacaaag ctaatcctta 2761 actatccaaa agccaaaatg gaagatggcc aggctgctga aagccttcac aagaccattg 2821 ttaagaggcg aatgtcccat gtgagtggag gaggatccat agatttgtct gacacagact 2881 ccctacagga atggatcaac atgactggct tcctttgtgc ccttggggga gtgtgcctcc 2941 agcagagaag caattctggc ctggcaacct atagcccacc catgggtcca gtcagtgaac 3001 gtaagggttc tatgatttca gtgatgtctt cagagggaaa cgcagataca cctgtcagca 3061 aatttatgga tcggctgttg tccttaatgg tgtgtaacca tgagaaagtg ggacttcaaa 3121 tacggaccaa tgttaaggat ctggtgggtc tagaattgag tcctgctctg tatccaatgc 3181 tatttaacaa attgaagaat accatcagca agttttttga ctcccaagga caggttttat 3241 tgactgatac caatactcaa tttgtagaac aaaccatagc tataatgaag aacttgctag 3301 ataatcatac tgaaggcagc tctgaacatc tagggcaagc tagcattgaa acaatgatgt 3361 taaatctggt caggtatgtt cgtgtgcttg ggaatatggt ccatgcaatt caaataaaaa 3421 cgaaactgtg tcaattagtt gaagtaatga tgcaaggag agatgacctc tcattttgcc 3481 aagagatgaa atttaggaat aagatggtag aatacctgac agactgggtt atgggaacat 3541 caaaccaagc agcagatgat gatgtaaaat gtcttacaag agatttggac caggcaagca 3601 tggaagcagt agtttcactt ctagctggtc tccctctgca gcctgaagaa ggagatggtg 3661 tggaattgat ggaagccaaa tcacagttat ttcttaaata cttcacatta tttatgaacc 3721 ttttgaatga ctgcagtgaa gttgaagatg aaagtgcgca aacaggtggc aggaaacgtg 3781 gcatgtctcg gaggctggca tcactgaggc actgtacggt ccttgcaatg tcaaacttac 3841 tcaatgccaa cgtagacagt ggtctcatgc actccatagg cttaggttac cacaaggatc
```

-continued

```
3901 tccagacaag agctacattt atggaagttc tgacaaaaat ccttcaacaa ggcacagaat
3961 ttgacacact tgcagaaaca gtattggctg atcggtttga gagattggtg aactggtca
4021 caatgatggg tgatcaagga gaactcccta tagcgatggc tctggccaat gtggttcctt
4081 gttctcagtg ggatgaacta gctcgagttc tggttactct gtttgattct cggcatttac
4141 tctaccaact gctctggaac atgttttcta agaagtaga attggcagac tccatgcaga
4201 ctctcttccg aggcaacagc ttggccagta aaataatgac attctgtttc aaggtatatg
4261 gtgctaccta tctacaaaaa ctcctggatc ctttattacg aattgtgatc acatcctctg
4321 attggcaaca tgttagcttt gaagtggatc ctaccaggtt agaaccatca gagagccttg
4381 aggaaaacca gcggaacctc cttcagatga ctgaaaagtt cttccatgcc atcatcagtt
4441 cctcctcaga attccccct caacttcgaa gtgtgtgcca ctgtttatac caggtggtta
4501 gccagcgttt ccctcagaac agcatcggtg cagtaggaag tgccatgttc ctcagattta
4561 tcaatcctgc cattgtctca ccgtatgaag cagggatttt agataaaaag ccaccaccta
4621 gaatcgaaag gggcttgaag ttaatgtcaa agatacttca gagtattgcc aatcatgttc
4681 tcttcacaaa agaagaacat atgcggcctt tcaatgattt tgtgaaaagc aactttgatg
4741 cagcacgcag gttttccttt gatatagcat ctgattgtcc tacaagtgat gcagtaaatc
4801 atagtctttc cttcataagt gacggcaatg tgcttgcttt acatcgtcta ctctggaaca
4861 atcaggagaa aattgggcag tatcttccca gcaacaggga tcataaagct gttggaagac
4921 gaccttttga taagatggca acacttcttg catacctggg tcctccagag cacaaacctg
4981 tggcagatac acactggtcc agccttaacc ttaccagttc aaagtttgag gaatttatga
5041 ctaggcatca ggtacatgaa aaagaagaat tcaaggcttt gaaaacgtta agtatttttct
5101 accaagctgg gacttccaaa gctgggaatc ctatttttta ttatgttgca cggaggttca
5161 aaactggtca aatcaatggt gatttgctga tataccatgt cttactgact ttaaagccat
5221 attatgcaaa gccatatgaa attgtagtgg accttaccca taccgggcct agcaatcgct
5281 ttaaaacaga ctttctctct aagtggtttg ttgttttttcc tggctttgct tacgacaacg
5341 tctccgcagt ctatatctat aactgtaact cctgggtcag ggagtacacc aagtatcatg
5401 agcggctgct gactggcctc aaaggtagca aaaggcttgt tttcatagac tgtcctggga
5461 aactggctga gcacatagag catgaacaac agaaactacc tgctgccacc ttggctttag
5521 aagaggacct gaaggtattc cacaatgctc tcaagctagc tcacaaagac accaaagttt
5581 ctattaaagt tggttctact gctgtccaag taacttcagc agagcgaaca aaagtcctag
5641 ggcaatcagt ctttctaaat gacatttatt atgcttcgga aattgaagaa atctgcctag
5701 tagatgagaa ccagttcacc ttaaccattg caaaccaggg cacgccgctc accttcatgc
5761 accaggagtg tgaagccatt gtccagtcta tcattcatat ccggacccgc tgggaactgt
5821 cacagcccga ctctatcccc caacacacca agattcggcc aaaagatgtc cctgggacac
5881 tgctcaatat cgcattactt aatttaggca gttctgaccc gagtttacgg tcagctgcct
5941 ataatcttct gtgtgcctta acttgtacct ttaatttaaa aatcgagggc cagttactag
6001 agacatcagg tttatgtatc cctgccaaca acaccctctt tattgtctct attagtaaga
6061 cactggcagc caatgagcca cacctcacgt tagaattttt ggaagagtgt atttctggat
6121 ttagcaaatc tagtattgaa ttgaaacacc tttgtttgga atacatgact ccatggctgt
6181 caaatctagt tcgtttttgc aagcataatg atgatgccaa acgacaaaga gttactgcta
6241 ttcttgacaa gctgataaca atgaccatca atgaaaaaca gatgtaccca tctattcaag
```

-continued

```
6301 caaaaatatg gggaagcctt gggcagatta cagatctgct tgatgttgta ctagacagtt
6361 tcatcaaaac cagtgcaaca ggtggcttgg gatcaataaa agctgaggtg atggcagata
6421 ctgctgtagc tttggcttct ggaaatgtga aattggtttc aagcaaggtt attggaagga
6481 tgtgcaaaat aattgacaag acatgcttat ctccaactcc tactttagaa caacatctta
6541 tgtgggatga tattgctatt ttagcacgct acatgctgat gctgtccttc aacaattccc
6601 ttgatgtggc agctcatctt ccctacctct tccacgttgt tactttctta gtagccacag
6661 gtccgctctc ccttagagct tccacacatg gactggtcat taatatcatt cactctctgt
6721 gtacttgttc acagcttcat tttagtgaag agaccaagca agttttgaga ctcagtctga
6781 cagagttctc attacccaaa ttttacttgc tgtttggcat tagcaaagtc aagtcagctg
6841 ctgtcattgc cttccgttcc agttaccggg acaggtcatt ctctcctggc tcctatgaga
6901 gagagacttt tgctttgaca tccttggaaa cagtcacaga agctttgttg agatcatgg
6961 aggcatgcat gagagatatt ccaacgtgca agtggctgga ccagtggaca gaactagctc
7021 aaagatttgc attccaatat aatccatccc tgcaaccaag agctcttgtt gtctttgggt
7081 gtattagcaa acgagtgtct catgggcaga taaagcagat aatccgtatt cttagcaagg
7141 cacttgagag ttgcttaaaa ggacctgaca cttacaacag tcaagttctg atagaagcta
7201 cagtaatagc actaaccaaa ttacagccac ttcttaataa ggactcgcct ctgcacaaag
7261 ccctcttttg ggtagctgtg gctgtgctgc agcttgatga ggtcaacttg tattcagcag
7321 gtaccgcact tcttgaacaa aacctgcata ctttagatag tctccgtata ttcaatgaca
7381 agagtccaga ggaagtattt atggcaatcc ggaatcctct ggagtggcac tgcaagcaaa
7441 tggatcattt tgttggactc aatttcaact ctaactttaa ctttgcattg gttggacacc
7501 ttttaaaagg gtacaggcat ccttcacctg ctattgttgc aagaacagtc agaattttac
7561 atacactact aactctggtt aacaaacaca gaaattgtga caaatttgaa gtgaatacac
7621 agagcgtggc ctacttagca gctttactta cagtgtctga agaagttcga agtcgctgca
7681 gcctaaaaca tagaaagtca cttcttctta ctgatatttc aatggaaaat gttcctatgg
7741 atacatatcc cattcatcat ggtgacccett cctataggac actaaaggag actcagccat
7801 ggtcctctcc caaaggttct gaaggatacc ttgcagccac ctatccaact gtcggccaga
7861 ccagtccccg agccaggaaa tccatgagcc tggacatggg gcaaccttct caggccaaca
7921 ctaagaagtt gcttggaaca aggaaaaagtt ttgatcactt gatatcagac acaaaggctc
7981 ctaaaaggca agaaatggaa tcagggatca caacaccccc caaaatgagg agagtagcag
8041 aaactgatta tgaaatggaa actcagagga tttcctcatc acaacagcac ccacatttac
8101 gtaaagtttc agtgtctgaa tcaaatgttc tcttggatga agaagtactt actgatccga
8161 agatccaggc gctgcttctt actgttctag ctacactggt aaaatatacc acagatgagt
8221 ttgatcaacg aattctttat gaatacttag cagaggccag tgttgtgttt cccaaagtct
8281 ttcctgttgt gcataatttg ttggactcta agatcaacac cctgttatca ttgtgccaag
8341 atccaaatttt gttaaatcca atccatgaa ttgtgcagag tgtggtgtac catgaagaat
8401 ccccaccaca ataccaaaca tcttacctgc aaagttttgg ttttaatggc ttgtggcggt
8461 ttgcaggacc gttttcaaag caaacacaaa ttccagacta tgctgagctt attgttaagt
8521 ttcttgatgc cttgattgac acgtacctgc ctggaattga tgaagaaacc agtgaagaat
8581 ccctcctgac tcccacatct ccttacccte ctgcactgca gagccagctt agtatcactg
8641 ccaaccttaa cctttctaat tccatgacct cacttgcaac ttcccagcat tccccaggaa
8701 tcgacaagga gaacgttgaa ctctccccta ccactggcca ctgtaacagt ggacgaactc
```

```
8761  gccacggatc cgcaagccaa gtgcagaagc aaagaagcgc tggcagtttc aaacgtaata
8821  gcattaagaa gatcgtgtga agcttgcttg ctttcttttt taaaatcaac ttaacatggg
8881  ctcttcacta gtgaccccct ccctgtcctt gccctttccc cccatgttgt aatgctgcac
8941  ttcctgtttt ataatgaacc catccggttt gccatgttgc cagatgatca actcttcgaa
9001  gccttgccta aatttaatgc tgccttttct ttaacttttt ttcttctact tttggcgtgt
9061  atctggtata tgtaagtgtt cagaacaact gcaaagaaag tgggaggtca ggaaactttt
9121  aactgagaaa tctcaattgt aagagaggat gaattcttga atactgctac tactggccag
9181  tgatgaaagc catttgcaca gagctctgcc ttctgtggtt ttcccttctt catcctacag
9241  agtaaagtgt tagtcctatt tatacatttt tcaagataca agtttatgag agaaatagta
9301  ttataacccc agtatgttta atcttttagc tgtggacttt ttttttaacc gtacaaaact
9361  gaaagaacca tagaggtcaa gcctcagtga cttgacacca taaagccaca gacaaggtac
9421  ttgggggggga gggcagggaa atttcatatt ttatagtgga ttcttaagaa atactaacac
9481  ttgagtatta gcaataatta caggaaaata agtgcgacca catatatctt aacattactg
9541  aattaaaact atggcttcta agtccttatc caaactcagt catccaaact agtttatttt
9601  tttctccagt tgattatctt ttaattttta attttgctaa aggtggtttt tttgtgtttt
9661  gttttttgta aaccaaaact atactaagta tagtaattat atatatatat atattttttc
9721  ccctccccct cttctttcct aactaattct gagcagggta atcagtgaac aaagtgttga
9781  aaattgttcc cagaaggtaa ttttcataga tgtttgcatt agctccatag caaaatggaa
9841  tggtacgtga catttagggt agctgatatt tttattttgt taaataattt ccaagaatag
9901  agtatggtgt atattataaa tttctttgat aagatgtatt ttgaatgtct tttaatcttc
9961  ctcctcctct ccaaaaaaat cagaaacctc tttaagaaaa catgtaggtt atatatgcta
10021 gaattgcatt taatcactgt gaaaagactg gtcagcctgc attagtatga cagtaggggg
10081 gctgttagaa ttgctgctat actggtggta tggattatca tggcattgga atttcatag
10141 taatgcagat ccaatttctt tgtggtacct gcagtttaca aaataatttg acttcagtga
10201 gcatattggt atctggatgt tccaatttag aactaaacca tatttattac aaaaagatat
10261 taatccctct actcccaggt tccctttata tgttaagata aatggctttg gagggggaa
10321 aaaataaacc taggggagag gggagtttcc tgtagtgctg tttcattaga ggatttcagt
10381 aaattaaatt ccacagctaa ttcaataaat aatggtacat ttaagtgttc tgattttaat
10441 aatatatttc acatttatcc acacagtaac aatgtaatat gttaatgtaa ataaaattgg
10501 ttttgatact cagaaataac aagaatttaa ttttttaaat ttgtttacag tcctgggaaa
10561 agtaagaatt atttgccaaa ataagaggaa agaaaacctt agtattatta atgagtttac
10621 catagaattg ttggaaatac tgaagacagg tgcaatttac taaactttg tttttaaact
10681 attgtagagg ctgcattaga agaaatgtt tataatgaca gagcaactat gactatataa
10741 aaaagctgaa attagaactg tgtttagaaa tagatcagta acccagtgcc aaggatgcca
10801 agctgccacc atggtcttgg ctctcccaca acccagtgtt tctggggtaa gtttcacagt
10861 ttctaggccc tggaatagca ggcagtgtaa gcctttgata actttagttc gatgttttc
10921 ttgttttgt ttgttggttt ggtgcatatg atagtgggtg ttatgctatt ttgctcttcc
10981 catcaaaata aagaaacttc cagaggttta ctgttaaaaa tactgatatt tccataaacg
11041 ggtttaccaa gggtgtagta tttcataccg cctgaaatga tcagcattgg cacaaatcaa
11101 aattcagccg cctttgaaat gcaaaaatac ctttgactag taagtacatc ctaggagttt
```

-continued

```
11161 gaaaacttaa ctaaggttta aaatttacct tgtttaaaga acttctgact tttgaggaaa 11221 atctagcttt ccaagtaact aaaatgtaca tgagataaac ctctcaccac tatgtgtccc 11281 ttgagaaatg caacactttt ttagtcttca tacttgtaat ctataaaaga aattctgaag 11341 tttagaccaa gttgcccatt tctgcgtaat tgacataagt tctgttaaaa atattataag 11401 taattcgttt cggtttgtag atgtttcccc tgacttgtta aagaggaaac caggaactca 11461 gtcatgtttt tgtcctggat aatctacctg ttatgccagt actcccatcc gaggggcatg 11521 cccttagttg cccagatgga gatgcagttc agtagatttg gggcaaagtg gctacagctc 11581 tgtcttccat tcactcaaca cctgttcatg actgagccag gtgcccagga cacatcctaa 11641 acagtcagct tctatcctgt gtcctagttg gggagacaga gtgccagcca gcaaccctcc 11701 caggtttgta ggtttagggg gttttcagtt ttgtttgggt tttttgtttt ttgtttttgt 11761 ttctacatcc ttccccgact cccaggcata atgaggcatg tcttactcaa tgttatgcaa 11821 tggatttagg caaaaattca ttcttagtgt cagccacaca attttttta atgcagtata 11881 ttcacctgta aatagtttgt gtaaaatttg acaaaaaaag tatatttact atactgtaaa 11941 tatatgtgat gatatattgt attattttgc tttttttgtaa agcagttagt tgctgcacat 12001 ggataacaac aaaaatttga ttattctcgt gttagtattg ttaacttctt tttgcgactg 12061 cgttacatca tttaaagaaa atgctgtgta ttgtaaactt aaattgtata tgataactta 12121 ctgtcctttc catccgggcc taaactttgg cagttccttt gtctacaacc ttgttaatac 12181 tgtaaacagt tgtacgccag caggaaaaat actgcccaac agacaaaatc gatcattgta 12241 ggggaaaatc atagaaatcc atttcagatc tttattgttc ctcaccccat tttcctcctt 12301 gtgtatgtac ttccccccacc cccctttttt taagtaaaat gtaaattcaa tctgctctaa 12361 gaaaaaaaaa aaaaaaaaa a
```

NM_005188 11241 bp mRNA *Homo sapiens* Cbl proto-oncogene (CBL), mRNA.

```
   1 tccgcccgga tagccggcgg cggcggcggc ggcggcggcg gcggcggccg ggagaggccc 61 ctccttcacg ccctgcttct ctccctcgct cgcagtcgag ccgagccggc ggacccgcct 121 gggctccgac cctgcccagg ccatggccgg caacgtgaag aagagctctg gggccggggg 181 cggcagcggc tccgggggct cgggttcggg tggcctgatt gggctcatga aggacgcctt 241 ccagccgcac caccaccacc accaccacct cagcccccac ccgccgggga cggtggacaa 301 gaagatggtg agaagtgct ggaagctcat ggacaaggtg gtgcggttgt gtcagaaccc 361 aaagctggcg ctaaagaata gcccaccttat atcttagac ctgctaccag atacctacca 421 gcatctccgt actatcttgt caagatatga ggggaagatg gagacacttg agaaaatga 481 gtatttagg gtgtttatgg agaatttgat gaagaaaact aagcaaacca taagcctctt 541 caaggaggga aaagaaagaa tgtatgagga gaattctcag cctaggcgaa acctaaccaa 601 actgtccctc atcttcagcc acatgctggc agaactaaaa ggaatctttc caagtggact 661 ctttcaggga gacacatttc ggattactaa agcagatgct gcggaatttt ggagaaaagc 721 ttttgggaa aagacaatag tcccttggaa gagctttcga caggctctac atgaagtgca 781 tcccatcagt tctgggctgg aggccatggc tctgaaatcc actattgatc tgacctgcaa 841 tgattatatt tcggttttg aatttgacat ctttacccga ctctttcagc cctggtcctc 901 tttgctcagg aattggaaca gccttgctgt aactcatcct ggctacatgg ctttttgac 961 gtatgacgaa gtgaaagctc ggctccagaa attcattcac aaacctggca gttatatctt 1021 ccggctgagc tgtactcgtc tgggtcagtg ggctattggg tatgttactg ctgatgggaa 1081 cattctccag acaatccctc acaataaacc tctcttccaa gcactgattg atggcttcag
```

-continued

```
1141 ggaaggcttc tatttgtttc ctgatggacg aaatcagaat cctgatctga ctggcttatg
1201 tgaaccaact ccccaagacc atatcaaagt gacccaggaa caatatgaat tatactgtga
1261 gatgggctcc acattccaac tatgtaaaat atgtgctgaa aatgataagg atgtaaagat
1321 tgagccctgt ggacacctca tgtgcacatc ctgtcttaca tcctggcagg aatcagaagg
1381 tcagggctgt cctttctgcc gatgtgaaat taaaggtact gaacccatcg tggtagatcc
1441 gtttgatcct agagggagtg gcagcctgtt gaggcaagga gcagagggag ctccctcccc
1501 aaattatgat gatgatgatg atgaacgagc tgatgatact ctcttcatga tgaaggaatt
1561 ggctggtgcc aaggtggaac ggccgccttc tccattctcc atggcccac aagcttccct
1621 tcccccggtg ccaccacgac ttgaccttct gccgcagcga gtatgtgttc cctcaagtgc
1681 ttctgctctt ggaactgctt ctaaggctgc ttctggctcc cttcataaag acaaaccatt
1741 gccagtacct cccacacttc gagatcttcc accaccaccg cctccagacc ggccatattc
1801 tgttggagca gaatcccgac ctcaaagacg cccctttgcct tgtacaccag gcgactgtcc
1861 ctccagagac aaaactgccc ctgtcccctc tagccgcctt ggagactcat ggctgccccg
1921 gccaatcccc aaagtaccag tatctgcccc aagttccagt gatccctgga caggaagaga
1981 attaaccaac cggcactcac ttccattttc attgccctca caaatggagc ccagaccaga
2041 tgtgcctagg ctcggaagca cgttcagtct ggatacctcc atgagtatga atagcagccc
2101 attagtaggt ccagagtgtg accaccccaa aatcaaacct tcctcatctg ccaatgccat
2161 ttattctctg gctgccagac ctcttcctgt gccaaaactg ccacctgggg agcaatgtga
2221 gggtgaagag gacacagagt acatgactcc ctcttccagg cctctacggc ctttggatac
2281 atcccagagt tcacgagcat gtgattgcga ccagcagatt gatagctgta cgtatgaagc
2341 aatgtataat attcagtccc aggcgccatc tatcaccgag agcagcacct ttggtgaagg
2401 gaatttggcc gcagcccatg ccaacactgg tcccgaggag tcagaaaatg aggatgatgg
2461 gtatgatgtc ccaaagccac ctgtgccggc cgtgctggcc cgccgaactc tctcagatat
2521 ctctaatgcc agctcctcct ttggctggtt gtctctggat ggtgatccta acaaaatgt
2581 cactgaaggt tcccaagttc ccgagaggcc tccaaaacca ttcccgcgga gaatcaactc
2641 tgaacggaaa gctggcagct gtcagcaagg tagtggtcct gccgcctctg ctgccaccgc
2701 ctcacctcag ctctccagtg agatcgagaa cctcatgagt caggggtact cctaccagga
2761 catccagaaa gctttggtca ttgcccagaa caacatcgag atggccaaaa acatcctccg
2821 ggaatttgtt tccatttctt ctcctgccca tgtagctacc tagcacacca tctccctgct
2881 gcaggtttag aggaccagtg agttgggagt tattactcaa gtggcaccta aagggcagg
2941 agttcctttg gtgacttcac agtgaagtct tgccctctct gtgggatatc acatcagtgg
3001 ttccaagatt tcaaagtggt gaaatgaaaa tggagcagct agtatgtttt attattttat
3061 gggtcttgag tgcatttgaa ggtgtccttc agttcccacg tagagagagt gtggattata
3121 ttacatgata acctacctgg ggaacagtcc agaaagctat agaacaagta ttttgctgga
3181 aatcctaatt gaggacttaa gacttcctgg gttaaggatg tggccgtgtg tgtgtgtgtc
3241 tgcctgtggt tgtatgtgtc cttgtgatta taagattaac ctgctgtgtg tgttaattcc
3301 aggcagggaa ttagcacaaa aggtttagga aggaatcttt ttttaaagac ttccatctac
3361 tgtggtatta tacccaagcc tagtgtgtat tacaacttca acactcccct ttggcttata
3421 ttaccatgtg catagctaaa gtcttctatt tttagaacac cttctgtctg ttctttcccc
3481 atcaactcct tcctcatcct tcttggtgtt ctgtcatggg ccatgggctt gctatggcca
3541 gccttactga ggccaagcag cttatgggat gttctttatt gtgtgtgatg gtattggttt
```

-continued

```
3601 gtttggtaga taagtgggag gaaaagtact gttgctacac tattataggc atgtttgata
3661 ctagcagcta acactggtca ctccaaagca ctgtttctat aggaacattg aagctattaa
3721 gatgttttga ttatcctaat tacataatga ccgatttgag atagaggcct ttaaatacat
3781 tccatgccct ccccagaaaa tagtctgtgg gagtcagttg ccttggtgcc aggtatgtgt
3841 tctgatgtag gtcatgagtc tttctactta atgggaaggg aagaacattt gtttccagga
3901 tgactttctg gccagaatac cggaaagctt ttaggaagct tcgttcacat gctatttaaa
3961 tgcacaaaat agacagtaag gatttatctg ttcagttttt cttcccagtg aattaatttc
4021 agcttatatg ggtgtcttca tttgaacatg aggaatatta ggttatattt tcagcagtgg
4081 ttttttcctt tgccctttaa ggagtgggga taatgtccac ggtggcccag cctcttgctg
4141 atggcacctt ccctgcattg ctgcctcccg atgatgtggt tcttttcttg tgcctgtggc
4201 tttgggaatg taacatctct ttcctccttt ccttcccttt tcctcttcac ctgaggtcct
4261 aaatactctc tgtaattact gtgttcttca cggtaattag acatcattca gtgaataaat
4321 tactgtagtc aaagacagta tgggctggca gtttgtgtaa ttgcaagttc ataaagagaa
4381 ttgagggtcc agttgggaga actattagtc agttctttta tatgctgata aatgatccct
4441 cgagttcagt tagtattctg tccagagtgt ttagctcact ttcttagcag tgtgtaagct
4501 ttctccatgt cagaagcaag cctgctcttt gataaatctg tcttcctgaa aatctaaatc
4561 atgcttttgt ctttagatct acacagaaat gaccctcctt ggatcagttt tctttccagt
4621 ctaatcatct ttggaactaa aacttgttct aactcgtctc ttggcattca gctactccta
4681 gatcttttgg ttttatcccc tggcctcaga gccatttata ttcccagagt aggcagtaca
4741 ggatctcgtg ttgatttgct gtggttaccc agtgtcttct ctacatggca taaagcggca
4801 aagcccacca ttaggtgagg cggtcccgag ttgaggtaga gtggggcaga ggaagatggc
4861 agtgaatatc aaacagtaga ccgccatcaa cttctaacag ccagtacaca cactgtttca
4921 ttttgaggta acgttcagtt ttgcattttg tttaaatatt gaaggcctag acaaagaact
4981 agaaaaaaaa aagcagtttc caggcccatc catattgtaa ttttctttta tctgcagata
5041 ttgcctgtag tctaaagatc tctttggaag acaaagcatt ggctatatat cttttgcctt
5101 ttccatgcat ctaaatcttc tctggagatt atctccctac tgtgtaggtt aagggcagtc
5161 tcgactttc cttttttgag tcctgtgtgg ctctttgaat cagcgtgaaa ctgaggctcc
5221 agctccctgt gttgtgtgtg tgtgccatcc atgggcttgg gtgtcagttt gtcacaggta
5281 tctgccagca ttcaaggttt tggatcattt catgaggatc tttcctttga ctgggtgctg
5341 tgaggacaca cctgggtctg tgcctgagat tgccaggcaa gattaaggaa agttttcatg
5401 tggcttttgt tttgaggtta ttctcaaaac cttaatttct tatattttct gttgactaag
5461 gcaccagtaa cccattcttc accctccatt tgtatggcaa tttaaaagtc tttggctttg
5521 ctctgaattt aattaaaact gccttttatg aacagacttc gagttttgcc attttgggca
5581 agcccttccg cttgtccctt cctagtggct aataaagtaa aaaaacccac actactttgt
5641 tctcttttttc tcatattcat tgggctgttg tattcagcca gtctcatgct ttccctgggt
5701 cttcacggat tgctttccaa gctgccttgt tgcggggttg ctgcagagca gcaactggac
5761 ctttccagct gtcgccatgt tccttccact aaagtagagg gttcttaaaa tggaaaaacc
5821 tgtgggctct tcatataccct ccctttagtt aagtaataga ccaggcagct tctcatctca
5881 gcatttacct gttaatatttt ttgtgaatag tgctctctac ctgtgggtgg ccgttctctt
5941 ccacttgctc gtctcccccc agccccattc tgcataatct accattcttc tcctctcttt
```

-continued

```
6001 ctcttcttat acagaccctc attactgggg cccaagatgt gggatactac tgttagtatt 6061 atttaactat tttgtagatt taaaagattt ctggttaagg gaggtggggg tcactgttca 6121 tcactcttaa aatatgtgtt ttctctatag aaaagtaaaa tgtgtttatg gtcccaaaca 6181 gtcaactcac aaattttat aacaaaattt ccttgtaaaa actagggacc atctatatat 6241 tcccttttaag atctagttct ttttgtaggt gttcagcaat ggtgataaag cagaatattc 6301 tcctacctca cgtcattaaa gtcagaagat tatagacctt ctcaaactat aagtccctct 6361 tcttgccgtt ggccttttctg actctggaat gaccactgtt cattgaaaaa tagttttctg 6421 actattggtc tggctctaac agtttgtttg ttcatccagc aaatgtttat gagtgatgac 6481 catgtgccag aaatgtcagg tatgtgtcct tcccttggcg ccacatagta gtttactaat 6541 gtttggggga ttgtacttgg actgtcatag cctctgcgtt tgaccttaaa atagctcttc 6601 ccagtaagat tgtgcaattt ttattcacag ctcttccatg tagacttacc tttcctcata 6661 gagctatcct ggttaataac aggccaagat tctcccatta tccctgttg tctcctgtag 6721 ctttgataat gcctgggaga ttccttggtg taagtgtcat ggataccgac tgtttttatg 6781 ttggaatttg ttccaacata attagaatct gtttggtgag ttgaaaggta agttggctca 6841 gagttgcaca gtagggcatt aaatgtttaa gcaaagcatc tgcccacact cccctttcca 6901 atctagtgcc ttccttgaac ttttttcctga gctgctacgt ccctaatccc ccttgttggg 6961 aggattttcg tatcaccctt atgggacctg tcaccatgtc ctgtactatt tggaattggt 7021 tttccagtct ttcaacaacc gttgtggcta actatgtttt agaagggctg gaggtgtggg 7081 ccctgtcttc gggtctcagg acccaaagat cctttagtca gttgttgggt cttccaagag 7141 ccagacatta atacagattg aactccatca gtcccctaat tgtcagcctt tacctccctc 7201 ccagagcaag gagtttaggg attctaaagc ttagtgtcca cacatcattc taccagacct 7261 tagagcttta gaagctcaat ctaaaatact gtaactcagc ataaactatt actatcactc 7321 ctttgaactc agtctccatg agcagtgttt tgttggaaat acatagaacg gcttaatgcc 7381 tagagggtgg tggatagtga aggacggtca aggttatatt tttgactgct tagggattct 7441 ttggatccaa gaaacagaaa tgttcaagcg gaataaagga gggagtggag ttgtggtaag 7501 gatgcagggt atttcgcaga acccaggacg ggaagtgcct ttggttcttg ggtggagctg 7561 gaactgcaga gctttgcacc tagtcctttc tcccgcttca cagtctgctt atggtatatg 7621 tggcccccaa ataggcactc tagtcctcaa gtctacacca ccttccaact ctggggatca 7681 ccatgaacaa attctcaatt tcccatactt aatttttttt ttttttgaga tggagtctcg 7741 ctgtgtcgcc caggctggag tgcagtggtg cagtctcaac tcaccacaac ctctgcctcc 7801 caggttcaag cagttctctg cctcaacctc ccgagtagct gggattacag gcgcctgcca 7861 ccatgcccag ctaatgttca tattttagt agagacaggg tttcaccgtc ttggctaggc 7921 tggtcttgaa ctcctgaccc tcatgatcca cccacctcgg cctcccaaag tgctaagatt 7981 acaggcgtga gccaccgcgc ccggcccata cttcgtattc ttaaaaaaaa ctacactcag 8041 cccagcacat tgatcaagta tctatctctg agcagttggc cttgccaggg agagcagaga 8101 tgtggcaggc tccttcagct ggagacaggg agcttctcag agaagtgagc agagactcca 8161 cagacaccct aaaaggcttt ctactcaaga agtaaagcca ctactcctgc ctttttgctt 8221 agtggacagg aaggcacagg agtttgtctg ggacatcata gaaattctta ggtttaactt 8281 aattctggtc attgtcttct ttatttcctg ttttttcttcc ctttgtcagt cttcgcatcc 8341 aagatttctt ccctccctct tgtgggccag cctgtcctgt tccagagcta gcctgttcct 8401 gggtagcctt ccttagcctc cattcagcct caggtctttt gccttcttcc gtgtttattt
```

```
8461 agagagcaga atctaataac gggttccact gtagccacta tccatggact tctgggtcct 8521 cttcaggttt gagtgcttga aaatgttcat tctctgggct tgtggcctgt ctcctccact 8581 ctcctcctca ccctctcgct ccttcctgtg tgagggccgc tctgcagtaa tgttctcagg 8641 caagccttcc taggcacctc agaaactact ttgccagagc cagtaagaat atataatatt 8701 ggagcagttg ccaggataga aattaaatat agattccagt ttaggataga gtttttaccg 8761 agagctcttt agacagtata cctgtgtctt ctctggcaat tgctttcatt ttagtcctat 8821 ataaaagctt tccttttctg tttttttta aaactatgct tttgcttgcc taaatctttt 8881 gatcttatat ttctctcatc tcagagcctg tcctgagttg taaggtattt catactgcct 8941 tacttaaaag ttttttaaac tactagagtc atttgataca cacagaagtt acctaataat 9001 ccaaagatgt ccatcaaggg aggaagggtg ggtcatcaga cttttgccttt gatgttgtag 9061 actaggctcc tgagttaagc agcagaggga cagcagtgcc atgtgccttc actgtgtccc 9121 aggaaatctg ggttggttcc agtgggaaat accagtattt cttggttctg gaaagtagca 9181 aaagagtagg agatggggaa atagggatgg ggagagcaag ccccgcatgt ccatggcgag 9241 tcaggtgggg agcacgggtg gaagggccgg ctgttgacag acagactaag ctgtgtggtg 9301 ctcttgccgc cccttcctgg gtacagagct tgagaaaaat gcagccgacc actccctgtg 9361 tttgtacaga gcaaagccca aaagccaacc tcagatctcc tgatttggca gctgaagaaa 9421 tcagcagagt cctgattgcc tgattcagtc ccaaaaatga atgtcaggcc ccgccccctc 9481 cccaccaaca ttgcctctcc tacattctcc ttctgcccct aaatcagaca ggaggccaga 9541 gaggagtatt gctcaatgcg tgctatgtgc aactcctcag gccttgtgcc acctccatgc 9601 tgagccctga agcagggtgt cctgggtgcc tgtgtgtcag ctccctcctc tctacctacc 9661 tctgaccttc ttgtgggtga gggtggccat gcttatggcc atcttaaaac tggagaggca 9721 gagaactact tatgagtctg tagaccacgt gttgtcttcc atggcctgtt tctcctgctg 9781 tctgggtgag tgagcctgca acgcaatgcc catgagagta aatgcctcct gacctaccct 9841 gctcagcact gttctagtgt cttggccttg aaagaaaagc ctgacttcct gctgacacat 9901 gtggtagggg catggcagct atgaggcacc tcctacgtct gttttctggc tgtggtgact 9961 tgggattttt aaccttatat atcttttttcc tttactcaaa acaaaacaat ttttagcaca 10021 ctgaaaaaaa aaaaaagcca aatgttttgt gcctttctaa ggcagcactg tatcccaggc 10081 tgcattttag gacttaatat ggaaatacca gagtctgagc tcctctacct tgagtttcat 10141 tagtccttag tgtctaggag acaggaaaga atgctctctg tgactggaga ggtgacatgc 10201 aggtgcagtg tgtctggagt ccctttcccc tgctgtgaga cttcagtgga ggagagaagc 10261 attgtaccct gggatcattt ggttggttcc aatcacaagc ttagttatca ggttgcatgc 10321 cttgtctcct gcaaaagaca gaatgtttca caattcccag gtaaactctg gaccattcca 10381 agtgtcctag ccttctgatg acattaatta cctagttgtg tcgaggagta taggatggac 10441 tctcctgaga agggggaggtt ggtggctttg tctttttcttt ttgctggatc ctgaactggt 10501 ctagacctcc tgcccccacc ccccagcccc catcagatgt ggctggcctt tcatttgaag 10561 gcttcagact taaagcatta agcagctagt gccctctgca gggcctggtt tccccaggga 10621 agggcagcaa ggaacatggg accagaagcc tgtcctcagt aatgtgacta tagtgagctt 10681 tagcaaaagt ttttctatat aatgacatct tacttatctt ttacccttttc ctcagttttc 10741 ccctgccttt aactaataaa gaattgggag acagaaattt taaagtcctc cttattcaag 10801 attttgaaat tcttagcctg ggagtgctgg agagaacctg atgctttctc cagaatgaag
```

-continued

```
10861 agtcccaatt tgtatatcag tgttaagaag aaaacaaaac aaacacatag gtgagatttt 10921 cgtggactat tttaaaaatg tgtcattaat ataaaaaatt tatattagca gtatttaatc 10981 attctcacct gtaaagaata agaaaaacag aaggtaaata ttcttacaga gaatagcaga 11041 gctttaagat tcattttcat tttaagtcca ttttattttg ccagtgtatt aatgtttaga 11101 agtctgtttt actaatgtta tttattaatt tttttttcatt tccatacaca gttagttaac 11161 taaagagctt tttcaagcac ccatgtctgt aaaaaaatat ttttaaataa agtttctttt 11221 gttgtagcag aaaaaaaaaa a
```

The RASopathies are a group of genetic heterogeneous disorders, which include but not limited to Noonan syndrome (NS), Cardiofaciocutaneous syndrome (CFC), neurofibromatosis type 1 (NF1), Noonan syndrome with multiple lentigines (NSML), Costello syndrome (CS), and Legius syndrome, with mutations in Ras/MAPK pathway involving PTPN11, SOS1, RAF1, KRAS, HRAS, MAP2K1, MAP2K2, NRAS, CBL, SHOC2, BRAF, RIT1, A2ML1, SPRED1 and NF1. Lymphatic defects in NS have been described in a subset of the NS patients, but vary in severity, location and time of onset. Reviewing the literature, we identified 52 prenatal and postnatal patients in total who present clinical features of Noonan or Noonan-like syndromes and lymphatic defects, including pleural effusion, pericardial effusions, chylothorax, hydrops, lymphangiectasis, and lymphedema. We identified mutations in PTPN11 that explain their disease. Accordingly, therapeutic interventions at the ras/MAPK ERK pathway should reverse the disease phenotype in these patients similar to what we have previously shown for ARAF mutations. Thus, our discovery that central conducting lymphatic anomaly patients have either germline or somatic mutations in the Ras/MAPK pathway is novel and identifies new targets for therapeutic development. Cellular and modeling data in support of these the RAS/MAPK pathway are described below.

A cellular model for studying the effects of potential ERK-activating mutations was developed. We have retrovirally expressed wild-type and mutant versions of proteins in the cell line Ea.hy926. The Ea.hy926 cell line is a fusion of human umbilical vein endothelial cells with a melanoma cell line. It is immortalized and retains some characteristics of endothelial cells. We have successfully used this cell line to demonstrate cellular consequences of a mutation in the ARAF gene, which causes a form of central conducting lymphatic anomaly. We have also shown reversal of the effects of the mutant ARAF in the same cell line using trametinib, a MEK inhibitor.

FIG. 1 shows the levels of activated ERK in EA.hy926 cells that express WT or mutant versions of the BRAF or PTPN11 proteins. When normalized to protein load, the cells expressing the mutant BRAF contain, in this experiment, more than 5 times the amount of phosphorylated ERK as cells expressing the wild type BRAF. Mutant BRAF is more highly expressed than WT, as was previously observed with ARAF.

Figure 2:
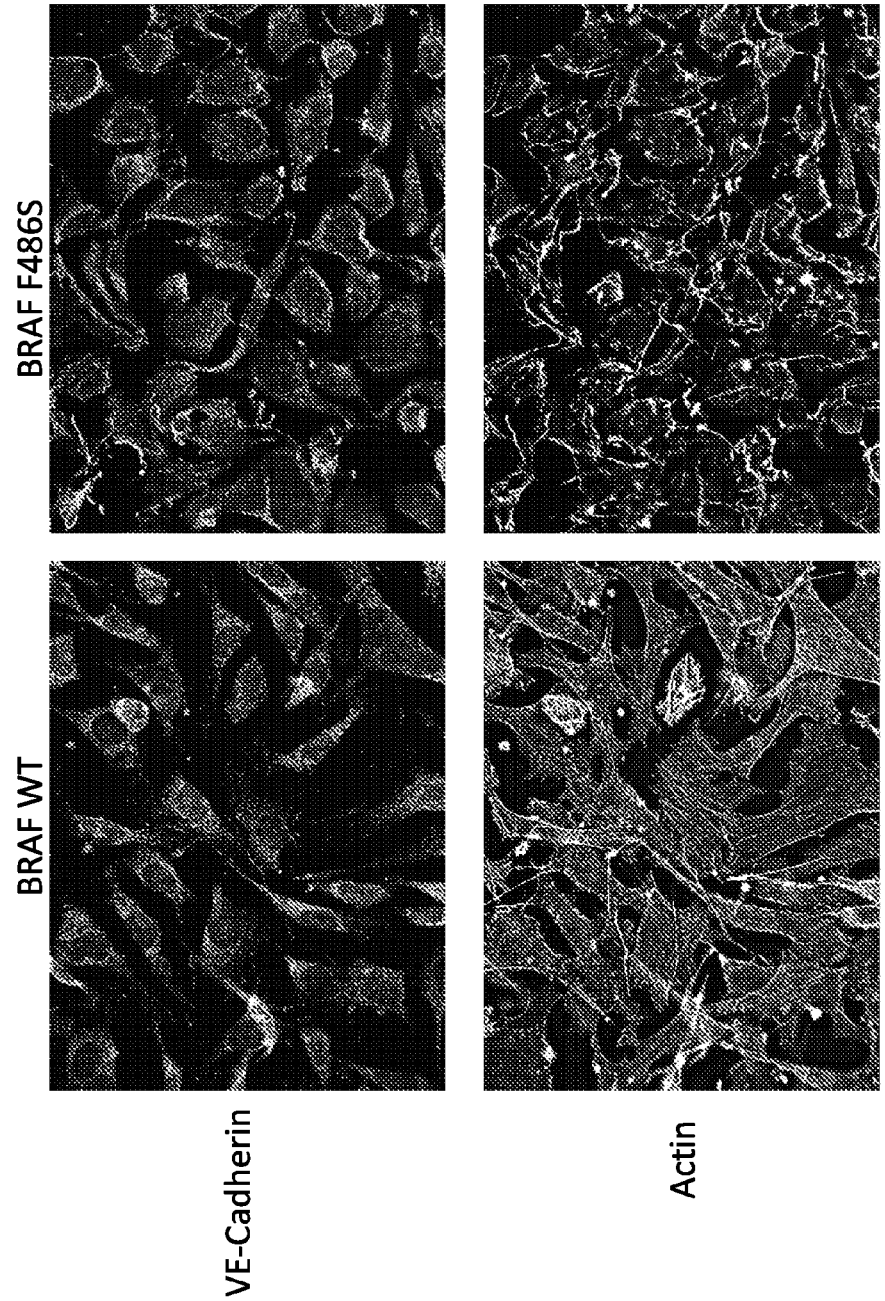
FIG. 2. Overexpression of BRAF F486S in the Ea.hy926 cell line alters cell morphology and actin organization.
Figure 3:
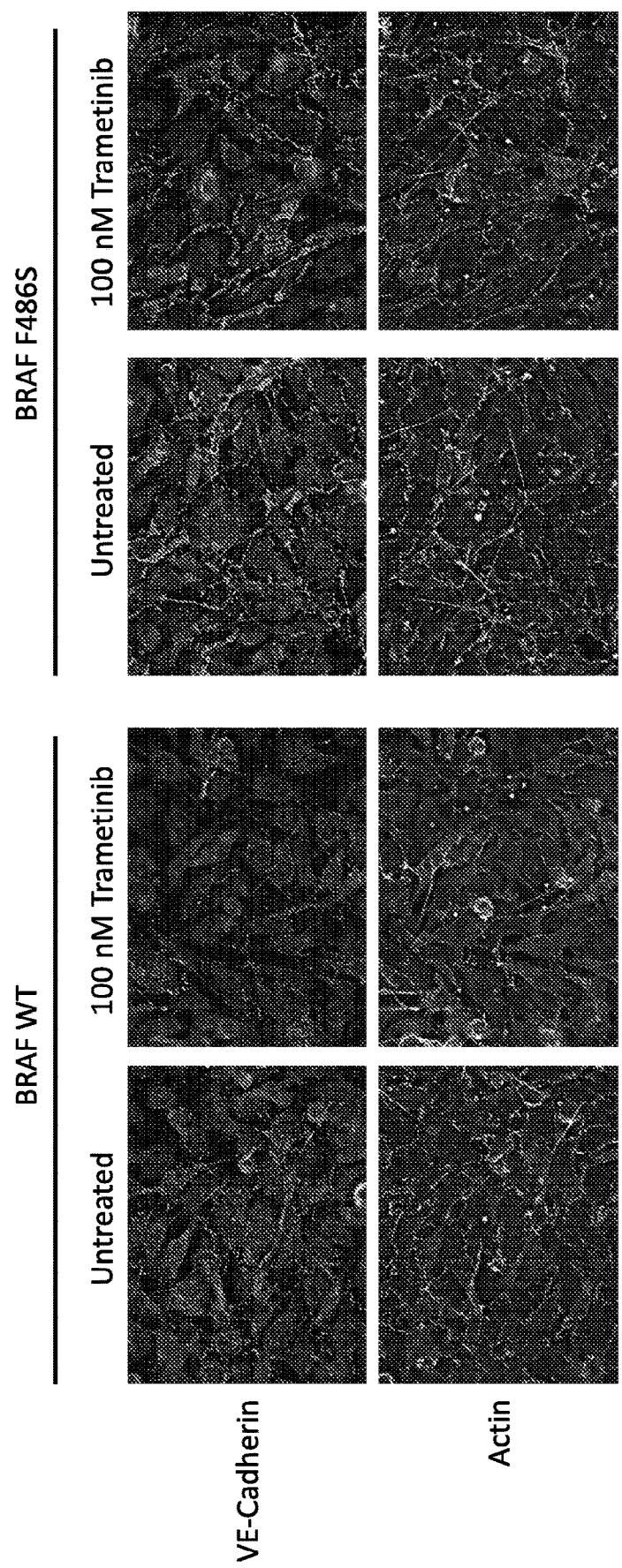
FIG. 3. Treatment with the MEK inhibitor Trametinib increases VE-cadherin surface staining and filamentous actin in cells overexpressing BRAF WT and F486S mutant.

In FIG. 2, cellular morphology changes can be observed in cells expressing the F486S BRAF mutant. Filamentous actin, as revealed by phalloidin staining, is present throughout the cell bodies of cells expressing the wild type BRAF. However, actin is largely limited to the periphery of cells expressing the BRAF mutant. This behavior is consistent with previous observations of ARAF-mutant-expressing cells. VE-cadherin staining is largely intracellular in cells expressing either WT or mutant BRAF. Our previous results with ARAF suggest that even expression of WT BRAF is inducing ERK activation in the Ea.hy926 cell line. This results in internalized VE-cadherin, although the cell morphology is not grossly changed by WT BRAF. FIG. 3 highlights the impact of ERK activation on both VE-cadherin localization and cell morphology. Treatment of cells expressing either WT or mutant BRAF results in dramatically increased cell surface staining for VE-cadherin and increased filamentous actin in the cell bodies. Morphological differences between WT and mutant-expressing cells are not as pronounced in this experiment, which may represent experiment-to-experiment variability or be due to the increased culture time and cell density in this experiment in comparison to FIG. 2. Cell morphology changes and distribution of VE-cadherin were not observed to be altered in cells expressing mutants of PTPN11.

Figure 4B:
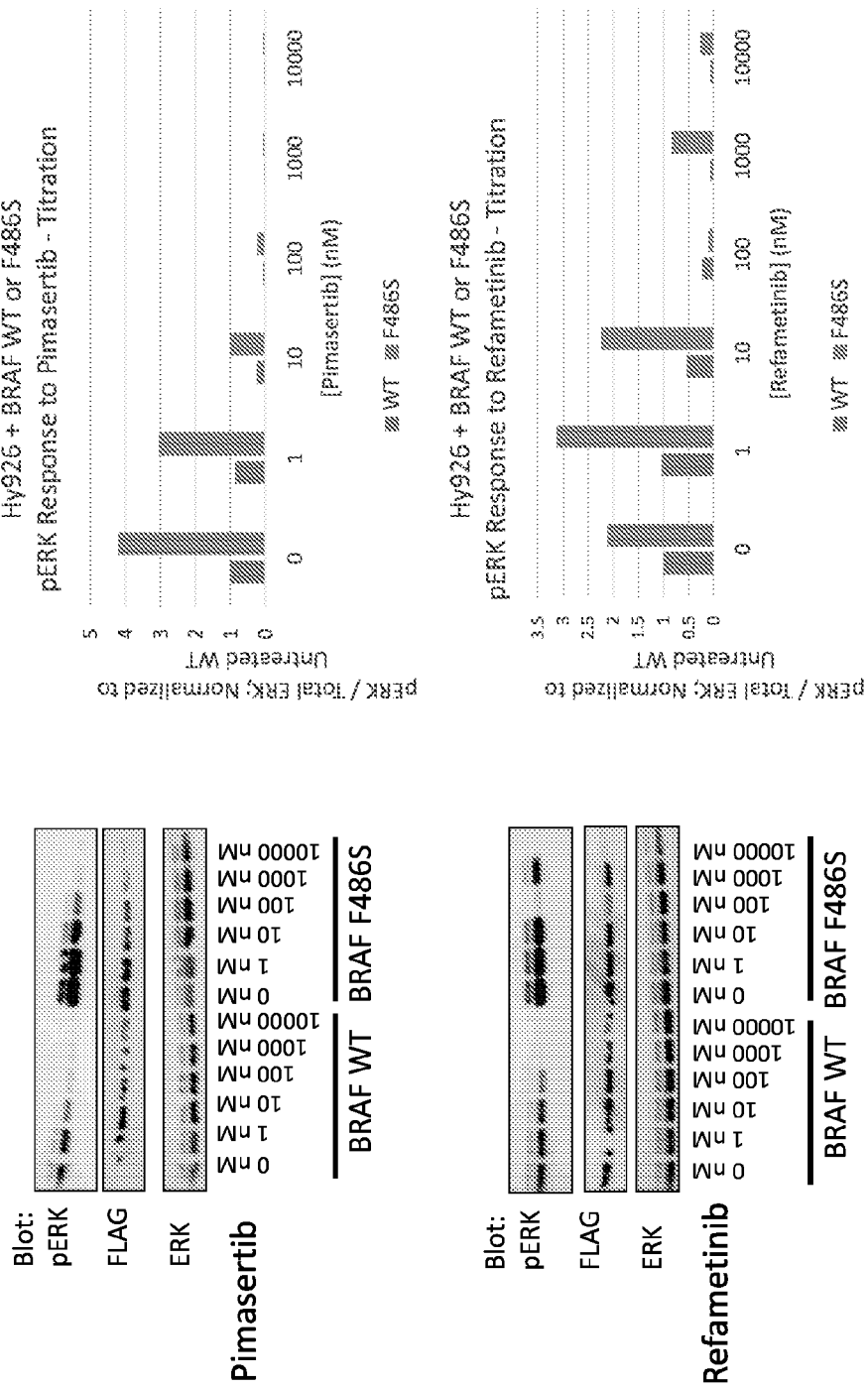
Figure 5A:
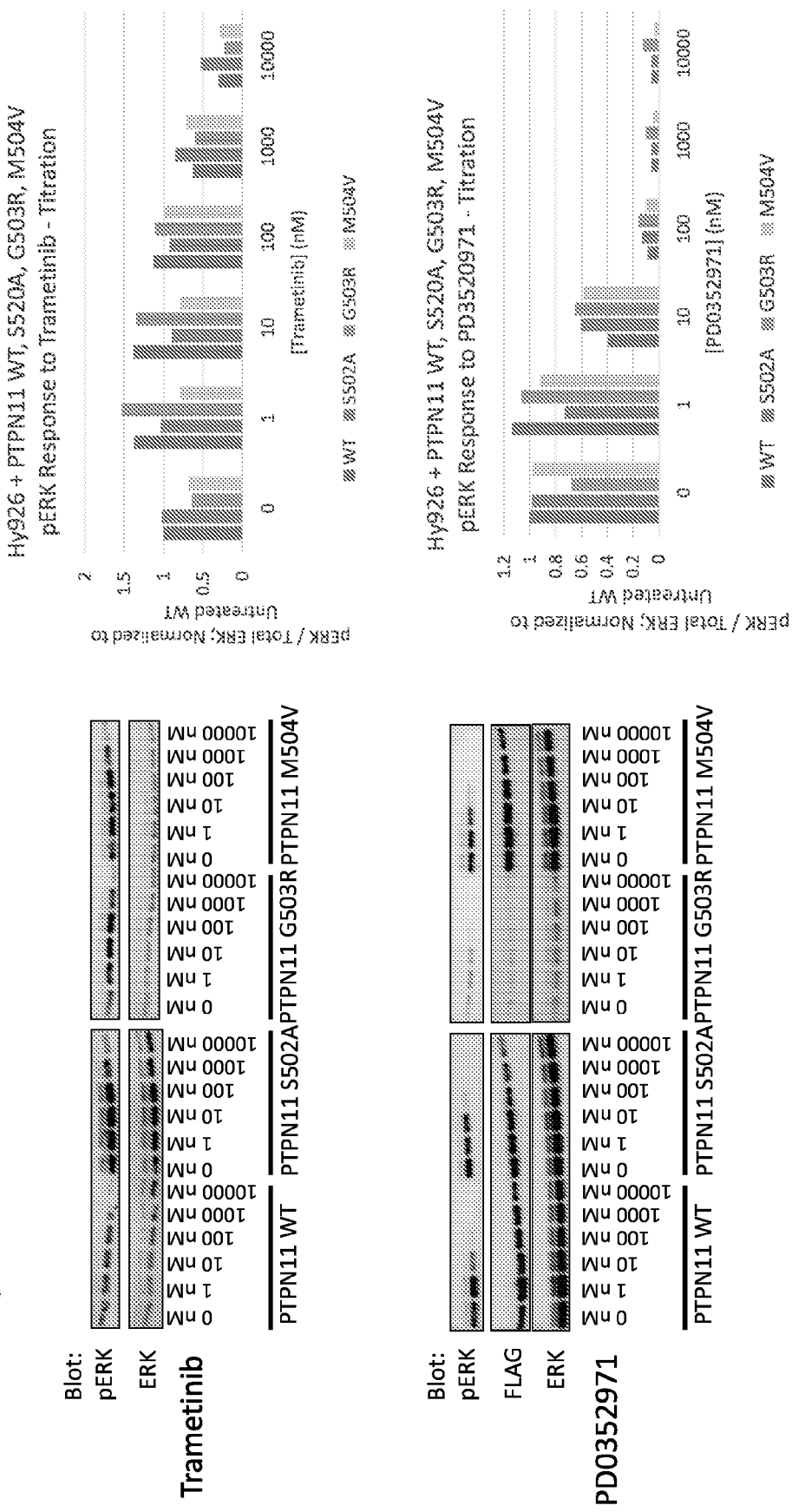
FIGS. 5A-5B. MEK inhibitors reduce ERK activation/ phosphorylation in cells overexpression PTPN11 mutants (FIG. 5A). MEK inhibitors reduce ERK activation/phosphorylation in cells overexpression PTPN11 mutants (FIG. 5B).
Figure 5B:
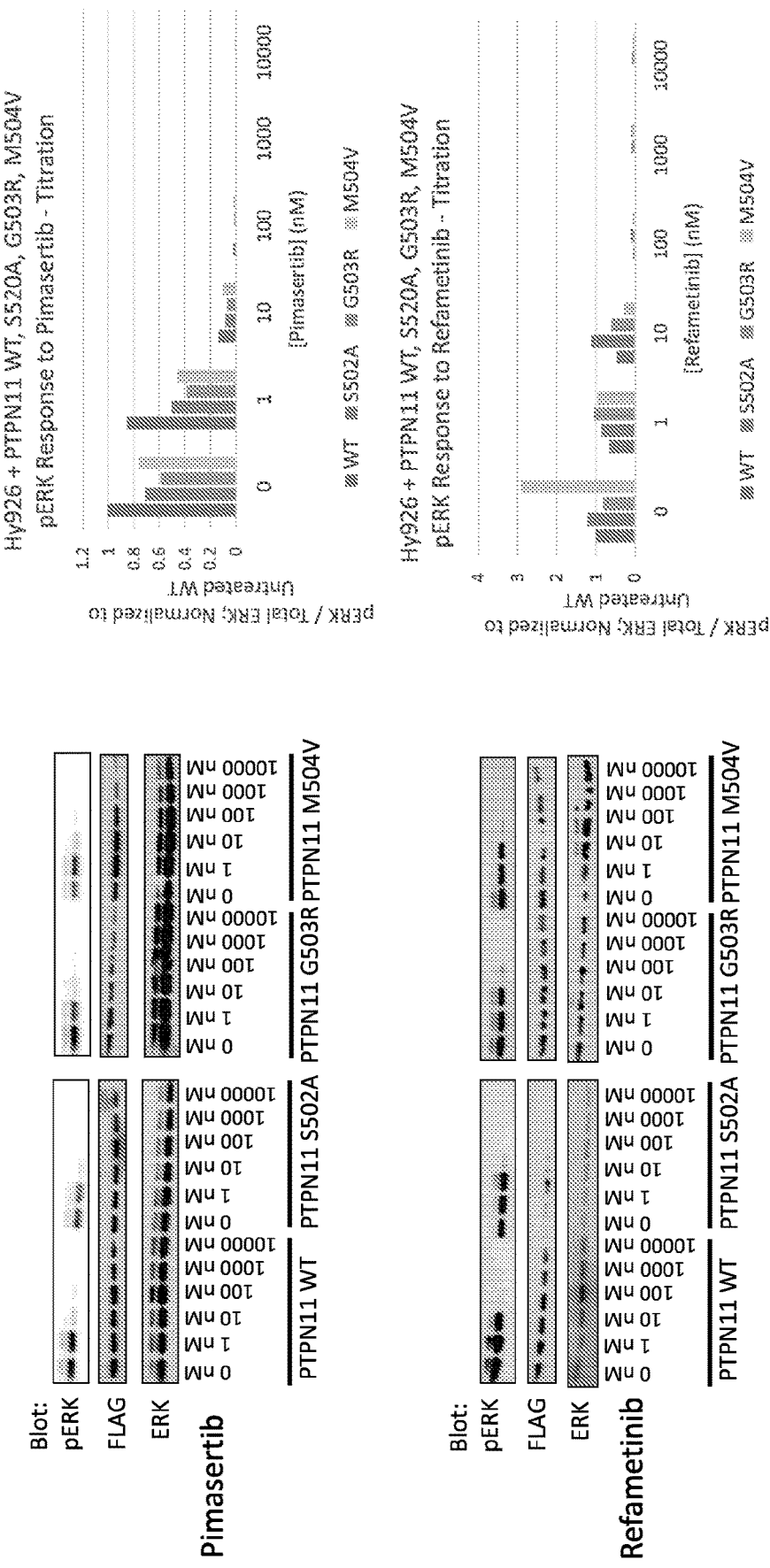

In an effort to identify inhibitors with greater therapeutic efficacy, we have treated cells expressing WT and mutant BRAF or PTPN11 with various MEK inhibitors. See FIGS. 4 and 5. We have performed titration curves with PD0352971, Pimasertib, and Refametinib, using Trametinib as a point of comparison. As expected, each inhibitor was capable of reducing pERK levels in cells in a dose dependent manner. Note that in this set of experiments, mutants of PTPN11 do not appear to activate ERK above and beyond levels seen with WT PTPN11. BRAF F486S consistently induces ERK activation over WT levels, although the specific fold increase varies from gel to gel.

Zebrafish Models of Lymphatic Vessel Disease

Clones were assembled using the gateway system (Invitrogen, Kwan 2007, Villefranc 2007 17937395, 17948311) in a vector with flanking Tol2 transposase sites to enable integration in the genome (Kawakami 1999, Ser. No. 10/564,832). Approximately 10 pl of 25 ng/ul Tol2 mRNA and vector DNA was injected in the 1st cell of freshly fertilized eggs. Construct was injected in mrc1a:GFP expressing casper fish to visualize lymphatic vessels. Confocal scans were performed using a Zeiss LSM710 confocal microscope and Zen software. Confocal z-stacks of images were superimposed using Zeiss Zen software's maximum intensity projection function. Images were compiled in imageJ (Fiji) {Schindelin 2012} and Powerpoint (Microsoft).

To assess if mutant human KRAS G12D can influence lymphatic vessel development in zebrafish we cloned both the mutant and WT gene after the lymphatic specific mrc1a promoter (Jung 2017, PMID: 28506987) and linked it to the mCherry fluorophore with a v2a autocatalytic cleavage site (Provost 2007, Ser. No. 17/941,043). We used flanking Tol2 transposase sites for genome integration. Injection of this construct with tol2 mRNA resulted in small patches of lymphatic vessels cells that express the transgenes and the mCherry marker in most injected fish when the phenotype was analyzed at 7 dpf (days post fertilization).

We investigated the phenotype in the trunk thoracic duct, one of the largest vessels at this stage that showed the most consistent expression of transgenic clones. WT KRAS expression did not show an influence on lymphatic development, however KRAS G12D causes expansion and dilation of the thoracic duct that appeared to fuse with the ventral cardinal vein In additional studies, we identified more genes/mutations in the RAS/MAPK pathway that explain lymphatic anomalies and present opportunities for new therapeutic interventions. As shown in Table 3, we identified germline or somatic mutations in RASA1, RAF1, RIT1, NF1, CBL1, and BRAF, which are all involved in the RAS/MAPK signaling pathway, further supporting the shared genetic etiology between these disease entities and the importance of mutations in the RAS/MAPK pathway in lymphatic anomalies. In addition, one homozygous missense variant was discovered in a patient with lymphedema and lymphatic conduction disorder. Accordingly, we present data demonstrating that therapeutic interventions at the linear RAS/MAPK pathway can reverse the elevated ERK1/2 activity and the lymphatic phenotype in zebrafish induced by the mutations similar to what we have previously shown for ARAF mutation.

Figure 7:
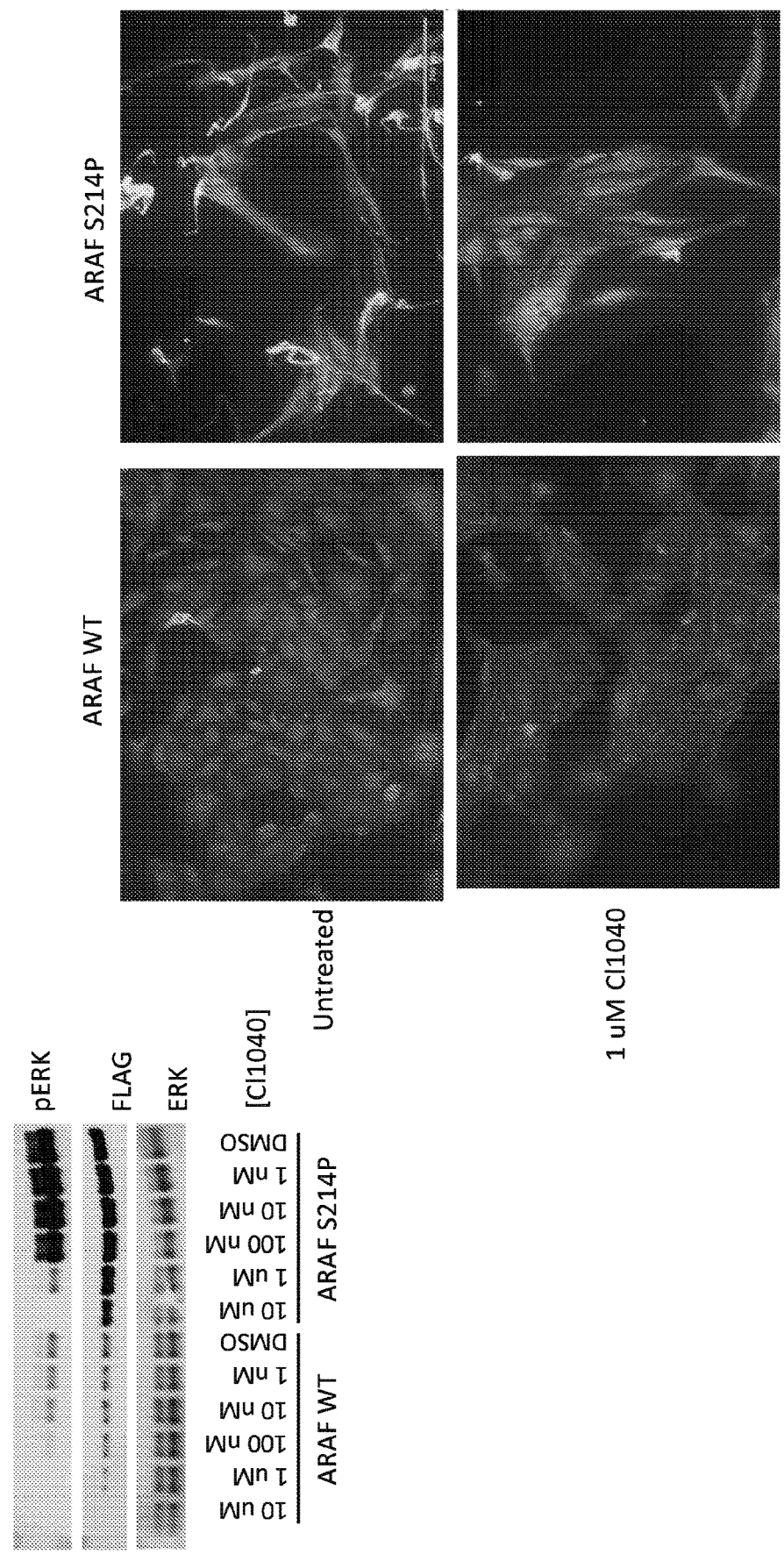
FIG. 7. Effects of CI1040 on HDLECs expressing ARAF mutation S214P. The cell morphological differences induced by ARAF-S214P was rescued by CI1040, as illustrated by reduced levels of pERK and increased VE-cadherin accumulation at the cell membrane. Green is for HA staining, which marks ARAF expressing cells; red is for VE-Cadherin staining.
Figure 8:
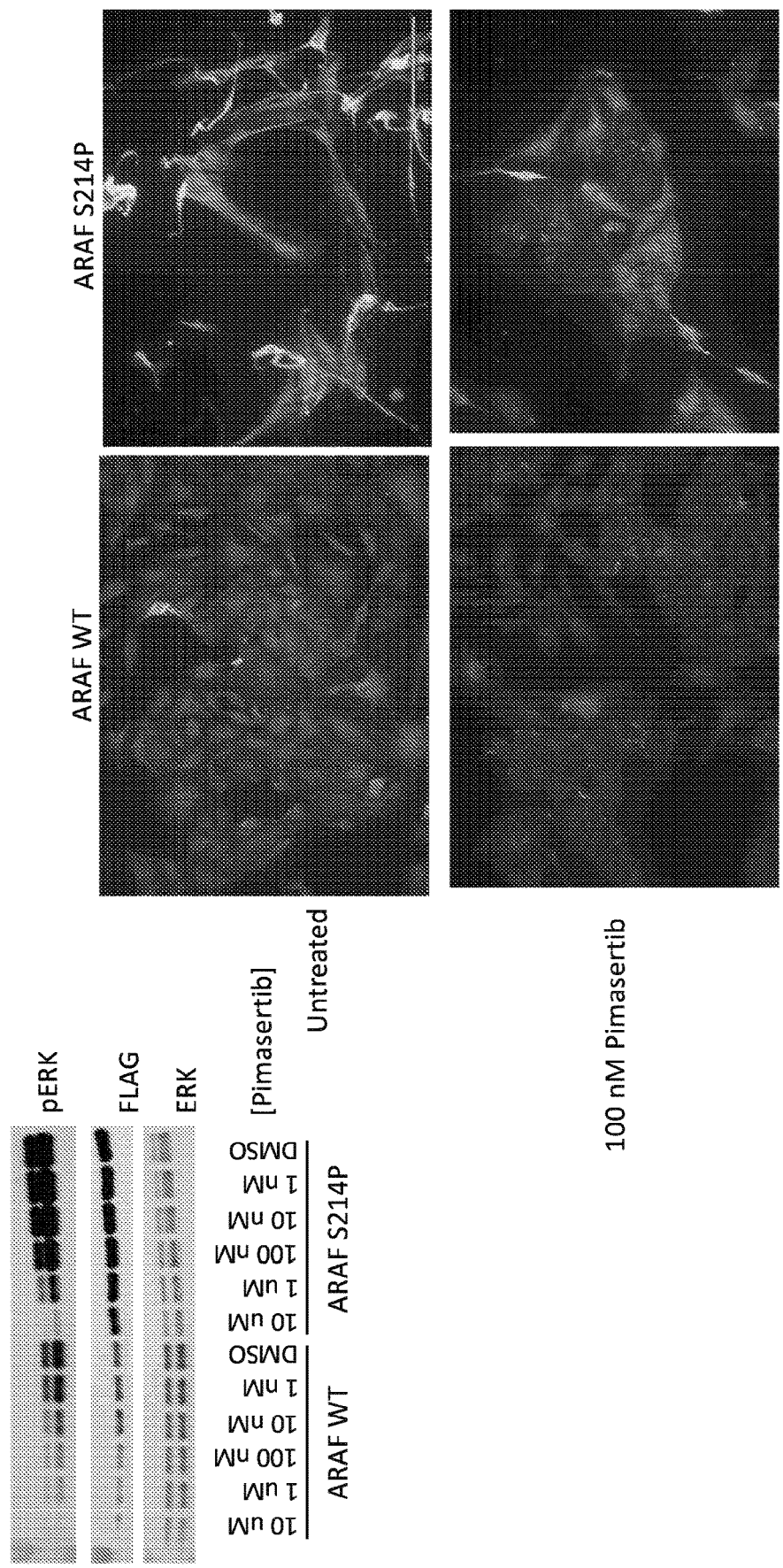
FIG. 8. Effects of Pimasertib on HDLECs expressing ARAF mutation S214P. The cell morphological differences induced by ARAF-S214P was rescued by Pimasertib, as illustrated by reduced levels of pERK and increased VE-cadherin accumulation at the cell membrane. Green is for HA staining, which marks ARAF expressing cells; red is for VE-Cadherin staining.
Figure 9:
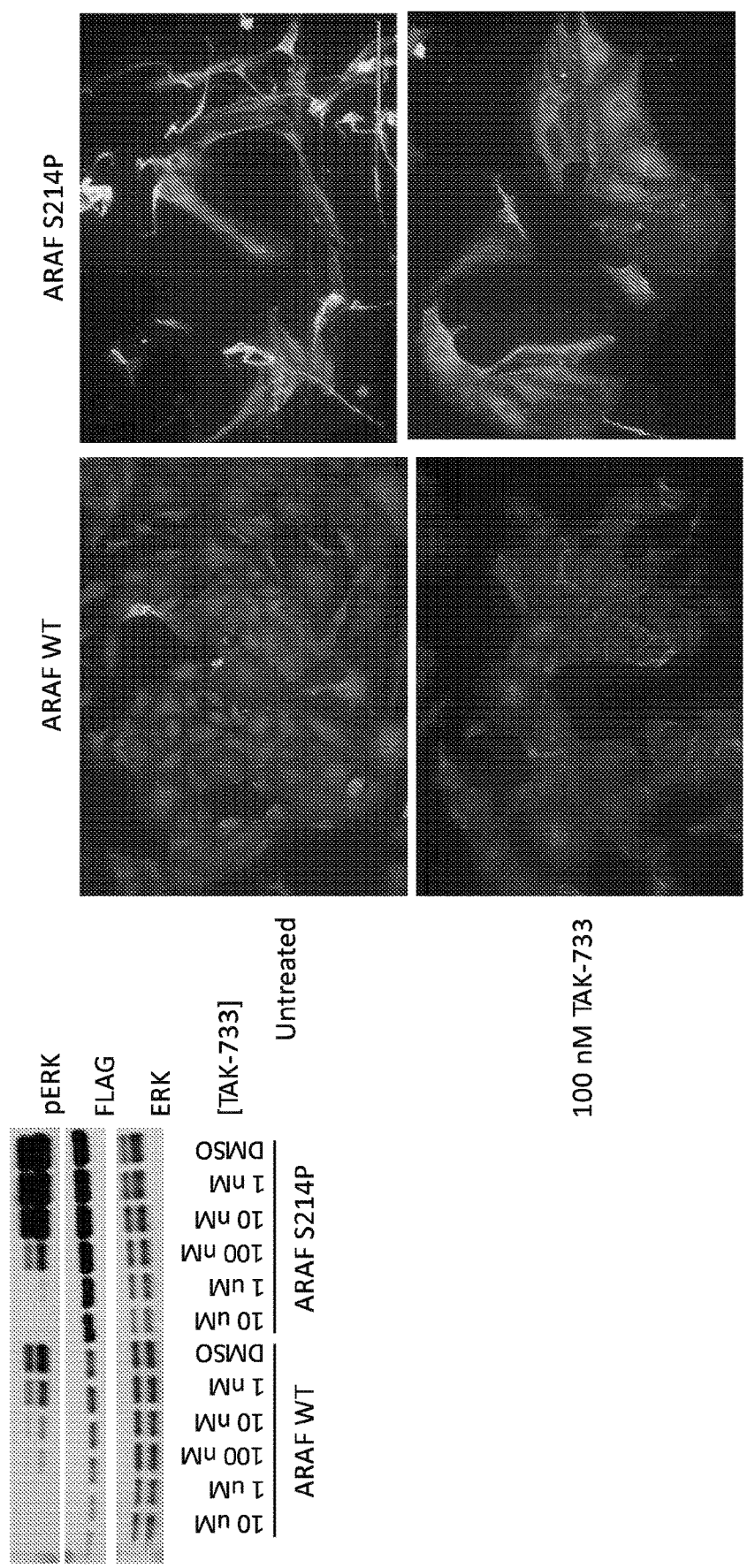
FIG. 9. Effects of TAK-733 on HDLECs expressing ARAF mutation S214P. The cell morphological differences induced by ARAF-S214P was rescued by TAK-733, as illustrated by reduced levels of pERK and increased VE-cadherin accumulation at the cell membrane. Green is for HA staining, which marks ARAF expressing cells; red is for VE-Cadherin staining.
Figure 10:
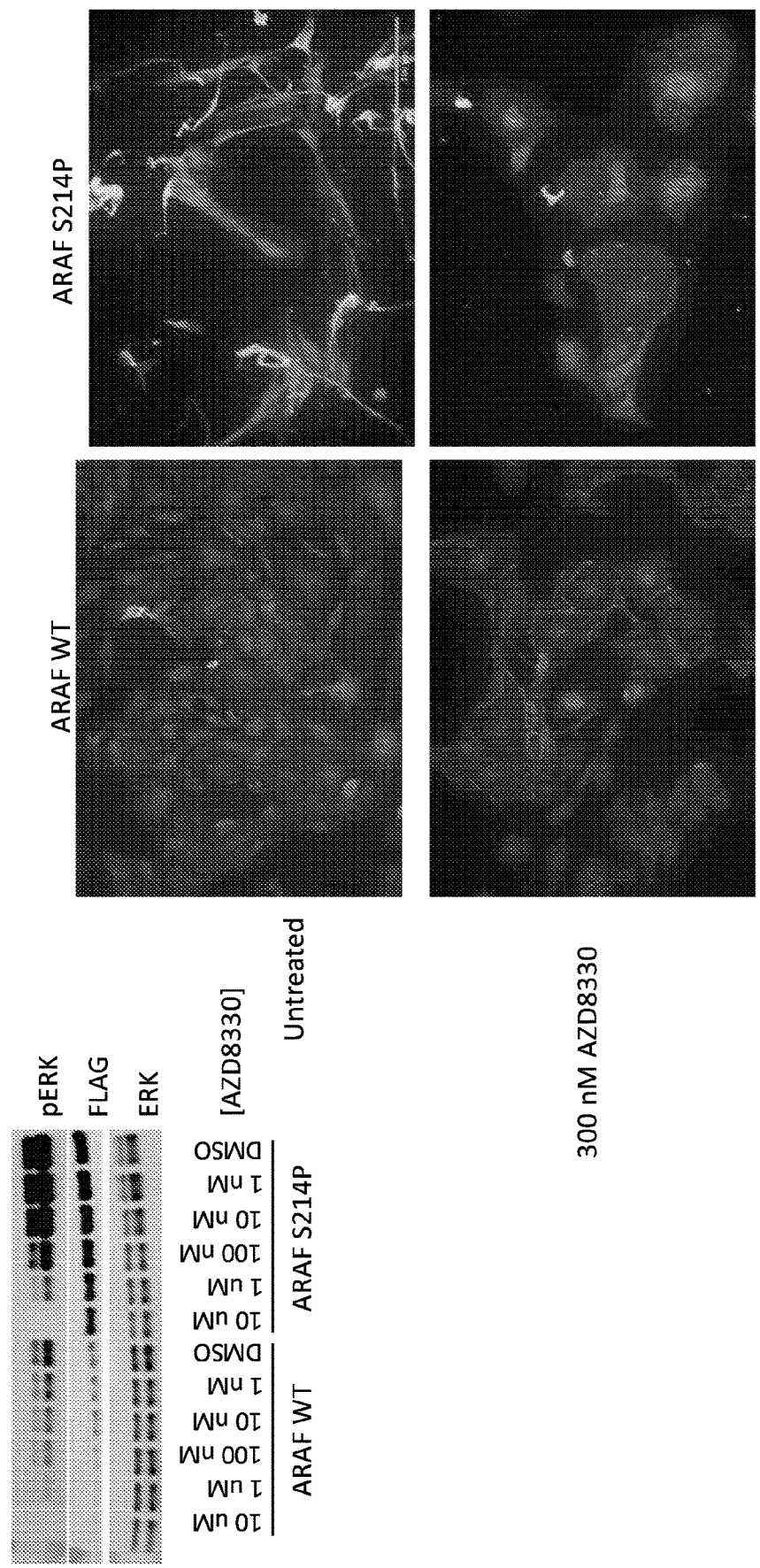
FIG. 10. Effects of AZD8330 on HDLECs expressing ARAF mutation S214P. The cell morphological differences induced by ARAF-S214P was rescued by AZD8330, as illustrated by reduced levels of pERK and increased VE-cadherin accumulation at the cell membrane. Green is for HA staining, which marks ARAF expressing cells; red is for VE-Cadherin staining.
Figure 11:
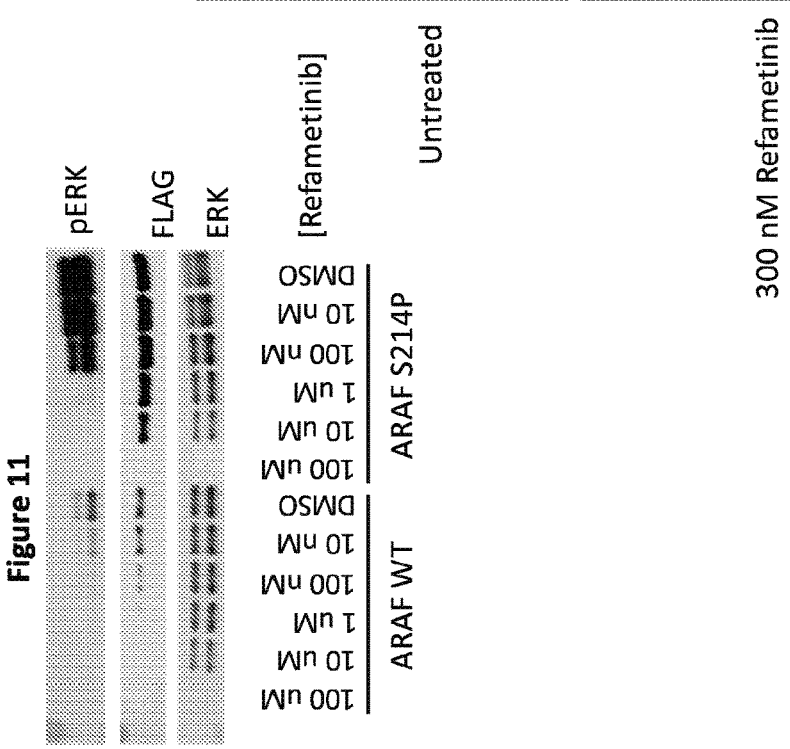
FIG. 11. Effects of Refametinib on HDLECs expressing ARAF mutation S214P. The cell morphological differences induced by ARAF-S214P was rescued by Refametinib, as illustrated by reduced levels of pERK and increased VE-cadherin accumulation at the cell membrane. Green is for HA staining, which marks ARAF expressing cells; red is for VE-Cadherin staining.
Figure 12:
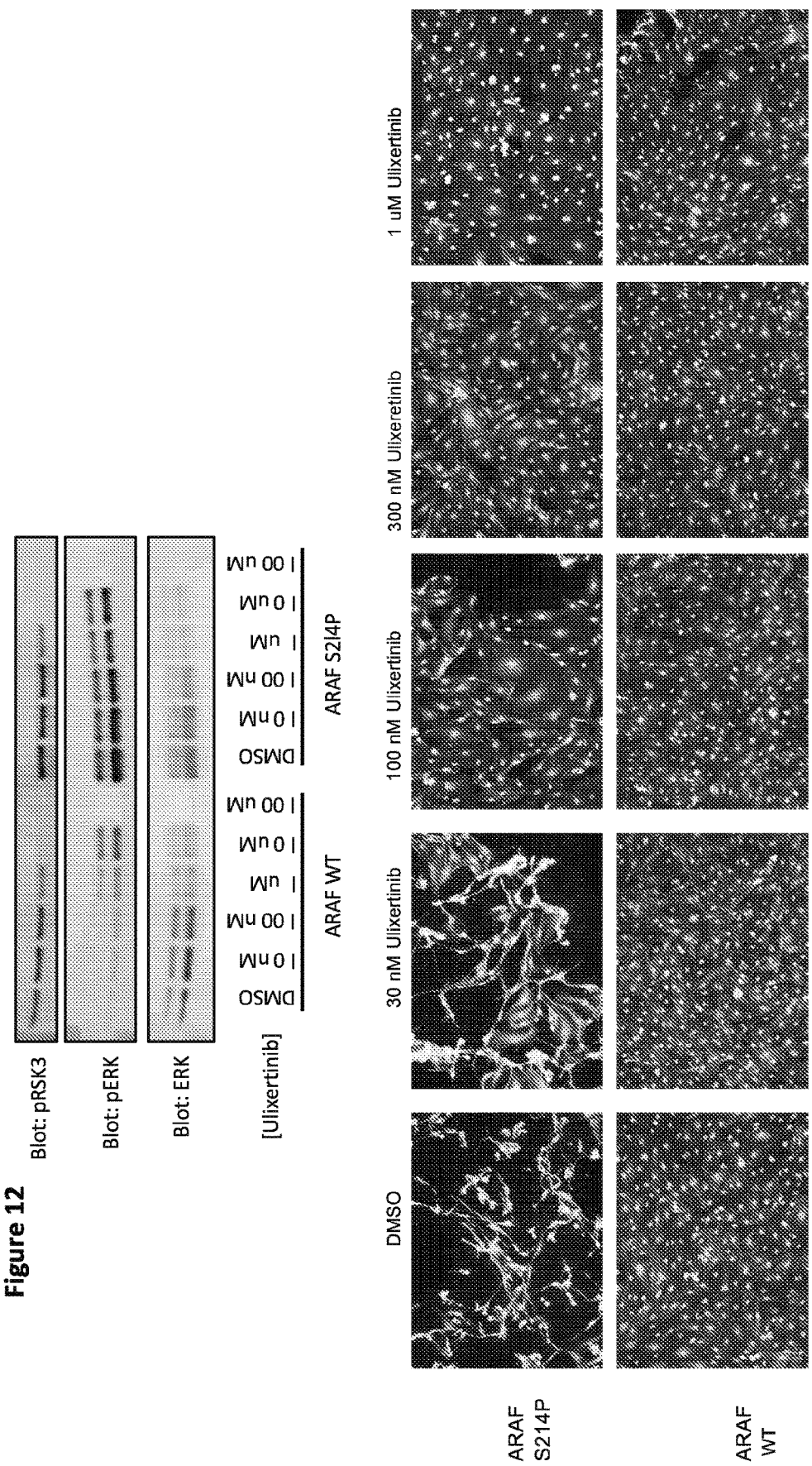
FIG. 12. Effects of Ulixertinib on HDLECs expressing ARAF mutation S214P. The cell morphological differences induced by ARAF-S214P was rescued by Ulixertinib, as illustrated by reduced levels of phosphorylation of the ERK substrate RSK3 and increased VE-cadherin accumulation at the cell membrane. Green is for HA staining, which marks ARAF expressing cells; red is for VE-Cadherin staining; and white is DAPI staining for nuclei.

We developed a cellular model to better understand and study the effects of potential ERK-activating mutations was developed by using primary lymphatic endothelial cells instead of established cell lines to capture the characteristics of mutations in the disease relevant cell type. We have retrovirally expressed wild-type and mutant versions of proteins in the human dermal lymphatic endothelial cells (HDLECs). We have successfully used these cells to demonstrate cellular consequences of a mutation in the ARAF gene, causing a form of central conducting lymphatic anomaly. We have also shown reversal of the effects of the mutant ARAF in the cells using trametinib, a MEK inhibitor, which we recently published in the Nature Medicine. Additionally, we tested seven additional MEK/ERK inhibitors in this model and showed biochemical and morphological reversal of the effects induced by the ARAF mutation, including PD0325901 (FIG. 6), CI1040/PD184352 (FIG. 7), Pimasertib (FIG. 8), TAK-733 (FIG. 9), AZD8330 (FIG. 10), Refametinib (FIG. 11), and Ulixertinib (FIG. 12), which is comparable to Trametinib.

FIGS. 6-11 show effects of each different drug (as shown on the figure) on HDLECs expressing ARAF mutation S214P. All of the drugs tested were sufficient to reverse the morphological differences induced by ARAF-S214P, demonstrating more VE-Cadherin accumulation at the cell membrane. Green is for HA staining, which marks ARAF expressing cells; red is for VE-Cadherin staining.

Figure 13:
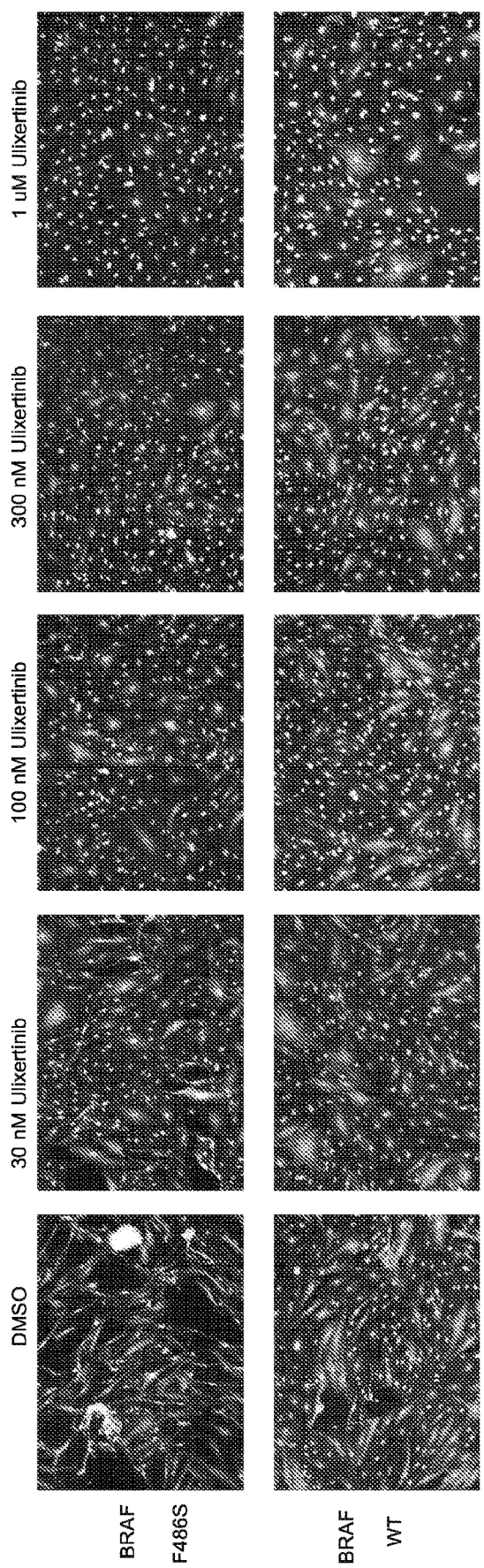
FIG. 13. Effects of Ulixertinib on HDLECs expressing BRAF mutation F486S. The cell morphological differences induced by BRAF-F486S was rescued by Ulixertinib, as illustrated by increased VE-cadherin accumulation at the cell membrane. Green is for HA staining, which marks BRAF expressing cells; red is for VE-Cadherin staining; and white is DAPI staining for nuclei.
Figure 14:
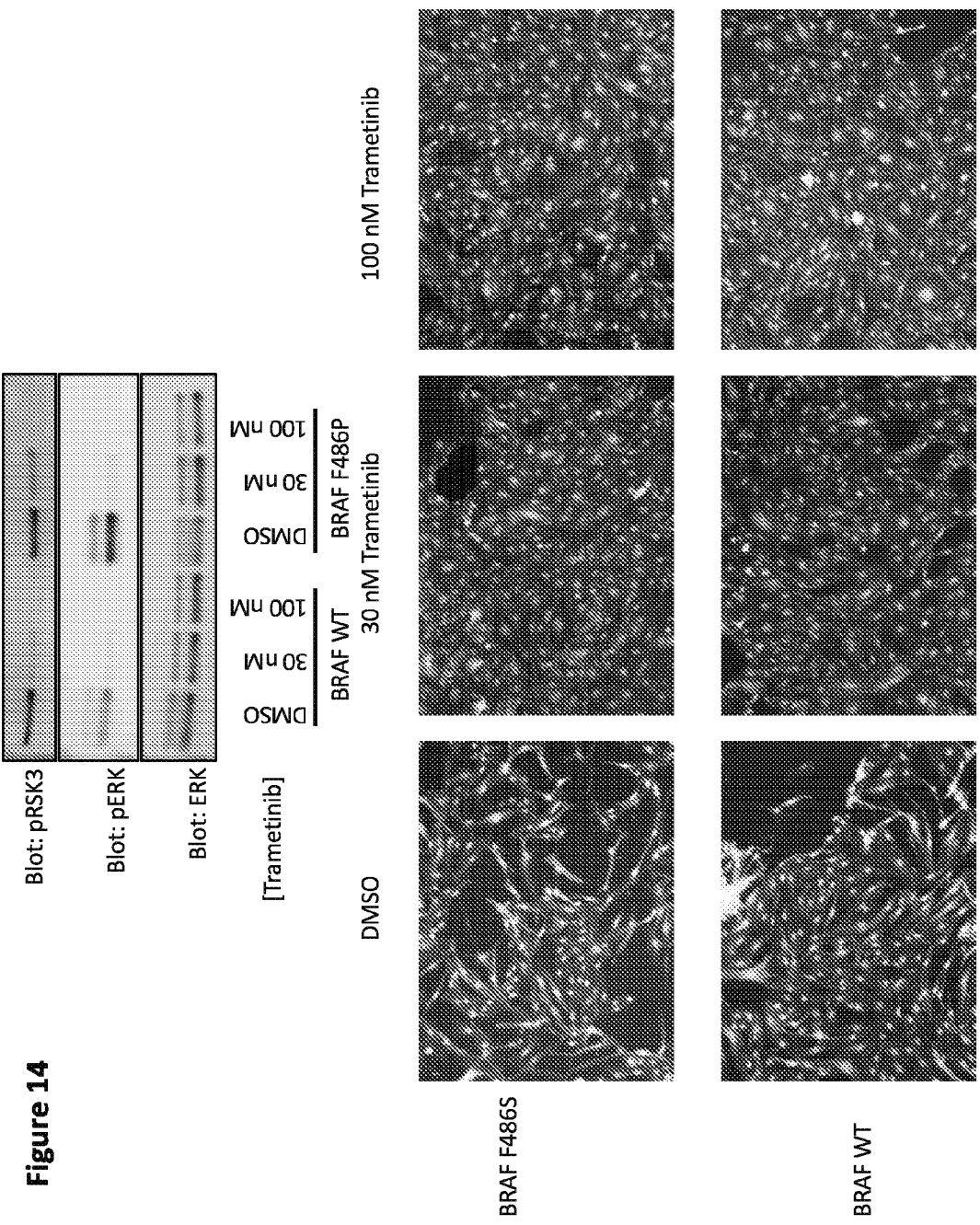
FIG. 14. Effects of Trametinib on HDLECs expressing BRAF mutation F486S. The cell morphological differences induced by BRAF-F486S was rescued by Trametinib, as illustrated by reduced levels of phosphorylation of the ERK and increased VE-cadherin accumulation at the cell membrane. Green is for HA staining, which marks BRAF expressing cells; red is for VE-Cadherin staining; and white is DAPI staining for nuclei.
Figure 15:
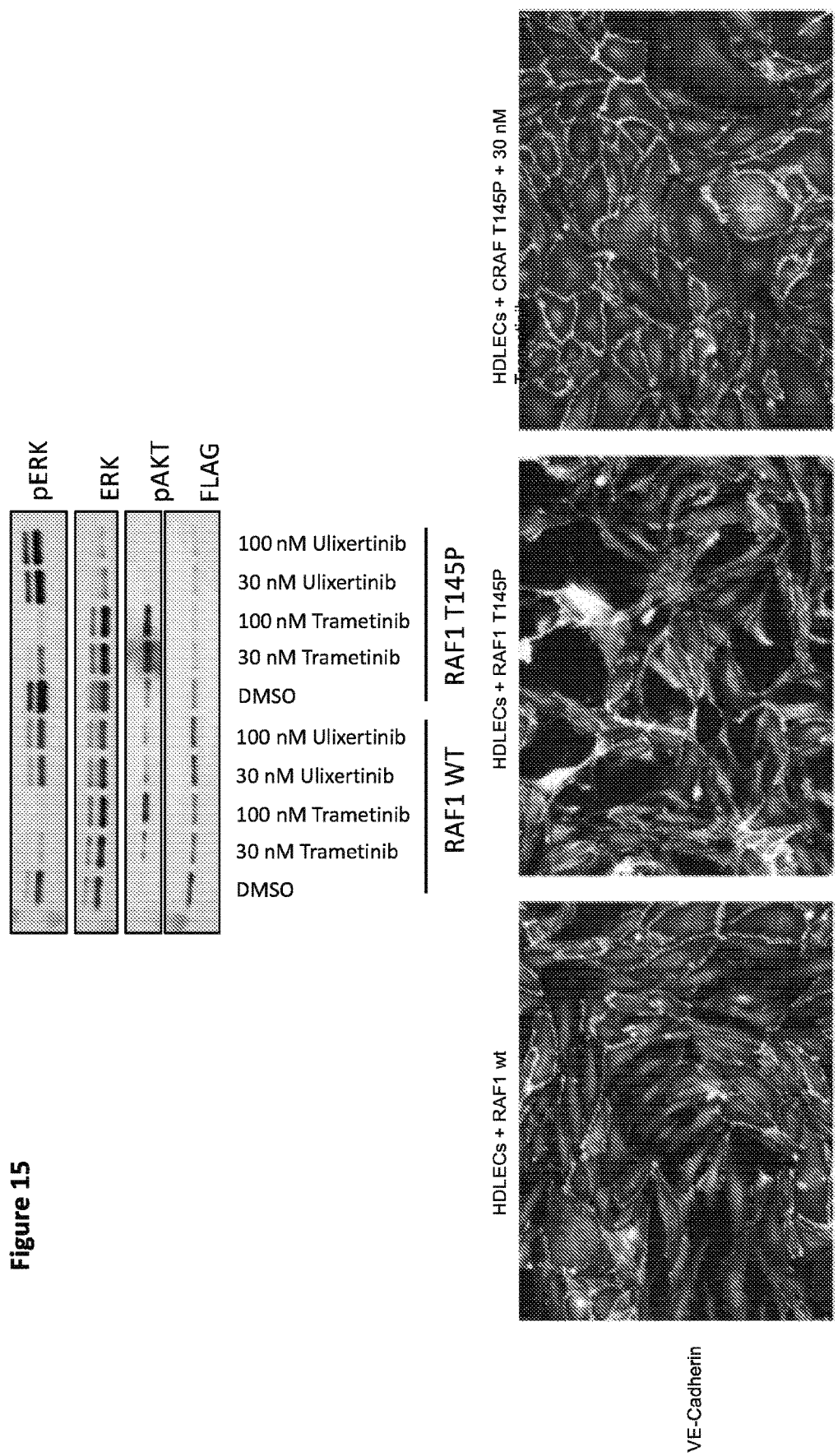
FIG. 15. Effects of Trametinib on HDLECs expressing RAF1 mutation T145P. The cell morphological differences induced by RAF1-T145P was rescued by Trametinib, as illustrated by reduced levels of phosphorylation of the ERK and increased VE-cadherin accumulation at the cell membrane.
Figure 16:
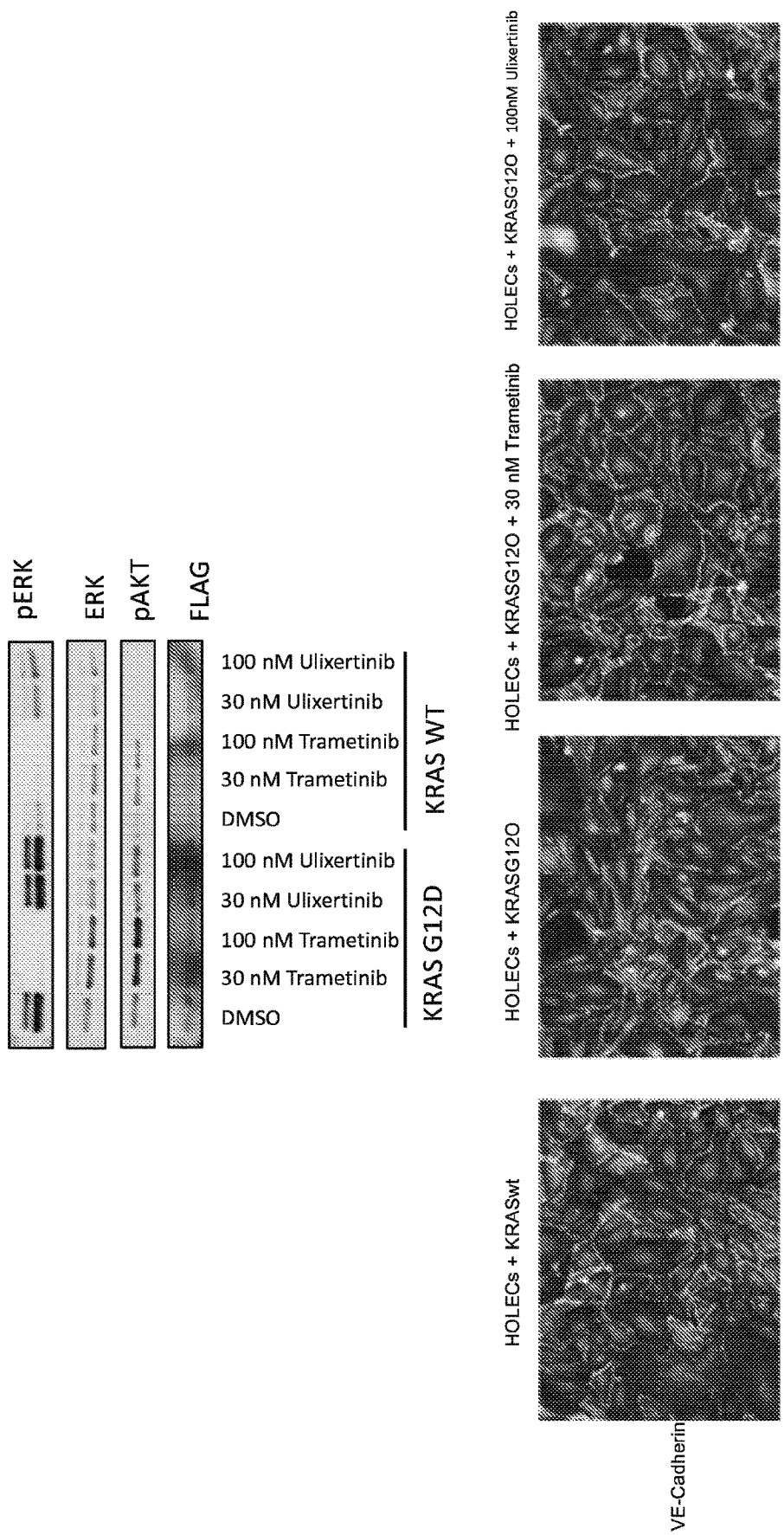
FIG. 16. Effects of Ulixertinib and Trametinib on HDLECs expressing KRAS mutation G12D. The cell morphological differences induced by KRAS-G12D was rescued by Trametinib and Ulixertinib, as illustrated by reduced levels of phosphorylation of the ERK and increased VE-cadherin accumulation at the cell membrane.
Figure 17:
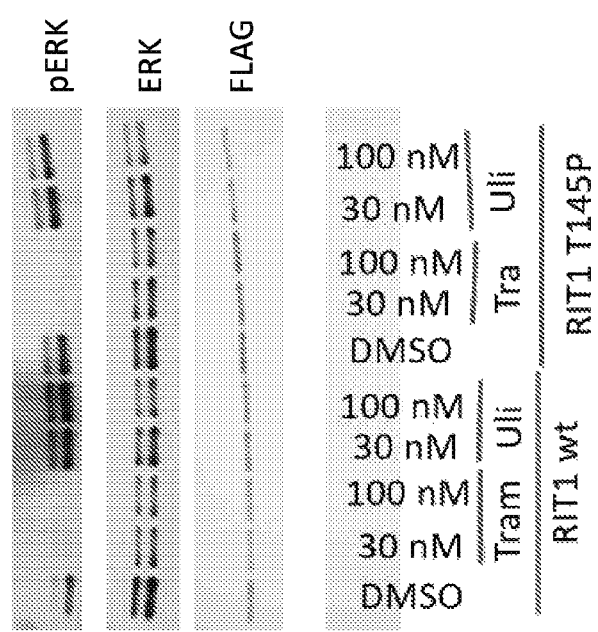
FIG. 17. Weak activation of p-ERK induced by the RIT1 mutation.

Ulixertinib is an orally effective inhibitor of ERK1/2. Previous study showed that p-ERK1/2 levels increased in various cancer cell lines after Ulixertinib treatment. However, phosphorylation of RSK (an ERK1/2 protein substrate) was reduced, which is consistent with sustained ERK1/2 inhibition. As shown on FIG. 12 upper panel, Ulixertinib treatment does reduce phosphorylation of the ERK substrate RSK3. And on the lower panel, Ulixertinib can rescue the loss of the VE-Cadherin from cell-cell junctions in HDLECs expressing ARAF-S214P with an almost complete restoration at a concentration of 300 nM (FIG. 12; green is for HA staining, which marks ARAF expressing cells; red is for VE-Cadherin staining; and white is DAPI staining for nuclei). Similarly, expressing BRAF-F486S in HDLECs causes a significant absence of VE-Cadherin accumulation between adjacent cells (FIGS. 13-14), which basically produces a similar phenotype as ARAF mutation. As expected, Ulixertinib (FIG. 13) or Trametinib (FIG. 14) treatment can rescue the phenotype, and Trametinib (FIG. 14 upper panel) can inhibit elevated ERK phosphorylation. Moreover, HDLECs expressing RAF1 or KRAS mutation showed similar morphological changes and similarly elevated p-ERKs, which could be normalized by Trametinib and Ulixertinib (FIGS. 15-16). On the other hand, weak activation of p-ERK is induced by the RIT1 mutation (FIG. 17).

Figure 18:
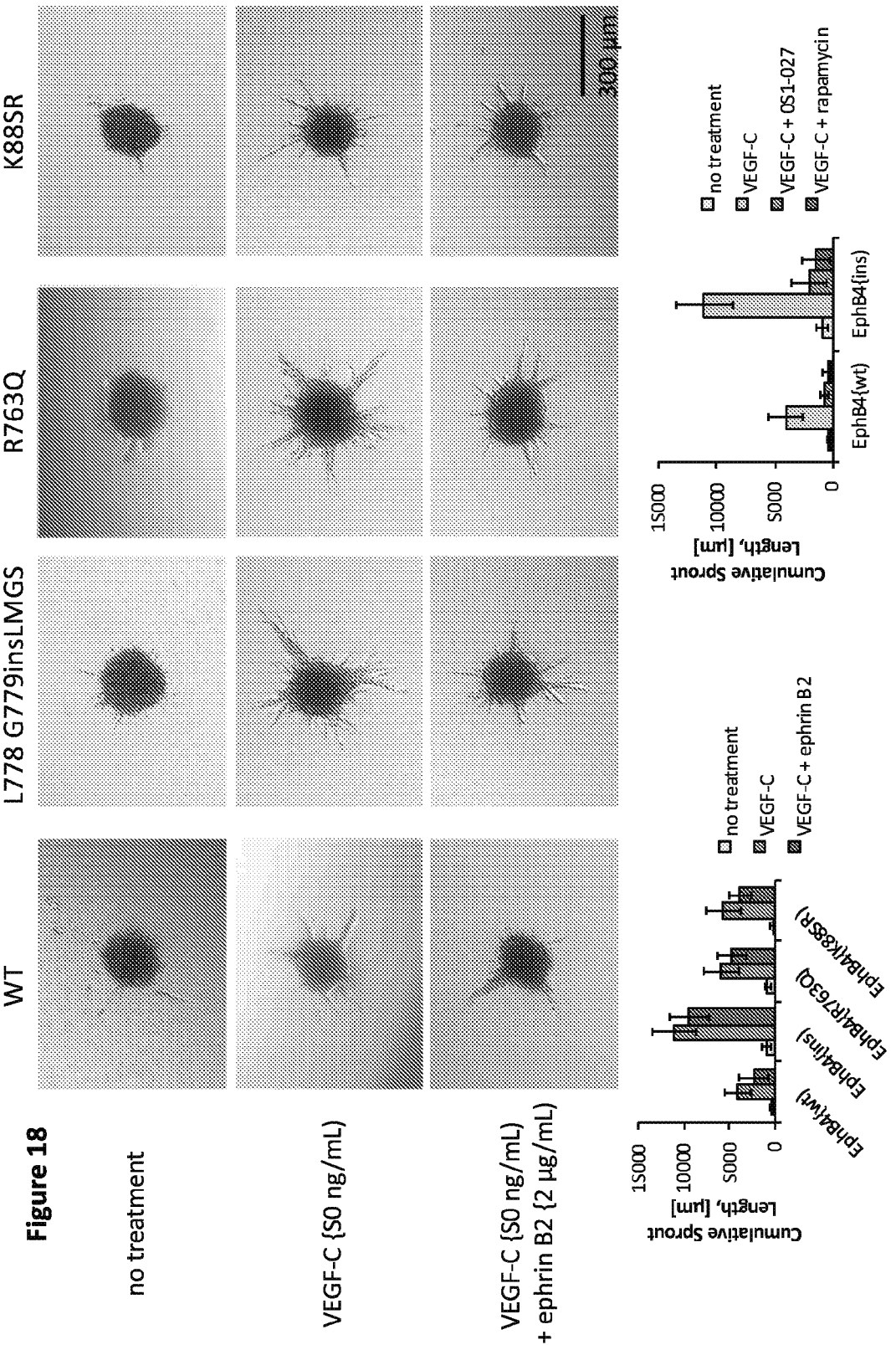
FIG. 18. Three-dimensional lymphatic spheroid sprouting assay shows the elevated sprouting activity in HDLECs expressing three different EPHB4 mutations compared with EPHB4-WT as measured by sprout length on the bottom. Both Rapamycin and OSI-027 could rescue the increased sprouting induced by the mutation L778_G779insLMGS.

We utilized a spheroid sprouting assay (3D lymphangiogenesis assay) with HDLECs to gain insights into the effects of the mutations on lymphangiogenesis. HDLECs expressing EPHB4-ins, EPHB4-R763Q, or EPHB4-K885 manifest enhanced lymphangiogenic capacity compared with HDLECs expressing EPHB4-WT, as measured by sprout length in the three-dimensional lymphatic spheroid sprouting assay conducted in the presence of vascular endothelial growth factor C (VEGFC) with or without Ephrin B2 (FIG. 18, upper panel and lower left panel). Both Rapamycin and OSI-027, a potent and selective inhibitor of mTORC1 and mTORC2, could rescue the increased sprouting in the mutants (FIG. 18, lower right panel).

Figure 19:
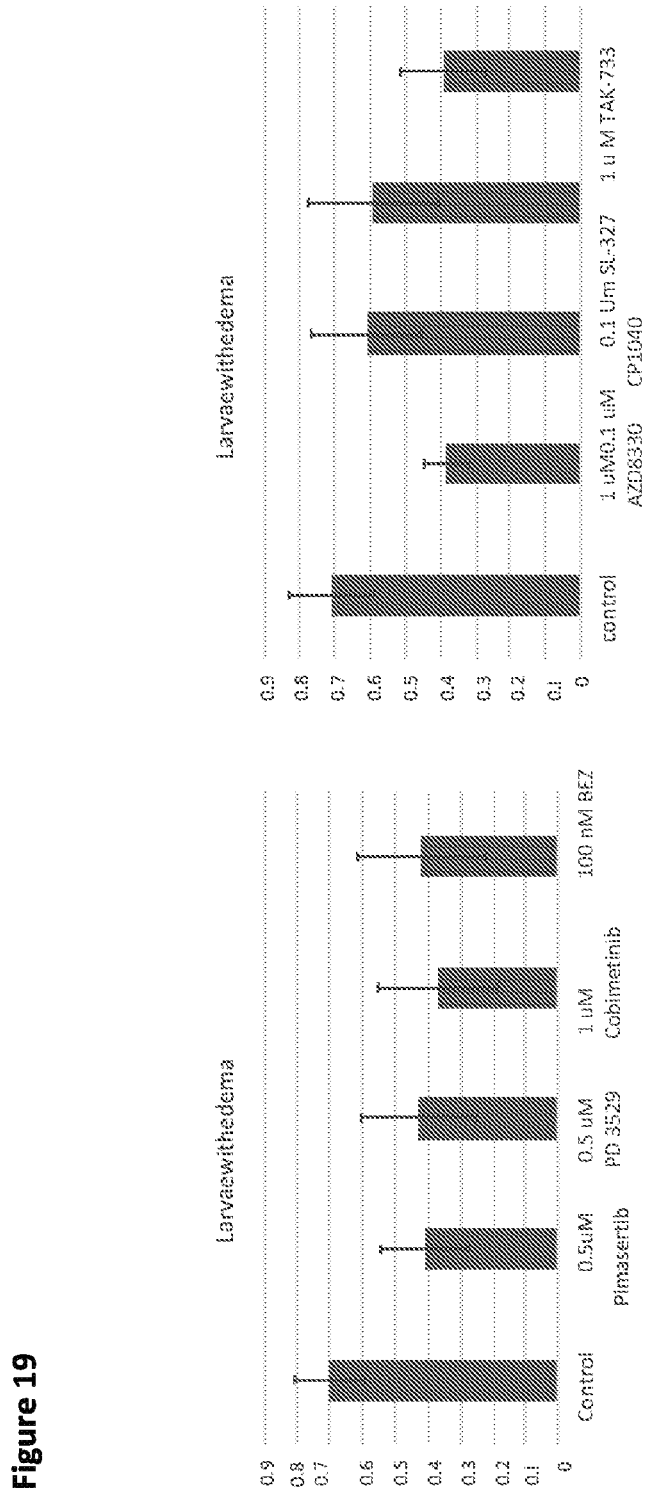
FIG. 19. Treatment with MEK inhibitors and BEZ235 resulted in significant improvement in the edema induced by KRAS mutation G12D FIG. 20. Mosaic expression of PTPN11 S502A or G503R mutation resulted in a mild lymphatic anomaly phenotype.

In the zebrafish model, overexpression of KRAS-G12D mutant, but not wild type KRAS, in lymphatics led to expansion of the thoracic duct and significant edema. We further investigated if any of the mTOR or MEK/ERK inhibitors could rescue the phenotype. Unlike rapamycin, CI1040, and SL-327 which had no significant effect, treatment with MEK inhibitors resulted in significant improvement in the phenotype. Specifically, treatment with Cobimetinib, Pimasertib, TAK-733, AZD8330, and PD0325901 led to a decrease in the edema and improvement in disorganized lymphatic branching (FIG. 19). Moreover, treatment with NVP-BEZ235, a dual inhibitor of PI3K and mTOR, showed a significant reduction of edematous larvae (FIG. 19).

Figure 20:
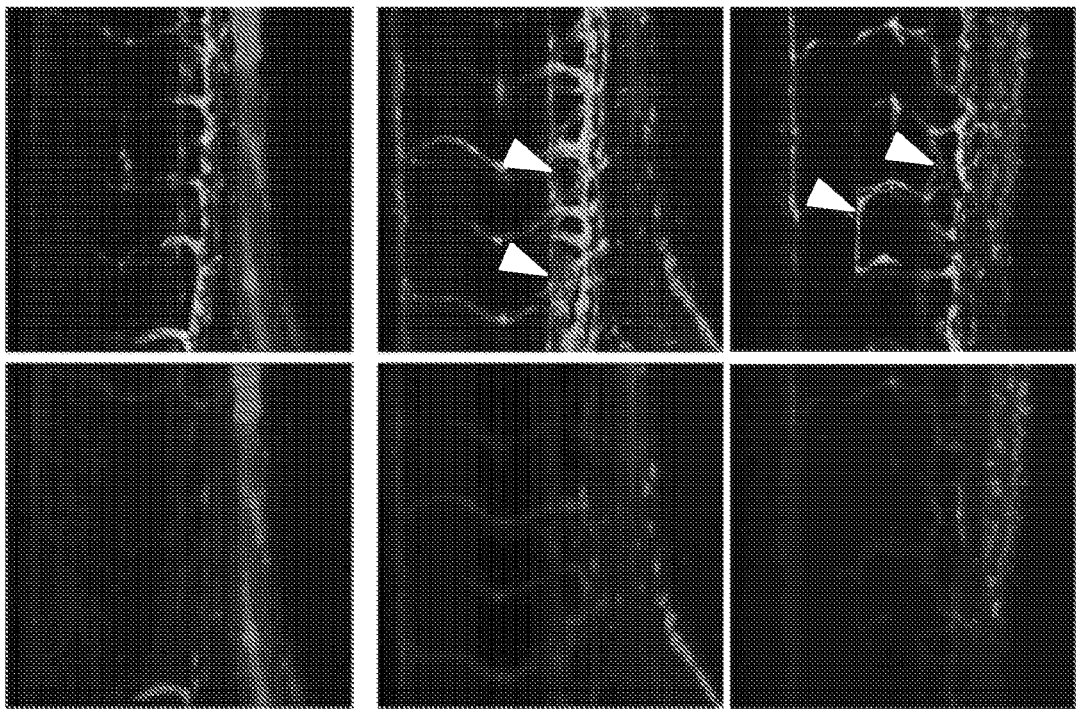

We also overexpressed PTPN11 mutations in the zebrafish model. FIG. 20 shows mosaic expression of PTPN11 5502A or G503R mutation resulted in a mild lymphatic anomaly phenotype. There were some expansions and misguiding of lymphatic tissues or fusion of posterior cardinal vein and thoracic duct.

Figure 21:
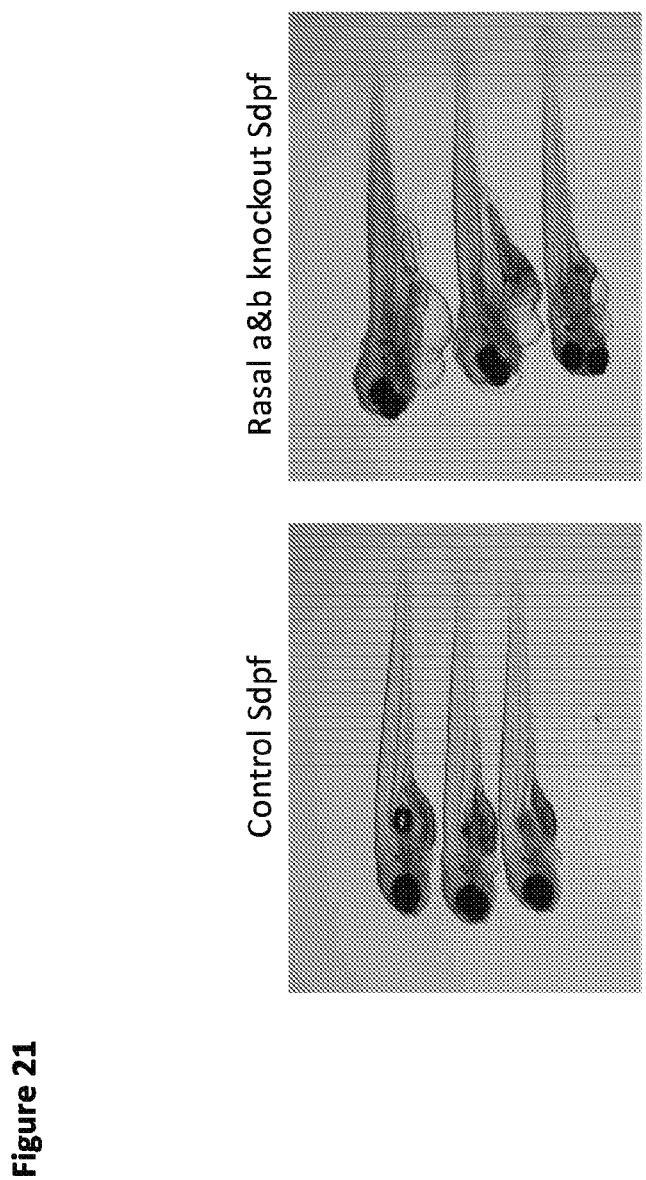
FIG. 21. CRISPR knockout target on rasa1a and rasa1b around residue 749 causes the formation of large edemas in zebrafish, single targeting (rasa1a or rasa1b) or ATG targeting does not result in any phenotypes.

There are two RASA1 homologs in zebrafish, rasa1a and rasa1b. We have designed gRNAs targeting both rasa1a and rasa1b genes, and injected into Cas9 transgenic embryos, which caused the formation of large edemas (FIG. 21).

REFERENCES FOR EXAMPLE I

1. Alitalo K, Tammela T, Petrova T V 2005 Lymphangiogenesis in development and human disease. Nature 438:946-953
2. Trenor C C, 3rd, Chaudry G 2014 Complex lymphatic anomalies. Semin Pediatr Surg 23:186-190
3. Levine C 1989 Primary disorders of the lymphatic vessels—a unified concept. J Pediatr Surg 24:233-240
4. Wassef M, Blei F, Adams D, Alomari A, Baselga E, Berenstein A, Burrows P, Frieden I J, Garzon M C, Lopez-Gutierrez J C, Lord D J, Mitchel S, Powell J, Prendiville J, Vikkula M 2015 Vascular Anomalies Classification: Recommendations From the International Society for the Study of Vascular Anomalies. Pediatrics 136:e203-214
5. Hilliard R I, McKendry J B, Phillips M J 1990 Congenital abnormalities of the lymphatic system: a new clinical classification. Pediatrics 86:988-994

6. Smeltzer D M, Stickler G B, Fleming R E 1986 Primary lymphatic dysplasia in children: chylothorax, chylous ascites, and generalized lymphatic dysplasia. Eur J Pediatr 145:286-292
7. Faul J L, Berry G J, Colby T V, Ruoss S J, Walter M B, Rosen G D, Raffin T A 2000 Thoracic lymphangiomas, lymphangiectasis, lymphangiomatosis, and lymphatic dysplasia syndrome. Am J Respir Crit Care Med 161:1037-1046
8. Brouillard P, Boon L, Vikkula M 2014 Genetics of lymphatic anomalies. J Clin Invest 124:898-904
9. Luks V L, Kamitaki N, Vivero M P, Uller W, Rab R, Bovee J V, Rialon K L, Guevara C J, Alomari A I, Greene A K, Fishman S J, Kozakewich H P, Maclellan R A, Mulliken J B, Rahbar R, Spencer S A, Trenor C C, 3rd, Upton J, Zurakowski D, Perkins J A, Kirsh A, Bennett J T, Dobyns W B, Kurek K C, Warman M L, McCarroll S A, Murillo R 2015 Lymphatic and other vascular malformative/overgrowth disorders are caused by somatic mutations in PIK3CA. J Pediatr 166:1048-1054 e1041-1045
10. Kurek K C, Luks V L, Ayturk U M, Alomari A I, Fishman S J, Spencer S A, Mulliken J B, Bowen M E, Yamamoto G L, Kozakewich H P, Warman M L 2012 Somatic mosaic activating mutations in PIK3CA cause CLOVES syndrome. Am J Hum Genet 90:1108-1115
11. Lindhurst M J, Sapp J C, Teer J K, Johnston J J, Finn E M, Peters K, Turner J, Cannons J L, Bick D, Blakemore L, Blumhorst C, Brockmann K, Calder P, Cherman N, Deardorff M A, Everman D B, Golas G, Greenstein R M, Kato B M, Keppler-Noreuil K M, Kuznetsov S A, Miyamoto R T, Newman K, Ng D, O'Brien K, Rothenberg S, Schwartzentruber D J, Singhal V, Tirabosco R, Upton J, Wientroub S, Zackai E H, Hoag K, Whitewood-Neal T, Robey P G, Schwartzberg P L, Darling T N, Tosi L L, Mullikin J C, Biesecker L G 2011 A mosaic activating mutation in AKT1 associated with the *Proteus* syndrome. N Engl J Med 365:611-619
12. Revencu N, Boon L M, Mendola A, Cordisco M R, Dubois J, Clapuyt P, Hammer F, Amor D J, Irvine A D, Baselga E, Dompmartin A, Syed S, Martin-Santiago A, Ades L, Collins F, Smith J, Sandaradura S, Barrio V R, Burrows P E, Blei F, Cozzolino M, Brunetti-Pierri N, Vicente A, Abramowicz M, Desir J, Vilain C, Chung W K, Wilson A, Gardiner C A, Dwight Y, Lord D J, Fishman L, Cytrynbaum C, Chamlin S, Ghali F, Gilaberte Y, Joss S, Boente Mdel C, Leaute-Labreze C, Delrue M A, Bayliss S, Martorell L, Gonzalez-Ensenat M A, Mazereeuw-Hautier J, O'Donnell B, Bessis D, Pyeritz R E, Salhi A, Tan O T, Wargon O, Mulliken J B, Vikkula M 2013 RASA1 mutations and associated phenotypes in 68 families with capillary malformation-arteriovenous malformation. Hum Mutat 34:1632-1641
13. Burrows P E, Gonzalez-Garay M L, Rasmussen J C, Aldrich M B, Guilliod R, Maus E A, Fife C E, Kwon S, Lapinski P E, King P D, Sevick-Muraca E M 2013 Lymphatic abnormalities are associated with RASA1 gene mutations in mouse and man. Proc Natl Acad Sci USA 110:8621-8626
14. Lo I F, Brewer C, Shannon N, Shorto J, Tang B, Black G, Soo M T, Ng D K, Lain S T, Kerr B 2008 Severe neonatal manifestations of Costello syndrome. J Med Genet 45:167-171
15. Fabretto A, Kutsche K, Harmsen M B, Demarini S, Gasparini P, Fertz M C, Zenker M 2010 Two cases of Noonan syndrome with severe respiratory and gastroenteral involvement and the SOS1 mutation F6231. Eur J Med Genet 53:322-324
16. Joyce S, Gordon K, Brice G, Ostergaard P, Nagaraja R, Short J, Moore S, Mortimer P, Mansour S 2016 The lymphatic phenotype in Noonan and Cardiofaciocutaneous syndrome. Eur J Hum Genet 24:690-696
17. Morcaldi G, Bellini T, Rossi C, Maghnie M, Boccardo F, Bonioli E, Bellini C 2015 Lymphodysplasia and Kras Mutation: A Case Report and Literature Review. Lymphology 48:121-127
18. Makinen T, Adams R H, Bailey J, Lu Q, Ziemiecki A, Alitalo K, Klein R, Wilkinson G A 2005 PDZ interaction site in ephrinB2 is required for the remodeling of lymphatic vasculature. Genes Dev 19:397-410
19. Kume T 2010 Specification of arterial, venous, and lymphatic endothelial cells during embryonic development. Histol Histopathol 25:637-646
20. Hashimoto T, Tsuneki M, Foster T R, Santana J M, Bai H, Wang M, Hu H, Hanisch J J, Dardik A 2016 Membrane-mediated regulation of vascular identity. Birth Defects Res C Embryo Today 108:65-84
21. Martin-Almedina S, Martinez-Corral I, Holdhus R, Vicente A, Fotiou E, Lin S, Petersen K, Simpson M A, Hoischen A, Gilissen C, Jeffery H, Atton G, Karapouliou C, Brice G, Gordon K, Wiseman J W, Wedin M, Rockson S G, Jeffery S, Mortimer P S, Snyder M P, Berland S, Mansour S, Makinen T, Ostergaard P 2016 EPHB4 kinase-inactivating mutations cause autosomal dominant lymphatic-related hydrops fetalis. J Clin Invest 126:3080-3088
22. Kettleborough R N, Busch-Nentwich E M, Harvey S A, Dooley C M, de Bruijn E, van Eeden F, Sealy I, White R J, Herd C, Nijman I J, Fenyes F, Mehroke S, Scahill C, Gibbons R, Wali N, Carruthers S, Hall A, Yen J, Cuppen E, Stemple D L 2013 A systematic genome-wide analysis of zebrafish protein-coding gene function. Nature 496:494-497
23. Sun S, Chen S, Liu F, Wu H, McHugh J, Bergin I L, Gupta A, Adams D, Guan J L 2015 Constitutive Activation of mTORC1 in Endothelial Cells Leads to the Development and Progression of Lymphangiosarcoma through VEGF Autocrine Signaling. Cancer Cell 28:758-772.

Example II

ARAF Recurrent Mutation Causes Central Conducting Lymphatic Anaomaly Treatable with a MEK Inhibitor Although recent studies have demonstrated the benefit of sirolimus in the treatment of generalized lymphatic anomaly (GLA) and central conducting lymphatic anomaly (CCLA) 3-5, the absence of clear clinical distinctions between these entities, due to their rarity and overlapping of diagnostic criteria, has hampered the development of innovative therapies6-9. GLA is defined as multifocal lymphatic anomaly that has multiple areas of micro/macrocystic lymphatic malformation and often involves bone destruction9-11. CCLA, on the other hand, describes dysfunction of the thoracic duct (TD) or cisterna chyli, leading to a retrograde flux of lymphatic fluid or abnormal drainage of lymphatic fluid1, 12, 13, Both conditions can manifest with chylothorax, effusions, chylous ascites or lymphedema. The overlap of these apparently disparate disorders suggests that a common pathway rather than a common gene is responsible for the various clinical syndromes, and implies that the distinction between entities may be artificial. Here we report the use of whole exome sequencing (WES) to identify a recurrent missense mutation in ARAF as the basis for a severely advanced lymphatic disease characterized by a complex lymphatic anomaly in two unrelated patients. Our results provide a representative demonstration of how genetic classification presents a way to categorize complex medical disorders, thereby guiding biologically based medical treatments, which in our instance was life-saving.

The following materials and methods are provided to facilitate the practice of example II.

Patients.

After obtaining approval from the Institutional Review Board at The Children's Hospital of Philadelphia (CHOP) and written informed consent, blood specimens from the lead proband (P1) and his parents were obtained for sequencing analysis. The proband had severe accumulation of lymphatic fluid in his chest, pericardium, abdomen, lower extremities and genitalia and was being followed and treated at the Center for Lymphatic Imaging and Interventions at CHOP. An unrelated second adult patient (P2) was recruited through the Patient Registry of the Lymphangiomatosis & Gorham's Disease Alliance (LGDA), together with available family members. Birth and family history for P1 were unremarkable except for a capillary malformation on the left side of his abdomen and his childhood growth and development milestones were normal. At age 10 years, he developed swelling of his lower abdomen, thighs, scrotum and penis. Two months later, he presented to a local hospital with shortness of breath and exercise intolerance. A chest radiograph demonstrated cardiomegaly and echocardiogram revealed a large pericardial effusion. Pericardiocentesis was performed with drainage of 1l of chylous fluid. Despite institution of total parenteral nutrition, the drainage continued and he was transferred to CHOP for further management. At CHOP, his initial evaluation included dynamic contrast-enhanced magnetic resonance lymphangiography that demonstrated large pericardial effusion and antegrade flow in dilated lumbar and retroperitoneal networks into a dilated and tortuous TD coursing towards the innominate vein on the left (FIG. 1a,c,d). An image of an unaffected person is shown in FIG. 1b as a reference. In addition, there was retrograde lymphatic flow into the liver, mesentery, penis and scrotum, and from the distal TD there was retrograde flow into the mediastinum and pericardium (FIG. 1c-e). He underwent placement of a stent in the distal TD and Lipiodol embolization with the aim of stopping the abnormal mediastinal and pericardial lymphatic effusion. He was discharged after a month with a stable pericardial effusion but then presented shortly thereafter in respiratory distress due to large fluid re-accumulation that necessitated an increasing requirement for supplemental oxygen (up to 5l by nasal cannula). He was started on sirolimus and was dosed based on trough levels tolerated well on a dose of 2.5 mg per day, which resulted in a median trough level of 11.8 between May and November 2016 (range 6.8-16.2 µg dl-1). Over the course of 1.5 years, he underwent multiple percutaneous interventional and surgical lymphatic procedures, including repetitive thoracentesis and pleural drains, multiple percutaneous lymphatic embolizations, bilateral surgical pleurodesis twice, surgical lymphovenous anastomosis in his thighs, abdomen and retroperitoneum and, due to worsening penile and scrotal edema, surgical ligation and embolization of groin lymph channels. Despite multiple attempts to control his pericardial effusions, his penile, scrotal, lower extremity and lower abdominal lymphedema worsened and his condition continued to deteriorate to the point that consideration of palliative care was discussed. The last procedure was performed and sirolimus was discontinued five months before trametinib.

|  |  | Baseline | | | | Post therapy | | | | | |
| --- | --- | --- | --- | --- | --- | --- | --- | --- | --- | --- | --- |
|  |  | Mar. 17, 2017 | | Apr. 4, 2017 | | May 4, 2017 | | Oct. 23, 2017 | | Mar. 8, 2018 | |
| Parameter | Unit | Per | % ref | Per | % ref | Per | % ref | Per | % ref | Per | % ref |
| Weight | kg | 38 |  | 40 |  | 42 |  | 40 |  | 39 |  |
| Height | cm | 142 |  | 142 |  | 143 |  | 145 |  | 148 |  |
| FVC | L | 0.58 | 23 | 0.88 | 35 | 0.88 | 31 | 0.95 | 35 | 1.18 | 40 |
| FEV$_1$ | L | 0.52 | 23 | 0.77 | 34 | 0.72 | 31 | 0.85 | 35 | 1.09 | 42 |
| FEV$_1$/FVC | % | 89.8 | 105 | 87 | 102 | 89.3 | 105 | 89.0 | 105 | 92.0 | 108 |
| FEF$_{25-35}$ | L/s | 0.8 | 29 | 1.12 | 41 | 1.10 | 39 | 1.46 | 50 | 1.79 | 58 |
| TLC | L | 0.93 | 29 | 1.23 | 38 | 1.28 | 39 | 1.51 | 45 | 1.89 | 56 |
| RV | L | 0.27 | 31 | 0.35 | 40 | 0.48 | 55 | 0.56 | 62 | 0.80 | 86 |
| RV/TLC | % | 28.94 | 107 | 28 | 104 | 37.67 | 140 | 37 | 137 | 40 | 154 |
| DLCO [Hb] | ml min$^{-2}$ mmHg$^{-1}$ | — | — | — | — | — | — | 9.99 | 54 | 9.9 | 52 |
| DLCO/VA | ml min$^{-2}$ mmHg$^{-1}$ | — | — | — | — | — | — | 9.08 | 135 | 7.67 | 116 |
| MIP | cmH$_2$O | 51.6 | 71 | — | — | 62.2 | 82 | 70.0 | 95 | 85.0 | 115 |
| MEP | cmH$_2$O | 69.4 | 66 | — | — | 77.6 | 74 | 89.0 | 85 | 83.0 | 75 |
| O$_2$ Bat | % | 92 |  | — |  | 97 |  | 100 |  | 97 |  |

Patient P2, an unrelated adult female, was diagnosed with lymphangiomatosis at the age of 31. She had extensive symptoms for many years before her diagnosis with prominent pulmonary involvement and required multiple pleurocentesis procedures before pleurodesis. She had widespread involvement of her gastrointestinal tract, requiring a specialized fat-restricted diet and medium-chain triglyceride oil supplementation with intermittent total parenteral nutrition. She underwent computed tomography and magnetic resonance imaging after persistent unexplained symptoms, which were consistent with lymphangiomatosis affecting her kidneys, liver, spleen and lungs.

A liver biopsy confirmed the diagnosis of lymphangiomatosis. She was additionally treated with albuterol and diuretics and used a motorized scooter because of fatigue and dyspnea. She was never confirmed to have bone involvement. As the patient was recruited from the Lymphangiomatosis & Gorham's Disease Alliance and was not local, she was lost to follow-up and was not available for a trial of other therapies as she had died from complications related to her underlying lymphatic disorder.

WES and Bioinformatics Analysis.

We examined mis sense, nonsense, splice altering and coding indels matching either the dominant or recessive inheritance models in the exome data. Results were filtered to exclude variants with the following factors: synonymous variants; variants in known pseudogenes; variants with a minor allele frequency (MAF) greater than 0.5% in either the 1000 Genomes Project or the 6,503 exomes from the National Heart, Lung, and Blood Institute Exome Sequencing Project (ESP6500SI); variants previously identified in controls by our in-house exome variant database. Subsequent gene prioritization was performed on the basis of deleterious prediction and biological relevance by referring to the Online Mendelian Inheritance in Man database.

Expression and Characterization of ARAF Mutation in Mammalian Cell Lines.

HEK293T and HeLa cells were obtained from the American Type Culture Collection and grown at 37° C. in Dulbecco's modified Eagle's medium supplemented with 10% fetal bovine serum. Primary adult HDLECs were obtained from Promocell, and were cultured in Endothelial Cell Growth Medium MV 2 (Promocell) according to the manufacturer's directions. The full-length ARAF cDNA obtained from Addgene (plasmid no. 23725)41 was amplified from the original vector and cloned as a BamHI/XhoI fragment into the pcDNA3.1 vector that contains two copies of the FLAG tag (DYKDDDDK), followed by two STREP tags (WSHPQFEK). The S214P mutation was introduced by site-directed mutagenesis using the Q5 mutagenesis kit from NEB following the manufacturer's instructions. Transfections in HEK293T and HeLa were performed using Fugene HD (Promega), with 3 µg DNA (empty vector, WT ARAF (ARAF-WT) or ARAF mutant (ARAF-S214P)) and 9 µl of the transfection reagent, according to the manufacturer's protocols. At 36-48 h after transfection, cells were washed twice with ice-cold phosphate-buffered saline (PBS) and lysed on ice using a freshly prepared ice-cold cell lysis buffer containing 50 mM Tris-HCl, pH 7.4, 100 mM NaCl, 50 mM β-glycerophosphate, 10% glycerol (w/v), 1% NP-40 (w/v), 1 mM EDTA, 2 mM NaVO4 and a complete, EDTA-free protease inhibitor cocktail (Roche Applied Science) at 20 µl per millilitre of lysis buffer. After clearing the cell lysates by centrifugation, the supernatants were collected and used for western blotting or immunoprecipitation with Anti-FLAG M2 Affinity Gel (cat. no. A2220, Sigma) followed by western blotting. Immunoprecipitates and lysates were run on NuPAGE 4-12% Bis-Tris gels (Thermo Fisher Scientific) and blotted with primary antibodies including anti-phospho-p70S6K-Thr389 (cat. no. 9205S, Cell Signaling Technology; 1:1,000), anti-phospho-mTOR Ser2448 (cat. no. 5536P, Cell Signaling Technology; 1:1,000), anti-FLAG (cat. no. F3165, Sigma; 1:4,000), antiphospho-p38 Thr180/Tyr182 (cat. no. 4511, Cell Signaling Technology; 1:1,000), anti-PAN-14-3-3 (cat. no. sc-629, Santa Cruz Biotechnology; 1:500), anti-phospho-Akt-Ser473 (cat. no. 4060, Cell Signaling Technology; 1:1,000), anti-phosphop44/42-(Erk1/2)-Thr202/Tyr204 (cat. no. 4376, Cell Signaling Technology; 1:1,000) or anti-β-actin (cat. no. sc-69879, Santa Cruz Biotechnology; 1:1,000) antibodies.

The ARAF sequence, from pCDNA3.1-F2S2-ARAF-WT or -S214P constructs as previously indicated, was cut with BamHI/XhoI and introduced into the BglII/XhoI sites of a modified version of the pMSCV plasmid that contains aminoterminal FLAG and HA tags. Viral production was performed using Fugene, with 8 µg of total DNA (pMSCV-ARAF-WT or -S214P together with envelope and packaging plasmids) and 18 µl of the transfection reagent in HEK293T.

After 72 h, viral supernatant was collected and filtered. HDLECs were infected by replacing the cell culture medium with the viral supernatant, supplemented with 8 µg ml$^{-1}$ Polybrene and filtered through a 0.45 µm filter. Cells were spinfected at 650 g for 90 min, and subsequently cultured for 6 h at which point the viral supernatant was replaced by standard culture medium. Transduced HDLECs were cultured for 48 h before use in experiments. Transduction efficiencies observed by HA staining were between 40% and 60%.

Immunofluorescence Staining and Western Blotting of HDLECs.

Round (12 mm) coverslips (VWR) were coated with 0.1% gelatin in water for 10 min in 24-well plates (Corning), and then air-dried for 15 min. Transduced HDLECs were plated at 100,000 cells per well in 0.5 ml of culture medium in the presence or absence of trametinib for 48 h. Cells were washed in warm serum-free Dulbecco's modified Eagle's medium and fixed in 4% paraformaldehyde. Fixed cells were washed twice with PBS and twice with 0.1% BSA in PBS. Cells were permeablized and blocked by incubation with 10% normal donkey serum (Jackson Immunoresearch) and 0.3% Triton X-100 (Sigma Aldrich) in PBS. VE-cadherin antibody (Thermo Fisher Scientific) was diluted (final concentration: 2 µg ml$^{-1}$) in 0.01% normal donkey serum, 0.1% BSA and 0.3% Triton X-100 in PBS, and staining was performed for 1 h. Coverslips were washed twice with 0.1% BSA in PBS. Goat-anti-rabbit Alexa546 (Thermo Fisher Scientific; final concentration: 8 µg ml-1) and phalloidin Alexa350 (Thermo Fisher Scientific; final concentration: 5 units ml-1) were diluted in 0.01% normal donkey serum, 0.1% BSA and 0.3% Triton X-100 in PBS, and staining was performed for 1 h. When used, HA-Tag (6E2) mouse antibody (cat. no. 2367, Cell Signaling Technology) was diluted 1:100 in 0.1% BSA and 0.3% Triton X-100 in PBS, and staining was performed for 1 h. Coverslips were washed twice with 0.1% BSA in PBS and twice with PBS. Coverslips were dipped in water to remove residual salts, and mounted to slides using Prolong Gold antifade reagent (Thermo Fisher Scientific). Image acquisition was performed on a Leica DM6000 motorized upright microscope with a Photometrics HQ2 high-resolution monochrome CCD (charge-coupled device) camera using LAS AF software (Leica Microsystems). Z-stacks were acquired at ×10 magnification. Images were further processed in the Fiji software package42. Brightness and contrast adjustments were made. Identical brightness and contrast settings were applied to all images. Fluorescence values were measured in regions of interest (ROIs) drawn to contain entire individual cells, or in ROIs drawn to contain the entire cell body but exclude the cell-cell junction. From those measured values, a value for the plasma membrane was derived (total cell-intracellular), and the ratio of plasma membrane to intracellular values was derived and plotted. Additionally, the length and width of cells were measured with the line tool and ROI manager. For both analyses, five clearly ARAF-expressing cells, as determined by HA staining, were analyzed per ×10 field. Five ×10 fields were acquired per condition per experiment. Experiments were conducted with cells from 3 independent thaws and transductions of HDLECs, for a total of 75 cells per condition. For western blotting of HDLECs with trametinib, 20,000 transduced HDLECs cells were plated into 96-well plates in the presence of increasing amounts of trametinib. Cells were cultured for 24 h in the presence of the drug, and then lysed with 40 mM HEPES pH 7.5, 120 mM NaCl, 0.3% CHAPS, 50 mM NaF, 1.5 mM NaVO3 and a protease inhibitor cocktail.

Lysates were cleared by centrifugation at 20,000 g for 5 min at 4° C. Proteins were separated on 4-12% NuPAGE Bis-Tris gels. Blotting was performed using the antibodies described above.

Three-Dimensional Lymphatic Spheroid Sprouting Assay.

Multicellular spheroids for the lymphatic sprouting assay were initiated by seeding 7,500 HDLECs expressing ARAF-WT or ARAF-S214P into wells of a 96-well plate that were precoated with 1.5% agarose. Under these conditions, all of the HDLECs would aggregate into a single spheroid by 24 h. After formation, each spheroid was transferred into a gelling solution comprised of type I collagen (cat. no. 354236, Corning; final concentration=1.5 mg ml-1; pH neutralized with NaOH) and trametinib at the indicated concentrations, which was then allowed to polymerize at 37° C. Once solidified, Endothelial Cell Growth Medium MV 2 (without VEGFC) containing trametinib at the appropriate concentration was added onto the collagen gels. After 2 days of incubation, z-stack images with a step size of ~8.5 μm were taken of the embedded spheroids using an EVOS FL Auto Imaging System (Thermo Fisher Scientific). The numbers and lengths of capillary-like sprouts growing from each spheroid were measured using the software ImageJ (https://imagej.nih.gov/ij/).

MTT Proliferation Assay with Transduced HDLECs.

Proliferation of transduced HDLECs was measured using Cell Proliferation Kit I (MTT) from Roche Applied Science. Briefly, at 2 d post retroviral transduction, ARAF-WT- and -S214P expressing HDLECs were collected, counted and replated into flat-bottom 96-well plates at 10,000 cells per well in 100 μl of medium. At the indicated times after plating, 10 μl of the MTT was added to the appropriate wells, and incubated for 4 h at 37° C. A 100 μl volume of the solubilization reagent was added followed by overnight incubation at 37° C. Absorbance at 550 nm and 700 nm was measured on a Spectramax i3 Multi Mode plate reader (Molecular Devices), and A550 nm-A700 nm was calculated. A time point of 4 h after plating was included as an approximate measure of cells loaded into the experiment with minimal proliferation.

Transgenic Expression of Human ARAF in Zebrafish.

All procedures using zebrafish were approved by the Institutional Animal Care and Use Committee of CHOP (IAC 001154) and were in accordance with the Guide for the Care and Use of Laboratory Animals by the National Institutes of Health. Human mutant and WT ARAF cDNAs were cloned without stop codons into the pDONR221 vector; a zebrafish-adapted kozak sequence (GCAAACATGG) was used43. Expression constructs were assembled using a Tol2 backbone vector including a gateway cloning cassette (44, 45). Constructs were co-injected with Tol2 messenger RNA (46).

ARAF was expressed in vein and lymphatic vessels using the zebrafish mrc1 apromoter, and expression was visualized by mCherry linked to ARAF by an autocatalytic V2a protein cleavage site. For imaging, larvae were mounted in low-melting agarose, and multiple Z-images were taken with a Zeiss LSM710 confocal microscope using a ×20 lens. Confocal z-stacks of images were superimposed using Zeiss Zen software's maximum intensity projection function.

To analyze dilation of the TD, body segments separated by intersegmental lymphatic vessels with expression of the transgene in the TD were selected. Morphology was scored as normal (WT), moderate dilation (TD expanded but separate from the PCV) or severe dilation (TD and PCV not distinguishable in Z-projections). Images were compiled in ImageJ (Fiji). Each experiment was performed 3 times, and a total of 40 animals were analyzed.

Inhibitory Drug Treatment in Zebrafish.

Drug treatments were performed in 6-well plates with up to 20 larvae per group. Cobimetinib was diluted in embryo medium containing 0.01 M Tris pH 7.2 and 0.1% DMSO. Cobimetinib was used at 1 μM.

p-ERK antibody staining in zebrafish. Fish were injected as described above and larvae with prominent WT or mutant ARAF/mcherry expression were selected for analysis. Larvae were fixed overnight in a 4% paraformaldehyde solution in PBS with Tween-20 (PBST). Larvae were washed with PBST and incubated in 2% Triton X-100 for 24 h at 4° C. Then, larvae were blocked in 10% bovine serum and stained with phospho-ERK T202/Y204 antibody (cat. no. 9101, Cell Signaling Technology, 1:200) overnight at 4° C., washed with PBST and stained with Alexa Fluor 488 goat anti-rabbit secondary antibody (cat. no. A11008, Thermo Fisher Scientific, 1:400).

Statistics. For all of the cell-based assays, significance was assessed by unpaired, two-tailed Student's t-tests for comparison of two groups. Statistical analysis was performed with GraphPad Prism 7.0d software. The data are represented as box-and-whisker plots with boxes ranging from the 25th to 75th percentile, whiskers from the minimum to maximum and the median as the center, or as dot plots with bar graphs for mean±s.e.m., as indicated. For all of the assays performed on HDLECs, three independent experiments were performed with independent transductions of HDLECs, except for the proliferation study, where no statistical analysis was performed. For the 14-3-3 protein association assay, three independent experiments were performed with independent transfection of HEK293T cells, while other results for HEK293T cells represent six independent experiments. All of the zebrafish-related assays were performed in three independent experiments and tested by unpaired, one-tailed Student's t-tests for comparison of two groups.

Results

Figure 22F:
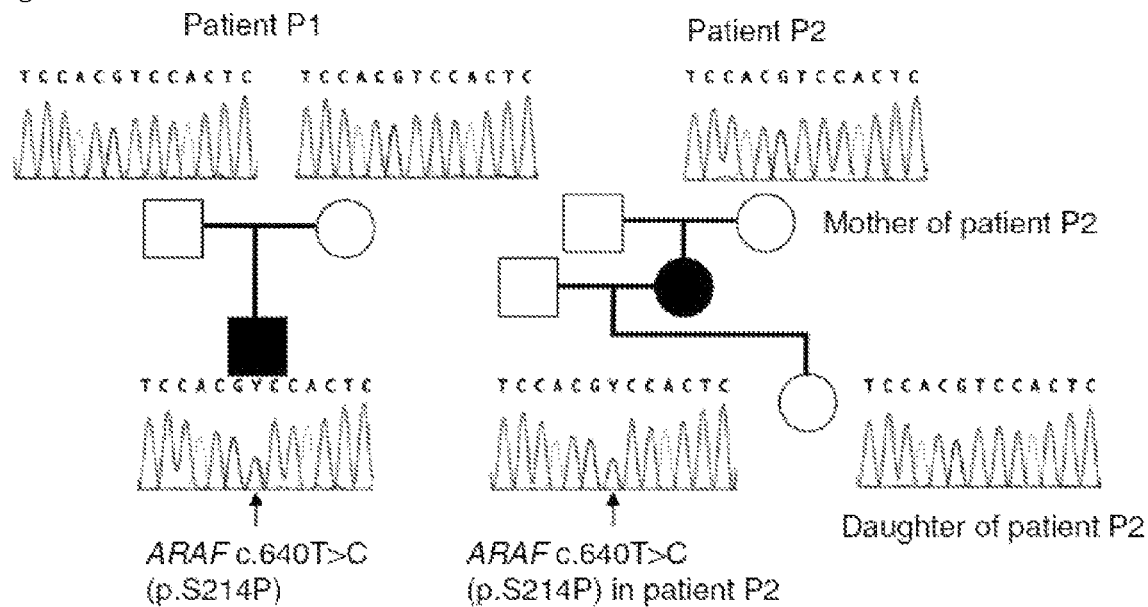

The first tier of WES analyses of the known lymphatic anomaly-associated genes was unrevealing, including mutation analysis of AKT1, PIK3CA, KRAS, HRAS, NRAS, BRAF, RAF1, PTPN11, SHOC2, CBL, RIT1 and SOS1. Subsequent gene prioritization revealed a novel X chromosomal ARAF mutation, c.640T>C:p. S214P, in both patient P1, a male with CCLA (FIG. 22A, 22C-22E; see Methods for a detailed clinical description; GenBank Accession No. NG_016339), and patient P2, a female previously diagnosed with lymphangiomatosis. The mutation affects a conserved phosphorylation site, which putatively resulted in a gain-of-function (GoF) effect as the residue Ser 214 is a paralogous regulatory site in its homologous protein C-RAF (also known as RAF1) for inhibition by 14-3-3 proteins. This missense mutation was absent from 1000 Genomes Project, ESP6500SI, ExAC v0.3, gnomAD v2.1 or additional exome-sequencing data from more than 5,000 samples that we had in our in-house database. Sanger sequencing of blood derived DNA from P1 and both parents confirmed that this X-linked ARAF mutation occurred as a somatic heterozygous event as shown in the male patient (FIG. 22F). Sanger sequencing of the ARAF mutation in P2, her unaffected daughter and mother confirmed the mutation was present only in P2 (FIG. 22F). The father was unavailable for sequencing; however, as her father had no reported respiratory symptoms it remains likely that the ARAF mutation arose as a de novo or somatic mutation in P2. Patient P2 was lost to follow-up and we were informed later that she subsequently died from complications of her lymphatic disease, five years after her diagnosis.

Figure 22G:
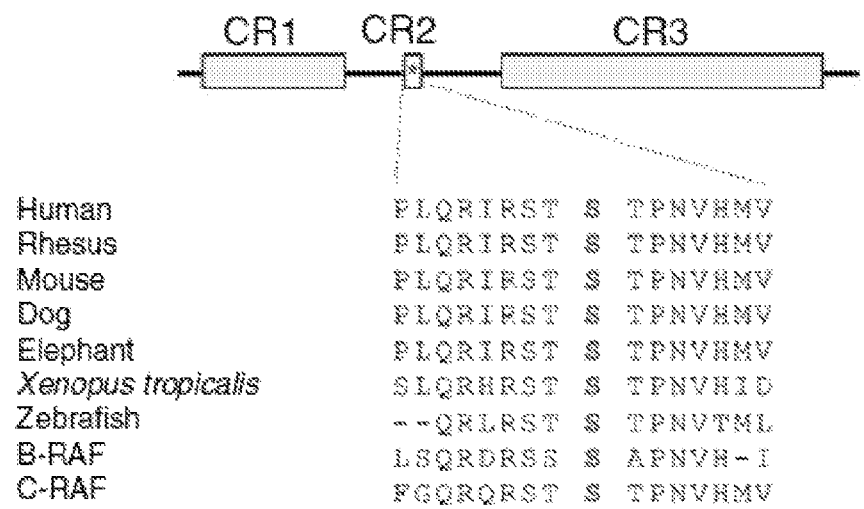
Figure 23A:
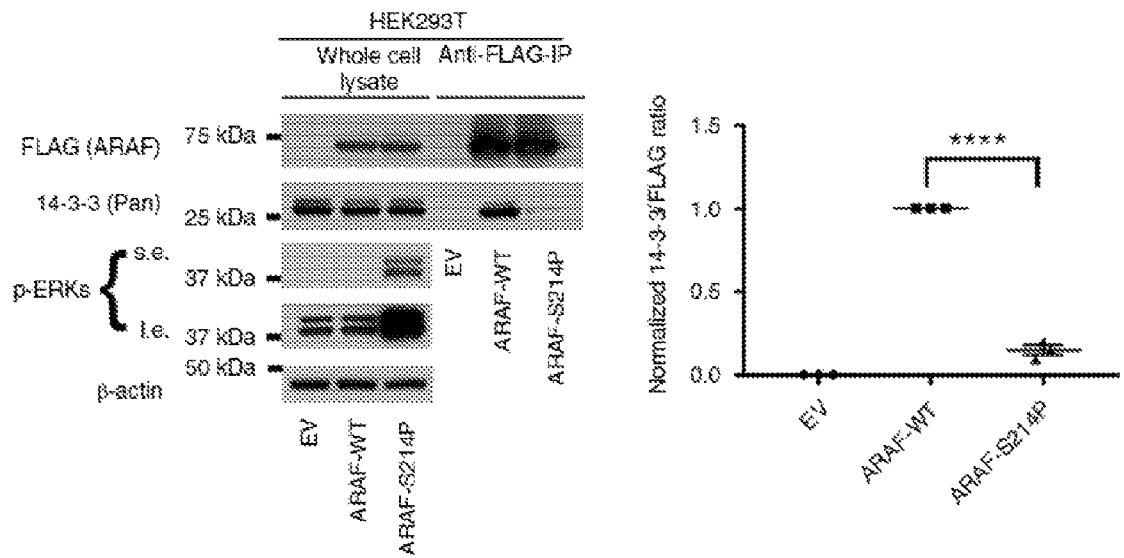
Figure 23B:
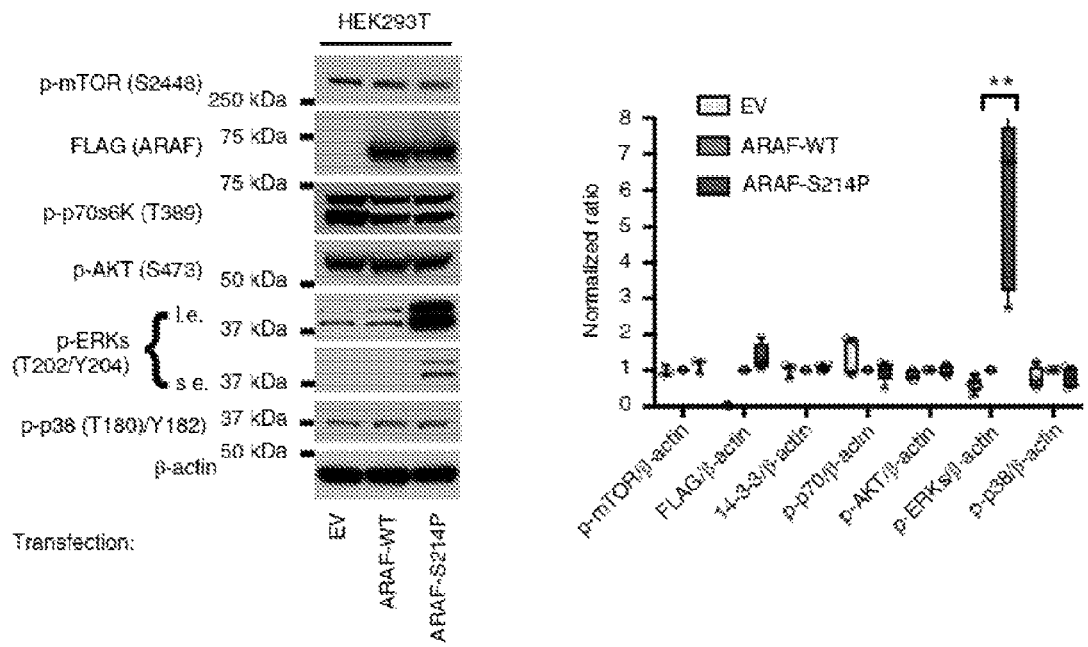

The Ser 214 residue, which is one of the 14-3-3 binding sites in conserved region 2 (CR2) (14), in ARAF is highly conserved across vertebrate species, as well as within the RAF proteins, suggesting that it may serve an essential role in the function of these kinases (FIG. 22G). The binding of 14-3-3 proteins to phosphorylated Ser 214 of ARAF would prevent recruitment of ARAF protein to the plasma membrane by activated Ras(15). Previous studies showed that the mutations in the ARAF-S214 paralogous residue Ser 259 in C-RAF impaired binding of 14-3-3 proteins, leading to plasma membrane localization and inducing ERK/MEK signaling(16). As shown in FIG. 23A, HEK293T cells transfected with ARAF-S214P showed reduced co-immunoprecipitation of 14-3-3 proteins, and in turn significantly greater activation of ERK1/2, as measured by increased phosphorylation, compared with HEK293T cells expressing wildtype (WT) ARAF (FIG. 23A, 23B). Phosphorylation of AKT, p70S6K, mTOR and p38 (another family of MAP kinases) was not altered by ARAF-S214P (FIG. 23B). Similar results were obtained in HeLa cells and in primary human dermal lymphatic endothelial cells (HDLECs) (FIG. 23C). This marked overactivation was also present even in the absence of cytokines or growth factors.

HDLECs expressing ARAF-S214P manifest enhanced lymphangiogenic capacity compared with HDLECs expressing ARAF-WT, as measured by the number of sprouts and the sprout length in the three-dimensional lymphatic spheroid sprouting assay conducted in the absence of vascular endothelial growth factor C (VEGFC) (FIG. 23D). The MEK inhibitor trametinib rescued the increased sprouting in the mutant (FIG. 23D). We then performed a morphological analysis of the endothelial adherens junctions of primary HDLECs expressing ARAF-S214P. As shown by immunofluorescence microscopy, ARAF-S214P expression caused a significant absence of VE-cadherin accumulation between adjacent cells suggesting increased VE-cadherin internalization (FIG. 23E, yellow arrowheads). Additionally, expression of ARAF-S214P altered actin organization, with mutant-expressing cells possessing fewer discrete F-actin filaments within the cell body.

We then examined the ability of MEK1/2 inhibitors to reverse these abnormalities. The MEK inhibitor trametinib, at a concentration of 100 nM, rescued the loss of VE-cadherin from cell-cell junctions observed in HDLECs expressing ARAF-S214P with an almost complete restoration of the cell monolayer integrity and a recovery of the normal appearance of VE-cadherin at junctions and actin filaments (FIG. 23E). Although ARAF-S214P clearly activates ERK in HDLECs, and ERK activation is typically associated with cell proliferation, we did not observe any measurable differences in proliferation between ARAF-WT- and -S214P-expressing HDLECs across two independent retroviral transductions (FIG. 23F).

Analysis of lymphatic development in zebrafish was performed in the Tg(mrc1a:egfp)y251 transgenic line17, where all lymphatic endothelial cells are labeled with EGFP. ARAF expression was targeted to lymphatic vessels with the mrc1a promoter, and ARAF-expressing cells were marked by mCherry expression. ARAF-S214P expression induced dilated lymphatic vessels in different locations, and most consistently we observed dilation of the trunk TD (FIG. 23H). Expression of ARAF-WT, in contrast, had no effect on lymphatic morphology (FIG. 23I). Expression of ARAF-S214P induces p-ERK in zebrafish.

To determine whether MEK signaling inhibitors can reverse the anomalies, we treated mrc1a:ARAFS214P larvae with cobimetinib from 3 d post fertilization (dpf), when the lymphatic progenitor cells sprout to form the TD (17). We analyzed body segments (somites) with ARAF expression in the TD at 7 dpf and found a significant rescue of duct morphology by cobimetinib (FIGS. 23J, 23K). Meanwhile, we treated WT Tg(mrc1a:egfp)y251 larvae with cobimetinib, and found that they tolerated the drug well.

In view of our demonstration that the ARAF mutation led to a gain of function effect in P1 that was unresponsive to sirolimus and that MEK inhibitors could rescue the lymphatic phenotype in both transduced endothelial cells and in a transgenic zebrafish model, we sought Institutional Review Board clearance to use MEK inhibitor therapy in P1. Trametinib (Mekinist), a Food and Drug Administration (FDA)-approved MEK inhibitor, was subsequently used off-label in this 12-year-old patient following comprehensive baseline evaluation.

Figures 24A, 24B:
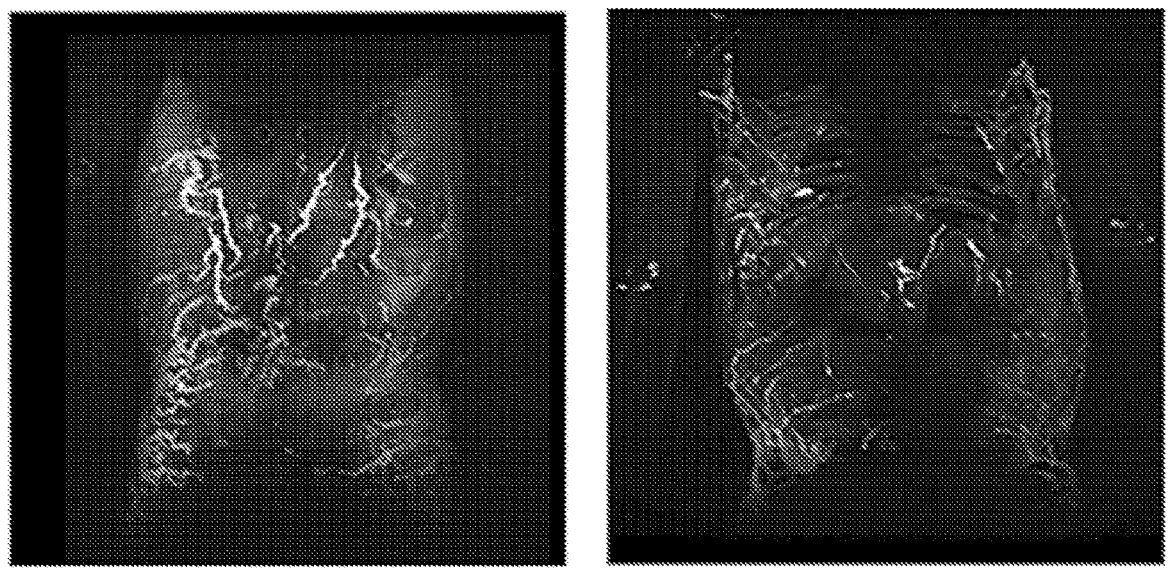
Figure 24E:
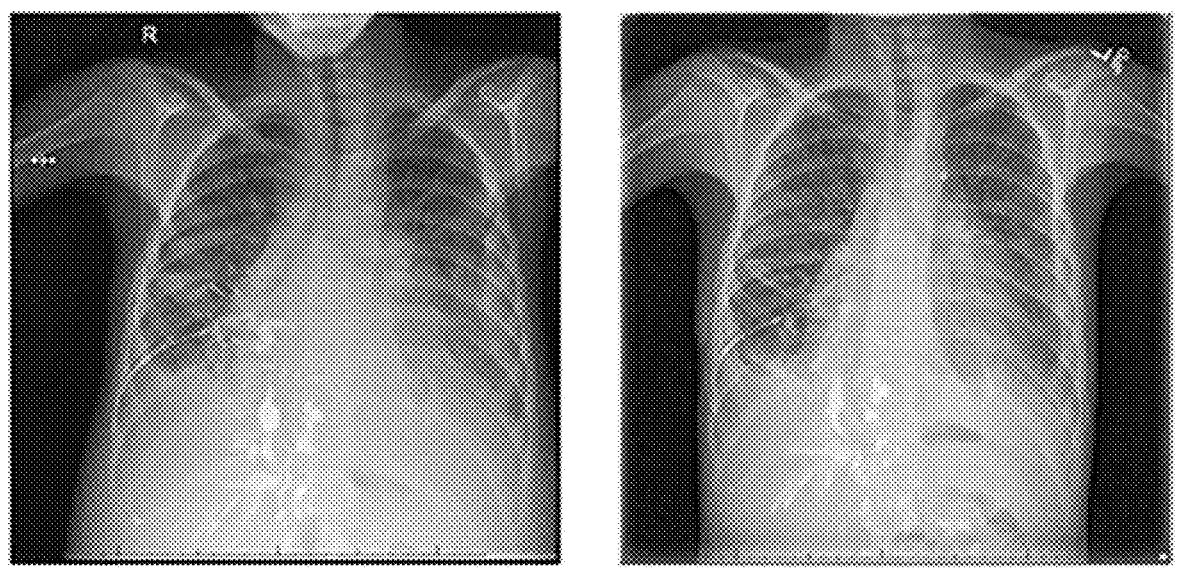
Figure 24F:
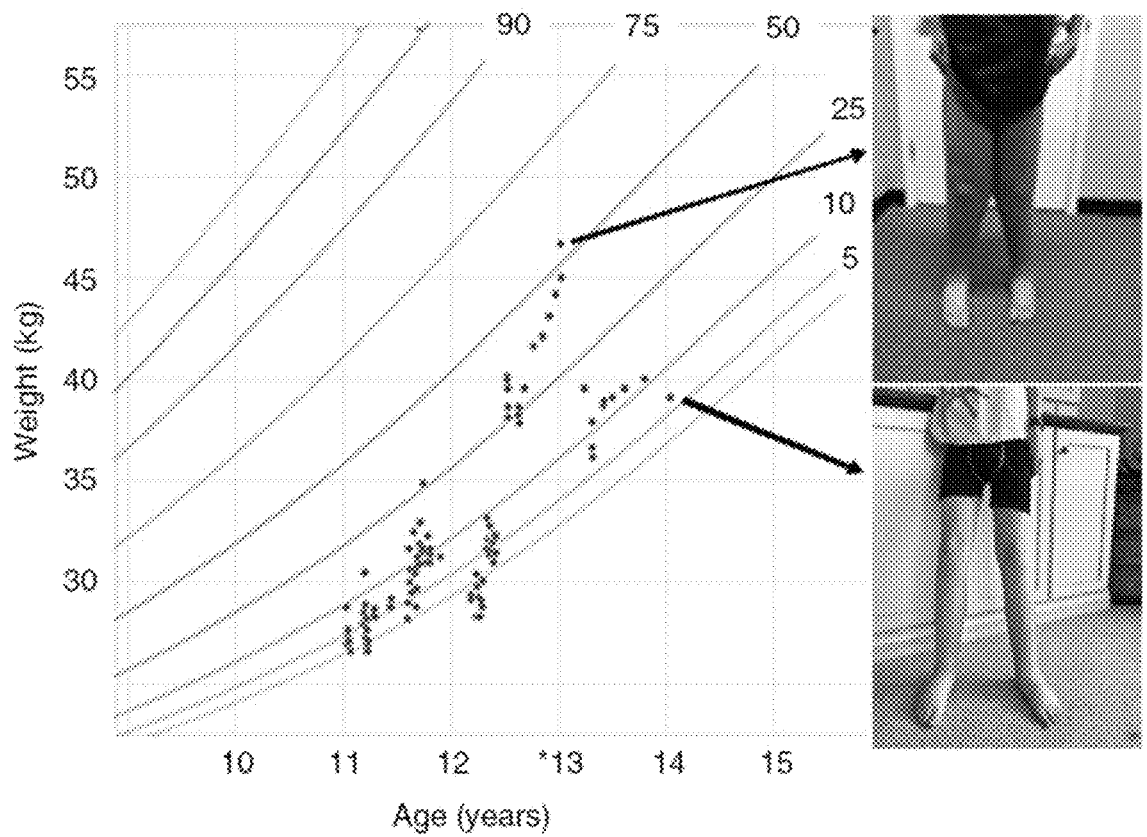

We used a starting dose of 1 mg $d^{-1}$ of trametinib and began observing improvement in pulmonary function testing within 2 months of therapy (FIG. 24A). Moreover, there were significant reductions in lymphatic fluid retention and supplemental oxygen requirements after three months of treatment, and he was able to wean to room air with improved levels of physical activity and without any adverse events being observed from trametinib. At 12 months of therapy, his pulmonary function tests showed near doubling of his total lung capacity (TLC) and his forced expiratory volume in 1 s (FEV1) improved from 23% to 42% predicted (FIG. 24A). Electrolytes (low Na and K) normalized and his magnetic resonance imaging scan showed lymphatic remodeling with restructuring of his lymphatic system (Fig. FIG. 24B-24F), a remarkable recovery in an doubling of his total lung capacity (TLC) and his forced expiratory volume in 1 s (FEV1) improved from 23% to 42% predicted (FIG. 24A). Electrolytes (low Na and K) normalized and his magnetic resonance imaging scan showed lymphatic remodeling with restructuring of his lymphatic system (FIG. 24B-24F), a remarkable recovery in an individual who was frequently hospitalized before initiation of this genetically guided therapy (FIG. 24F).

In sum, we performed WES for two unrelated patients with lymphatic anomaly and identified a recurrent gain of function mutation in the ARAF gene, including in a 12-year-old male with an advanced lymphatic disease unresponsive to sirolimus therapy. HDLECs transduced with the mutant ARAF showed elevated ERK1/2 activity, enhanced lymphangiogenic capacity, and disassembly of actin skeleton and VE-cadherin junctions, which were rescued using the MEK inhibitor trametinib. Sprouting was observed in ARAF-S214P-expressing HDLECs in the absence of VEGFC (a potent lymphangiogenic factor) (18). Under the same conditions, sprouting was absent in cells expressing ARAF-WT. This suggests that the ARAF mutant is mimicking the stimulatory behavior of VEGFC or inducing the expression of VEGFC by the HDLECs, which is necessary for endothelial cell sprouting, as seen in many stromal cell types (19-21). We reproduced the anomalous lymphatic phenotype, which is attributed to a GoF mutation in ARAF, in a zebrafish model observing rescue of the phenotype using MEK inhibitor therapy. Remarkably, therapy of the lead proband with the ARAF mutation using trametinib resulted in dramatic improvement in patient symptoms, with remodeling of his dilated and torturous lymphatic vasculature, resolution of the lymphatic edema and resumption of regular daily activities within 12 months of therapy.

From ongoing patient recruitment, we investigated additional lymphatic anomaly patients, including patients with Noonan (or Noonan-related) syndrome, Gorham-Stout disease, kaposiform lymphangiomatosis (KLA), lymphangiectasia and CCLA. On sequencing 43 additional patients, we identified 7 additional mutations in KRAS, BRAF, RASA1, PTPN11 and SOS1 (Table 3), suggesting that the RAS-MAPK signaling is a common pathway responsible for the various clinical lymphatic disease manifestations. Indeed, it has been increasingly acknowledged that the RAS-MAPK pathway plays a key role in the signaling of lymphangiogenesis (21-23). Reviewing the literature, we identified more than 50 patients who have mutations in KRAS, HRAS, BRAF, RAF1, PTPN11, SHOC2, CBL, RIT1 and SOS1, and present clinical features of Noonan or Noonan-related syndromes with lymphatic defects, including pleural effusion, pericardial effusions, chylothorax, hydrops, lymphangiectasis and lymphedema (21-23) While our work was in progress, a recurrent NRAS variant was implicated in GLA(37) and also in KLA(38), lending further support for the shared genetic etiology between these disease entities and the importance of mutations in the RAS-MAPK pathway in lymphatic anomalies.

The widespread prevalence of mutations in RASopathies in human cancer has been recognized for decades. A close scrutiny of the ARAF mutation we uncovered, using the cBioPortal (39) database (n=71,857 subjects and queried on Feb. 6, 2019), reveals 2 patients with the same exact mutation in ARAF. Interestingly, they both have concurrent TP53 mutations, which are considered as oncogenic drivers. Different mutations at this residue (S214T, S214A, S214Y, S214C and S214F), three of which have been shown to result in elevated MEK/ERK phosphorylation (40), were also observed in ten patients with different types of cancer. However, nine out of ten patients have co-occurring oncogenic mutations in TP53, GNAS, AKT2, APC, EGFR, ATM, CHEK2, KIT or U2AF1, raising the possibility that these oncogenic drivers may be responsible for the excessive proliferation in cancer cells. The lead proband with the ARAF mutation has dilated lymphatic vessels but the lesion shows no increase in size over years of follow-up. Thus, these data are consistent with our observation that the ARAF mutation we uncovered may not drive increased proliferation in lymphatic endothelial cells in vitro.

Regarding the prevalence of mutation-positive lymphatic anomalies, among 11 centers in the USA forming a lymphatic anomaly consortium to facilitate multi-center clinical trials for this group of lymphatic anomalies, including but not limited to GLA, Gorham-Stout disease, CCLA, KLA, Klippel-Trenaunay syndrome and kaposiform hemangioendothelioma, there are more than 3,000 patients recruited with moderate to severe disease course, and the number of new patients per year is about 300 combined. Based on the current molecular diagnostic yield (20%), we anticipate that about 20% of them will have defects in the RAS-MAPK pathway, suggesting that a few thousand patients overall in the USA may benefit from MEK inhibitor therapy. Thus, our work exemplifies how genetic discoveries can impact disease classification and uncover novel biological and life-saving treatments as represented here in a patient with lymphatic anomaly of a previously unknown etiology, a realization of a precision medicine approach.

REFERENCES

1. Trenor, C. C. 3rd & Chaudry, G. Complex lymphatic anomalies. *Semin. Pediatr. Surg.* 23, 186-190 (2014).
2. Collins, F. S. & Varmus, H. A new initiative on precision medicine. *N. Engl. J. Med.* 372, 793-795 (2015).
3. Adams, D. M. et al. Efficacy and safety of sirolimus in the treatment of complicated vascular anomalies. *Pediatrics* 137, e20153257 (2016).
4. Hammill, A. M. et al. Sirolimus for the treatment of complicated vascular anomalies in children. *Pediatr. Blood Cancer* 57, 1018-1024 (2011).
5. McCormick, A., Rosenberg, S., Trier, K. & Balest, A. A case of a central conducting lymphatic anomaly responsive to sirolimus. *Pediatrics* 137, e20152694 (2016).
6. Hilliard, R. I., McKendry, J. B. & Phillips, M. J. Congenital abnormalities of the lymphatic system: a new clinical classification. *Pediatrics* 86, 988-994 (1990).
7. Levine, C. Primary disorders of the lymphatic vessels—a unified concept. *J. Pediatr. Surg.* 24, 233-240 (1989).
8. Smeltzer, D. M., Stickler, G. B. & Fleming, R. E. Primary lymphatic dysplasia in children: chylothorax, chylous ascites, and generalized lymphatic dysplasia. *Eur. J. Pediatr.* 145, 286-292 (1986).
9. Wassef, M. et al. Vascular anomalies classification: recommendations from the International Society for the Study of Vascular Anomalies. *Pediatrics* 136, e203-e214 (2015).
10. Chen, W., Adams, D., Patel, M., Gupta, A. & Dasgupta, R. Generalized lymphatic malformation with chylothorax: long-term management of a highly morbid condition in a pediatric patient. *J. Pediatr. Surg.* 48, e9-e12 (2013).
11. Lala, S. et al. Gorham-Stout disease and generalized lymphatic anomaly—clinical, radiologic, and histologic differentiation. *Skeletal Radiol.* 42, 917-924 (2013).
12. Clemens, R. K., Pfammatter, T., Meier, T. O., Alomari, A. I. & Amann-Vesti, B. R. Combined and complex vascular malformations. *Vasa* 44, 92-105 (2015).
13. Li, D. et al. Pathogenic variant in EPHB4 results in central conducting lymphatic anomaly. *Hum. Mol. Genet.* 27, 3233-3245 (2018).
14. Wellbrock, C., Karasarides, M. & Marais, R. The RAF proteins take centre stage. *Nat. Rev. Mol. Cell Biol.* 5, 875-885 (2004).
15. Lavoie, H. & Therrien, M. Regulation of RAF protein kinases in ERK signalling. *Nat. Rev. Mol. Cell Biol.* 16, 281-298 (2015).
16. Molzan, M. et al. Impaired binding of 14-3-3 to C-RAF in Noonan syndrome suggests new approaches in diseases with increased Ras signaling. *Mol. Cell Biol.* 30, 4698-4711 (2010).
17. Jung, H. M. et al. Development of the larval lymphatic system in zebrafish. *Development* 144, 2070-2081 (2017).
18. Karkkainen, M. J. et al. Vascular endothelial growth factor C is required for sprouting of the first lymphatic vessels from embryonic veins. *Nat. Immunol.* 5, 74-80 (2004).
19. Carmeliet, P. & Jain, R. K. Molecular mechanisms and clinical applications of angiogenesis. *Nature* 473, 298-307 (2011).
20. Karaman, S., Leppanen, V. M. & Alitalo, K. Vascular endothelial growth factor signaling in development and disease. *Development* 145, dev151019 (2018).

21. Potente, M. & Makinen, T. Vascular heterogeneity and specialization in development and disease. *Nat. Rev. Mol. Cell Biol.* 18, 477-494 (2017).
22. Coso, S., Bovay, E. & Petrova, T. V. Pressing the right buttons: signaling in lymphangiogenesis. *Blood* 123, 2614-2624 (2014).
23. Brouillard, P., Boon, L. & Vikkula, M. Genetics of lymphatic anomalies. *J. Clin. Invest.* 124, 898-904 (2014).
24. Bulow, L. et al. Hydrops, fetal pleural effusions and chylothorax in three patients with CBL mutations. *Am. J. Med. Genet.* A 167A, 394-399 (2015).
25. Gargano, G. et al. Hydrops fetalis in a preterm newborn heterozygous for the c.4A>G SHOC2 mutation. *Am. J. Med. Genet.* A 164A, 1015-1020 (2014).
26. Gos, M. et al. Contribution of RIT1 mutations to the pathogenesis of Noonan syndrome: four new cases and further evidence of heterogeneity. *Am. J. Med. Genet. A* 164A, 2310-2316 (2014).
27. Hanson, H. L. et al. Germline CBL mutation associated with a Noonan-like syndrome with primary lymphedema and teratoma associated with acquired uniparental isodisomy of chromosome 11q23. *Am. J. Med. Genet. A* 164A, 1003-1009 (2014).
28. Milosavljevic, D. et al. Two cases of RIT1 associated Noonan syndrome: further delineation of the clinical phenotype and review of the literature. *Am. J. Med. Genet. A* 170, 1874-1880 (2016).
29. Koenighofer, M. et al. Mutations in RIT1 cause Noonan syndrome—additional functional evidence and expanding the clinical phenotype. *Clin. Genet.* 89, 359-366 (2016).
30. Lee, K. A. et al. PTPN11 analysis for the prenatal diagnosis of Noonan syndrome in fetuses with abnormal ultrasound findings. *Clin. Genet.* 75, 190-194 (2009).
31. Croonen, E. A. et al. Prenatal diagnostic testing of the Noonan syndrome genes in fetuses with abnormal ultrasound findings. *Eur. J. Hum. Genet.* 21, 936-942 (2013).
32. Joyce, S. et al. The lymphatic phenotype in Noonan and cardiofaciocutaneous syndrome. *Eur. J. Hum. Genet.* 24, 690-696 (2016).
33. Yaoita, M. et al. Spectrum of mutations and genotype-phenotype analysis in Noonan syndrome patients with RIT1 mutations. *Hum. Genet.* 135, 209-222 (2016).
34. Lo, I. F. et al. Severe neonatal manifestations of Costello syndrome. *J. Med. Genet.* 45, 167-171 (2008).
35. Ebrahimi-Fakhari, D. et al. Congenital chylothorax as the initial presentation of PTPN11-associated Noonan syndrome. *J. Pediatr.* 185, 248-248.e1 (2017).
36. Morcaldi, G. et al. Lymphodysplasia and Kras mutation: a case report and literature review. *Lymphology* 48, 121-127 (2015).
37. Manevitz-Mendelson, E. et al. Somatic NRAS mutation in patient with generalized lymphatic anomaly. *Angiogenesis* 21, 287-298 (2018).
38. Barclay S. F. et al. A somatic activating NRAS variant associated with kaposiform lymphangiomatosis. *Genet. Med.* https://doi.org/10.1038/s41436-018-0390-0 (2018).
39. Gao, J. et al. Integrative analysis of complex cancer genomics and clinical profiles using the cBioPortal. *Sci. Signal.* 6, p 11 (2013).
40. Imielinski, M. et al. Oncogenic and sorafenib-sensitive ARAF mutations in lung adenocarcinoma. *J. Clin. Invest.* 124, 1582-1586 (2014).

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for treating a lymphatic anomaly in a human patient, the method comprising:
   a) detecting a single nucleotide variant (SNV) in a nucleic acid of a biological sample obtained from the patient, wherein the SNV is selected from:
   i) c.1504T>G:pS502A, C1510A>G:pM504V and c.1507G>C:pG503R in PTPN11;
   ii) c.35G>A:pG12D in KRAS;
   iii) c.1403T>C:pF468S and c.2128-G>T in BRAF;
   iv) c.2536G>A:pE846K in SOS1;
   v) c.1236+4A>G and c.289T>G:p.C97G in ITGA9;
   vi) c.475_476del:p.(L159Gfs*20) and c.2246G>C p.R749P in RASA1;
   vii) c.433A>C:p.T145P in RAF1;
   viii) c.270G>T:p.M90I in RIT1;
   ix) c.7289C>T:p.P2430L in PEIZ01;
   x) c.1034_1043del:p.(L345Pfs*28) in NF1; and
   xi) c.1096-1G>T and c.2322T>G:p.Y774* in CBL; and
   b) administering one or more agents suitable for treatment of said lymphatic anomaly to the patient, thereby treating the lymphatic anomaly,
   wherein said one or more agents suitable for treatment of said lymphatic anomaly are selected from the group consisting of one or more mTOR inhibitors, one or more PIK3K inhibitors, one or more MEK/ERK inhibitors, and a combination of one or more of any of said inhibitors.

2. The method of claim 1, wherein said one or more agents is an inhibitor selected from the group consisting of trametinib (GSK1120212), rapamycin (sirolimus), everolimus (RAD001), AZD8055, temsirolimus (CCI-779, NSC 683864), KU-0063794, MHY1485, BEZ235 (NVP-BEZ235, dactolisib), PI-103, torkinib (PP242), tacrolimus (FK506), selumetinib (AZD6244), PD0325901, PD184352 (CI-1040), pimasertib (AS-703026), TAK-733, AZD8330, binimetinib (MEK162, ARRY-162, ARRY-438162), SL-327, refametinib (RDEA119, Bay 86-9766), cobimetinib (GDC-0973, RG7420), ulixertinib, ridaforolimus (deforolimus, MK-8669), INK 128 (MLN0128), voxtalisib (SAR245409, XL765), torin 1, omipalisib (GSK2126458, GSK458), OSI-027, PF-04691502, apitolisib (GDC-0980, RG7422), GSK 1059615, Gedatolisib (PF-05212384, PKI-587), WYE-354, AZD2014, torin 2, WYE-125132 (WYE-132), PP121, WYE-687, CH5132799, WAY-600, ETP-46464, GDC-0349, XL388, zotarolimus (ABT-578), tacrolimus (FK506), BGT226 (NVP-BGT226), palomid 529 (P529), chrysophanic acid, TAK-733, PD-325901), pimasertib (AS-70326), and PD184352, (SL-327), or a combination thereof.

3. The method of claim 1, wherein the lymphatic anomaly is characterized by abnormal formation of lymphatic vessels and/or tissue overgrowth.

4. The method of claim 1, wherein the lymphatic anomaly is lymphangiomatosis (LAM).

5. The method of claim 1, wherein the lymphatic anomaly is generalized lymphatic anomaly (GLA).

6. The method of claim 1, wherein the lymphatic anomaly is characterized by chylous effusions, including pericardial, pleural, or peritoneal effusions.

7. The method of claim 1, wherein the method further comprises generating a report identifying the SNV after detection in the biological sample.

8. The method of claim 1, wherein the method further comprises generating a report identifying suggested treatment(s) for the lymphatic anomaly based upon the SNV identified in the method.

9. The method of claim 1, wherein a MEK inhibitor selected from pimasertib, refametinib and/or Trametinib is administered.

10. The method of claim 1, wherein the agent has an $IC_{50}$ of less than 100 μM, less than 10 μM, less than 1 μM, less than 100 nM, less than 10 nM, or less than 1 nM.

11. The method of claim 1, wherein the patient does not have an SNV in one selected from the group consisting of PTPN11, KRAS, BRAF, SOS1, and ITGA9.

12. The method of claim 1, wherein the treatment further comprises administering systemic chemotherapy, interferon alfa, radiotherapy, and/or surgery.

13. The method of claim 1, wherein the method further comprises the step of analyzing a polynucleotide sample to determine the presence of said SNV by performing a process selected from the group consisting of detection of specific hybridization, measurement of allele size, restriction fragment length polymorphism analysis, allele-specific hybridization analysis, single base primer extension reaction, and sequencing of an amplified polynucleotide.

14. The method of claim 1, wherein in the biological sample comprises DNA or RNA.

15. The method of claim 1, wherein nucleic acids comprising said SNV(s) are obtained from an isolated cell of the human patient.

\* \* \* \* \*

SEQUENCE LISTING

```
<160> NUMBER OF SEQ ID NOS: 19

<210> SEQ ID NO 1
<211> LENGTH: 1782
<212> TYPE: DNA
<213> ORGANISM: Homo sapiens

<400> SEQUENCE: 1
atgacatcgc ggagatggtt tcacccaaat atcactggtg tggaggcaga aaacctactg      60
ttgacaagag gagttgatgg cagttttttg gcaaggccta gtaaaagtaa ccctggagac     120
ttcacacttt ccgttagaag aaatggagct gtcacccaca tcaagattca gaacactggt     180
gattactatg acctgtatgg aggggagaaa tttgccactt tggctgagtt ggtccagtat     240
tacatggaac atcacgggca attaaaagag aagaatggag atgtcattga gcttaaatat     300
cctctgaact gtgcagatcc tacctctgaa aggtggtttc atggacatct ctctgggaaa     360
gaagcagaga aattattaac tgaaaaagga aaacatggta gttttcttgt acgagagagc     420
cagagccacc ctggagattt tgttctttct gtgcgcactg tgatgacaa aggggagagc     480 aatgacggca agtctaaagt gacccatgtt atgattcgct gtcaggaact gaaatacgac     540
gttggtggag gagaacggtt tgattctttg acagatcttg tggaacatta taagaagaat     600
cctatggtgg aaacattggg tacagtacta caactcaagc agcccttaa cacgactcgt     660
```

| | |
|---|---|
| ataaatgctg ctgaaataga aagcagagtt cgagaactaa gcaaattagc tgagaccaca | 720 |
| gataaagtca acaaggctt ttgggaagaa tttgagacac tacaacaaca ggagtgcaaa | 780 |
| cttctctaca gccgaaaaga gggtcaaagg caagaaaaca aaaacaaaaa tagatataaa | 840 |
| aacatcctgc cctttgatca taccaggggtt gtcctacacg atggtgatcc caatgagcct | 900 |
| gtttcagatt acatcaatgc aaatatcatc atgcctgaat ttgaaaccaa gtgcaacaat | 960 |
| tcaaagccca aaaagagtta cattgccaca caaggctgcc tgcaaaacac ggtgaatgac | 1020 |
| ttttggcgga tggtgttcca agaaaactcc cgagtgattg tcatgacaac gaaagaagtg | 1080 |
| gagagaggaa agagtaaatg tgtcaaatac tggcctgatg agtatgctct aaaagaatat | 1140 |
| ggcgtcatgc gtgttaggaa cgtcaaagaa agcgccgctc atgactatac gctaagagaa | 1200 |
| cttaaacttt caaggttgg acaagggaat acggagagaa cggtctggca ataccacttt | 1260 |
| cggacctggc cggaccacgg cgtgcccagc gaccctgggg gcgtgctgga cttcctggag | 1320 |
| gaggtgcacc ataagcagga gagcatcatg gatgcagggc cggtcgtggt gcactgcagt | 1380 |
| gctggaattg gccggacagg gacgttcatt gtgattgata ttcttattga catcatcaga | 1440 |
| gagaaaggtg ttgactgcga tattgacgtt cccaaaacca tccagatggt gcggtctcag | 1500 |
| aggtcaggga tggtccagac agaagcacag taccgatttta tctatatggc ggtccagcat | 1560 |
| tatattgaaa cactacagcg caggattgaa gaagagcaga aaagcaagag gaaagggcac | 1620 |
| gaatatacaa atattaagta ttctctagcg gaccagacga gtggagatca gagccctctc | 1680 |
| ccgccttgta ctccaacgcc accctgtgca gaaatgagag aagacagtgc tagagtctat | 1740 |
| gaaaacgtgg gcctgatgca acagcagaaa agtttcagat ga | 1782 |

<210> SEQ ID NO 2
<211> LENGTH: 567
<212> TYPE: DNA
<213> ORGANISM: Homo sapiens

<400> SEQUENCE: 2

| | |
|---|---|
| atgactgaat ataaacttgt ggtagttgga gctggtggcg taggcaagag tgccttgacg | 60 |
| atacagctaa ttcagaatca ttttgtggac gaatatgatc caacaataga ggattcctac | 120 |
| aggaagcaag tagtaattga tggagaaacc tgtctcttgg atattctcga cacagcaggt | 180 |
| caagaggagt acagtgcaat gagggaccag tacatgagga ctggggaggg ctttctttgt | 240 |
| gtatttgcca taaataatac taaatcattt gaagatattc accattatag agaacaaatt | 300 |
| aaaagagtta aggactctga agatgtacct atggtcctag taggaaataa atgtgatttg | 360 |
| ccttctagaa cagtagacac aaaacaggct caggacttag caagaagtta tggaattcct | 420 |
| tttattgaaa catcagcaaa gacaagacag gtgttgatg atgccttcta tacattagtt | 480 |
| cgagaaattc gaaaacataa agaaaagatg agcaaagatg gtaaaaagaa gaaaaagaag | 540 |
| tcaaagacaa agtgtgtaat tatgtaa | 567 |

<210> SEQ ID NO 3
<211> LENGTH: 2301
<212> TYPE: DNA
<213> ORGANISM: Homo sapiens

<400> SEQUENCE: 3

| | |
|---|---|
| atggcggcgc tgagcggtgg cggtggtggc ggcgcggagc cgggccaggc tctgttcaac | 60 |
| ggggacatgg agcccgaggc cggcgccggc gccggcgccg cggcctcttc ggctgcggac | 120 |
| cctgccattc cggaggaggt gtggaatatc aaacaaatga ttaagttgac acaggaacat | 180 |

-continued

```
atagaggccc tattggacaa atttggtggg gagcataatc caccatcaat atatctggag       240
gcctatgaag aatacaccag caagctagat gcactccaac aaagagaaca acagttattg       300
gaatctctgg ggaacggaac tgattttttct gtttctagct ctgcatcaat ggataccgtt     360
acatcttctt cctcttctag cctttcagtg ctaccttcat ctctttcagt ttttcaaaat      420
cccacagatg tggcacggag caaccccaag tcaccacaaa acctatcgt tagagtcttc       480 ctgcccaaca aacagaggac agtggtacct gcaaggtgtg gagttacagt ccagacagt       540 ctaaagaaag cactgatgat gagaggtcta atcccagagt gctgtgctgt ttacagaatt     600
caggatggag agaagaaacc aattggttgg gacactgata tttcctggct tactggagaa     660
gaattgcatg tggaagtgtt ggagaatgtt ccacttacaa cacacaactt tgtacgaaaa     720 acgttttttca ccttagcatt ttgtgacttt tgtcgaaagc tgcttttcca gggtttccgc   780
tgtcaaacat gtggttataa atttcaccag cgttgtagta cagaagttcc actgatgtgt    840
gttaattatg accaacttga tttgctgttt gtctccaagt tctttgaaca ccacccaata    900
ccacaggaag aggcgtcctt agcagagact gccctaacat ctggatcatc cccttccgca    960
cccgcctcgg actctattgg gccccaaatt ctcaccagtc cgtctccttc aaaatccatt   1020
ccaattccac agcccttccg accagcagat gaagatcatc gaaatcaatt tgggcaacga   1080
gaccgatcct catcagctcc caatgtgcat ataaacacaa tagaacctgt caatattgat   1140
gacttgatta gagaccaagg atttcgtggt gatggaggat caaccacagg tttgtctgct   1200
accccccctg cctcattacc tggctcacta actaacgtga aagccttaca gaaatctcca   1260
ggacctcagc gagaaaggaa gtcatcttca tcctcagaag acaggaatcg aatgaaaaca   1320
cttggtagac gggactcgag tgatgattgg gagattcctg atgggcagat tacagtggga   1380
caaagaattg gatctggatc atttggaaca gtctacaagg gaaagtggca tggtgatgtg   1440
gcagtgaaaa tgttgaatgt gacagcacct acacctcagc agttacaagc cttcaaaaat   1500
gaagtaggag tactcaggaa aacacgacat gtgaatatcc tactcttcat gggctattcc   1560
acaaagccac aactggctat tgttacccag tggtgtgagg gctccagctt gtatcaccat   1620
ctccatatca ttgagaccaa atttgagatg atcaaactta tagatattgc acgacagact   1680
gcacagggca tggattactt acacgccaag tcaatcatcc acagagacct caagagtaat   1740
aatatatttc ttcatgaaga cctcacagta aaaataggtg attttggtct agctacagtg   1800
aaatctcgat ggagtgggtc ccatcagttt gaacagttgt ctggatccat tttgtggatg   1860
gcaccagaag tcatcagaat gcaagataaa aatccataca gctttcagtc agatgtatat   1920
gcatttggaa ttgttctgta tgaattgatg actggacagt taccttattc aaacatcaac   1980
aacagggacc agataatttt tatggtggga cgaggatacc tgtctccaga tctcagtaag   2040
gtacggagta actgtccaaa agccatgaag agattaatgg cagagtgcct caaaaagaaa   2100
agagatgaga gaccactctt tccccaaatt ctcgcctcta ttgagctgct ggcccgctca   2160
ttgccaaaaa ttcaccgcag tgcatcagaa ccctccttga atcgggctgg tttccaaaca   2220 gaggattta gtctatatgc ttgtgcttct ccaaaaacac ccatccaggc agggggatat   2280
ggtgcgtttc ctgtccactg a                                              2301
```

<210> SEQ ID NO 4
<211> LENGTH: 4002
<212> TYPE: DNA
<213> ORGANISM: Homo sapiens

```
<400> SEQUENCE: 4
atgcaggcgc agcagctgcc ctacgagttt tcagcgaag agaacgcgcc caagtggcgg        60
ggactactgg tgcctgcgct gaaaaaggtc caggggcaag ttcatcctac tctcgagtct      120
aatgatgatg ctcttcagta tgttgaagaa ttaattttgc aattattaaa tatgctatgc      180
caagctcagc cccgaagtgc ttcagatgta gaggaacgtg ttcaaaaaag tttccctcat      240
ccaattgata aatgggcaat agctgatgcc caatcagcta ttgaaaagag gaagcgaaga      300
aacccttat ctctcccagt agaaaaaatt catcctttat aaaggaggt cctaggttat        360
aaaattgacc accaggtttc tgtttacata gtagcagtct tagaatacat ttctgcagac      420
attttaaagc tggttgggaa ttatgtaaga aatatacggc attatgaaat tacaaaacaa      480
gatattaaag tggcaatgtg tgctgacaag gtattgatgg atatgtttca tcaagatgta      540
gaagatatta atatattatc tttaactgac gaagagcctt ccacctcagg agaacaaact      600
tactatgatt tggtaaaagc atttatggca gaaattcgac aatatataag ggaactaaat      660
ctaattataa aagttttttag agagcccttt gtctccaatt caaaattgtt ttcagctaat      720
gatgtagaaa atatatttag tcgcatagta gatatacatg aacttagtgt aaagttactg      780
ggccatatag aagatacagt agaaatgaca gatgaaggca gtccccatcc actagtagga      840
agctgctttg aagacttagc agaggaactg gcatttgatc catatgaatc gtatgctcga      900
gatattttgc gacctggttt tcatgatcgt ttccttagtc agttatcaaa gcctggggca      960
gcactttatt tgcagtcaat aggcgaaggt ttcaagaag ctgttcaata tgttttaccc      1020
aggctgcttc tggcccctgt ttaccactgt ctccattact ttgaactttt gaagcagtta      1080
gaagaaaaaa gtgaagatca agaagacaag gaatgtttaa acaagcaat aacagctttg      1140
cttaatgttc agagtggtat ggaaaaata tgttctaaaa gtcttgcaaa acgaagactg      1200
agtgaatctg catgtcggtt ttatagtcag caaatgaagg ggaaacaact agcaatcaag      1260
aagatgaacg agattcagaa gaatattgat ggttgggagg gaaaagacat ggacagtgt      1320
tgtaatgaat ttataatgga aggaactctt acacgtgtag gagccaaaca tgagagacac      1380
atatttctct tgatggcttt aatgatttgc tgtaaatcaa atcatgggca gccaagactt      1440
cctggtgcta gcaatgcaga atatcgtctt aaagaaaagt ttttatgcg aaaggtacaa      1500
attaatgata aagatgacac caatgaatac aagcatgctt tgaaataat tttaaaagat      1560
gaaaatagtg ttatattttc tgccaagtca gctgaagaga aaacaattg gatggcagca      1620
ttgatatctt tacagtaccg gagtacactg gaaaggatgc ttgatgtaac aatgctacag      1680
gaagagaaag aggagcagat gaggctgcct agtgctgatg tttatagatt tgcagagcct      1740
gactctgaag agaatattat atttgaagag aacatgcagc ccaaggctgg aattccaatt      1800
atcaaagcag gaactgttat taaacttata gagaggctta cgtaccatat gtacgcagat      1860
cccaattttg ttcggacatt tcttacaaca tacagatcct tttgcaaacc tcaagaacta      1920
ctgagtctta atagaaag gtttgaaatt ccagagcctg agccaacaga agctgatcgc      1980
atagctatag agaatggaga tcaacccttg agtgcagaac tgaaaagatt tagaaaagaa      2040
tatatacagc ctgtgcaact gcgagtatta atgtatgtc ggcactgggt agagcaccac      2100
ttctatgatt ttgaaagaga tgcatatctt ttgcaacgaa tggaagaatt tattggaaca      2160
gtaagaggta agcaatgaa aaatgggtt gaatccatca ctaaaataat ccaaaggaaa      2220
aaattgcaa gagacaatgg accaggtcat aatattacat ttcagagttc acctcccaca      2280
gttgagtggc atataagcag acctgggcac atagagactt ttgacctgct caccttacac      2340
```

| | |
|---|---|
| ccaatagaaa ttgctcgaca actcacttta cttgaatcag atctataccg agctgtacag | 2400 |
| ccatcagaat tagttggaag tgtgtggaca aagaagaca aagaaattaa ctctcctaat | 2460 |
| cttctgaaaa tgattcgaca taccaccaac ctcactctgt ggtttgagaa atgtattgta | 2520 |
| gaaactgaaa atttagaaga aagagtagct gtggtgagtc gaattattga gattctacaa | 2580 |
| gtctttcaag agttgaacaa ctttaatggt gtccttgagg ttgtcagtgc tatgaattca | 2640 |
| tcacctgttt acagactaga ccacacattt gagcaaatac caagtcgcca gaagaaaatt | 2700 |
| ttagaagaag ctcatgaatt gagtgaagat cactataaga atatttggc aaaactcagg | 2760 |
| tctattaatc caccatgtgt gcctttcttt ggaatttatc tcactaatat cttgaaaaca | 2820 |
| gaagaaggca accctgaggt cctaaaaaga catggaaaag agcttataaa ctttagcaaa | 2880 |
| aggaggaaag tagcagaaat aacaggagag atccagcagt accaaaatca gccttactgt | 2940 |
| ttacgagtag aatcagatat caaaaggttc tttgaaaact tgaatccgat gggaaatagc | 3000 |
| atggagaagg aatttacaga ttatcttttc aacaaatccc tagaaataga accacgaaac | 3060 |
| cctaagcctc tcccaagatt tccaaaaaaa tatagctatc ccctaaaatc tcctggtgtt | 3120 |
| cgtccatcaa acccaagacc aggtaccatg aggcatccca cacctctgca gcaggagcca | 3180 |
| aggaaaatta gttatagtag gatccctgaa agtgaaacag aaagtacagc atctgcacca | 3240 |
| aattctccaa gaacaccgtt aacacctccg cctgcttctg gtgcttccag taccacagat | 3300 |
| gtttgcagtg tatttgattc cgatcattcg agccctttc actcaagcaa tgataccgtc | 3360 |
| tttatccaag ttactctgcc ccatggccca agatctgctt ctgtatcatc tataagttta | 3420 |
| accaaaggca ctgatgaagt gcctgtccct cctcctgttc ctccacgaag acgaccagaa | 3480 |
| tctgccccag cagaatcttc accatctaag attatgtcta agcatttgga cagtccccca | 3540 |
| gccattcctc ctaggcaacc cacatcaaaa gcctattcac cacgatattc aatatcagac | 3600 |
| cggacctcta tctcagaccc tcctgaaagc cctcccttat taccaccacg agaacctgtg | 3660 |
| aggacacctg atgttttctc aagctcacca ctacatctcc aacctccccc tttgggcaaa | 3720 |
| aaaagtgacc atggcaatgc cttcttccca acagcccctt ccccctttac accacctcct | 3780 |
| cctcaaacac cttctcctca cggcacaaga aggcatctgc catcaccacc attgacacaa | 3840 |
| gaagtggacc ttcattccat tgctgggccg cctgttcctc cacgacaaag cacttctcaa | 3900 |
| catatcccta aactccctcc aaaaacttac aaaagggagc acacacaccc atccatgcac | 3960 |
| agagatggac caccactgtt ggagaatgcc cattcttcct ga | 4002 |

<210> SEQ ID NO 5
<211> LENGTH: 3108
<212> TYPE: DNA
<213> ORGANISM: Homo sapiens

<400> SEQUENCE: 5

| | |
|---|---|
| atgggcggcc cggctgcgcc gagggcgcc gggaggctcc gcgcgctgct gctggcgctg | 60 |
| gtggtcgcgg ggatccccgc gggcgcctac aacctcgacc cgcagcgccc cgtgcacttc | 120 |
| cagggccccg ctgactcgtt cttcggctac gcagttctgg agcatttcca cgacaacacg | 180 |
| cgctgggtcc ttgtgggcgc accaaaggca gattccaaat acagcccttc agtgaagtct | 240 |
| cctgggggctg tgtttaagtg ccgtgttcac accaaccctg accggagatg caccgaactg | 300 |
| gacatggctc gagggaagaa tcggggcacg tcctgcggaa agaccctgcc ggaagaccgc | 360 |
| gatgatgagt ggatgggggt gagcctggcc cgacagccca aggctgatgg ccgtgtgttg | 420 |

```
gcctgtgctc atcgctggaa gaacatctac tatgaagccg accacatcct accccatggc      480
ttctgctaca tcatcccctc caacctccag gccaaaggca ggacgctgat cccttgctat      540
gaagagtata agaagaagta cggagaggaa cacggctcct gccaggctgg gatagcgggc      600
ttcttcaccg aggagctggt ggtgatgggg gctccaggt cattttattg ggctggaacc      660
atcaaagtgc tgaaccttac ggacaacacc tatttaaaac tgaacgacga agtgatcatg      720
aacaggcggt acacctacct gggctacgca gtgaccgctg gccacttctc tcacccgtcc      780
accattgatg tggtaggagg tgccccacag gacaaaggca tcggcaaggt ttatattttc      840
agagctgacc gaagatcagg caccttaatt aagatctttc aagcatcagg taaaaagatg      900
ggctcttact tcggctcctc cttgtgcgca gttgacctga atggggacgg cctctctgac      960
ctgctggtgg gggccccccat gttttctgag atcaggatg agggacaggt cactgtctac     1020
atcaacagag gaaatggagc cctcgaggag cagctggctc tgactgggga tggtgcctac     1080
aatgcgcact ttggagagag cattgccagc ctggacgatc tggacaatga tgggttccca     1140
gatgtggcca ttggtgcacc caaggaggat gacttcgcag gggcggtcta tatctatcat     1200
ggtgatgccg gtgggatagt ccctcagtac tcaatgaaac tgtctgggca gaagataaat     1260
ccagtgctcc ggatgtttgg tcagtccata tcggaggca ttgatatgga tggaaatggc     1320
tatcctgatg tcactgttgg agccttcatg tccgacagcg tggttcttct cagagcaagg     1380
cctgtcatta cggtggatgt ctccatcttc ctcccgggct ccatcaacat cacagcgcct     1440
cagtgtcacg acggacagca gcctgtgaac tgcctgaacg tcaccacctg cttcagcttc     1500
catggcaaac acgttccagg agagattggc ctgaattatg ttctgatggc tgacgtggcc     1560
aaaaaggaga agggccagat gcccagggtc tactttgtgc tgctgggaga gaccatgggt     1620
caggtcacag agaagctgca gctgacttac atggaggaga cgtgtcgtca ctatgtggcc     1680
catgtgaagc ggagggtgca ggacgtcatc agcccgatcg tgtttgaagc agcctacagc     1740
ctcagtgagc atgtgactgg agaggaggag agggaactgc cgcctctgac accagttctc     1800
cgctggaaaa agggacaaaa gattgcccaa aagaatcaga ctgtttttga aaggaattgc     1860
cgttcagagg actgtgccgc agacctgcag cttcagggta aactgctgct ctccagtatg     1920
gatgagaaaa ccctgtatct agctttgggg gctgtgaaga acatctccct aaacatctct     1980
atctccaacc tcgagatgga tgcctatgat gccaacgtgt ccttcaatgt ttcccgggag     2040
ctcttcttca tcaacatgtg gcagaaggag gagatgggca tctcctgtga gctgctggaa     2100
tcggacttcc tcaaatgcag cgtgggattt cctttcatga ggtcaaagtc aaagtatgaa     2160
ttcagcgtga tctttgatac aagccaccag tctggggaag aggaagttct cagcttcatt     2220
gttactgctc agagtggcaa cacggagcgc tctgaatccc tgcatgacaa caccctcgtg     2280
ctgatggtgc cactgatgca cgaggtggac acgtccatca ccggaatcat gtctccaacc     2340
tcctttgtat atggcgagtc cgtggacgca gccaacttca ttcagctgga tgacctggag     2400
tgtcactttc agcccatcaa tatcacccct caggtctaca cactggccc aagcacccTT     2460 ccagggtcat ctgtcagcat ctcttttcct aatcgactct catctggtgg tgcagagatg     2520
tttcatgtcc aggaaatggt ggtgggccaa gagaagggaa actgctcttt ccagaaaaac     2580
ccaactccct gcatcatccc tcaagaacaa gaaaatatct ccacacaat atttgctttt     2640 ttcacaaagt ctggaagaaa agtcttggac tgtgaaaaac caggaatttc ttgcctaaca     2700
gcacactgta actttagtgc tcttgctaaa gaagaaagtc gtactataga catttacatg     2760
ctgctgaaca cagaaatact gaaaaaggac agttcgtctg tcatccagtt catgtcccgc     2820
```

```
gccaaggtga aggtggatcc tgccctaagg gtggtggaaa tagctcatgg gaacccagaa    2880
gaggtgacgg tggtcttcga ggccctgcac aatctggagc cccgtggcta cgtcgtgggg    2940
tggatcatcg ccatcagttt gttggtggga atcctcatct tcctgctgct ggccgtgctg    3000
ctctggaaga tgggcttctt tcgccgaagg tacaaagaaa ttatcgaagc tgagaagaac    3060
cggaaagaga atgaagacag ttgggactgg gtccagaaaa accagtga                3108

<210> SEQ ID NO 6
<211> LENGTH: 4402
<212> TYPE: DNA
<213> ORGANISM: Homo sapiens

<400> SEQUENCE: 6
cgtaacccag gcagctgggg agcctgggct gtggccctag gagggggcgc ggcggcgggc      60
tctctccttt tgttgttgtt tcctcagcct ggggagctga aggggagacg cgtctgggtg     120
gggctgctcg gagcccgggc ctggtggccc ctggggctcc cggcgcggca gggtagggca     180
gagtagagcg ggcttcaaca tgatggcggc cgaggccggc agtgaggagg gcggcccggt     240
aacagccgga gctggaggag gcggcgcggc agcgggctcc agtgcctatc ccgcagtgtg     300
tcgggtgaag atacccgcgg ccctgcctgt ggcagccgcc ccctatcctg ggctggtgga     360
gaccggagtg gctggaactc tgggtggcgg agccgctttg gggtcagagt tcctaggagc     420
cgggtctgtg gcaggggcac tggggggagc tggactgaca gggggaggta ctgctgctgg     480
cgtagctggt gctgctgctg gcgtggccgg tgctgctgtt gctggaccta gtggagacat     540
ggctctcacc aaaactgccca cttcgttgct tgctgagact ctcgggccag gcggcggttt     600 tcccctctg ccccctcccc cttacctgcc ccctttgggg gcgggcctcg ggacagtgga     660
cgaaggtgac tctctggatg gaccagaata cgaggaggaa gaggtggcca taccgttgac     720
cgctcctcca actaaccagt ggtatcacgg aaaacttgac agaacgatag cagaagaacg     780
cctcaggcag gcagggaagt ctggcagtta tcttataaga gagagtgatc ggaggccagg     840
gtcctttgta ctttcatttc ttagccagat gaatgttgtc aaccattta ggattattgc     900 tatgtgtgga gattactaca ttggtggaag acgttttct tcactgtcag acctaatagg     960
ttattacagt catgtttctt gtttgcttaa aggagaaaaa ttactttacc cagttgcacc    1020
accagagcca gtagaagata gaaggcgtgt acgagctatt ctaccttaca caaagtacc    1080 agacactgat gaaataagtt tcttaaaagg agatatgttc attgttcata atgaattaga    1140
agatggatgg atgtgggtta caaatttaag aacagatgaa caaggcctta ttgttgaaga    1200
cctagtagaa gaggtgggcc gggaagaaga tccacatgaa ggaaaaatat ggttccatgg    1260
gaagatttcc aaacaggaag cttataattt actaatgaca gttggtcaag tctgcagttt    1320
tcttgtgagg ccctcagata atactcctgg cgattattca ctttatttcc ggaccaatga    1380
aaatattcag cgatttaaaa tatgtccaac gccaaacaat cagtttatga tgggaggccg    1440
gtattataac agcattgggg acatcataga tcactatcga aagaacagaa ttgttgaagg    1500
atattatctt aaggaacctg taccaatgca ggatcaagaa caagtactca atgacacagt    1560
ggatggcaag gaaatctata ataccatccg tcgtaaaaca aaggatgcct tttataaaaa    1620
cattgttaag aaaggttatc ttctgaaaaa gggcaaagga aaacgttgga aaaattata    1680 ttttatctta gagggtagtg atgccccaact tatttatttt gaaagcgaaa aacgagctac    1740
caaaccaaaa ggattaatag atctcagtgt atgttctgtc tatgtcgttc atgatagtct    1800
```

```
ctttggcagg ccaaactgtt ttcagatagt agttcagcac tttagtgaag aacattacat    1860
cttttacttt gcaggagaaa ctccagaaca agcagaggat tggatgaaag gtctgcaggc    1920
attttgcaat ttacggaaaa gtagtccagg gacatccaat aaacgccttc gtcaggtcag    1980
cagccttgtt ttacatattg aagaagccca taaactccca gtaaaacatt ttactaatcc    2040
atattgtaac atctacctga atagtgtcca agtagcaaaa actcatgcaa gggaagggca    2100
aaacccagta tggtcagaag agtttgtctt tgatgatctt cctcctgaca tcaatagatt    2160
tgaaataact cttagtaata aacaaagaa aagcaaagat cctgatatct tatttatgcg     2220
ctgccagttg agccgattac agaaagggca tgccacagat gaatggtttc tgctcagctc    2280
ccatatacca ttaaaaggta ttgaaccagg gtccctgcgt gttcgagcac gatactctat    2340
ggaaaaaatc atgccagaag aagagtacag tgaatttaaa gagcttatac tgcaaaagga    2400
acttcatgta gtctatgctt tatcacatgt atgtggacaa gaccgaacac tactggccag    2460
catcctactg aggattttc ttcacgaaaa gcttgaatcg ttgttgttat gcacactaaa     2520
tgacagagaa ataagcatgg aagatgaagc cactacccta tttcgagcca caacacttgc    2580
aagcaccttg atggagcagt atatgaaagc cactgctaca cagtttgttc atcatgcttt    2640
gaaagactct attttaaaga taatggaaag caagcagtct tgtgagttaa gtccatcaaa    2700
gttagaaaaa aatgaagatg tgaacactaa tttaacacac ctattgaaca tacttttcaga   2760
gcttgtggag aaaatattca tggcttcaga aatacttcca ccgacattga gatatatttta   2820
tgggtgttta cagaaatctg ttcagcataa gtggcctaca aataccacca tgagaacaag    2880
agttgttagt ggttttgttt ttcttcgact catctgtcct gccatcctga atccacggat    2940
gttcaatatc atctcagatt ctccatctcc tattgctgca agaacactga tattagtggc    3000
taaatcgtgt cagaacttag caaatcttgt ggaatttgga gctaaggagc cctacatgga    3060
aggtgtcaat ccattcatca aaagcaacaa acatcgtatg atcatgtttt tagatgaact    3120
tgggaatgta cctgaacttc cggacactac agagcattct agaacggacc tgtcccgtga    3180
tttagcagca ttgcatgaga tttgcgtggc tcattcagat gaacttcgaa cgctcagtaa    3240
tgagcgtggt gcacagcagc acgtattgaa aaagcttctg gctataacag aactgcttca    3300
acaaaaacaa aaccagtata caaaaaccaa tgatgtcagg tagcagcctt cgccccagtg    3360
ttctgcatgg attcagcatg tccaacatgg taattcactt cagtttaatg tctccttttgc   3420
tcttgccaaa aaatagcaca ctttttccaca ttccagtgat gtgtgagcta tgcaaacaaa   3480
atccaagatt ctgctggtga ataactatgc cagcaacctt gtaagctatc tgtgcaggat    3540
atttgcacta tttccacatg gaatcaatct ttaacaacct ctgagccttg gtgtacagac    3600
cacctttcac aaaacgaaat gctatgactg tatcttgata tctcgaactt tcaaaatata    3660
ttttcagtac acccagttgc caaagttttg ctgtctctta gagaaagaac tatgaaatca    3720
actgacaaga aacacattct tattgacaat tgtgtataac tggattgcag actgttctta    3780
ctgtaactac ttcctgatta ggaatatgac catttgactg ttcaatgatt atttgtattt    3840
acagtttcca gagtttgtca ttataatagg aacaatcttt gctgtatact tttaaaaaat    3900
actctgctat ttctcttgct ggaactgttg aaagaaaata tatagaatga tctattgctc    3960
atcagcttta ttttttaaac atacgactta ttttgttgaa attgtcaaag actgtattta    4020
gatctcataa tgctttgtta aatgtttaca agtaaatagt ttgaattcag taaatattat    4080
tggttgttgt attgatcaat gcatgttacc cattcaacca ttttatagac taccaatttc    4140
ttttatgtta actagaatgc ttttgttaaa agttatttgt tcattatttg tgctacccct    4200
```

```
ttgattatgc agacaacctc atcagctgcc taacttatcc atctttgaac ttctgactac    4260
ttgttgtatc tgctggatat ttagttcaac tgtatagttt tatttacttc tgtatgtgta    4320
tttttgtgaa gtattcacaa aggttaagtt aaaataaaac caagggatat cttgcataat    4380
tgattaaaaa aaaaaaaaaa aa                                             4402

<210> SEQ ID NO 7
<211> LENGTH: 3291
<212> TYPE: DNA
<213> ORGANISM: Homo sapiens

<400> SEQUENCE: 7
agaatcggag agccggtggc gtcgcaggtc gggaggacga gcaccgagtc gagggctcgc      60
tcgtctgggc cgcccgagag tcttaatcgc gggcgcttgg gccgccatct tagatggcgg     120
gagtaagagg aaaacgattg tgaggcggga acggctttct gctgcctttt ttgggccccg     180
aaaagggtca gctggccggg ctttggggcg cgtgccctga ggcgcggagc gcgtttgcta     240
cgatgcgggg gctgctcggg gctccgtccc ctgggctggg gacgcgccga atgtgaccgc     300
ctcccgctcc ctcacccgcc gcggggagga ggagcgggcg agaagctgcc gccgaacgac     360
aggacgttgg ggcggcctgg ctccctcagg tttaagaatt gtttaagctg catcaatgga     420
gcacatacag ggagcttgga agacgatcag caatggtttt ggattcaaag atgccgtgtt     480
tgatggctcc agctgcatct ctcctacaat agttcagcag tttggctatc agcgccgggc     540
atcagatgat ggcaaactca cagatccttc taagacaagc aacactatcc gtgttttctt     600
gccgaacaag caaagaacag tggtcaatgt gcgaaatgga atgagcttgc atgactgcct     660
tatgaaagca ctcaaggtga ggggcctgca accagagtgc tgtgcagtgt tcagacttct     720
ccacgaacac aaaggtaaaa aagcacgctt agattggaat actgatgctg cgtctttgat     780
tggagaagaa cttcaagtag atttcctgga tcatgttccc ctcacaacac acaactttgc     840
tcggaagacg ttcctgaagc ttgccttctg tgacatctgt cagaaattcc tgctcaatgg     900
atttcgatgt cagacttgtg gctacaaaat tcatgagcac tgtagcacca aagtacctac     960
tatgtgtgtg gactggagta acatcagaca actcttattg tttccaaatt ccactattgg    1020
tgatagtgga gtcccagcac taccttcttt gactatgcgt cgtatgcgag agtctgtttc    1080
caggatgcct gttagttctc agcacagata ttctacacct cacgccttca cctttaacac    1140
ctccagtccc tcatctgaag gttccctctc ccagaggcag aggtcgacat ccacacctaa    1200
tgtccacatg gtcagcacca ccctgcctgt ggacagcagg atgattgagg atgcaattcg    1260
aagtcacagc gaatcagcct caccttcagc cctgtccagt agcccaaca atctgagccc     1320 aacaggctgg tcagccgga aaccccgt gccagcacaa agagagcggg caccagtatc      1380
tgggacccag gagaaaaaca aaattaggcc tcgtggacag agagattcaa gctattattg    1440
ggaaatagaa gccagtgaag tgatgctgtc cactcggatt gggtcaggct cttttggaac    1500
tgtttataag ggtaaatggc acggagatgt tgcagtaaag atcctaaagg ttgtcgaccc    1560 aacccccagag caattccagg ccttcaggaa tgaggtggct gttctgcgca aaacacggca    1620
tgtgaacatt ctgctttca tggggtacat gacaaaggca aacctggcaa ttgtgaccca    1680
gtggtgcgag ggcagcagcc tctacaaaca cctgcatgtc caggagacca gtttcagat     1740 gttccagcta attgacattg cccggcagac ggctcaggga atggactatt tgcatgcaaa    1800
gaacatcatc catagagaca tgaaatccaa caatatattt ctccatgaag gcttaacagt    1860
```

| | |
|---|---|
| gaaaattgga gattttggtt tggcaacagt aaagtcacgc tggagtggtt ctcagcaggt | 1920 |
| tgaacaacct actggctctg tcctctggat ggccccagag gtgatccgaa tgcaggataa | 1980 |
| caacccattc agtttccagt cggatgtcta ctcctatggc atcgtattgt atgaactgat | 2040 |
| gacggggag cttccttatt ctcacatcaa caaccgagat cagatcatct tcatggtggg | 2100 |
| ccgaggatat gcctcccag atcttagtaa gctatataag aactgcccca agcaatgaa | 2160 |
| gaggctggta gctgactgtg tgaagaaagt aaaggaagag aggcctcttt tccccagat | 2220 |
| cctgtcttcc attgagctgc tccaacactc tctaccgaag atcaaccgga gcgcttccga | 2280 |
| gccatccttg catcgggcag cccacactga ggatatcaat gcttgcacgc tgaccacgtc | 2340 |
| cccgaggctg cctgtcttct agttgacttt gcacctgtct tcaggctgcc aggggaggag | 2400 |
| gagaagccag caggcaccac ttttctgctc cctttctcca gaggcagaac acatgttttc | 2460 |
| agagaagctg ctgctaagga ccttctagac tgctcacagg gccttaactt catgttgcct | 2520 |
| tcttttctat ccctttgggc cctgggagaa ggaagccatt tgcagtgctg gtgtgtcctg | 2580 |
| ctccctcccc acattcccca tgctcaaggc ccagccttct gtagatgcgc aagtggatgt | 2640 |
| tgatggtagt acaaaaagca ggggcccagc cccagctgtt ggctacatga gtatttagag | 2700 |
| gaagtaaggt agcaggcagt ccagcccctga tgtggagaca catgggattt tggaaatcag | 2760 |
| cttctggagg aatgcatgtc acaggcggga cttttcttcag agagtggtgc agcgccagac | 2820 |
| attttgcaca taaggcacca aacagcccag gactgccgag actctggccg cccgaaggag | 2880 |
| cctgctttgg tactatggaa cttttcttag gggacacgtc ctcctttcac agcttctaag | 2940 |
| gtgtccagtg cattgggatg gttttccagg caaggcactc ggccaatccg catctcagcc | 3000 |
| ctctcaggga gcagtcttcc atcatgctga attttgtctt ccaggagctg cccctatggg | 3060 |
| gcggggccgc agggccagcc ttgtttctct aacaaacaaa caaacaaaca gccttgtttc | 3120 |
| tctagtcaca tcatgtgtat acaaggaagc caggaataca ggttttcttg atgatttggg | 3180 |
| ttttaatttt gttttttattg cacctgacaa aatacagtta tctgatggtc cctcaattat | 3240 |
| gttattttaa taaaataaat taaatttagg tgtaaaaaa aaaaaaaaa a | 3291 |

<210> SEQ ID NO 8
<211> LENGTH: 7833
<212> TYPE: DNA
<213> ORGANISM: Homo sapiens

<400> SEQUENCE: 8

| | |
|---|---|
| atggagccgc acgtgctcgg cgcggtcctg tactggctgc tgctgccctg cgcgctgctg | 60 |
| gctgcctgcc tgctccgctt cagcggactc tcgctggtct acctgctctt cctgctgctg | 120 |
| ctgcctggt tccccggccc caccgatgc ggcctccaag gtcacacagg ccgcctcctg | 180 |
| cgggcattgc tgggcctcag cctgctcttc ctggtggccc atctcgccct ccagatctgc | 240 |
| ctgcatattg tgccccgcct ggaccagctc tgggaccca gctgcagccg ctgggagacc | 300 |
| ctctcgcgac acatagggt cacaaggctg gacctgaagg acatccccaa cgccatccgg | 360 |
| ctggtggccc ctgacctggg catcttggtg gtctcctctg tctgcctcgg catctgcggg | 420 |
| cgccttgcaa ggaacacccg gcagagccca catccacggg agctggatga tgatgagagg | 480 |
| gatgtggatg ccagcccgac ggcagggctg caggaagcag caacgctggc ccctacacgg | 540 |
| aggtcacggc tggccgctcg tttccgagtc acgccccact ggctgctggt ggcggctggg | 600 |
| cgggtcctgg ccgtaacact gcttgcactg gcaggcatcg cccacccctc ggccctctcc | 660 |
| agtgtctacc tgctgctctt cctggccctc tgcacctggt gggcctgcca ctttcccatc | 720 |

```
agcactcggg gcttcagcag actctgcgtc gcggtggggt gcttcggcgc cggccatctc    780
atctgcctct actgctacca gatgcccttg cacaggctc  tgctcccgcc tgccggcatc    840
tgggctaggg tgctgggtct caaggacttc gtgggtccca ccaactgctc cagccccac    900 gcgctggtcc tcaacaccgg cctggactgg cctgtgtatg ccagcccggg cgtcctcctg    960
ctgctgtgct acgccacggc ctctctgcgc aagctccgcg cgtaccgccc ctccggccag   1020
aggaaggagg cggcaaaggg gtatgaggct cgggagctgg agctagcaga gctgaccag    1080 tggccccagg aacgggagtc tgaccagcac gtggtgccca cagcacccga caccgaggct   1140
gataactgca tcgtgcacga gctgaccggc cagagctccg tcctgcggcg gcctgtgcgg   1200
cccaagcggg ctgagcccag ggaggcgtct ccgctccaca gcctgggcca cctcatcatg   1260
gaccagagct atgtgtgcgc gctcattgcc atgatggtat ggagcatcac ctaccacagc   1320
tggctgacct tcgtactgct gctctgggcc tgcctcatct ggacggtgcg cagccgccac   1380
caactggcca tgctgtgctc gccctgcatc ctgctgtatg ggatgacgct gtgctgccta   1440
cgctacgtgt gggccatgga cctgcgccct gagctgccca ccaccctggg ccccgtcagc   1500
ctgcgccagc tggggctgga gcacaccgc  taccccctgtc tggaccttgg tgccatgttg   1560
ctctacaccc tgaccttctg gctcctgctg cgccagtttg tgaaagagaa gctgctgaag   1620
tgggcagagt ctccagctgc gctgacggag gtcaccgtgg cagacacaga gcccacgcgg   1680
acgcagacgc tgttgcagag cctggggggag ctggtgaagg gcgtgtacgc caagtactgg   1740
atctatgtgt gtgctggcat gttcatcgtg gtcagcttcg ccggccgcct cgtggtctac   1800
aagattgtct acatgttcct cttcctgctc tgcctcaccc tcttccaggt ctactacagc   1860
ctgtggcgga agctgctcaa ggccttctgg tggctcgtgg tggcctacac catgctggtc   1920
ctcatcgccg tctacacctt ccagttccag gacttccctg cctactggcg caacctcact   1980
ggcttcaccg acgagcagct gggggacctg ggcctggagc agttcagcgt gtccgagctc   2040
ttctccagca tcctggtgcc cggcttcttc ctcctggcct gcatcctgca gctgcactac   2100
ttccacaggc ccttcatgca gctcaccgac atggagcacg tgtccctgcc tggcacgcgc   2160
ctcccgcgct gggctcacag gcaggatgca gtgagtggga ccccactgct gcgggaggag   2220
cagcaggagc atcagcagca gcagcaggag gaggaggagg aggaggagga ctccagggac   2280
gaggggctgg gcgtggccac tccccaccag gccacgcagg tgcctgaagg ggcagccaag   2340
tggggcctgg tggctgagcg gctgctggag ctggcagccg gcttctcgga cgtcctctca   2400
cgcgtgcagg tgttcctgcg gcggctgctg gagcttcacg tttcaagct  ggtggccctg   2460 tacaccgtct gggtggccct gaaggaggtg tcggtgatga acctgctgct ggtggtgctg   2520
tgggccttcg ccctgccctg cccacgcttc cggcccatgg cctcctgcct gtccaccgtg   2580
tggacctgcg tcatcatcgt gtgtaagatg ctgtaccagc tcaaggttgt caacccccag   2640
gagtattcca gcaactgcac cgagcccttc cccaacagca ccaacttgct gcccacggag   2700
atcagccagt ccctgctgta ccgggggccc gtggaccctg ccaactggtt tggggtgcgg   2760
aaagggttcc ccaacctggg ctacatccag aaccacctgc aagtgctgct gctgctggta   2820
ttcgaggcca tcgtgtaccg gcgccaggag cactaccgcc ggcagcacca gctggccccg   2880
ctgcctgccc aggccgtgtt tgccagcggc acccgccagc agctggacca ggatctgctc   2940
ggctgcctca gtacttcat  caacttcttc ttctacaaat tcgggctgga gatctgcttc   3000
ctgatggccg tgaacgtgat cgggcagcgc atgaactttc tggtgaccct gcacggttgc   3060
```

```
tggctggtgg ccatcctcac ccgcaggcac cgccaggcca ttgcccgcct ctggcccaac   3120
tactgcctct tcctggcgct gttcctgctg taccagtacc tgctgtgcct ggggatgccc   3180
ccggccctgt gcattgatta tccctggcgc tggagccggg ccgtccccat gaactccgca   3240
ctcatcaagt ggctgtacct gcctgatttc ttccgggccc ccaactccac caacctcatc   3300
agcgactttc tcctgctgct gtgcgcctcc cagcagtggc aggtgttctc agctgagcgc   3360
acagaggagt ggcagcgcat ggctggcgtc aacaccgacc gcctggagcc gctgcggggg   3420
gagcccaacc ccgtgcccaa ctttatccac tgcaggtcct accttgacat gctgaaggtg   3480
gccgtcttcc gatacctgtt ctggctggtg ctggtggtgg tgtttgtcac gggggccacc   3540
cgcatcagca tcttcgggct gggctacctg ctggcctgct tctacctgct gctcttcggc   3600
acggccctgc tgcagaggga cacacgggcc cgcctcgtgc tgtgggactg cctcattctg   3660
tacaacgtca ccgtcatcat ctccaagaac atgctgtcgc cctggcctg cgtcttcgtg   3720 gagcagatgc agaccggctt ctgctgggtc atccagctct tcagccttgt atgcaccgtc   3780
aagggctact atgaccccaa ggagatgatg acagagacc aggactgcct gctgcctgtg   3840
gaggaggctg gcatcatctg ggacagcgtc tgcttcttct tcctgctgct gcagcgccgc   3900
gtcttcctta gccattacta cctgcacgtc agggccgacc tccaggccac cgccctgcta   3960
gcctccaggg gcttcgccct ctacaacgct gccaacctca agagcattga ctttcaccgc   4020
aggatagagg agaagtccct ggcccagctg aaaagacaga tggagcgtat ccgtgccaag   4080
caggagaagc acaggcaggg ccgggtggac cgcagtcgcc cccaggacac cctgggcccc   4140
aaggaccccg gcctggagcc agggcccgac agtccagggg gctcctcccc gccacggagg   4200
cagtggtggc ggccctggct ggaccacgcc acagtcatcc actccgggga ctacttcctg   4260
tttgagtccg acagtgagga agaggaggag gctgttcctg aagacccgag gccgtcggca   4320
cagagtgcct tccagctggc gtaccaggca tgggtgacca cgcccaggc ggtgctgagg   4380 cggcggcagc aggagcagga gcaggcaagg caggaacagg caggacagct acccacagga   4440
ggtggtccca gccaggaggt ggagccagca gagggccccg aggaggcagc ggcaggccgg   4500
agccatgtgg tgcagagggt gctgagcacg gcgcagttcc tgtggatgct ggggcaggcg   4560
ctagtggatg agctgacacg ctggctgcag gagttcaccc ggcaccacgg caccatgagc   4620
gacgtgctgc gggcagagcg ctacctcctc acacaggagc tcctgcaggg cggcgaagtg   4680
cacaggggcg tgctggatca gctgtacaca agccaggccg aggccacgct gccaggcccc   4740
accgaggccc ccaatgcccc aagcaccgtg tccagtgggc tgggcgcgga ggagccactc   4800
agcagcatga cagacgacat gggcagcccc ctgagcaccg gctaccacac gcgcagtggc   4860
agtgaggagg cagtcaccga ccccggggag cgtgaggctg gtgcctctct gtaccaggga   4920
ctgatgcgga cggccagcga gctgctcctg gacaggcgcc tgcgcatccc agagctggag   4980
gaggcagagc tgtttgcgga ggggcaggc cgggcgctgc ggctgctgcg ggccgtgtac   5040
cagtgtgtgg ccgcccactc ggagctgctc tgctacttca tcatcatcct caaccacatg   5100
gtcacggcct ccgccggctc gctggtgctg cccgtgctcg tcttcctgtg ggccatgctg   5160
tcgatcccga ggcccagcaa gcgcttctgg atgacggcca tcgtcttcac cgagatcgcg   5220
gtggtcgtca agtacctgtt ccagtttggg ttcttcccct ggaacagcca cgtggtgctg   5280
cggcgctacg agaacaagcc ctacttcccg ccccgcatcc tgggcctgga aagactgac   5340 ggctacatca agtacgacct ggtgcagctc atggcccttt tcttccaccg ctcccagctg   5400
ctgtgctatg gcctctggga ccatgaggag gactcaccat ccaaggagca tgacaagagc   5460
```

| | |
|---|---|
| ggcgaggagg agcagggagc cgaggagggg ccagggtgc ctgcggccac caccgaagac | 5520 |
| cacattcagg tggaagccag ggtcggaccc acggacggga ccccagaacc ccaagtggag | 5580 |
| ctcaggcccc gtgatacgag gcgcatcagt ctacgtttta gaagaaggaa gaaggagggc | 5640 |
| ccagcacgga aaggagcggc agccatcgaa gctgaggaca gggaggaaga agaggggag | 5700 |
| gaagagaaag aggccccac ggggagagag aagaggccaa gccgctctgg aggaagagta | 5760 |
| agggcggccg ggcggcggct gcagggcttc tgcctgtccc tggcccaggg cacatatcgg | 5820 |
| ccgctacggc gcttcttcca cgacatcctg cacaccaagt accgcgcagc caccgacgtc | 5880 |
| tatgccctca tgttcctggc tgatgttgtc gacttcatca tcatcatttt tggcttctgg | 5940 |
| gcctttggga agcactcggc ggccacagac atcacgtcct ccctatcaga cgaccaggta | 6000 |
| cccgaggctt tcctggtcat gctgctgatc cagttcagta ccatggtggt tgaccgcgcc | 6060 |
| ctctacctgc gcaagaccgt gctgggcaag ctggccttcc aggtggcgct ggtgctggcc | 6120 |
| atccacctat ggatgttctt catcctgccc gccgtcactg agaggatgtt caaccagaat | 6180 |
| gtggtggccc agctctggta cttcgtgaag tgcatctact tcgccctgtc cgcctaccag | 6240 |
| atccgctgcg gctaccccac ccgcatcctc ggcaacttcc tcaccaagaa gtacaatcat | 6300 |
| ctcaacctct tcctcttcca ggggttccgg ctggtgccgt tcctggtgga gctgcgggca | 6360 |
| gtgatggact gggtgtggac ggacaccacg ctgtccctgt ccagctggat gtgtgtggag | 6420 |
| gacatctatg ccaacatctt catcatcaaa tgcagccgag agacagagaa gaaatacccg | 6480 |
| cagcccaaag ggcagaagaa gaagaagatc gtcaagtacg gcatgggtgg cctcatcatc | 6540 |
| ctcttcctca tcgccatcat ctggttccca ctgctcttca tgtcgctggt gcgctccgtg | 6600 |
| gttgggttg tcaaccagcc catcgatgtc accgtcaccc tgaagctggg cggctatgag | 6660 |
| ccgctgttca ccatgagcgc ccagcagccg tccatcatcc ccttcacggc ccaggcctat | 6720 |
| gaggagctgt cccggcagtt tgaccccag ccgctggcca tgcagttcat cagccagtac | 6780 |
| agccctgagg acatcgtcac ggcgcagatt gagggcagct ccggggcgct gtggcgcatc | 6840 |
| agtcccccca gccgtgccca gatgaagcgg gagctctaca acggcacggc cgacatcacc | 6900 |
| ctgcgcttca cctggaactt ccagagggac ctggcgaagg gaggcactgt ggagtatgcc | 6960 |
| aacgagaagc acatgctggc cctggccccc aacagcactg cacggcggca gctggccagc | 7020 |
| ctgctcgagg gcacctcgga ccagtctgtg gtcatcccta atctcttccc caagtacatc | 7080 |
| cgtgccccca cgggcccga agccaaccct gtgaagcagc tgcagcccaa tgaggaggcc | 7140 |
| gactacctcg gcgtgcgtat ccagctgcgg agggagcagg tgcggggc caccggcttc | 7200 |
| ctcgaatggt gggtcatcga gctgcaggag tgccggaccg actgcaacct gctgccatg | 7260 |
| gtcatttttca gtgacaaggt cagcccaccg agcctcggct tcctggctgg ctacggcatc | 7320 |
| atggggctgt acgtgtccat cgtgctggtc atcggcaagt tcgtgcgcgg attcttcagc | 7380 |
| gagatctcgc actccattat gttcgaggag ctgccgtgcg tggaccgcat cctcaagctc | 7440 |
| tgccaggaca tcttcctggt gcgggagact cgggagctgg agctggagga ggagttgtac | 7500 |
| gccaagctca tcttcctcta ccgctcaccg gagaccatga tcaagtggac tcgtgagaag | 7560 |
| gagtaggagc tgctgctggc gcccgagagg gaaggagccg gcctgctggg cagcgtggcc | 7620 |
| acaaggggcg gcactcctca ggccggggga gccactgccc cgtccaaggc cgccagctgt | 7680 |
| gatgcatcct cccggcctgc ctgagccctg atgctgctgt cagagaagga cactgcgtcc | 7740 |
| ccacggcctg cgtggcgctg ccgtccccca cgtgtactgt agagttttt ttttaattaa | 7800 | aaaatgtttt atttatacaa atggacaatc aga        7833

<210> SEQ ID NO 9
<211> LENGTH: 4369
<212> TYPE: DNA
<213> ORGANISM: Homo sapiens

<400> SEQUENCE: 9

| | | | | | |
|---|---|---|---|---|---|
| ttccagcgca | gctcagcccc | tgcccggccc | ggcccgcccg | gctccgcgcc | gcagtctccc      60 |
| tccctcccgc | tccgtccccg | ctcgggctcc | caccatcccc | gcccgcgagg | agagcactcg     120 |
| gcccggcggc | gcgagcagag | ccactccagg | gaggggggga | gaccgcgagc | ggccggctca     180 |
| gcccccgcca | cccggggcgg | gaccccgagg | ccccggaggg | accccaactc | cagccacgtc     240 |
| ttgctgcgcg | cccgcccggc | gcggccactg | ccagcacgct | ccgggcccgc | cgcccgcgcg     300 |
| cgcggcacag | acgcggggcc | acacttggcg | ccgccgcccg | gtgccccgca | cgctcgcatg     360 |
| ggcccgcgct | gagggccccg | acgaggagtc | ccgcgcggag | tatcggcgtc | cacccgccca     420 |
| gggagagtca | gacctggggg | ggcgagggcc | ccccaaactc | agttcggatc | ctacccgagt     480 |
| gaggcggcgc | catggagctc | cgggtgctgc | tctgctgggc | ttcgttggcc | gcagctttgg     540 |
| aagagaccct | gctgaacaca | aaattggaaa | ctgctgatct | gaagtgggtg | acattccctc     600 |
| aggtggacgg | gcagtgggag | gaactgagcg | gcctggatga | ggaacagcac | agcgtgcgca     660 |
| cctacgaagt | gtgtgacgtg | cagcgtgccc | cgggccaggc | ccactggctt | cgcacaggtt     720 |
| gggtcccacg | gcggggcgcc | gtccacgtgt | acgccacgct | gcgcttcacc | atgctcgagt     780 |
| gcctgtccct | gcctcgggct | gggcgctcct | gcaaggagac | cttcaccgtc | ttctactatg     840 |
| agagcgatgc | ggacacggcc | acggccctca | cgccagcctg | gatggagaac | ccctacatca     900 |
| aggtggacac | ggtggccgcg | gagcatctca | cccggaagcg | ccctggggcc | gaggccaccg     960 |
| ggaaggtgaa | tgtcaagacg | ctgcgtctgg | gaccgctcag | caaggctggc | ttctacctgg    1020 |
| ccttccagga | ccagggtgcc | tgcatggccc | tgctatccct | gcacctcttc | tacaaaaagt    1080 |
| gcgcccagct | gactgtgaac | ctgactcgat | cccgggagac | tgtgcctcgg | gagctggttg    1140 |
| tgcccgtggc | cggtagctgc | gtggtggatg | ccgtccccgc | ccctggcccc | agccccagcc    1200 |
| tctactgccg | tgaggatggc | cagtgggccg | aacagccggt | cacgggctgc | agctgtgctc    1260 |
| cggggttcga | ggcagctgag | gggaacacca | agtgccgagc | ctgtgcccag | gcaccttca    1320 |
| agcccctgtc | aggagaaggg | tcctgccagc | catgcccagc | caatagccac | tctaacacca    1380 |
| ttggatcagc | cgtctgccag | tgccgcgtcg | ggtacttccg | ggcacgcaca | daccccggg    1440 |
| gtgcaccctg | caccacccct | ccttcggctc | cgcggagcgt | ggtttcccgc | ctgaacggct    1500 |
| cctccctgca | cctggaatgg | agtgcccccc | tggagtctgg | tggccgagag | gacctcacct    1560 |
| acgccctccg | ctgccgggag | tgccgacccg | gaggctcctg | tgcgccctgc | gggggagacc    1620 |
| tgactttga | ccccggcccc | cgggacctgg | tggagccctg | ggtggtggtt | cgagggctac    1680 |
| gtcctgactt | cacctatacc | tttgaggtca | ctgcattgaa | cggggtatcc | tccttagcca    1740 |
| cggggcccgt | cccatttgag | cctgtcaatg | tcaccactga | ccgagaggta | cctcctgcag    1800 |
| tgtctgacat | ccgggtgacg | cggtcctcac | ccagcagctt | gagcctggcc | tgggctgttc    1860 |
| cccgggcacc | cagtggggct | gtgctggact | acgaggtcaa | ataccatgag | aagggcgccg    1920 |
| agggtcccag | cagcgtgcgg | ttcctgaaga | cgtcagaaaa | ccgggcagag | ctgcgggggc    1980 |
| tgaagcgggg | agccagctac | ctggtgcagg | tacgggcgcg | ctctgaggcc | ggctacgggc    2040 |
| ccttcggcca | ggaacatcac | agccagacce | aactggatga | gagcgagggc | tggcgggagc    2100 |

```
agctggccct gattgcgggc acggcagtcg tgggtgtggt cctggtcctg gtggtcattg    2160
tggtcgcagt tctctgcctc aggaagcaga gcaatgggag agaagcagaa tattcggaca    2220
aacacggaca gtatctcatc ggacatggta ctaaggtcta catcgacccc ttcacttatg    2280
aagaccctaa tgaggctgtg agggaatttg caaaagagat cgatgtctcc tacgtcaaga    2340
ttgaagaggt gattggtgca ggtgagtttg gcgaggtgtg ccggggggcgg ctcaaggccc    2400 cagggaagaa ggagagctgt gtggcaatca agaccctgaa gggtggctac acggagcggc    2460
agcggcgtga gtttctgagc gaggcctcca tcatgggcca gttcgagcac cccaatatca    2520
tccgcctgga gggcgtggtc accaacagca tgcccgtcat gattctcaca gagttcatgg    2580
agaacggcgc cctggactcc ttcctgcggc taaacgacgg acagttcaca gtcatccagc    2640
tcgtgggcat gctgcgggc atcgcctcgg gcatgcggta ccttgccgag atgagctacg    2700
tccaccgaga cctggctgct cgcaacatcc tagtcaacag caacctcgtc tgcaaagtgt    2760
ctgactttgg ccttcccga ttcctggagg agaactcttc cgatcccacc tacacgagct    2820
ccctgggagg aaagattccc atccgatgga ctgccccgga ggccattgcc ttccggaagt    2880
tcacttccgc cagtgatgcc tggagttacg ggattgtgat gtgggaggtg atgtcatttg    2940
gggagaggcc gtactgggac atgagcaatc aggacgtgat caatgccatt gaacaggact    3000
accggctgcc cccgccccca gactgtccca cctccctcca ccagtcatg ctggactgtt     3060 ggcagaaaga ccggaatgcc cggccccgct ccccccaggt ggtcagcgcc ctggacaaga    3120
tgatccggaa ccccgccagc ctcaaaatcg tggcccggga gaatggcggg gcctcacacc    3180
ctctcctgga ccagcggcag cctcactact cagcttttgg ctctgtgggc gagtggcttc    3240
gggccatcaa aatgggaaga tacgaagaaa gtttcgcagc cgctggcttt ggctccttcg    3300
agctggtcag ccagatctct gctgaggacc tgctccgaat cggagtcact ctggcgggac    3360
accagaagaa aatcttggcc agtgtccagc acatgaagtc ccaggccaag ccgggaaccc    3420
cgggtgggac aggaggaccg gccccgcagt actgacctgc aggaactccc cacccccaggg   3480 acaccgcctc cccattttcc ggggcagagt ggggactcac agaggccccc agccctgtgc    3540
cccgctggat tgcactttga gcccgtgggg tgaggagttg gcaatttgga gagacaggat    3600 ttggggggttc tgccataata ggaggggaaa atcacccccc agccacctcg gggaactcca    3660
gaccaagggt gagggcgcct ttccctcagg actgggtgtg accagaggaa aaggaagtgc    3720
ccaacatctc ccagcctccc caggtgcccc cctcaccttg atgggtgcgt tcccgcagac    3780
caaagagagt gtgactccct tgccagctcc agagtgggg ggctgtccca gggggcaaga     3840
aggggtgtca gggcccagtg acaaaatcat tggggtttgt agtcccaact tgctgctgtc    3900
accaccaaac tcaatcattt ttttccttg taaatgcccc tccccagct gctgccttca       3960 tattgaaggt ttttgagttt tgtttttggt cttaattttt ctccccgttc ccttttttgtt   4020 tcttcgtttt gtttttctac cgtccttgtc ataactttgt gttggaggga acctgtttca    4080
ctatggcctc ctttgcccaa gttgaaacag gggcccatca tcatgtctgt tccagaaca     4140 gtgccttggt catcccacat ccccggaccc cgcctgggac ccccaagctg tgtcctatga    4200
aggggtgtgg ggtgaggtag tgaaaagggc ggtagttggt ggtggaaccc agaaacggac    4260
gccggtgctt ggagggggttc ttaaattata tttaaaaaag taacttttttg tataaataaa  4320 agaaaatggg acgtgtccca gctccagggg taaaaaaaaa aaaaaaaa                 4369
```

<210> SEQ ID NO 10

<211> LENGTH: 12381
<212> TYPE: DNA
<213> ORGANISM: Homo sapiens

<400> SEQUENCE: 10

```
aatctctagc tcgctcgcgc tccctctccc cgggccgtgg aaaggatccc acttccggtg      60
gggtgtcatg gcggcgtctc ggactgtgat ggctgtgggg agacggcgct agtggggaga     120
gcgaccaaga ggcccctcc cctcccggg tccccttccc ctatccccct cccccagcc        180 tccttgccaa cgcccccttt ccctctcccc ctcccgctcg gcgctgaccc cccatcccca     240
cccccgtggg aacactggga gcctgcactc cacagaccct ctccttgcct cttccctcac     300
ctcagcctcc gctccccgcc ctcttcccgg cccagggcgc cggcccaccc ttccctccgc     360
cgccccccgg ccgcggggag gacatggccg cgcacaggcc ggtggaatgg gtccaggccg     420
tggtcagccg cttcgacgag cagcttccaa taaaaacagg acagcagaac acacatacca     480
aagtcagtac tgagcacaac aaggaatgtc taatcaatat ttccaaatac aagttttctt     540
tggttataag cggcctcact actattttaa agaatgttaa caatatgaga atatttggag     600
aagctgctga aaaaaattta tatctctctc agttgattat attggataca ctggaaaaat     660
gtcttgctgg gcaaccaaag gacacaatga gattagatga aacgatgctg gtcaaacagt     720
tgctgccaga atctgccat tttcttcaca cctgtcgtga aggaaaccag catgcagctg      780
aacttcggaa ttctgcctct gggggtttat tttctctcag ctgcaacaac ttcaatgcag     840
tctttagtcg catttctacc aggttacagg aattaactgt tgttcagaa gacaatgttg      900 atgttcatga tatagaattg ttacagtata tcaatgtgga ttgtgcaaaa ttaaaacgac     960
tcctgaagga acagcattt aaatttaaag ccctaagaa ggttgcgcag ttagcagtta     1020
taaatagcct ggaaaaggca ttttggaact gggtagaaaa ttatccagat gaatttacaa    1080
aactgtacca gatcccacag actgatatgg ctgaatgtgc agaaaagcta tttgacttgg    1140
tggatggttt tgctgaaagc accaaaacgta agcagcagt ttggccacta caaatcattc    1200
tccttatctt gtgtccagaa ataatccagg atatatccaa agacgtggtt gatgaaaaca    1260
acatgaataa gaagttattt ctggacagtc tacgaaaagc tcttgctggc catggaggaa    1320
gtaggcagct gacagaaagt gctgcaattg cctgtgtcaa actgtgtaaa gcaagtactt    1380
acatcaattg ggaagataac tctgtcattt tcctacttgt tcagtccatg gtggttgatc    1440
ttaagaacct gcttttttaat ccaagtaagc cattctcaag aggcagtcag cctgcagatg    1500
tggatctaat gattgactgc cttgtttctt gctttcgtat aagccctcac aacaaccaac    1560
actttaagat ctgcctggct cagaattcac cttctacatt tcactatgtg ctggtaaatt    1620
cactccatcg aatcatcacc aattccgcat tggattggtg gcctaagatt gatgctgtgt    1680
attgtcactc ggttgaactt cgaaatatgt ttggtgaaac acttcataaa gcagtgcaag    1740
gttgtggagc acacccagca atacgaatgg caccgagtct tacatttaaa gaaaaagtaa    1800
caagccttaa atttaaagaa aaacctacag acctggagac aagaagctat aagtatcttc    1860
tcttgtccat ggtgaaacta attcatgcag atccaaagct cttgctttgt aatccaagaa    1920
aacaggggcc cgaaacccaa ggcagtacag cagaattaat tacagggctc gtccaactgg    1980
tccctcagtc acacatgcca gagattgctc aggaagcaat ggaggctctg ctggttcttc    2040
atcagttaga tagcattgat ttgtggaatc ctgatgctcc tgtagaaaca ttttgggaga    2100
ttagctcaca aatgctttt tacatctgca agaaattaac tagtcatcaa atgcttagta    2160
gcacagaaat tctcaagtgg ttgcgggaaa tattgatctg caggaataaa tttcttctta    2220
```

```
aaaataagca ggcagataga agttcctgtc actttctcct ttttacggg gtaggatgtg   2280 atattccttc tagtggaaat accagtcaaa tgtccatgga tcatgaagaa ttactacgta   2340
ctcctggagc ctctctccgg aagggaaaag ggaactcctc tatggatagt gcagcaggat   2400
gcagcggaac cccccgatt tgccgacaag cccagaccaa actagaagtg gccctgtaca    2460
tgtttctgtg gaaccctgac actgaagctg ttctggttgc catgtcctgt ttccgccacc   2520
tctgtgagga agcagatatc cggtgtgggg tggatgaagt gtcagtgcat aacctcttgc   2580
ccaactataa cacattcatg gagtttgcct ctgtcagcaa tatgatgtca acaggaagag   2640
cagcacttca gaaaagagtg atggcactgc tgaggcgcat tgagcatccc actgcaggaa   2700
acactgaggc ttgggaagat acacatgcaa aatgggaaca agcaacaaag ctaatcctta   2760
actatccaaa agccaaaatg gaagatggcc aggctgctga aagccttcac aagaccattg   2820
ttaagaggcg aatgtcccat gtgagtggag gaggatccat agatttgtct gacacagact   2880
ccctacagga atggatcaac atgactggct ccttttgtgc ccttggggga gtgtgcctcc   2940
agcagagaag caattctggc ctggcaacct atagcccacc catgggtcca gtcagtgaac   3000
gtaagggttc tatgatttca gtgatgtctt cagagggaaa cgcagataca cctgtcagca   3060
aatttatgga tcggctgttg tccttaatgg tgtgtaacca tgagaaagtg ggacttcaaa   3120 tacgaccaa tgttaaggat ctggtgggtc tagaattgag tcctgctctg tatccaatgc    3180
tatttaacaa attgaagaat accatcagca agttttttga ctcccaagga caggttttat   3240
tgactgatac caatactcaa tttgtagaac aaaccatagc tataatgaag aacttgctag   3300
ataatcatac tgaaggcagc tctgaacatc tagggcaagc tagcattgaa acaatgatgt   3360
taaatctggt caggtatgtt cgtgtgcttg ggaatatggt ccatgcaatt caaataaaaa   3420
cgaaactgtg tcaattagtt gaagtaatga tggcaaggag agatgacctc tcattttgcc   3480
aagagatgaa atttaggaat aagatggtag aatacctgac agactgggtt atgggaacat   3540
caaaccaagc agcagatgat gatgtaaaat gtcttacaag agatttggac caggcaagca   3600
tggaagcagt agtttcactt ctagctggtc tccctctgca gcctgaagaa ggagatggtg   3660
tggaattgat ggaagccaaa tcacagttat ttcttaaata cttcacatta tttatgaacc   3720
ttttgaatga ctgcagtgaa gttgaagatg aaagtgcgca aacaggtggc aggaaacgtg   3780
gcatgtctcg gaggctggca tcactgaggc actgtacggt ccttgcaatg tcaaacttac   3840
tcaatgccaa cgtagacagt ggtctcatgc actccatagg cttaggttac cacaaggatc   3900
tccagacaag agctacattt atggaagttc tgacaaaaat ccttcaacaa ggcacagaat   3960
ttgacacact tgcagaaaca gtattggctg atcggtttga gagattggtg aactggtca    4020 caatgatggg tgatcaagga gaactcccta tagcgatggc tctggccaat gtggttcctt   4080
gttctcagtg ggatgaacta gctcgagttc tggttactct gtttgattct cggcatttac   4140
tctaccaact gctctggaac atgtttttcta aagaagtaga attggcagac tccatgcaga   4200
ctctcttccg aggcaacagc ttggccagta aaataatgac attctgtttc aaggtatatg   4260
gtgctaccta tctacaaaaa ctcctggatc ctttattacg aattgtgatc acatcctctg   4320
attggcaaca tgttagcttt gaagtggatc ctaccaggtt agaaccatca gagagccttg   4380
aggaaaacca gcggaacctc cttcagatga ctgaaaagtt cttccatgcc atcatcagtt   4440
cctcctcaga attccccct caacttcgaa gtgtgtgcca ctgtttatac caggtggtta   4500
gccagcgttt ccctcagaac agcatcggtg cagtaggaag tgccatgttc ctcagattta   4560
```

-continued

```
tcaatcctgc cattgtctca ccgtatgaag cagggatttt agataaaaag ccaccaccta      4620
gaatcgaaag gggcttgaag ttaatgtcaa agatacttca gagtattgcc aatcatgttc      4680
tcttcacaaa agaagaacat atgcggcctt tcaatgattt tgtgaaaagc aactttgatg      4740
cagcacgcag gttttccctt gatatagcat ctgattgtcc tacaagtgat gcagtaaatc      4800
atagtctttc cttcataagt gacggcaatg tgcttgcttt acatcgtcta ctctggaaca      4860
atcaggagaa aattgggcag tatctttcca gcaacaggga tcataaagct gttggaagac      4920
gaccttttga taagatggca acacttcttg catacctggg tcctccagag cacaaacctg      4980
tggcagatac acactggtcc agccttaacc ttaccagttc aaagtttgag gaatttatga      5040
ctaggcatca ggtacatgaa aaagaagaat tcaaggcttt gaaaacgtta agtatttttct     5100 accaagctgg gacttccaaa gctgggaatc ctatttttta ttatgttgca cggaggttca      5160
aaactggtca aatcaatggt gatttgctga tataccatgt cttactgact ttaaagccat      5220
attatgcaaa gccatatgaa attgtagtgg accttaccca taccgggcct agcaatcgct      5280
ttaaaacaga ctttctctct aagtggtttg ttgttttttcc tggctttgct tacgacaacg      5340
tctccgcagt ctatatctat aactgtaact cctgggtcag ggagtacacc aagtatcatg      5400
agcggctgct gactggcctc aaaggtagca aaaggcttgt tttcatagac tgtcctggga      5460
aactggctga gcacatagag catgaacaac agaaactacc tgctgccacc ttggctttag      5520
aagaggacct gaaggtattc cacaatgctc tcaagctagc tcacaaagac accaaagttt      5580
ctattaaagt tggttctact gctgtccaag taacttcagc agagcgaaca aaagtcctag      5640
ggcaatcagt ctttctaaat gacatttatt atgcttcgga aattgaagaa atctgcctag      5700
tagatgagaa ccagttcacc ttaaccattg caaaccaggg cacgccgctc accttcatgc      5760
accaggagtg tgaagccatt gtccagtcta tcattcatat ccggacccgc tgggaactgt      5820
cacagcccga ctctatcccc caacacacca agattcggcc aaaagatgtc cctgggacac      5880
tgctcaatat cgcattactt aatttaggca gttctgaccc gagtttacgg tcagctgcct      5940
ataatcttct gtgtgcctta acttgtacct ttaatttaaa aatcgagggc cagttactag      6000
agacatcagg tttatgtatc cctgccaaca acaccctctt tattgtctct attagtaaga      6060
cactggcagc caatgagcca cacctcacgt tagaattttt ggaagagtgt atttctggat      6120
ttagcaaatc tagtattgaa ttgaaacacc tttgtttgga atacatgact ccatggctgt      6180
caaatctagt tcgttttttgc aagcataatg atgatgccaa acgacaaaga gttactgcta      6240
ttcttgacaa gctgataaca atgaccatca atgaaaaaca gatgtaccca tctattcaag      6300
caaaaatatg gggaagcctt gggcagatta cagatctgct tgatgttgta ctagacagtt      6360
tcatcaaaac cagtgcaaca ggtggcttgg gatcaataaa agctgaggtg atggcagata      6420
ctgctgtagc tttggcttct ggaaatgtga aattggtttc aagcaaggtt attggaagga      6480
tgtgcaaaat aattgacaag acatgcttat ctccaactcc tactttagaa caacatctta      6540
tgtgggatga tattgctatt ttagcacgct acatgctgat gctgtccttc aacaattccc      6600
ttgatgtggc agctcatctt ccctacctct tccacgttgt tactttctta gtagccacag      6660
gtccgctctc ccttagagct tccacacatg gactggtcat taatatcatt cactctctgt      6720
gtacttgttc acagcttcat tttagtgaag agaccaagca agttttgaga ctcagtctga      6780
cagagttctc attacccaaa ttttacttgc tgtttggcat tagcaaagtc aagtcagctg      6840
ctgtcattgc cttccgttcc agttaccggg acaggtcatt ctctcctggc tcctatgaga      6900
gagagacttt tgctttgaca tccttggaaa cagtcacaga agctttgttg gagatcatgg      6960
```

```
aggcatgcat gagagatatt ccaacgtgca agtggctgga ccagtggaca gaactagctc   7020
aaagatttgc attccaatat aatccatccc tgcaaccaag agctcttgtt gtctttgggt   7080
gtattagcaa acgagtgtct catgggcaga taaagcagat aatccgtatt cttagcaagg   7140
cacttgagag ttgcttaaaa ggacctgaca cttacaacag tcaagttctg atagaagcta   7200
cagtaatagc actaaccaaa ttacagccac ttcttaataa ggactcgcct ctgcacaaag   7260
ccctcttttg ggtagctgtg gctgtgctgc agcttgatga ggtcaacttg tattcagcag   7320
gtaccgcact tcttgaacaa aacctgcata ctttagatag tctccgtata ttcaatgaca   7380
agagtccaga ggaagtattt atggcaatcc ggaatcctct ggagtggcac tgcaagcaaa   7440
tggatcattt tgttggactc aatttcaact ctaactttaa ctttgcattg gttggacacc   7500
ttttaaaagg gtacaggcat ccttcacctg ctattgttgc aagaacagtc agaattttac   7560
atacactact aactctggtt aacaaacaca gaaattgtga caaatttgaa gtgaatacac   7620
agagcgtggc ctacttagca gctttactta cagtgtctga agaagttcga agtcgctgca   7680
gcctaaaaca tagaaagtca cttcttctta ctgatatttc aatggaaaat gttcctatgg   7740
atacatatcc cattcatcat ggtgacccct cctataggac actaaaggag actcagccat   7800
ggtcctctcc caaaggttct gaaggatacc ttgcagccac ctatccaact gtcggccaga   7860
ccagtccccg agccaggaaa tccatgagcc tggacatggg gcaaccttct caggccaaca   7920
ctaagaagtt gcttggaaca aggaaaagtt ttgatcactt gatatcagac acaaaggctc   7980
ctaaaaggca agaaatggaa tcagggatca caacaccccc caaaatgagg agagtagcag   8040
aaactgatta tgaaatggaa actcagagga tttcctcatc acaacagcac ccacatttac   8100
gtaaagtttc agtgtctgaa tcaaatgttc tcttggatga agaagtactt actgatccga   8160
agatccaggc gctgcttctt actgttctag ctacactggt aaaatatacc acagatgagt   8220
ttgatcaacg aattctttat gaatacttag cagaggccag tgttgtgttt cccaaagtct   8280
ttcctgttgt gcataaattg ttggactcta agatcaacac cctgttatca ttgtgccaag   8340
atccaaattt gttaaatcca atccatggaa ttgtgcagag tgtggtgtac catgaagaat   8400
ccccaccaca ataccaaaca tcttacctgc aaagttttgg ttttaatggc ttgtggcggt   8460
ttgcaggacc gttttcaaag caaacacaaa ttccagacta tgctgagctt attgttaagt   8520
ttcttgatgc cttgattgac acgtacctgc ctggaattga tgaagaaacc agtgaagaat   8580
ccctcctgac tcccacatct ccttaccctc ctgcactgca gagccagctt agtatcactg   8640
ccaaccttaa cctttctaat tccatgacct cacttgcaac ttcccagcat tccccaggaa   8700
tcgacaagga gaacgttgaa ctctccccta ccactggcca ctgtaacagt ggacgaactc   8760
gccacggatc cgcaagccaa gtgcagaagc aaagaagcgc tggcagtttc aaacgtaata   8820
gcattaagaa gatcgtgtga agcttgcttg ctttcttttt taaaatcaac ttaacatggg   8880
ctcttcacta gtgaccccctt ccctgtcctt gcccttccc cccatgttgt aatgctgcac   8940
ttcctgtttt ataatgaacc catccggttt gccatgttgc cagatgatca actcttcgaa   9000
gccttgccta aatttaatgc tgccttttct ttaacttttt ttcttctact tttggcgtgt   9060
atctggtata tgtaagtgtt cagaacaact gcaagaaaag tgggaggtca ggaaacttttt  9120 aactgagaaa tctcaattgt aagagaggat gaattcttga atactgctac tactggccag   9180
tgatgaaagc catttgcaca gagctctgcc ttctgtggtt ttccttcttt catcctacag   9240
agtaaagtgt tagtcctatt tatacatttt tcaagataca agtttatgag agaaatagta   9300
```

| | |
|---|---|
| ttataacccc agtatgttta atcttttagc tgtggacttt tttttaacc gtacaaaact | 9360 |
| gaaagaacca tagaggtcaa gcctcagtga cttgacacca taaagccaca gacaaggtac | 9420 |
| ttgggggga gggcagggaa atttcatatt ttatagtgga ttcttaagaa atactaacac | 9480 |
| ttgagtatta gcaataatta caggaaaata agtgcgacca catatatctt aacattactg | 9540 |
| aattaaaact atggcttcta agtccttatc caaactcagt catccaaact agtttatttt | 9600 |
| tttctccagt tgattatctt ttaattttta attttgctaa aggtggtttt tttgtgtttt | 9660 |
| gttttttgta aaccaaaact atactaagta tagtaattat atatatatat atattttttc | 9720 |
| ccctccccct cttctttcct aactaattct gagcagggta atcagtgaac aaagtgttga | 9780 |
| aaattgttcc cagaaggtaa ttttcataga tgtttgcatt agctccatag caaaatggaa | 9840 |
| tggtacgtga catttagggt agctgatatt tttattttgt taaataattt ccaagaatag | 9900 |
| agtatggtgt atattataaa tttctttgat aagatgtatt ttgaatgtct tttaatcttc | 9960 |
| ctcctcctct ccaaaaaaat cagaaacctc tttaagaaaa catgtaggtt atatatgcta | 10020 |
| gaattgcatt taatcactgt gaaaagactg gtcagcctgc attagtatga cagtaggggg | 10080 |
| gctgttagaa ttgctgctat actggtggta tggattatca tggcattgga attttcatag | 10140 |
| taatgcagat ccaatttctt tgtggtacct gcagtttaca aaataatttg acttcagtga | 10200 |
| gcatattggt atctggatgt tccaatttag aactaaacca tatttattac aaaaagatat | 10260 |
| taatccctct actcccaggt tcccttata tgttaagata aatggctttt gagggggaa | 10320 |
| aaaataaacc tagggagag gggagtttcc tgtagtgctg tttcattaga ggatttcagt | 10380 |
| aaattaaatt ccacagctaa ttcaataaat aatggtacat ttaagtgttc tgattttaat | 10440 |
| aatatatttc acatttatcc acacagtaac aatgtaatat gttaatgtaa ataaaattgg | 10500 |
| ttttgatact cagaaataac aagaatttaa ttttttaaat ttgtttacag tcctgggaaa | 10560 |
| agtaagaatt atttgccaaa ataagaggaa agaaaacctt agtattatta atgagtttac | 10620 |
| catagaattg ttggaaatac tgaagacagg tgcaatttac taaacttttg tttttaaact | 10680 |
| attgtagagg ctgcattaga agaaaatgtt tataatgaca gagcaactat gactatataa | 10740 |
| aaaagctgaa attagaactg tgtttagaaa tagatcagta acccagtgcc aaggatgcca | 10800 |
| agctgccacc atggtcttgg ctctcccaca acccagtgtt tctggggtaa gtttcacagt | 10860 |
| ttctaggccc tggaatagca ggcagtgtaa gcctttgata actttagttc gatgttttc | 10920 |
| ttgtttttgt ttgttggttt ggtgcatatg atagtgggtg ttatgctatt ttgctcttcc | 10980 |
| catcaaaata aagaaacttc cagaggttta ctgttaaaaa tactgatatt tccataaacg | 11040 |
| ggtttaccaa gggtgtagta tttcataccg cctgaaatga tcagcattgg cacaaatcaa | 11100 |
| aattcagccg cctttgaaat gcaaaaatac ctttgactag taagtacatc ctaggagttt | 11160 |
| gaaaacttaa ctaaggttta aaatttacct tgtttaaaga acttctgact tttgaggaaa | 11220 |
| atctagctttt ccaagtaact aaaatgtaca tgagataaac ctctcaccac tatgtgtccc | 11280 |
| ttgagaaatg caacactttt ttagtcttca tacttgtaat ctataaaaga aattctgaag | 11340 |
| tttagaccaa gttgcccatt tctgcgtaat tgacataagt tctgttaaaa atattataag | 11400 |
| taattcgttt cggtttgtag atgtttcccc tgacttgtta aagaggaaac caggaactca | 11460 |
| gtcatgtttt tgtcctggat aatctacctg ttatgccagt actccatcc gagggcatg | 11520 |
| cccttagttg cccagatgga gatgcagttc agtagatttg gggcaaagtg gctacagctc | 11580 |
| tgtcttccat tcactcaaca cctgttcatg actgagccag gtgcccagga cacatcctaa | 11640 |
| acagtcagct tctatcctgt gtcctagttg gggagacaga gtgccagcca gcaaccctcc | 11700 |

```
caggtttgta ggttttaggg gttttcagtt ttgtttgggt ttttttgtttt ttgtttttgt    11760
ttctacatcc ttccccgact cccaggcata atgaggcatg tcttactcaa tgttatgcaa    11820
tggatttagg caaaaattca ttcttagtgt cagccacaca attttttta atgcagtata     11880
ttcacctgta aatagtttgt gtaaaatttg acaaaaaaag tatatttact atactgtaaa   11940
tatatgtgat gatatattgt attattttgc ttttttgtaa agcagttagt tgctgcacat    12000
ggataacaac aaaaatttga ttattctcgt gttagtattg ttaacttctt tttgcgactg   12060
cgttacatca tttaaagaaa atgctgtgta ttgtaaactt aaattgtata tgataactta   12120
ctgtcctttc catccgggcc taaactttgg cagttccttt gtctacaacc ttgttaatac   12180
tgtaaacagt tgtacgccag caggaaaaat actgcccaac agacaaaatc gatcattgta   12240
ggggaaaatc atagaaatcc atttcagatc tttattgttc ctcacccat tttcctcctt    12300
gtgtatgtac ttccccacc cccttttttt taagtaaaat gtaaattcaa tctgctctaa   12360
gaaaaaaaaa aaaaaaaaa a                                              12381

<210> SEQ ID NO 11
<211> LENGTH: 11241
<212> TYPE: DNA
<213> ORGANISM: Homo sapiens

<400> SEQUENCE: 11
tccgcccgga tagccggcgg cggcggcggc ggcggcggcg gcggcggccg ggagaggccc      60
ctccttcacg ccctgcttct ctccctcgct cgcagtcgag ccgagccggc ggacccgcct    120
gggctccgac cctgcccagg ccatggccgg caacgtgaag aagagctctg gggccggggg    180
cggcagcggc tccgggggct cgggttcggg tggcctgatt gggctcatga aggacgcctt    240
ccagccgcac caccaccacc accaccacct cagccccca ccgccgggga cggtggacaa    300
gaagatggtg gagaagtgct ggaagctcat ggacaaggtg gtgcggttgt gtcagaaccc    360
aaagctggcg ctaaagaata gcccaccta tatcttagac ctgctaccag atacctacca    420
gcatctccgt actatcttgt caagatgatga ggggaagatg gagacacttg agaaaaatga    480
gtattttagg gtgtttatgg agaatttgat gaagaaaact aagcaaacca taagcctctt    540
caaggaggga aaagaaagaa tgtatgagga gaattctcag cctaggcgaa acctaaccaa    600
actgtccctc atcttcagcc acatgctggc agaactaaaa ggaatctttc caagtggact    660
ctttcaggga gacacatttc ggattactaa agcagatgct gcggaatttt ggagaaaagc    720
ttttgggaa aagacaatag tcccttggaa gagctttcga caggctctac atgaagtgca    780
tcccatcagt tctgggctgg aggccatggc tctgaaatcc actattgatc tgacctgcaa    840
tgattatatt tcggtttttg aatttgacat ctttacccga ctctttcagc cctggtcctc    900
tttgctcagg aattggaaca gccttgctgt aactcatcct ggctacatgg ctttttttgac   960
gtatgacgaa gtgaaagctc ggctccagaa attcattcac aaacctggca gttatatctt   1020
ccggctgagc tgtactcgtc tgggtcagtg ggctattggg tatgttactg ctgatgggaa   1080
cattctccag acaatccctc acaataaacc tctcttccaa gcactgattg atggcttcag   1140
ggaaggcttc tatttgtttc ctgatggacg aaatcagaat cctgatctga ctggcttatg   1200
tgaaccaact ccccaagacc atatcaaagt gacccaggaa caatatgaat tatactgtga   1260
gatgggctcc acattccaac tatgtaaaat atgtgctgaa aatgataagg atgtaaagat   1320
tgagccctgt ggacacctca gtgcacatc ctgtctttaca tcctggcagg aatcagaagg   1380
```

```
tcagggctgt cctttctgcc gatgtgaaat taaaggtact gaacccatcg tggtagatcc     1440
gtttgatcct agagggagtg gcagcctgtt gaggcaagga gcagagggag ctccctcccc     1500
aaattatgat gatgatgatg atgaacgagc tgatgatact ctcttcatga tgaaggaatt     1560
ggctggtgcc aaggtggaac ggccgccttc tccattctcc atggcccac aagcttccct      1620 tcccccggtg ccaccacgac ttgaccttct gccgcagcga gtatgtgttc cctcaagtgc     1680
ttctgctctt ggaactgctt ctaaggctgc ttctggctcc cttcataaag acaaaccatt     1740
gccagtacct cccacacttc gagatcttcc accaccacg cctccagacc ggccatattc      1800
tgttggagca gaatcccgac ctcaaagacg ccccttgcct tgtacaccag gcgactgtcc     1860
ctccagagac aaactgcccc ctgtcccctc tagccgcctt ggagactcat ggctgccccg     1920
gccaatcccc aaagtaccag tatctgcccc aagttccagt gatccctgga caggaagaga     1980
attaaccaac cggcactcac ttccattttc attgccctca caaatggagc ccagaccaga     2040
tgtgcctagg ctcggaagca cgttcagtct ggatacctcc atgagtatga atagcagccc     2100
attagtaggt ccagagtgtg accaccccaa aatcaaacct tcctcatctg ccaatgccat     2160
ttattctctg gctgccagac ctcttcctgt gccaaaactg ccacctgggg agcaatgtga     2220
gggtgaagag gacacagagt acatgactcc ctcttccagg cctctacggc ctttggatac     2280
atcccagagt tcacgagcat gtgattgcga ccagcagatt gatagctgta cgtatgaagc     2340
aatgtataat attcagtccc aggcgccatc tatcaccgag agcagcacct ttggtgaagg     2400
gaatttggcc gcagcccatg ccaacactgg tcccgaggag tcagaaaatg aggatgatgg     2460
gtatgatgtc ccaaagccac ctgtgccggc cgtgctggcc cgccgaactc tctcagatat     2520
ctctaatgcc agctcctcct ttggctggtt gtctctggat ggtgatccta caacaaatgt     2580
cactgaaggt tcccaagttc ccgagaggcc tccaaaacca ttcccgcgga gaatcaactc     2640
tgaacggaaa gctggcagct gtcagcaagg tagtggtcct gccgcctctg ctgccaccgc     2700
ctcacctcag ctctccagtg agatcgagaa cctcatgagt caggggtact cctaccagga     2760
catccagaaa gctttggtca ttgcccagaa caacatcgag atggccaaaa acatcctccg     2820
ggaatttgtt tccatttctt ctcctgccca tgtagctacc tagcacacca tctccctgct     2880
gcaggtttag aggaccagtg agttgggagt tattactcaa gtggcaccta aagggcagg     2940 agttcctttg gtgacttcac agtgaagtct tgccctctct gtgggatatc acatcagtgg     3000
ttccaagatt tcaaagtggt gaaatgaaaa tggagcagct agtatgtttt attattttat     3060
gggtcttgag tgcatttgaa ggtgtccttc agttccacg tagagagagt gtggattata      3120
ttacatgata acctacctgg ggaacagtcc agaaagctat agaacaagta ttttgctgga     3180
aatcctaatt gaggacttaa gacttcctgg gttaaggatg tggccgtgtg tgtgtgtgtc     3240
tgcctgtggt tgtatgtgtc cttgtgatta taagattaac ctgctgtgtg tgttaattcc     3300
aggcagggaa ttagcacaaa aggtttagga aggaatcttt ttttaaagac ttccatctac     3360
tgtggtatta tacccaagcc tagtgtgtat tacaacttca acactcccct ttggcttata     3420
ttaccatgtg catagctaaa gtcttctatt tttagaacac cttctgtctg ttctttcccc     3480
atcaactcct tcctcatcct tcttggtgtt ctgtcatggg ccatgggctt gctatggcca     3540
gccttactga ggccaagcag cttatgggat gttctttatt gtgtgtgatg gtattggttt     3600
gtttggtaga taagtgggag gaaaagtact gttgctacac tattataggc atgtttgata     3660
ctagcagcta acactggtca ctccaaagca ctgtttctat aggaacattg aagctattaa     3720
gatgttttga ttatcctaat tacataatga ccgatttgag atagaggcct ttaaatacat     3780
```

```
tccatgccct ccccagaaaa tagtctgtgg gagtcagttg ccttggtgcc aggtatgtgt   3840
tctgatgtag gtcatgagtc tttctactta atgggaaggg aagaacattt gtttccagga   3900 tgacttttctg gccagaatac cggaaagctt ttaggaagct tcgttcacat gctatttaaa   3960
tgcacaaaat agacagtaag gatttatctg ttcagttttt cttcccagtg aattaatttc   4020
agcttatatg ggtgtcttca tttgaacatg aggaatatta ggttatattt tcagcagtgg   4080
ttttttcctt tgccctttaa ggagtgggga taatgtccac ggtggcccag cctcttgctg   4140
atggcacctt ccctgcattg ctgcctcccg atgatgtggt tcttttcttg tgcctgtggc   4200
tttgggaatg taacatctct ttcctccttt ccttcccttt tcctcttcac ctgaggtcct   4260
aaatactctc tgtaattact gtgttcttca cggtaattag acatcattca gtgaataaat   4320
tactgtagtc aaagacagta tgggctggca gttttgtgtaa ttgcaagttc ataaagagaa   4380
ttgagggtcc agttgggaga actattagtc agttctttta tatgctgata aatgatccct   4440
cgagttcagt tagtattctg tccagagtgt ttagctcact ttcttagcag tgtgtaagct   4500
ttctccatgt cagaagcaag cctgctcttt gataaatctg tcttcctgaa aatctaaatc   4560
atgcttttgt ctttagatct acacagaaat gaccctcctt ggatcagttt tctttccagt   4620
ctaatcatct ttggaactaa aacttgttct aactcgtctc ttggcattca gctactccta   4680
gatcttttgg ttttatcccc tggcctcaga gccatttata ttcccagagt aggcagtaca   4740
ggatctcgtg ttgatttgct gtggttaccc agtgtcttct ctacatggca taaagcggca   4800
aagcccacca ttaggtgagg cggtcccgag ttgaggtaga gtggggcaga ggaagatggc   4860
agtgaatatc aaacagtaga ccgccatcaa cttctaacag ccagtacaca cactgtttca   4920
ttttgaggta acgttcagtt ttgcattttg tttaaatatt gaaggcctag acaaagaact   4980
agaaaaaaaa aagcagtttc caggcccatc catattgtaa ttttttcttta tctgcagata   5040 ttgcctgtag tctaaagatc tcttttggaag acaaagcatt ggctatatat cttttgcctt   5100
ttccatgcat ctaaatcttc tctggagatt atctccctac tgtgtaggtt aagggcagtc   5160
tcgacttttc cttttttgag tcctgtgtgg ctctttgaat cagcgtgaaa ctgaggctcc   5220
agctccctgt gttgtgtgtg tgtgccatcc atgggcttgg gtgtcagttt gtcacaggta   5280
tctgccagca ttcaaggttt tggatcattt catgaggatc tttcctttga ctgggtgctg   5340
tgaggacaca cctgggtctg tgcctgagat tgccaggcaa gattaaggaa agttttcatg   5400
tggcttttgt tttgaggtta ttctcaaaac cttaatttct tatattttct gttgactaag   5460
gcaccagtaa cccattcttc accctccatt tgtatggcaa tttaaaagtc tttggctttg   5520
ctctgaattt aattaaaact gccttttatg aacagacttc gagttttgcc attttgggca   5580
agcccttccg cttgtccctt cctagtggct aataaagtaa aaaaacccac actactttgt   5640 tctcttttctc tcatattcat tgggctgttg tattcagcca gtctcatgct ttccctgggt   5700
cttcacggat tgctttccaa gctgccttgt tgcggggttg ctgcagagca gcaactggac   5760 cttttccagct gtcgccatgt tccttccact aaagtagagg gttcttaaaa tggaaaaacc   5820
tgtgggctct tcatatacct ccctttagtt aagtaataga ccaggcagct tctcatctca   5880
gcatttacct gttaatattt ttgtgaatag tgctctctac ctgtgggtgg ccgttctctt   5940
ccacttgctc gtctccccccc agccccattc tgcataatct accattcttc tcctctcttt   6000
ctcttcttat acagaccctc attactgggg cccaagatgt gggatactac tgttagtatt   6060
atttaactat tttgtagatt taaaagattt ctggttaagg gaggtgggggg tcactgttca   6120
```

```
tcactcttaa aatatgtgtt ttctctatag aaaagtaaaa tgtgtttatg gtcccaaaca    6180
gtcaactcac aaatttttat aacaaaattt ccttgtaaaa actagggacc atctatatat    6240
tcccttaag  atctagttct ttttgtaggt gttcagcaat ggtgataaag cagaatattc    6300
tcctacctca cgtcattaaa gtcagaagat tatagacctt ctcaaactat aagtccctct    6360
tcttgccgtt ggcctttctg actctggaat gaccactgtt cattgaaaaa tagttttctg    6420
actattggtc tggctctaac agtttgtttg ttcatccagc aaatgtttat gagtgatgac    6480
catgtgccag aaatgtcagg tatgtgtcct tcccttggcg ccacatagta gtttactaat    6540
gtttggggga ttgtacttgg actgtcatag cctctgcgtt tgaccttaaa atagctcttc    6600
ccagtaagat tgtgcaattt ttattcacag ctcttccatg tagacttacc tttcctcata    6660
gagctatcct ggttaataac aggccaagat tctcccatta tccctgttg  tctcctgtag    6720
ctttgataat gcctgggaga ttccttggtg taagtgtcat ggataccgac tgtttttatg    6780
ttggaatttg ttccaacata attagaatct gtttggtgag ttgaaaggta agttggctca    6840
gagttgcaca gtagggcatt aaatgtttaa gcaaagcatc tgcccacact ccctttcca    6900
atctagtgcc ttccttgaac ttttcctga  gctgctacgt ccctaatccc ccttgttggg    6960
aggattttcg tatcacccttatgggacctg  tcaccatgtc ctgtactatt tggaattggt    7020
tttccagtct ttcaacaacc gttgtggcta actatgtttt agaagggctg gaggtgtggg    7080
ccctgtcttc gggtctcagg acccaaagat cctttagtca gttgttgggt cttccaagag    7140
ccagacatta atacagattg aactccatca gtcccctaat tgtcagcctt acctccctc     7200
ccagagcaag gagtttaggg attctaaagc ttagtgtcca cacatcattc taccagacct    7260
tagagcttta gaagctcaat ctaaaatact gtaactcagc ataaactatt actatcactc    7320
ctttgaactc agtctccatg agcagtgttt tgttggaaat acatagaacg gcttaatgcc    7380
tagagggtgg tggatagtga aggacggtca aggttatatt tttgactgct tagggattct    7440
ttggatccaa gaaacagaaa tgttcaagcg gaataaagga gggagtggag ttgtggtaag    7500
gatgcagggt atttcgcaga acccaggacg ggaagtgcct ttggttcttg ggtggagctg    7560
gaactgcaga gctttgcacc tagtcctttc tcccgcttca cagtctgctt atggtatatg    7620
tggcccccaa ataggcactc tagtcctcaa gtctacacca ccttccaact ctgggatca    7680
ccatgaacaa attctcaatt tcccatactt aattttttt  ttttttgaga tggagtctcg    7740
ctgtgtcgcc caggctggag tgcagtggtg cagtctcaac tcaccacaac ctctgcctcc    7800
caggttcaag cagttctctg cctcaacctc ccgagtagct gggattacag gcgcctgcca    7860
ccatgcccag ctaatgttca tatttttagt agagacaggg tttcaccgtc ttggctaggc    7920
tggtcttgaa ctcctgaccc tcatgatcca cccacctcgg cctcccaaag tgctaagatt    7980
acaggcgtga gccaccgcgc ccggcccata cttcgtattc ttaaaaaaaa ctacactcag    8040
cccagcacat tgatcaagta tctatctctg agcagttggc cttgccaggg agagcagaga    8100
tgtggcaggc tccttcagct ggagacaggg agcttctcag agaagtgagc agagactcca    8160
cagacaccct aaaaaggctt ctactcaaga agtaaagcca ctactcctgc cttttttgctt   8220
agtggacagg aaggcacagg agtttgtctg ggacatcata gaaattctta ggtttaactt    8280
aattctggtc attgtcttct ttatttcctg ttttttcttcc ctttgtcagt cttcgcatcc   8340
aagatttctt ccctcctct  tgtgggccag cctgtcctgt tccagagcta gcctgttcct    8400
gggtagcctt ccttagcctc cattcagcct caggtctttt gccttcttcc gtgtttattt    8460
agagagcaga atctaataac gggttccact gtagccacta tccatggact tctgggtcct    8520
```

```
cttcaggttt gagtgcttga aaatgttcat tctctgggct tgtggcctgt ctcctccact   8580
ctcctcctca ccctctcgct ccttcctgtg tgagggccgc tctgcagtaa tgttctcagg   8640
caagccttcc taggcacctc agaaactact ttgccagagc cagtaagaat atataatatt   8700
ggagcagttg ccaggataga aattaaatat agattccagt ttaggataga gttttaccg    8760 agagctcttt agacagtata cctgtgtctt ctctggcaat tgctttcatt ttagtcctat   8820
ataaaagctt tccttttctg ttttttttta aaactatgct tttgcttgcc taaatctttt   8880
gatcttatat ttctctcatc tcagagcctg tcctgagttg taaggtattt catactgcct   8940
tacttaaaag ttttttaaac tactagagtc atttgataca cacagaagtt acctaataat   9000
ccaaagatgt ccatcaaggg aggaagggtg ggtcatcaga ctttgccttt gatgttgtag   9060
actaggctcc tgagttaagc agcagaggga cagcagtgcc atgtgccttc actgtgtccc   9120
aggaaatctg ggttggttcc agtgggaaat accagtattt cttggttctg gaaagtagca   9180
aaagagtagg agatggggaa atagggatgg ggagagcaag ccccgcatgt ccatggcgag   9240
tcaggtgggg agcacgggtg gaagggccgg ctgttgacag acagactaag ctgtgtggtg   9300
ctcttgccgc cccttcctgg gtacagagct tgagaaaaat gcagccgacc actccctgtg   9360
tttgtacaga gcaaagccca aaagccaacc tcagatctcc tgatttggca gctgaagaaa   9420
tcagcagagt cctgattgcc tgattcagtc caaaaatga atgtcaggcc ccgcccctc    9480 cccaccaaca ttgcctctcc tacattctcc ttctgcccct aaatcagaca ggaggccaga   9540
gaggagtatt gctcaatgcg tgctatgtgc aactcctcag ccttgtgcc acctccatgc    9600 tgagccctga agcagggtgt cctgggtgcc tgtgtgtcag ctccctcctc tctacctacc   9660
tctgaccttc ttgtgggtga gggtggccat gcttatggcc atcttaaaac tggagaggca   9720
gagaactact tatgagtctg tagaccacgt gttgtcttcc atggcctgtt tctcctgctg   9780
tctgggtgag tgagcctgca acgcaatgcc catgagagta aatgcctcct gacctaccct   9840
gctcagcact gttctagtgt cttggccttg aaagaaaagc ctgacttcct gctgacacat   9900
gtggtagggg catggcagct atgaggcacc tcctacgtct gttttctggc tgtggtgact   9960
tgggattttt aaccttatat atctttttcc tttactcaaa acaaaacaat ttttagcaca  10020 ctgaaaaaa aaaaaagcca aatgttttgt gcctttctaa ggcagcactg tatcccaggc   10080
tgcattttag gacttaatat ggaaatacca gagtctgagc tcctctacct tgagtttcat  10140
tagtccttag tgtctaggag acaggaaaga atgctctctg tgactggaga ggtgacatgc  10200
aggtgcagtg tgtctggagt ccctttcccc tgctgtgaga cttcagtgga ggagagaagc  10260
attgtaccct gggatcattt ggttggttcc aatcacaagc ttagttatca ggttgcatgc  10320
cttgtctcct gcaaaagaca gaatgtttca caattcccag gtaaactctg gaccattcca  10380
agtgtcctag ccttctgatg acattaatta cctagttgtg tcgaggagta taggatggac  10440
tctcctgaga aggggaggtt ggtggctttg tcttttcttt ttgctggatc ctgaactggt  10500
ctagacctcc tgcccccacc cccagccccc catcagatgt ggctggcctt tcatttgaag  10560
gcttcagact taaagcatta agcagctagt gccctctgca gggcctggtt tccccaggga  10620
agggcagcaa ggaacatggg accagaagcc tgtcctcagt aatgtgacta tagtgagctt  10680
tagcaaaagt ttttctatat aatgacatct tacttatctt ttacccttc ctcagttttc   10740 ccctgccttt aactaataaa gaattgggag acagaaattt taaagtcctc cttattcaag  10800
attttgaaat tcttagcctg ggagtgctgg agagaacctg atgctttctc cagaatgaag  10860
```

-continued

```
agtcccaatt tgtatatcag tgttaagaag aaaacaaaac aaacacatag gtgagatttt    10920
cgtggactat tttaaaaatg tgtcattaat ataaaaaatt tatattagca gtatttaatc    10980
attctcacct gtaaagaata agaaaaacag aaggtaaata ttcttacaga gaatagcaga    11040
gctttaagat tcattttcat tttaagtcca ttttattttg ccagtgtatt aatgtttaga    11100
agtctgtttt actaatgtta tttattaatt tttttttcatt tccatacaca gttagttaac    11160
taaagagctt tttcaagcac ccatgtctgt aaaaaaatat ttttaaataa agtttctttt    11220
gttgtagcag aaaaaaaaaa a                                              11241
```

<210> SEQ ID NO 12
<211> LENGTH: 10
<212> TYPE: DNA
<213> ORGANISM: Artificial Sequence
<220> FEATURE:
<223> OTHER INFORMATION: a zebrafish-adapted kozak sequence

<400> SEQUENCE: 12
gcaaacatgg                                                           10

<210> SEQ ID NO 13
<211> LENGTH: 13
<212> TYPE: DNA
<213> ORGANISM: Homo sapiens

<400> SEQUENCE: 13
tccacgtcca ctc                                                       13

<210> SEQ ID NO 14
<211> LENGTH: 13
<212> TYPE: DNA
<213> ORGANISM: Homo sapiens

<400> SEQUENCE: 14
tccacgycca ctc                                                       13

<210> SEQ ID NO 15
<211> LENGTH: 16
<212> TYPE: PRT
<213> ORGANISM: Homo sapiens

<400> SEQUENCE: 15

Pro Leu Gln Arg Ile Arg Ser Thr Ser Thr Pro Asn Val His Met Val
1               5                   10                  15

<210> SEQ ID NO 16
<211> LENGTH: 16
<212> TYPE: PRT
<213> ORGANISM: Xenopus tropicalis

<400> SEQUENCE: 16

Ser Leu Gln Arg His Arg Ser Thr Ser Thr Pro Asn Val His Ile Asp
1               5                   10                  15

<210> SEQ ID NO 17
<211> LENGTH: 14
<212> TYPE: PRT
<213> ORGANISM: Danio rerio

<400> SEQUENCE: 17

Gln Arg Leu Arg Ser Thr Ser Thr Pro Asn Val Thr Met Leu
1               5                   10

```
<210> SEQ ID NO 18
<211> LENGTH: 15
<212> TYPE: PRT
<213> ORGANISM: Homo sapiens

<400> SEQUENCE: 18

Leu Ser Gln Arg Asp Arg Ser Ser Ser Ala Pro Asn Val His Ile
1               5                   10                  15

<210> SEQ ID NO 19
<211> LENGTH: 16
<212> TYPE: PRT
<213> ORGANISM: Homo sapiens

<400> SEQUENCE: 19

Phe Gly Gln Arg Gln Arg Ser Thr Ser Thr Pro Asn Val His Met Val
1               5                   10                  15
```